(12) United States Patent
Koerber et al.

(10) Patent No.: US 12,312,415 B2
(45) Date of Patent: May 27, 2025

(54) ANTI-KLK7 ANTIBODIES, ANTI-KLK5 ANTIBODIES, MULTISPECIFIC ANTI-KLK5/KLK7 ANTIBODIES, AND METHODS OF USE

(71) Applicant: Genentech, Inc., South San Francisco, CA (US)

(72) Inventors: James Thomas Koerber, San Mateo, CA (US); Wyne Pun Lee, Millbrae, CA (US); Tangsheng Yi, Belmont, CA (US); Juan Zhang, Palo Alto, CA (US); Cary Dean Austin, San Carlos, CA (US); Cecilia P.C. Chiu, Redwood City, CA (US); Joseph Edward Chavarria-Smith, San Francisco, CA (US); Jawahar Sudhamsu, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 18/389,748

(22) Filed: Dec. 19, 2023

(65) Prior Publication Data
US 2024/0150491 A1    May 9, 2024

Related U.S. Application Data

(62) Division of application No. 17/024,094, filed on Sep. 17, 2020.

(60) Provisional application No. 62/901,990, filed on Sep. 18, 2019.

(51) Int. Cl.
*C07K 16/40* (2006.01)
*A61K 39/395* (2006.01)
*A61P 17/00* (2006.01)
*A61K 39/00* (2006.01)

(52) U.S. Cl.
CPC .......... *C07K 16/40* (2013.01); *A61K 39/3955* (2013.01); *A61P 17/00* (2018.01); *A61K 2039/507* (2013.01); *C07K 2317/24* (2013.01); *C07K 2317/31* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,834,290 A | 11/1998 | Egelrud et al. | |
| 6,180,370 B1 * | 1/2001 | Queen | A61P 19/02 435/69.6 |
| 8,088,376 B2 | 1/2012 | Chamberlain et al. | |
| 8,318,907 B2 | 11/2012 | Chamberlain et al. | |
| 8,324,351 B2 | 12/2012 | Chamberlain et al. | |
| 8,329,867 B2 | 12/2012 | Lazar et al. | |
| 8,338,574 B2 | 12/2012 | Chamberlain et al. | |
| 8,362,210 B2 | 1/2013 | Lazar et al. | |
| 8,367,805 B2 | 2/2013 | Chamberlain et al. | |
| 8,394,925 B2 | 3/2013 | Chamberlain et al. | |
| 8,435,517 B2 | 5/2013 | Desjarlais | |
| 8,546,543 B2 | 10/2013 | Lazar et al. | |
| 8,629,113 B2 | 1/2014 | Lazar et al. | |
| 8,802,820 B2 | 8/2014 | Chamberlain et al. | |
| 8,852,586 B2 | 10/2014 | Chamberlain et al. | |
| 8,883,973 B2 | 11/2014 | Chamberlain et al. | |
| 9,062,117 B2 | 6/2015 | Desjarlais et al. | |
| 9,200,079 B2 | 12/2015 | Chamberlain et al. | |
| 9,221,916 B2 | 12/2015 | Desjarlais et al. | |
| 9,266,966 B2 | 2/2016 | Desjarlais et al. | |
| 9,371,397 B2 | 6/2016 | Lazar et al. | |
| 9,475,881 B2 | 10/2016 | Lazar et al. | |
| 9,493,578 B2 | 11/2016 | Lazar et al. | |
| 9,540,451 B2 | 1/2017 | Desjarlais et al. | |
| 9,617,348 B2 | 4/2017 | Desjarlais et al. | |
| 9,803,023 B2 | 10/2017 | Chamberlain et al. | |
| 10,155,800 B2 | 12/2018 | Lazar et al. | |
| 10,336,818 B2 | 7/2019 | Chamberlain et al. | |
| 10,821,094 B2 | 11/2020 | Azouz et al. | |
| 2004/0106120 A1 * | 6/2004 | Tazi-Ahnini | A61P 11/06 435/6.18 |
| 2007/0135620 A1 | 6/2007 | Chamberlain et al. | |
| 2009/0018033 A1 | 1/2009 | Morgan et al. | |
| 2010/0098730 A1 | 4/2010 | Lowman et al. | |
| 2010/0234575 A1 | 9/2010 | Chamberlain et al. | |
| 2011/0189178 A1 | 8/2011 | Desjarlais et al. | |
| 2014/0212435 A1 | 7/2014 | Moore et al. | |
| 2014/0294810 A1 | 10/2014 | Lowman et al. | |

(Continued)

FOREIGN PATENT DOCUMENTS

| | | |
|---|---|---|
| JP | 2007-500744 A | 1/2007 |
| JP | 2008-508862 A | 3/2008 |

(Continued)

OTHER PUBLICATIONS

Kipriyanov, Sergey M., and Fabrice Le Gall. "Generation and production of engineered antibodies." Molecular biotechnology 26.1 (2004): 39-60. (Year: 2004).*

(Continued)

*Primary Examiner* — Michael Szperka
*Assistant Examiner* — Lia E Taylor
(74) *Attorney, Agent, or Firm* — Genentech, Inc.

(57) ABSTRACT

The invention provides anti-KLK7 antibodies, anti-KLK5 antibodies, anti-KLK5/KLK7 multispecific antibodies, and methods of using the same.

48 Claims, 26 Drawing Sheets
Specification includes a Sequence Listing.

(56) References Cited

U.S. PATENT DOCUMENTS

| | | |
|---|---|---|
| 2015/0071948 A1 | 3/2015 | Lazar et al. |
| 2015/0099863 A1 | 4/2015 | Chamberlain et al. |
| 2017/0058053 A1 | 3/2017 | Lazar et al. |
| 2017/0166655 A1 | 6/2017 | Lazar et al. |
| 2017/0335013 A1 | 11/2017 | Desjarlais et al. |
| 2018/0360981 A1 | 12/2018 | Lazar et al. |
| 2019/0127437 A1 | 5/2019 | Lazar et al. |
| 2019/0183989 A1 | 6/2019 | Deperthes et al. |
| 2020/0040103 A1 | 2/2020 | Chiu et al. |
| 2020/0123274 A1 | 4/2020 | Lazar et al. |
| 2021/0032313 A1 | 2/2021 | Nishimiya et al. |
| 2021/0162029 A1 | 6/2021 | Sampson |
| 2021/0163577 A1 | 6/2021 | Lazar |
| 2021/0163627 A1 | 6/2021 | Moore et al. |
| 2021/0171608 A1 | 6/2021 | Moore et al. |

FOREIGN PATENT DOCUMENTS

| | | |
|---|---|---|
| JP | 2010-518039 A | 5/2010 |
| WO | WO 95/00651 A1 | 1/1995 |
| WO | WO 01/64747 A1 | 9/2001 |
| WO | 02/044736 A2 | 6/2002 |
| WO | WO 02/44736 A2 | 6/2002 |
| WO | 02/062135 A2 | 8/2002 |
| WO | WO 2004/075723 A2 | 9/2004 |
| WO | WO 2005/001025 A2 | 1/2005 |
| WO | 2005/075667 A1 | 8/2005 |
| WO | WO 2005/078123 A1 | 8/2005 |
| WO | WO 2006/000448 A2 | 1/2006 |
| WO | WO 2008/098720 A1 | 8/2008 |
| WO | 2009/000878 A1 | 12/2008 |
| WO | 2009/024527 A1 | 2/2009 |
| WO | 2009/024528 A1 | 2/2009 |
| WO | 2009/093119 A2 | 7/2009 |
| WO | 2010/097066 A1 | 9/2010 |
| WO | 2011/050276 A1 | 4/2011 |
| WO | 2012/083385 A1 | 6/2012 |
| WO | 2012/174569 A2 | 12/2012 |
| WO | WO 2015/061441 A1 | 4/2015 |
| WO | 2015/112079 A1 | 7/2015 |
| WO | 2015/112081 A1 | 7/2015 |
| WO | 2015/114144 A1 | 8/2015 |
| WO | WO 2018/195472 A1 | 10/2018 |
| WO | WO 2019/178316 A1 | 9/2019 |
| WO | 2019/234075 A1 | 12/2019 |
| WO | 2020/095921 A1 | 5/2020 |
| WO | WO 2021/009204 A1 | 1/2021 |
| WO | WO 2021/055577 A2 | 3/2021 |
| WO | WO 2021/067335 A1 | 4/2021 |
| WO | WO 2021/092050 A1 | 5/2021 |
| WO | WO 2021/226695 A1 | 11/2021 |
| WO | 2022/192647 A1 | 9/2022 |

OTHER PUBLICATIONS

Janeway, A. C., et al. "Immunobiology: the immune system in health and disease. London." Current Biology (1997): 3:1-3:11. (Year: 1997).*

Goettig et al., "Natural and synthetic inhibitors of kallikrein-related peptidases (KLKs)" Biochimie 92:1546-1567 ( 2010).

Oliveira et al., "Isomannide-Based Peptidomimetics as Inhibitors for Human Tissue Kallikreins 5 and 7" ACS Medicinal Chemistry Letters 5:128-132 ( 2014).

Anonymous, "Human Kallikrein 7 Antibody," rndsystems.com, Feb. 7, 2018, retrieved from https://resources.rndsystems.com/pdfs/datasheets/mab2624.pdf, 1 page.

Invitation to Pay Additional Fees and, Where Applicable, Protest Fee for PCT application No. PCT/US2020/051233, mailed Dec. 17, 2020, 18 pages.

Arron et al., "Noninvasive Biomarkers That Predict Treatment Benefit from Biologic Therapies in Asthma," Ann. Am. Thorac. Soc., 10(Suplement):S206-S213 (2013).

Arron et al., "Stratified medicine in inflammatory disorders: From theory to practice," Clinical Immunology, 161: 11-22 (2015).

Auton et al., "A global reference for human genetic variation," Nature, 526: 68-74 (2015).

Birben et al., "The role of SPINK5 in asthma related physiological events in the airway epithelium," Respiratory Medicine, 106: 349-355 (2012).

Bitoun et al., "Netherton syndrome: Disease Expression and Spectrum of SPINK5 Mutations in 21 Families," J. Invest. Dermatol. 118(2):352-361 (2002).

Bobrova, "Human Kallikrein Gene Family: Biology and the role in development of ovarian cancer and other diseases," Bulletin of RONTS im. N. N. Blokhin RAMS, 17(4): 3-11 (2006).

Bønnelykke et al., "A genome-wide association study identifies CDHR3 as a susceptibility locus for early childhood asthma with severe exacerbations," Nat. Genet., 46(1): 51-55 with online methods (3 pages) (2014).

Bønnelykke et al., "Leveraging gene-environment interactions and endotypes for asthma gene discovery," J. Allergy Clin. Immunol., 137: 667-679 (2016).

Briot et al., "Kallikrein 5 induces atopic dermatitis-like lesions through PAR2-mediated thymic stromal lymphopoietin expression in Netherton syndrome," J. Exp. Med., 206: 1135-1147 (2009).

Church et al., "I am atopic, but why don't I develop allergy? the association between atopy and clinical expression of allergic disease," Clin. Exp. All. Rev., 5(1): 12-15 (2005).

Corren et al., "Lebrikizumab Treatment in Adults with Asthma," N. Engl. J. Med., 365(12): 1088-1098 (2011).

Debela et al., "Structural Basis of the Zinc Inhibition of Human Tissue Kallikrein 5," J. Mol. Biol. 373:1017-1031 (2007).

Debela et al., "Structures and specificity of the human kallikrein-related peptidases KLK 4, 5, 6, and 7," Biol. Chem. 389(6):623-632 (2008).

Deraison et al., "LEKTI Fragments Specifically Inhibit KLK5, KLK7, and KLK14 and Control Desquamation through a pH-dependent Interaction," Mol. Biol. Cell, 18: 3607-3619 (2007).

Descargues et al., "Spink5-deficient mice mimic Netherton syndrome through degradation of desmoglein 1 by epidermal protease hyperactivity," Nat. Genet., 37: 56-65 (2005).

Fahy et al., "Type 2 inflammation in asthma—present in most, absent in many," Nat. Rev. Immunol. 15(1):57-65 (2015).

Furio et al., "KLK5 Inactivation Reverses Cutaneous Hallmarks of Netherton Syndrome," PLoS Genet. 11(9):e1005389 (20 pages) (2015).

Furio et al., "Transgenic kallikrein 5 mice reproduce major cutaneous and systemic hallmarks of Netherton syndrome," J. Exp. Med., 211(3): 499-513 (2014).

Gudbjartsson et al., "Sequence variants affecting eosinophil Nos. associate with asthma and myocardial infarction," Nat. Genet., 41(3): 342-347 (2009).

Hovnanian, "Netherton syndrome: skin inflammation and allergy by loss," Cell Tissue Res., 351: 289-300 (2013).

Jia et al., "Periostin is a systemic biomarker of eosinophilic airway inflammation in asthmatic patients," J. Allergy Clin. Immunol., 130: 647-654 (2012).

Judge et al., "A clinical and immunological study of Netherton's syndrome," British Journal of Dermatology, 131: 615-621 (1994).

Kasparek et al., "KLK5 and KLK7 Ablation Fully Rescues Lethality of Netherton Syndrome-Like Phenotype," PLoS Genet. 13(1):e1006566 (21 pages) (2017).

Komatsu et al., "Aberrant human tissue kallikrein levels in the stratum corneum and serum of patients with psoriasis: dependence on phenotype, severity and therapy," Br. J. Dermatol., 156: 875-883 (2007).

Manolio et al., "Finding the missing heritability of complex diseases," Nature, 461: 747-753 (2009).

Meyer-Hoffert et al., "Identification of lympho-epithelial Kazal-type inhibitor 2 in human skin as a kallikrein-related peptidase 5-specific protease inhibition," PLoS One 4(2):e4372 (12 pages) (2009).

(56) References Cited

OTHER PUBLICATIONS

Morizane et al., "Kallikrein Expression and Cathelicidin Processing Are Independently Controlled in Keratinocytes by Calcium, Vitamin D3, and Retinoic Acid," J. Invest. Dermatol., 130(5): 1297-1306 (2010).

Myers et al., "Further replication studies of the EVE Consortium meta-analysis identifies 2 asthma risk loci in European Americans," J. Allergy Clin. Immunol., 130: 1294-1301 (2012).

Myers et al., "Epistasis between serine protease inhibitor Kazal-type 5 (SPINK5) and thymic stromal lymphopoietin (TSLP) genes contributes to childhood asthma," J. Allergy Clin. Immunol., 134(4): 891-899 (2014).

Redelfs et al., "The serine protease inhibitor of Kazal-type 9 (SPINK9) is expressed in lichen simplex chronicus, actinic keratosis and squamous cell carcinoma," Arch. Dermatol. Res., 308: 133-137 (2016).

Schechter et al., "Inhibition of human kallikreins 5 and 7 by the serine protease inhibitor lympho-epithelial Kazal-type inhibitor (LEKTI)," Biol. Chem., 386: 1173-1184 (2005).

Sun et al., "Inhibition of the kinase ITK in a mouse model of asthma reduces cell death and fails to inhibit the inflammatory response," Sci. Signal., 8(405):ra122 (13 pages) (2015).

Takayama et al., "Periostin: A novel component of subepithelial fibrosis of bronchial asthma downstream of IL-4 and IL-13 signals," J. Allergy Clin. Immunol., 118: 98-104 (2006).

Tan et al., "Toward the first class of suicide inhibitors of kallikreins involved in skin diseases," J. Med. Chem. 58(2):598-612 (2015).

Thibaut et al., "Topical Treatment of Rosacea with Ivermectin Inhibits Gene Expression of Cathelicidin Innate Immune Mediators, LL-37 and KLK5, in Reconstructed and Ex Vivo Skin Models," Dermatol. Ther. (Heidelb), 7: 213-225 (2017).

Ullemar et al., "Heritability and confirmation of genetic association studies for childhood asthma in twins," Allergy, 71: 230-238 (2016).

Wan et al., "Biomarkers in Severe Asthma," Immunol Allergy Clin. N. Am., 36: 547-557 (2016).

Wang et al., "SPINK5 knockdown in organotypic human skin culture as a model system for Netherton syndrome: effect of genetic inhibition of serine proteases kallikrein 5 and kallikrein 7," Exp. Dermatol., 23(7): 524-526 (2014).

Weber et al., "P017: Characterization of the protease inhibitor SPINK7in human skin," Experimental Dermatology, P017, 23: e4 (2014).

Wu et al., "Structural insight into distinct mechanisms of protease inhibition by antibodies," PNAS USA 104(50):19784-19789 (2007).

Wu et al., "BioGPS: building your own mash-up of gene annotations and expression profiles," Nucleic Acids Research, 44: D313-D316 (2016).

Yousef et al., "Human Kallikrein 5: A Potential Novel Serum Biomarker for Breast and Ovarian Cancer," Cancer Res., 63(14): 3958-3965 (2003).

Zhu et al., "Persistent kallikrein 5 activation induces atopic dermatitis-like skin architecture independent of PAR2 activity," J. Allergy Clin. Immunol., 140(5): 1310-1322, 1322e1-5 (2017).

International Search Report and Written Opinion for PCT Application No. PCT/US2018/028637, mailed Jul. 6, 2018, 10 pages.

International Search Report and Written Opinion for PCT Application No. PCT/US2020/051233, mailed Mar. 24, 2021, 26 pages.

International Search Report and Written Opinion for PCT Application No. PCT/US2019/022192, mailed Jul. 8, 2019, 20 pages.

Laureano et al., "Generation of recombinant antibodies against human tissue kallikrein 7 to treat skin diseases," Bioorganic Med. Chem. Letters, 30: 127626 (5 pages) (2020).

Laureano et al., "Generation of soluble antibodies against human tissue kallikrein 7 and the evaluation of their biopharmaceutical use with a poloxamer-based hydrogel drug delivery system," retreived from the internet: https://d197for5662m48.cloudfront.net/documents/publicationstatus/29066/preprint_pdf/acfa6b3a2c882a5171b04c31255fea06.pdf.

International Search Report and Written Opinion for PCT Application No. PCT/US2022/019912, mailed Aug. 19, 2022, 21 pages.

Janeway, Jr, C., et al. IMMUNOBIOLOGY: The Immune System in Health and Disease "Chapter 3:Antigen Recognition by B-cell and T-cell Receptors" Fifth Edition, New York, NY-US: Garland Publishing,:93-104 ( 2001).

Kipriyanov, S., et al. "Generation and production of engineered antibodies" Mole Biol 26(1):39-60 (Jan. 1, 2004).

R&D Systems et al., "Human Kallikrein 7 Antibody—Monoclonal Mouse IgG2A Clone#33393'" (Product Spec. Sheet; Catalog No. MAB2624),:1 (Feb. 7, 2018).

* cited by examiner

Figure 2B:
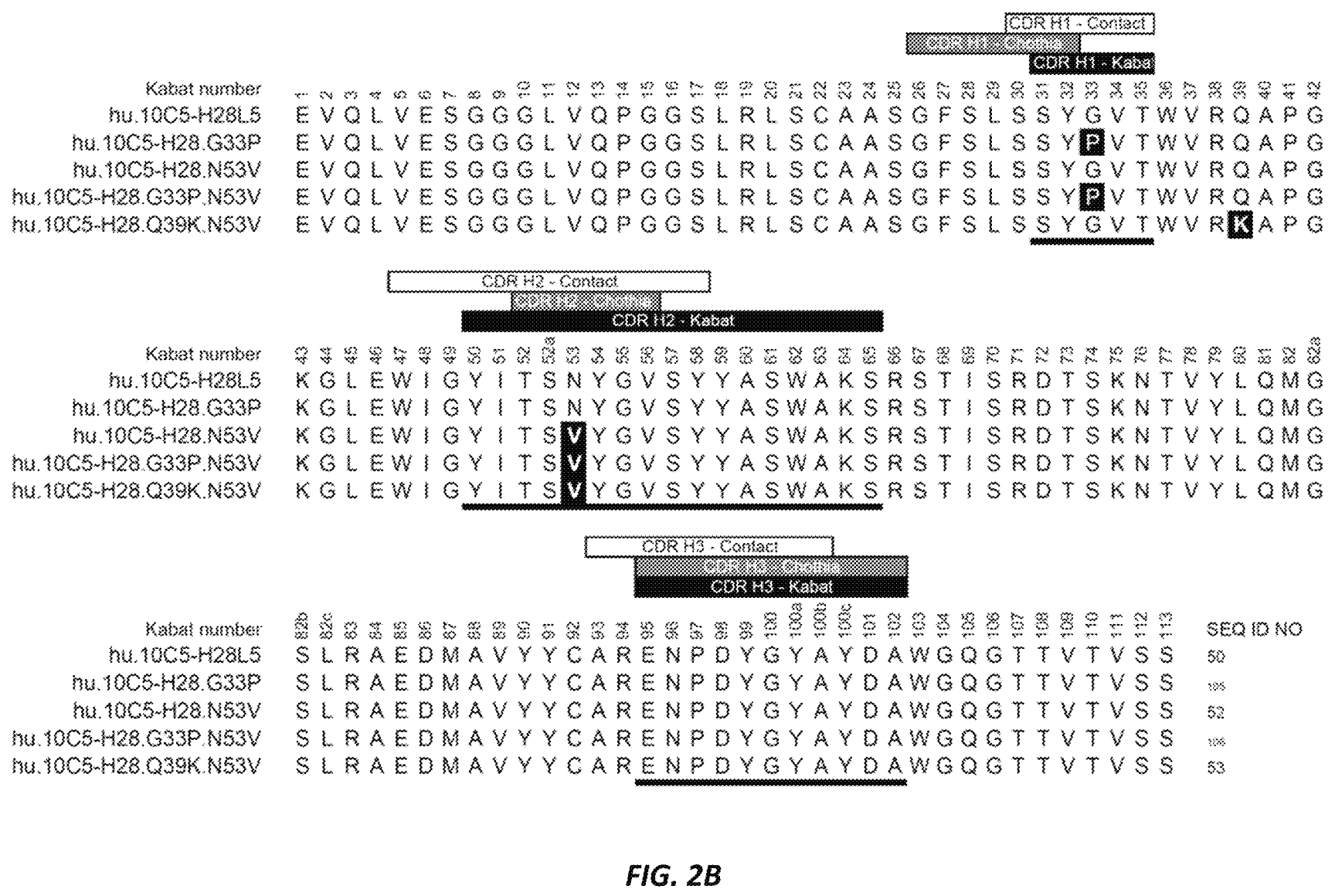

| Kabat number | Sequence (positions 1–113) | SEQ ID NO |
|---|---|---|
| hu.10C5-H28L5 | EVQLVESGGGLVQPGGSLRLSCAASGFSLSSYGVTWVRQAPGKGLEWIGYITSNYGVSYYASWAKSRSTI-SRDTSKNTVYLQMGRAEDMAVYYCARENPDYGYAYDAWGQGTTVTVSS | 50 |
| hu.10C5-H28.G33P | EVQLVESGGGLVQPGGSLRLSCAASGFSLSSYPVTWVRQAPGKGLEWIGYITSNYGVSYYASWAKSRSTI-SRDTSKNTVYLQMGRAEDMAVYYCARENPDYGYAYDAWGQGTTVTVSS | |
| hu.10C5-H28.N53V | EVQLVESGGGLVQPGGSLRLSCAASGFSLSSYGVTWVRQAPGKGLEWIGYITSVYGVSYYASWAKSRSTI-SRDTSKNTVYLQMGRAEDMAVYYCARENPDYGYAYDAWGQGTTVTVSS | 51 |
| hu.10C5-H28.G33P.N53V | EVQLVESGGGLVQPGGSLRLSCAASGFSLSSYPVTWVRQAPGKGLEWIGYITSVYGVSYYASWAKSRSTI-SRDTSKNTVYLQMGRAEDMAVYYCARENPDYGYAYDAWGQGTTVTVSS | 52 |
| hu.10C5-H28.Q39K.N53V | EVQLVESGGGLVQPGGSLRLSCAASGFSLSSYGVTWVRKAPGKGLEWIGYITSVYGVSYYASWAKSRSTI-SRDTSKNTVYLQMGRAEDMAVYYCARENPDYGYAYDAWGQGTTVTVSS | 53 |

CDR H1 (Contact / Kabat), CDR H2 (Contact / Kabat), CDR H3 (Contact / Kabat) regions indicated.

KLK7 and 14H11c Fab interface

ANTI-KLK7 ANTIBODIES, ANTI-KLK5 ANTIBODIES, MULTISPECIFIC ANTI-KLK5/KLK7 ANTIBODIES, AND METHODS OF USE

CROSS-REFERENCE TO RELATED APPLICATIONS

This application is a Divisional of U.S. application Ser. No. 17/024,094, filed Sep. 17, 2020, which claims the benefit of priority of U.S. Provisional Application No. 62/901,990, filed Sep. 18, 2019, each of which is incorporated herein by reference in its entirety.

SEQUENCE LISTING

This application contains a Sequence Listing, which has been submitted electronically in XML format and is hereby incorporated by reference in its entirety. Said XML copy, created on Dec. 19, 2023, is named P35683-US-2_Seq-Listing.xml and is 268,010 bytes in size.

Entry of the amendments to the specification is respectfully requested.

FIELD

The present invention relates to anti-KLK7 antibodies, anti-KLK5 antibodies, anti-KLK5/KLK7 multispecific antibodies, and methods of using the same.

BACKGROUND

Human kallikrein-related peptidases (KLKs) are (chymo)-trypsin-like serine proteases that are expressed in a variety of tissues such as prostate, ovary, breast, testis, brain, and skin. KLKs belong to a subgroup of the chymotrypsin-like serine protease family S1A of clan PA(S). The 15 human KLK genes are located on chromosome 19q13.4 and constitute the largest contiguous serine protease cluster in the human genome. These genes, generally composed of five coding exons and in some cases one or two 5' non-coding exons, encode the kallikrein-related peptidases KLK1 to KLK15. All KLK genes encode single-chain pre-pro-proteins containing a chymotrypsin- or trypsin-like catalytic domain of 224-237 residues with an amino acid sequence identity of approximately 40% among KLK4 to KLK15. KLK1 and its close homologs KLK2 and KLK3 form a clade of their own, KLK4, 5, and 7 belong to another subgroup, whereas KLK6 shares more similarity with KLK13 and KLK14. See Debela et al., Biol Chem 389, 623-632 (2008).

KLK5 is a secreted trypsin-like serine protease that appears to be most abundantly expressed in human skin, specifically in the upper spinous and granular layers of the skin, where keratinocytes undergo terminal differentiation and are transformed into flattened brick-like structures that form the stratum corneum, the outermost epidermal layer and the barrier to the outside environment. See Debela et al., J Mol Biol, 373, 1017-1031 (2007); and Tan et al., J Med Chem. 2015 Jan. 22; 58(2):598-612 (2014). KLK7 is a chymotrypsin-like serine protease also expressed in skin. KLK5 is described to play pathological roles in skin disorders such as Netherton Syndrome. See Furio et al., PLOS Genet 11(9), e1005389 (2015). Netherton Syndrome is caused by loss-of-function mutations in the SPINK5 gene, encoding the serine protease inhibitor Kazal-type 5 (SPINK5). See Descargues et al., Nat Genet. 2005 January; 37(1):56-65 (2004). SPINK5 has been shown to inhibit several members of the KLK serine protease family (e.g. KLK5 and KLK7). See Wang et al., Exp Dermatol. Jul; 23(7):524-6 (2014). The absence of SPINK5 in Netherton Syndrome results in unopposed KLKs activities. KLK5 hyperactivity is thought to be a key element in the pathophysiology of Netherton Syndrome as KLK5 is a regulator of proteolysis in the epidermis. Ablation of KLK5 and KLK7 rescues lethality of Netherton Syndrome-like phenotype. See Briot et al., J Exp Med. May 11; 206(5):1135-47 (2009); Furio et al., J Exp Med. Mar 10; 211(3):499-513 (2014); and Kasparek et al., PLoS Genet. 2017 Jan. 17; 13(1):e1006566 (2017). Netherton Syndrome is a complex systemic disease with multiple effects for which currently no satisfactory treatment is available.

Asthma is a clinically heterogeneous disorder associated with both genetic and environmental risk factors. Estimates of heritability from asthma twin studies vary from 35% to 80%, indicating an important role for genetic risk. See e.g., Ullemar et al., Allergy 71, 230-238 (2016). Several large scale GWAS have been performed for asthma and asthma related phenotypes, and many of the loci identified such as those near ORMDL3, IL13, IL1RL1 and TSLP genes have been confirmed in multiple study populations. See e.g., Bonnelykke et al., Nat Genet 46, 51-55 (2014). Recent studies identified a SNP at the KLK4/5 locus which is protective for the risk regarding periostin low, or type 2 low inflammation asthma. In the same study, KLK5 levels were found to be elevated in bronchoalveolar lavage of severe asthma patients supporting the hypothesis that KLK5 plays a role in bronchial obstruction and asthma pathogenesis.

Despite the advances in the field of diseases such as Netherton Syndrome and asthma, there remains a need to identify targets and develop means that can supplement or enhance the efficacy of existing therapies.

SUMMARY

The invention provides anti-KLK7 antibodies, anti-KLK5 antibodies, anti-KLK5/KLK7 multispecific antibodies, and methods of using the same.

Embodiment 1. An isolated antibody that binds to human kallikrein related peptidase 7 (KLK7), wherein the antibody:
  a) inhibits human KLK7-mediated cleavage of a substrate comprising the amino acid sequence RPKPVE-Nval-WRK (SEQ ID NO: 121), wherein Nval is norvaline;
  b) binds human KLK7 with an $K_D$ of less than 10 pM, or less than 9 pM, or less than 8 pM, or less than 7 pM, or less than 6 pM, or less than 5 pM as measured by surface plasmon resonance;
  c) binds an epitope within amino acids R71-N82, K152-S158, and/or Q211-K222 of KLK7 (SEQ ID NO: 4); and/or
  d) binds an epitope comprising one or more of amino acids H72, P73, G74, S76, Q78, N82, N157, K211, and/or T213 of KLK7 (SEQ ID NO: 4), or an epitope comprising one or more of amino acids H91, P92, G93, S95, Q97, N101, N178, K233, and/or T235 of KLK7, by chymotrypsin numbering.

Embodiment 2. An antibody that binds to human KLK7, wherein the antibody comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12.

Embodiment 3. The antibody of embodiment 1, comprising a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12.

Embodiment 4. The antibody of any one of embodiments 1 to 3, which is a monoclonal antibody.

Embodiment 5. The antibody of any one of embodiments 1 to 4, which is a humanized, or chimeric antibody.

Embodiment 6. The antibody of any one of embodiments 1 to 5, which is an antibody fragment that binds to human KLK7.

Embodiment 7. The antibody of any of embodiments 1 to 6, wherein the antibody binds human KLK7 with a $K_D$ of less than 10 pM, or less than 9 pM, or less than 8 pM, or less than 7 pM, or less than 6 pM, or less than 5 pM as measured by surface plasmon resonance; and/or binds to cynomolgus monkey KLK7 with a $K_D$ of less than 10 pM, or less than 9 pM, or less than 8 pM, or less than 7 pM, or less than 6 pM, or less than 5 pM as measured by surface plasmon resonance.

Embodiment 8. The antibody of any one of embodiments 1 to 7, wherein the heavy chain variable region comprises an FR1 comprising an amino acid sequence selected from SEQ ID NO: 123-128, an FR2 comprising an amino acid sequence selected from SEQ ID NO: 130-133, an FR3 comprising an amino acid sequence of SEQ ID NO: 135-143, and/or an FR4 comprising an amino acid sequence selected from SEQ ID NO: 144-145.

Embodiment 9. The antibody of any one of embodiments 1 to 8, wherein the light chain variable region comprises an FR1 comprising an amino acid sequence selected from SEQ ID NO: 147-150, an FR2 comprising an amino acid sequence selected from SEQ ID NO: 152-154, an FR3 comprising an amino acid sequence selected from SEQ ID NO: 156-158, and/or an FR4 comprising an amino acid sequence selected from SEQ ID NO: 160.

Embodiment 10. The antibody of any of embodiments 1 to 9, comprising a sequence selected from:
(a) a VH sequence having at least 95% sequence identity to an amino acid sequence selected from SEQ ID NOs: 15-30;
(b) a VL sequence having at least 95% sequence identity to an amino acid sequence selected from SEQ ID NO:31-38; and
(c) a VH sequence as defined in (a) and a VL sequence as defined in (b).

Embodiment 11. The antibody of any of embodiments 1 to 10, comprising a sequence selected from:
(a) a VH sequence comprising an amino acid sequence selected from SEQ ID NOs: 15-30;
(b) a VL sequence comprising an amino acid sequence selected from SEQ ID NO:31-38; and
(c) a VH sequence as defined in (a) and a VL sequence as defined in (b).

Embodiment 12. The antibody of any of embodiments 1 to 11, comprising a VH sequence of SEQ ID NO: 29 and a VL sequence of SEQ ID NO: 32.

Embodiment 13. The antibody of any of embodiments 1 to 11, comprising a VH sequence of SEQ ID NO: 30 and a VL sequence of SEQ ID NO: 38.

Embodiment 14. An antibody that specifically binds to human KLK7 comprising a VH sequence of SEQ ID NO: 29 and a VL sequence of SEQ ID NO: 32.

Embodiment 15. An antibody that specifically binds to human KLK7 comprising a VH sequence of SEQ ID NO: 30 and a VL sequence of SEQ ID NO: 38.

Embodiment 16. The antibody of any one of embodiments 1 to 15, wherein the antibody comprises a heavy chain constant region and a light chain constant region, wherein the heavy chain constant region comprises a S183K substitution (EU numbering) and/or an S183E substitution (EU numbering); and/or the light chain constant region comprises a V133K substitution (EU numbering) and/or a V133E substitution (EU numbering).

Embodiment 17. The antibody of any of embodiments 1 to 16, which is a full length IgG1 antibody.

Embodiment 18. The antibody of embodiment 17, wherein the antibody comprises a N297G substitution (EU numbering).

Embodiment 19. The antibody of any one of embodiments 16 to 18, wherein the antibody comprises a M428L substitution (EU numbering) and/or an N434S substitution (EU numbering).

Embodiment 20. The antibody of any one of embodiments 1 to 19, wherein the antibody binds human KLK7 with a $K_D$ of less than 20 pM, or less than 15 pM, or less than 10 pM, less than 5 pM, or less than 3 pM, or less than 2 pM, or less than 1 pM, as measured by surface plasmon resonance.

Embodiment 21. The antibody of any one of embodiments 1 to 20, wherein the antibody inhibits human KLK7 protease activity with an IC50 of less than 5 nM, or less than 3 nM, or less than 2 nM, or less than 1 nM.

Embodiment 22. The antibody of any one of embodiments 1 to 21, wherein the antibody binds human KLK7 with a $K_D$ of less than 20 pM, or less than 15 pM, or less than 10 pM, less than 5 pM, or less than 3 pM, or less than 2 pM, or less than 1 pM, as measured by surface plasmon resonance; and wherein the antibody inhibits human KLK7 protease activity with an IC50 of less than 5 nM, or less than 3 nM, or less than 2 nM, or less than 1 nM.

Embodiment 23. The antibody of embodiment 21 or embodiment 22, wherein inhibition of human KLK7 protease activity is inhibition of human KLK7-mediated cleavage of a substrate comprising the amino acid sequence RPKPVE-Nval-WRK (SEQ ID NO: 121), wherein Nval is norvaline.

Embodiment 24. The antibody of any of embodiments 1 to 23, wherein the antibody is a multispecific antibody.

Embodiment 25. The antibody of embodiment 24, which is a bispecific antibody.

Embodiment 26. An antibody that specifically binds human KLK7, which competes for binding to human KLK7 with the antibody of any one of embodiments 1 to 25.

Embodiment 27. The antibody of embodiment 26, wherein the antibody:
a) inhibits human KLK7-mediated cleavage of a substrate comprising the amino acid sequence RPKPVE-Nval-WRK (SEQ ID NO: 121), wherein Nval is norvaline with an IC50 of less than 5 nM, or less than 3 nM, or less than 2 nM, or less than 1 nM; and/or
b) binds human KLK7 with a $K_D$ of less than 10 pM, or less than 9 pM, or less than 8 pM, or less than 7 pM, or less than 6 pM, or less than 5 pM as measured by surface plasmon resonance.

Embodiment 28. An isolated nucleic acid encoding the antibody of any of embodiments 1 to 27.

Embodiment 29. An isolated host cell comprising the nucleic acid of embodiment 28.

Embodiment 30. An isolated host cell that expresses the antibody of any one of embodiments 1 to 27.

Embodiment 31. A method of producing an antibody that binds to human KLK7 comprising culturing the host cell of embodiment 29 or embodiment 30 under conditions suitable for the expression of the antibody.

Embodiment 32. The method of embodiment 31, further comprising recovering the antibody from the host cell.

Embodiment 33. An antibody produced by the method of embodiment 32.

Embodiment 34. An antibody that binds to human KLK5, wherein the antibody comprises:
- a) a heavy chain variable domain (VH) comprising (a) CDR-H1 comprising the amino acid sequence of SEQ ID NO: 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 46-49; or
- b) a heavy chain variable domain (VH) comprising (a) CDR-H1 comprising an amino acid sequence selected from SEQ ID NOs: 39 and 107, (b) CDR-H2 comprising the amino acid sequence of SEQ ID NO: 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 46-49; or
- c) a heavy chain variable domain (VH) comprising (a) CDR-H1 comprising an amino acid sequence selected from SEQ ID NOs: 39 and 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising the amino acid sequence of SEQ ID NOs: 44, (e) CDR-L2 comprising the amino acid sequence of SEQ ID NO: 45, and (f) CDR-L3 comprising an amino acid sequence selected from SEQ ID NOs: 46-49; or
- d) a heavy chain variable domain (VH) comprising (a) CDR-H1 comprising an amino acid sequence selected from SEQ ID NOs: 39 and 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 47-49; or
- e) a heavy chain variable domain (VH) comprising (a) CDR-H1 comprising the amino acid sequence of SEQ ID NO: 68, (b) CDR-H2 comprising the amino acid sequence of SEQ ID NO: 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78; or
- f) a heavy chain variable domain (VH) comprising (a) CDR-H1 comprising the amino acid sequence of SEQ ID NO: 68, (b) CDR-H2 comprising an amino acid sequence selected from SEQ ID NOs: 69 and 70, and (c) CDR-H3 comprising the amino acid sequence of SEQ ID NO: 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78; or
- g) a heavy chain variable domain (VH) comprising (a) CDR-H1 comprising the amino acid sequence of SEQ ID NO: 68, (b) CDR-H2 comprising an amino acid sequence selected from SEQ ID NOs: 69 and 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 76-78.

Embodiment 35. The antibody of embodiment 34, wherein the antibody comprises a heavy chain variable domain (VH) comprising (a) CDR-H1 comprising the amino acid sequence of SEQ ID NO: 39, (b) CDR-H2 comprising the amino acid sequence of SEQ ID NO: 41, and (c) CDR-H3 comprising the amino acid sequence of SEQ ID NO: 42, and a light chain variable domain (VL) comprising (d) CDR-L1 comprising the amino acid sequence of SEQ ID NOs: 43, (e) CDR-L2 comprising the amino acid sequence of SEQ ID NO: 45, and (f) CDR-L3 comprising the amino acid sequence of SEQ ID NO: 47.

Embodiment 36. The antibody of embodiment 34, wherein the antibody comprises a heavy chain variable domain (VH) comprising (a) CDR-H1 comprising the amino acid sequence of SEQ ID NO: 68, (b) CDR-H2 comprising the amino acid sequence of SEQ ID NO: 70, and (c) CDR-H3 comprising the amino acid sequence of SEQ ID NO: 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 76.

Embodiment 37. The antibody of any one of embodiments 34 to 36, which is a monoclonal antibody.

Embodiment 38. The antibody of any one of embodiments 34 to 37, which is a humanized, or chimeric antibody.

Embodiment 39. The antibody of any one of embodiments 34 to 38, which is an antibody fragment that binds human KLK5.

Embodiment 40. The antibody of any of embodiments 34 to 39, wherein the antibody binds human KLK5 with a $K_D$ of less than 1 nM, or less than 500 pM, or less than 300 pM, or less than 200 pM, or less than 100 pM, or less than 50 pM as measured by surface plasmon resonance; and/or binds to cynomolgus monkey KLK5 with a $K_D$ of less than 1 nM, or less than 500 pM, or less than 300 pM, or less than 200 pM, or less than 100 pM, or less than 50 pM as measured by surface plasmon resonance.

Embodiment 41. The antibody of any one of embodiments 34 to 40, wherein the heavy chain variable region comprises:

a) an FR1 comprising the amino acid sequence selected of SEQ ID NO: 161, an FR2 comprising the amino acid sequence of SEQ ID NO: 162-163, an FR3 comprising the amino acid sequence of SEQ ID NO: 164, and/or an FR4 comprising the amino acid sequence of SEQ ID NO: 165; or b) an FR1 comprising the amino acid sequence of SEQ ID NO: 171, an FR2 comprising an amino acid sequence selected from SEQ ID NO: 172-173, an FR3 comprising the amino acid sequence of SEQ ID NO: 174, and/or an FR4 comprising the amino acid sequence of SEQ ID NO: 175.

Embodiment 42. The antibody of any one of embodiments 34 to 41, wherein the light chain variable region comprises:

a) an FR1 comprising the amino acid sequence of SEQ ID NO: 166, an FR2 comprising an amino acid sequence selected from SEQ ID NO: 167-168, an FR3 comprising the amino acid sequence of SEQ ID NO: 169, and/or an FR4 comprising the amino acid sequence of SEQ ID NO: 170; or b) an FR1 comprising the amino acid sequence of SEQ ID NO: 176, an FR2 comprising an amino acid sequence selected from SEQ ID NO: 177-178, an FR3 comprising the amino acid sequence of SEQ ID NO: 179, and/or an FR4 comprising the amino acid sequence of SEQ ID NO: 180.

Embodiment 43. The antibody of any of embodiments 34 to 42, comprising a sequence selected from:

a) a VH sequence having at least 95% sequence identity to an amino acid sequence selected from SEQ ID NOs: 50, 52, 53, 105, and 106;

b) a VL sequence having at least 95% sequence identity to an amino acid sequence selected from SEQ ID NOs: 51 and 54-67; and c) a VH sequence as defined in (a) and a VL sequence as defined in (b);

d) a VH sequence having at least 95% sequence identity to an amino acid sequence selected from SEQ ID NOs: 79 and 81-87;

e) a VL sequence having at least 95% sequence identity to an amino acid sequence selected from SEQ ID NOs: 80 and 88-94; and f) a VH sequence as defined in (d) and a VL sequence as defined in (e).

Embodiment 44. The antibody of any of embodiments 34 to 43, comprising a sequence selected from:

a) a VH sequence comprising an amino acid sequence selected from SEQ ID NOs: 50, 52, 53, 105, and 106;

b) a VL sequence comprising an amino acid sequence selected from SEQ ID NOs: 51 and 54-67; and c) a VH sequence as defined in (a) and a VL sequence as defined in (b);

d) a VH sequence comprising an amino acid sequence selected from SEQ ID NOs: 79 and 81-87;

e) a VL sequence comprising an amino acid sequence selected from SEQ ID NOs: 80 and 88-94; and f) a VH sequence as defined in (d) and a VL sequence as defined in (e).

Embodiment 45. The antibody of any of embodiments 34 to 44, comprising a VH sequence of SEQ ID NO: 52 and a VL sequence of SEQ ID NO: 55.

Embodiment 46. The antibody of any of embodiments 34 to 44, comprising a VH sequence of SEQ ID NO: 53 and a VL sequence of SEQ ID NO: 62.

Embodiment 47. An antibody that specifically binds to human KLK5 comprising a VH sequence of SEQ ID NO: 52 and a VL sequence of SEQ ID NO: 55.

Embodiment 48. An antibody that specifically binds to human KLK5 comprising a VH sequence of SEQ ID NO: 53 and a VL sequence of SEQ ID NO: 62.

Embodiment 49. The antibody of any of embodiments 34 to 44, comprising a VH sequence of SEQ ID NO: 83 and a VL sequence of SEQ ID NO: 88.

Embodiment 50. The antibody of any of embodiments 34 to 44, comprising a VH sequence of SEQ ID NO: 87 and a VL sequence of SEQ ID NO: 92.

Embodiment 51. An antibody that specifically binds to human KLK5 comprising a VH sequence of SEQ ID NO: 83 and a VL sequence of SEQ ID NO: 88.

Embodiment 52. An antibody that specifically binds to human KLK5 comprising a VH sequence of SEQ ID NO: 87 and a VL sequence of SEQ ID NO: 92.

Embodiment 53. The antibody of any one of embodiments 34 to 52, wherein the antibody comprises a heavy chain constant region and a light chain constant region, wherein the heavy chain constant region comprises a S183K substitution (EU numbering) and/or an S183E substitution (EU numbering); and/or the light chain constant region comprises a V133K substitution (EU numbering) and/or a V133E substitution (EU numbering).

Embodiment 54. The antibody of any of embodiments 34 to 53, which is a full length IgG1 antibody.

Embodiment 55. The antibody of embodiment 54, wherein the antibody comprises a N297G substitution (EU numbering).

Embodiment 56. The antibody of any one of embodiments 53 to 55, wherein the antibody comprises a M428L substitution (EU numbering) and/or an N434S substitution (EU numbering).

Embodiment 57. The antibody of any of embodiments 34 to 56, wherein the antibody binds human KLK5 with a $K_D$ of less than 60 pM, less than 30 pM, less than 20 pM, less than 10 pM, or less than 5 pM, as measured by surface plasmon resonance.

Embodiment 58. The antibody of any one of embodiments 34 to 57, wherein the antibody inhibits human KLK5 protease activity with an IC50 of less than 5 nM, or less than 3 nM, or less than 2 nM, or less than 1 nM.

Embodiment 59. The antibody of any one of embodiments 34 to 58, wherein the antibody binds human KLK5 with a $K_D$ of less than 60 pM, less than 30 pM, less than 20 pM, less than 10 pM, or less than 5 pM, as measured by surface plasmon resonance; and wherein the antibody inhibits human KLK5 protease activity with an IC50 of less than 5 nM, or less than 3 nM, or less than 2 nM, or less than 1 nM.

Embodiment 60. The antibody of embodiment 58 or embodiment 59, wherein inhibition of human KLK5 protease activity is inhibition of human KLK5-mediated cleavage of the substrate Boc-Val-Pro-Arg-AMC.

Embodiment 61. The antibody of any of embodiments 34 to 60, wherein the antibody is a multispecific antibody.

Embodiment 62. The antibody of embodiment 61, wherein the antibody is a bispecific antibody.

Embodiment 63. An isolated nucleic acid encoding the antibody of any of embodiments 34 to 62.

Embodiment 64. An isolated host cell comprising the nucleic acid of embodiment 63.

Embodiment 65. An isolated host cell that expresses the antibody of any one of embodiments 34 to 62.

Embodiment 66. A method of producing an antibody that binds to human KLK5 comprising culturing the host cell of embodiment 64 or embodiment 65 under conditions suitable for the expression of the antibody.

Embodiment 67. The method of embodiment 66, further comprising recovering the antibody from the host cell.

Embodiment 68. An antibody produced by the method of embodiment 67.

Embodiment 69. A bispecific antibody comprising a first binding domain and a second binding domain, wherein the first binding domain binds human KLK7 and the second binding domain binds human KLK5, wherein the first binding domain comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12.

Embodiment 70. The bispecific antibody of embodiment 69, wherein the first binding domain is humanized.

Embodiment 71. The bispecific antibody of embodiment 69 or embodiment 70, wherein the first binding domain comprises a sequence selected from:
(a) a VH sequence having at least 95% sequence identity to an amino acid sequence selected from SEQ ID NOs: 15-30;
(b) a VL sequence having at least 95% sequence identity to an amino acid sequence selected from SEQ ID NO:31-38; and
(c) a VH sequence as defined in (a) and a VL sequence as defined in (b).

Embodiment 72. The bispecific antibody of any one of embodiments 69 to 71, wherein the first binding domain comprises a sequence selected from:
(a) a VH sequence comprising an amino acid sequence selected from SEQ ID NOs: 15-30;
(b) a VL sequence comprising an amino acid sequence selected from SEQ ID NO: 31-38; and
(c) a VH sequence as defined in (a) and a VL sequence as defined in (b).

Embodiment 73. The bispecific antibody of any one of embodiments 69 to 72, wherein the first binding domain comprises a VH sequence of SEQ ID NO: 29 and a VL sequence of SEQ ID NO: 32.

Embodiment 74. The bispecific antibody of any one of embodiments 69 to 72, wherein the first binding domain comprises a VH sequence of SEQ ID NO: 30 and a VL sequence of SEQ ID NO: 38.

Embodiment 75. The bispecific antibody of any one of embodiments 69 to 74, wherein the second binding domain comprises:
a) a heavy chain variable domain (VH) comprising (a) CDR-H1 comprising an amino acid sequence selected from SEQ ID NOs: 39 and 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 46-49; or
b) a heavy chain variable domain (VH) comprising (a) CDR-H1 comprising the amino acid sequence of SEQ ID NO: 68, (b) CDR-H2 comprising an amino acid sequence selected from SEQ ID NOs: 69 and 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78.

Embodiment 76. The bispecific antibody of any one of embodiments 69 to 75, wherein the second binding domain comprises a heavy chain variable domain (VH) comprising (a) CDR-H1 comprising the amino acid sequence of SEQ ID NO: 39, (b) CDR-H2 comprising the amino acid sequence of SEQ ID NO: 41, and (c) CDR-H3 comprising the amino acid sequence of SEQ ID NO: 42, and a light chain variable domain (VL) comprising (d) CDR-L1 comprising the amino acid sequence of SEQ ID NOs: 43, (e) CDR-L2 comprising the amino acid sequence of SEQ ID NO: 45, and (f) CDR-L3 comprising the amino acid sequence of SEQ ID NO: 47.

Embodiment 77. The bispecific antibody of any one of embodiments 69 to 75, wherein the second binding domain comprises a heavy chain variable domain (VH) comprising (a) CDR-H1 comprising the amino acid sequence of SEQ ID NO: 68, (b) CDR-H2 comprising the amino acid sequence of SEQ ID NO: 70, and (c) CDR-H3 comprising the amino acid sequence of SEQ ID NO: 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 76.

Embodiment 78. The bispecific antibody of any one of embodiments 69 to 77, wherein the second binding domain is humanized.

Embodiment 79. The bispecific antibody of any one of embodiments 75 to 78, wherein the second binding domain comprises a sequence selected from:
a) a VH sequence having at least 95% sequence identity to an amino acid sequence selected from SEQ ID NOs: 50, 52, 53, 105, and 106;
b) a VL sequence having at least 95% sequence identity to an amino acid sequence selected from SEQ ID NOs: 51 and 54-67; and
c) a VH sequence as defined in (a) and a VL sequence as defined in (b);
d) a VH sequence having at least 95% sequence identity to an amino acid sequence selected from SEQ ID NOs: 79 and 81-87;
e) a VL sequence having at least 95% sequence identity to an amino acid sequence selected from SEQ ID NOs: 80 and 88-94; and
f) a VH sequence as defined in (d) and a VL sequence as defined in (e).

Embodiment 80. The bispecific antibody of any one of embodiments 75 to 78, wherein the second binding domain comprises a sequence selected from:
a) a VH sequence having at least 95% sequence identity to an amino acid sequence selected from SEQ ID NOs: 52, 53, 105, and 106;
b) a VL sequence having at least 95% sequence identity to an amino acid sequence selected from SEQ ID NOs: 54-67; and
c) a VH sequence as defined in (a) and a VL sequence as defined in (b);
d) a VH sequence having at least 95% sequence identity to an amino acid sequence selected from SEQ ID NOs: 81-87;

e) a VL sequence having at least 95% sequence identity to an amino acid sequence selected from SEQ ID NOs: 88-94; and f) a VH sequence as defined in (d) and a VL sequence as defined in (e).

Embodiment 81. The bispecific antibody of any one of embodiments 69 to 78, wherein the second binding domain comprises a sequence selected from:
a) a VH sequence comprising an amino acid sequence selected from SEQ ID NOs: 50, 52, 53, 105, and 106;
b) a VL sequence comprising an amino acid sequence selected from SEQ ID NOs: 51 and 54-67; and
c) a VH sequence as defined in (a) and a VL sequence as defined in (b);
d) a VH sequence comprising an amino acid sequence selected from SEQ ID NOs: 79 and 81-87;
e) a VL sequence comprising an amino acid sequence selected from SEQ ID NOs: 80 and 88-94; and
f) a VH sequence as defined in (d) and a VL sequence as defined in (e).

Embodiment 82. The bispecific antibody of any one of embodiments 69 to 78, wherein the second binding domain comprises a sequence selected from:
a) a VH sequence comprising an amino acid sequence selected from SEQ ID NOs: 52, 53, 105, and 106;
b) a VL sequence comprising an amino acid sequence selected from SEQ ID NOs: 54-67; and
c) a VH sequence as defined in (a) and a VL sequence as defined in (b);
d) a VH sequence comprising an amino acid sequence selected from SEQ ID NOs: 81-87; e) a VL sequence comprising an amino acid sequence selected from SEQ ID NOs: 88-94; and
f) a VH sequence as defined in (d) and a VL sequence as defined in (e).

Embodiment 83. The bispecific antibody of any one of embodiments 69 to 79, wherein the first binding domain comprises a VH amino acid sequence of SEQ ID NO: 29 or SEQ ID NO: 30 and a VL amino acid sequence of SEQ ID NO: 32 or SEQ ID NO: 38, and the second binding domain comprises a VH sequence of SEQ ID NO: 52 or SEQ ID NO: 53 and a VL amino acid sequence of SEQ ID NO: 55 or SEQ ID NO: 62.

Embodiment 84. The bispecific antibody of embodiment 83, wherein (i) the first binding domain comprises a VH amino acid sequence of SEQ ID NO: 29 and a VL amino acid sequence of SEQ ID NO: 32, or a VH amino acid sequence of SEQ ID NO: 30 and a VL amino acid sequence of SEQ ID NO: 38; and (ii) the second binding domain comprises a VH sequence of SEQ ID NO: 52 and a VL amino acid sequence of SEQ ID NO: 55; or a VH sequence of SEQ ID NO: 53 and a VL amino acid sequence of SEQ ID NO: 62.

Embodiment 85. The bispecific antibody of any one of embodiments 69 to 79, wherein the first binding domain comprises a VH sequence of SEQ ID NO: 30 and a VL sequence of SEQ ID NO: 38, and the second binding domain comprises a VH sequence of SEQ ID NO: 53 and a VL sequence of SEQ ID NO: 62.

Embodiment 86. A bispecific antibody comprising a first binding domain and a second binding domain, wherein the first binding domain binds human KLK7 and the second binding domain binds human KLK5, wherein the first binding domain comprises a heavy chain variable domain (VH) amino acid sequence of SEQ ID NO: 30 and a light chain variable domain (VL) amino acid sequence of SEQ ID NO: 38, and the second binding domain comprises a VH amino acid sequence of SEQ ID NO: 53 and a VL amino acid sequence of SEQ ID NO: 62.

Embodiment 87. The bispecific antibody of any one of embodiments 69 to 86, wherein the first binding domain comprises a first heavy chain variable domain and a first light chain variable domain, wherein the first heavy chain variable domain is linked to a first heavy chain constant region and the first light chain variable domain is linked to a first light chain constant region; and the second binding domain comprises a second heavy chain variable domain and a second light chain variable domain, wherein the second heavy chain variable domain is linked to a second heavy chain constant region and the second light chain variable domain is linked to a second light chain constant region.

Embodiment 88. The bispecific antibody of embodiment 87, wherein the first heavy chain constant region comprises a knob mutation and the second heavy chain constant region comprises a hole mutation; or wherein the first heavy chain constant region comprises a hole mutation and the second heavy chain constant region comprises a knob mutation.

Embodiment 89. The bispecific antibody of embodiment 88, wherein the antibody is an IgG1 antibody and wherein the knob mutation comprises a T366W substitution.

Embodiment 90. The bispecific antibody of embodiment 88 or embodiment 89, wherein the antibody is an IgG1 antibody and wherein the hole mutation comprises at least one, at least two, or three substitutions selected from T366S, L368A, and Y407V.

Embodiment 91. The bispecific antibody of embodiment 90, wherein the antibody is an IgG1 antibody and wherein the hole mutation comprises T366S, L368A, and Y407V substitutions.

Embodiment 92. The bispecific antibody of any one of embodiments 87 to 91, wherein the first heavy chain constant region and/or the second heavy chain constant region comprises a N297G substitution (EU numbering).

Embodiment 93. The bispecific antibody of embodiment 92, wherein the first heavy chain constant region and the second heavy chain constant region each comprises a N297G substitution (EU numbering).

Embodiment 94. The bispecific antibody of any one of embodiments 87 to 93, wherein:
a) the first heavy chain constant region further comprises a S183K substitution (EU numbering) and the first light chain constant region comprises a V133E substitution (EU numbering), and the second heavy chain constant region further comprises a S183E substitution (EU numbering) and the second light chain constant region comprises a V133K substitution (EU numbering); or
b) the first heavy chain constant region further comprises a S183E substitution (EU numbering) and the first light chain constant region comprises a V133K substitution (EU numbering), and the second heavy chain constant region further comprises a S183K substitution (EU numbering) and the second light chain constant region comprises a V133E substitution (EU numbering).

Embodiment 95. The bispecific antibody of any one of embodiments 87 to 94, wherein the first heavy chain constant region and/or the second heavy chain constant region further comprises at least one substitution selected from M428L and N434S (EU numbering).

Embodiment 96. The bispecific antibody of embodiment 95, wherein the first heavy chain constant region and the second heavy chain constant region each further comprises at least one substitution selected from M428L and N434S (EU numbering).

Embodiment 97. The bispecific antibody of embodiment 96, wherein the first heavy chain constant region and the second heavy chain constant region each further comprises M428L and N434S substitutions (EU numbering).

Embodiment 98. The bispecific antibody of any one of embodiments 87 to 97, wherein:
  a) the first heavy chain constant region comprises an amino acid sequence selected from SEQ ID NOs: 96, 184, 98, 186, 117, 188, 119, and 190 and the first light chain constant region comprises the amino acid sequence of SEQ ID NO: 103; and the heavy chain constant region comprises an amino acid sequence selected from SEQ ID NOs: 97, 185, 99, 187, 118, 189, 120, and 191 and the second light chain constant region comprising the amino acid sequence of SEQ ID NO: 104; or
  b) the second heavy chain constant region comprises an amino acid sequence selected from SEQ ID NOs: 96, 184, 98, 186, 117, 188, 119, and 190 and the second light chain constant region comprises the amino acid sequence of SEQ ID NO: 103; and the first heavy chain constant region comprises an amino acid sequence selected from SEQ ID NOs: 97, 185, 99, 187, 118, 189, 120, and 191 and the first light chain constant region comprises the amino acid sequence of SEQ ID NO: 104.

Embodiment 99. The bispecific antibody of embodiment 98, wherein:
  a) the first heavy chain constant region comprises the amino acid sequence of SEQ ID NOs: 96 or 184 and the first light chain constant region comprises the amino acid sequence of SEQ ID NO: 103, and the second heavy chain constant region comprises the amino acid sequence of SEQ ID NO: 97 or 185 and the second light chain constant region comprises the amino acid sequence of SEQ ID NO: 104; or
  b) the first heavy chain constant region comprises the amino acid sequence of SEQ ID NO: 98 or 186 and the first light chain constant region comprises the amino acid sequence of SEQ ID NO: 103, and the second heavy chain constant region comprises the amino acid sequence of SEQ ID NO: 99 or 187 and the second light chain constant region comprises the amino acid sequence of SEQ ID NO: 104; or
  c) the second heavy chain constant region comprises the amino acid sequence of SEQ ID NOs: 96 or 184 and the second light chain constant region comprises the amino acid sequence of SEQ ID NO: 103, and the first heavy chain constant region comprises the amino acid sequence of SEQ ID NO: 97 or 185 and the first light chain constant region comprises the amino acid sequence of SEQ ID NO: 104; or
  d) the second heavy chain constant region comprises the amino acid sequence of SEQ ID NO: 98 or 186 and the second light chain constant region comprises the amino acid sequence of SEQ ID NO: 103, and the first heavy chain constant region comprises the amino acid sequence of SEQ ID NO: 99 or 187 and the first light chain constant region comprises the amino acid sequence of SEQ ID NO: 104; or
  e) the first heavy chain constant region comprises the amino acid sequence of SEQ ID NOs: 118 or 189 and the first light chain constant region comprises the amino acid sequence of SEQ ID NO: 103, and the second heavy chain constant region comprises the amino acid sequence of SEQ ID NO: 117 or 188 and the second light chain constant region comprises the amino acid sequence of SEQ ID NO: 104; or
  f) the first heavy chain constant region comprises the amino acid sequence of SEQ ID NO: 120 or 191 and the first light chain constant region comprises the amino acid sequence of SEQ ID NO: 103, and the second heavy chain constant region comprises the amino acid sequence of SEQ ID NO: 119 or 190 and the second light chain constant region comprises the amino acid sequence of SEQ ID NO: 104; or
  g) the second heavy chain constant region comprises the amino acid sequence of SEQ ID NOs: 118 or 189 and the second light chain constant region comprises the amino acid sequence of SEQ ID NO: 103, and the first heavy chain constant region comprises the amino acid sequence of SEQ ID NO: 117 or 188 and the first light chain constant region comprises the amino acid sequence of SEQ ID NO: 104; or
  h) the second heavy chain constant region comprises the amino acid sequence of SEQ ID NO: 120 or 191 and the second light chain constant region comprises the amino acid sequence of SEQ ID NO: 103, and the first heavy chain constant region comprises the amino acid sequence of SEQ ID NO: 119 or 190 and the first light chain constant region comprises the amino acid sequence of SEQ ID NO: 104.

Embodiment 100. A bispecific antibody comprising a first binding domain and a second binding domain, wherein the first binding domain binds human KLK7 and the second binding domain binds human KLK5, wherein the first binding domain comprises a heavy chain amino acid sequence of SEQ ID NO: 108 or 192, and a light chain amino acid sequence of SEQ ID NO: 109, and the second binding domain comprises a heavy chain amino acid sequence of SEQ ID NO: 110 or 193, and a light chain amino acid sequence of SEQ ID NO: 111.

Embodiment 101. A bispecific antibody comprising a first binding domain and a second binding domain, wherein the first binding domain binds human KLK7 and the second binding domain binds human KLK5, wherein the first binding domain comprises a heavy chain amino acid sequence of SEQ ID NO: 112 or 194, and a light chain amino acid sequence of SEQ ID NO: 113, and the second binding domain comprises a heavy chain amino acid sequence of SEQ ID NO: 114 or 195, and a light chain amino acid sequence of SEQ ID NO: 115.

Embodiment 102. A bispecific antibody comprising a first binding domain and a second binding domain, wherein the first binding domain binds human KLK7 and the second binding domain binds human KLK5, wherein the first binding domain comprises a heavy chain amino acid sequence of SEQ ID NO: 108 and a light chain amino acid sequence of SEQ ID NO: 109, and the second binding domain comprises a heavy chain amino acid sequence of SEQ ID NO: 110 and a light chain amino acid sequence of SEQ ID NO: 111.

Embodiment 103. A bispecific antibody comprising a first binding domain and a second binding domain, wherein the first binding domain binds human KLK7 and the second binding domain binds human KLK5, wherein the first binding domain comprises a heavy chain amino acid sequence of SEQ ID NO: 112 and a light chain amino acid sequence of SEQ ID NO: 113, and the second binding domain comprises a heavy chain amino acid sequence of SEQ ID NO: 114 and a light chain amino acid sequence of SEQ ID NO: 115.

Embodiment 104. A bispecific antibody comprising a first binding domain and a second binding domain, wherein the first binding domain binds human KLK7 and the second binding domain binds human KLK5, wherein the second binding domain comprises
- a) a heavy chain variable domain (VH) comprising (a) CDR-H1 comprising the amino acid sequence of SEQ ID NO: 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising the amino acid sequence of SEQ ID NOs: 43 or 44, (e) CDR-L2 comprising the amino acid sequence of SEQ ID NO: 45, and (f) CDR-L3 comprising an amino acid sequence selected from SEQ ID NOs: 46-49; or
- b) a heavy chain variable domain (VH) comprising (a) CDR-H1 comprising an amino acid sequence selected from SEQ ID NOs: 39 and 107, (b) CDR-H2 comprising the amino acid sequence of SEQ ID NO: 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 46-49; or
- c) a heavy chain variable domain (VH) comprising (a) CDR-H1 comprising the amino acid sequence of SEQ ID NO: 39 or 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising the amino acid sequence of SEQ ID NOs: 44, (e) CDR-L2 comprising the amino acid sequence of SEQ ID NO: 45, and (f) CDR-L3 comprising an amino acid sequence selected from SEQ ID NOs: 46-49; or
- d) a heavy chain variable domain (VH) comprising (a) CDR-H1 comprising an amino acid sequence selected from SEQ ID NOs: 39 and 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 47-49; or
- e) a heavy chain variable domain (VH) comprising (a) CDR-H1 comprising the amino acid sequence of SEQ ID NO: 68, (b) CDR-H2 comprising the amino acid sequence of SEQ ID NO: 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78; or
- f) a heavy chain variable domain (VH) comprising (a) CDR-H1 comprising the amino acid sequence of SEQ ID NO: 68, (b) CDR-H2 comprising an amino acid sequence selected from SEQ ID NOs: 69 and 70, and (c) CDR-H3 comprising the amino acid sequence of SEQ ID NO: 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78; or
- g) a heavy chain variable domain (VH) comprising (a) CDR-H1 comprising the amino acid sequence of SEQ ID NO: 68, (b) CDR-H2 comprising an amino acid sequence selected from SEQ ID NOs: 69 and 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 76-78.

Embodiment 105. The bispecific antibody of embodiment 104, wherein the second binding domain comprises a heavy chain variable domain (VH) comprising (a) CDR-H1 comprising the amino acid sequence of SEQ ID NO: 39, (b) CDR-H2 comprising the amino acid sequence of SEQ ID NO: 41, and (c) CDR-H3 comprising the amino acid sequence of SEQ ID NO: 42, and a light chain variable domain (VL) comprising (d) CDR-L1 comprising the amino acid sequence of SEQ ID NOs: 43, (e) CDR-L2 comprising the amino acid sequence of SEQ ID NO: 45, and (f) CDR-L3 comprising the amino acid sequence of SEQ ID NO: 47.

Embodiment 106. The bispecific antibody of embodiment 104, wherein the second binding domain comprises a heavy chain variable domain (VH) comprising (a) CDR-H1 comprising the amino acid sequence of SEQ ID NO: 68, (b) CDR-H2 comprising the amino acid sequence of SEQ ID NO: 70, and (c) CDR-H3 comprising the amino acid sequence of SEQ ID NO: 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 76.

Embodiment 107. The bispecific antibody of any one of embodiments 104 to 106, wherein the second binding domain is humanized.

Embodiment 108. The bispecific antibody of any one of embodiments 104 to 107, wherein the second binding domain comprises a sequence selected from:
- a) a VH sequence having at least 95% sequence identity to an amino acid sequence selected from SEQ ID NOs: 50, 52, 53, 105, and 106;
- b) a VL sequence having at least 95% sequence identity to an amino acid sequence selected from SEQ ID NOs: 51 and 54-67; and
- c) a VH sequence as defined in (a) and a VL sequence as defined in (b);
- d) a VH sequence having at least 95% sequence identity to an amino acid sequence selected from SEQ ID NOs: 79 and 81-87;
- e) a VL sequence having at least 95% sequence identity to an amino acid sequence selected from SEQ ID NOs: 80 and 88-94; and
- f) a VH sequence as defined in (d) and a VL sequence as defined in (e).

Embodiment 109. The bispecific antibody of any one of embodiments 104 to 107, wherein the second binding domain comprises a sequence selected from:
- a) a VH sequence having at least 95% sequence identity to an amino acid sequence selected from SEQ ID NOs: 52, 53, 105, and 106;
- b) a VL sequence having at least 95% sequence identity to an amino acid sequence selected from SEQ ID NOs: 54-67; and c) a VH sequence as defined in (a) and a VL sequence as defined in (b);
d) a VH sequence having at least 95% sequence identity to an amino acid sequence selected from SEQ ID NOs: 81-87;
e) a VL sequence having at least 95% sequence identity to an amino acid sequence selected from SEQ ID NOs: 88-94; and
f) a VH sequence as defined in (d) and a VL sequence as defined in (e).

Embodiment 110. The bispecific antibody of any one of embodiments 104 to 107, wherein the second binding domain comprises a sequence selected from:
a) a VH sequence comprising an amino acid sequence selected from SEQ ID NOs: 50, 52, 53, 105, and 106;
b) a VL sequence comprising an amino acid sequence selected from SEQ ID NOs: 51 and 54-67; and
c) a VH sequence as defined in (a) and a VL sequence as defined in (b);
d) a VH sequence comprising an amino acid sequence selected from SEQ ID NOs: 79 and 81-87;
e) a VL sequence comprising an amino acid sequence selected from SEQ ID NOs: 80 and 88-94; and
f) a VH sequence as defined in (d) and a VL sequence as defined in (e).

Embodiment 111. The bispecific antibody of any one of embodiments 104 to 107, wherein the second binding domain comprises a sequence selected from:
a) a VH sequence comprising an amino acid sequence selected from SEQ ID NOs: 52, 53, 105, and 106;
b) a VL sequence comprising an amino acid sequence selected from SEQ ID NOs: 54-67; and
c) a VH sequence as defined in (a) and a VL sequence as defined in (b);
d) a VH sequence comprising an amino acid sequence selected from SEQ ID NOs: 81-87; e) a VL sequence comprising an amino acid sequence selected from SEQ ID NOs: 88-94; and
f) a VH sequence as defined in (d) and a VL sequence as defined in (e).

Embodiment 112. The bispecific antibody of any one of embodiments 104 to 107, wherein the second half amino acid antibody comprises a VH sequence of SEQ ID NO: 52 or SEQ ID NO: 53 and a VL amino acid sequence of SEQ ID NO: 55 or SEQ ID NO: 62.

Embodiment 113. The bispecific antibody of embodiment 112, wherein the second half amino acid antibody comprises a VH sequence of SEQ ID NO: 52 and a VL amino acid sequence of SEQ ID NO: 55; or a VH sequence of SEQ ID NO: 53 and a VL amino acid sequence of SEQ ID NO: 62.

Embodiment 114. The bispecific antibody of any one of embodiments 104 to 113, wherein the first binding domain is humanized.

Embodiment 115. The bispecific antibody of any one of embodiments 104 to 114, wherein the first binding domain comprises a first heavy chain variable domain and a first light chain variable domain, wherein the first heavy chain variable domain is linked to a first heavy chain constant region and the first light chain variable domain is linked to a first light chain constant region; and the second binding domain comprises a second heavy chain variable domain and a second light chain variable domain, wherein the second heavy chain variable domain is linked to a second heavy chain constant region and the second light chain variable domain is linked to a second light chain constant region.

Embodiment 116. The bispecific antibody of embodiment 115, wherein the first heavy chain constant region comprises a knob mutation and the second heavy chain constant region comprises a hole mutation; or wherein the first heavy chain constant region comprises a hole mutation and the second heavy chain constant region comprises a knob mutation.

Embodiment 117. The bispecific antibody of embodiment 116, wherein the antibody is an IgG1 antibody and wherein the knob mutation comprises a T366W mutation.

Embodiment 118. The bispecific antibody of embodiment 116 or embodiment 117, wherein the antibody is an IgG1 antibody and wherein the hole mutation comprises at least one, at least two, or three mutations selected from T366S, L368A, and Y407V.

Embodiment 119. The bispecific antibody of embodiment 118, wherein the antibody is an IgG1 antibody and wherein the hole mutation comprises T366S, L368A, and Y407V mutations.

Embodiment 120. The bispecific antibody of any one of embodiments 115 to 119, wherein the first heavy chain constant region and/or the second heavy chain constant region comprises a N297G substitution (EU numbering).

Embodiment 121. The bispecific antibody of embodiment 120, wherein the first heavy chain constant region and the second heavy chain constant region each comprises a N297G substitution (EU numbering).

Embodiment 122. The bispecific antibody of any one of embodiments 115 to 121, wherein:
a) the first heavy chain constant region further comprises a S183K substitution (EU numbering) and the first light chain constant region comprises a V133E substitution (EU numbering), and the second heavy chain constant region further comprises a S183E substitution (EU numbering) and the second light chain constant region comprises a V133K substitution (EU numbering); or
b) the first heavy chain constant region further comprises a S183E substitution (EU numbering) and the first light chain constant region comprises a V133K substitution (EU numbering), and the second heavy chain constant region further comprises a S183K substitution (EU numbering) and the second light chain constant region comprises a V133E substitution (EU numbering).

Embodiment 123. The bispecific antibody of any one of embodiments 115 to 122, wherein the first heavy chain constant region and/or the second heavy chain constant region further comprises at least one substitution selected from M428L and N434S (EU numbering).

Embodiment 124. The bispecific antibody of embodiment 123, wherein the first heavy chain constant region and the second heavy chain constant region each further comprises at least one substitution selected from M428L and N434S (EU numbering).

Embodiment 125. The bispecific antibody of embodiment 124, wherein the first heavy chain constant region and the second heavy chain constant region each further comprises M428L and N434S substitutions (EU numbering).

Embodiment 126. The bispecific antibody of any one of embodiments 115 to 125, wherein:
a) the first heavy chain constant region comprises an amino acid sequence selected from SEQ ID NOs: 96, 184, 98, 186, 117, 188, 119, and 190 and the first light chain constant region comprises the amino acid sequence of SEQ ID NO: 103; and the heavy chain constant region comprises an amino acid sequence selected from SEQ ID NOs: 97, 185, 99, 187, 118, 189, 120, and 191 and the second light chain constant region comprising the amino acid sequence of SEQ ID NO: 104; or b) the second heavy chain constant region comprises an amino acid sequence selected from SEQ ID NOs: 96, 184, 98, 186, 117, 188, 119, and 190 and the second light chain constant region comprises the amino acid sequence of SEQ ID NO: 103; and the first heavy chain constant region comprises an amino acid sequence selected from SEQ ID NOs: 97, 185, 99, 187, 118, 189, 120, and 191 and the first light chain constant region comprises the amino acid sequence of SEQ ID NO: 104.

Embodiment 127. The bispecific antibody of embodiment 126, wherein:

a) the first heavy chain constant region comprises the amino acid sequence of SEQ ID NOs: 96 or 184 and the first light chain constant region comprises the amino acid sequence of SEQ ID NO: 103, and the second heavy chain constant region comprises the amino acid sequence of SEQ ID NO: 97 or 185 and the second light chain constant region comprises the amino acid sequence of SEQ ID NO: 104; or b) the first heavy chain constant region comprises the amino acid sequence of SEQ ID NO: 98 or 186 and the first light chain constant region comprises the amino acid sequence of SEQ ID NO: 103, and the second heavy chain constant region comprises the amino acid sequence of SEQ ID NO: 99 or 187 and the second light chain constant region comprises the amino acid sequence of SEQ ID NO: 104; or c) the second heavy chain constant region comprises the amino acid sequence of SEQ ID NOs: 96 or 184 and the second light chain constant region comprises the amino acid sequence of SEQ ID NO: 103, and the first heavy chain constant region comprises the amino acid sequence of SEQ ID NO: 97 or 185 and the first light chain constant region comprises the amino acid sequence of SEQ ID NO: 104; or d) the second heavy chain constant region comprises the amino acid sequence of SEQ ID NO: 98 or 186 and the second light chain constant region comprises the amino acid sequence of SEQ ID NO: 103, and the first heavy chain constant region comprises the amino acid sequence of SEQ ID NO: 99 or 187 and the first light chain constant region comprises the amino acid sequence of SEQ ID NO: 104; or e) the first heavy chain constant region comprises the amino acid sequence of SEQ ID NOs: 118 or 189 and the first light chain constant region comprises the amino acid sequence of SEQ ID NO: 103, and the second heavy chain constant region comprises the amino acid sequence of SEQ ID NO: 117 or 188 and the second light chain constant region comprises the amino acid sequence of SEQ ID NO: 104; or f) the first heavy chain constant region comprises the amino acid sequence of SEQ ID NO: 120 or 191 and the first light chain constant region comprises the amino acid sequence of SEQ ID NO: 103, and the second heavy chain constant region comprises the amino acid sequence of SEQ ID NO: 119 or 190 and the second light chain constant region comprises the amino acid sequence of SEQ ID NO: 104; or g) the second heavy chain constant region comprises the amino acid sequence of SEQ ID NOs: 118 or 189 and the second light chain constant region comprises the amino acid sequence of SEQ ID NO: 103, and the first heavy chain constant region comprises the amino acid sequence of SEQ ID NO: 117 or 188 and the first light chain constant region comprises the amino acid sequence of SEQ ID NO: 104; or h) the second heavy chain constant region comprises the amino acid sequence of SEQ ID NO: 120 or 191 and the second light chain constant region comprises the amino acid sequence of SEQ ID NO: 103, and the first heavy chain constant region comprises the amino acid sequence of SEQ ID NO: 119 or 190 and the first light chain constant region comprises the amino acid sequence of SEQ ID NO: 104.

Embodiment 128. The bispecific antibody of any one of embodiments 69 to 127, wherein the antibody binds human KLK5 with a $K_D$ of less than 60 pM, less than 30 pM, less than 20 pM, less than 10 pM, or less than 5 pM, as measured by surface plasmon resonance.

Embodiment 129. The bispecific antibody of any one of embodiments 69 to 128, wherein the antibody inhibits human KLK5 protease activity with an IC50 of less than 5 nM, or less than 3 nM, or less than 2 nM, or less than 1 nM.

Embodiment 130. The antibody of any one of embodiments 69 to 129, wherein the antibody binds human KLK5 with a $K_D$ of less than 60 pM, less than 30 pM, less than 20 pM, less than 10 pM, or less than 5 pM, as measured by surface plasmon resonance; and wherein the antibody inhibits human KLK5 protease activity with an IC50 of less than 5 nM, or less than 3 nM, or less than 2 nM, or less than 1 nM.

Embodiment 131. The bispecific antibody of embodiment 129 or embodiment 130, wherein inhibition of human KLK5 protease activity is inhibition of human KLK5-mediated cleavage of the substrate Boc-Val-Pro-Arg-AMC.

Embodiment 132. The bispecific antibody of any one of embodiments 69 to 131, wherein the antibody binds human KLK7 with a $K_D$ of less than 20 pM, or less than 15 pM, or less than 10 pM, less than 5 pM, or less than 3 pM, or less than 2 pM, or less than 1 pM, as measured by surface plasmon resonance.

Embodiment 133. The bispecific antibody of any one of embodiments 69 to 132, wherein the antibody inhibits human KLK7 protease activity with an IC50 of less than 5 nM, or less than 3 nM, or less than 2 nM, or less than 1 nM.

Embodiment 134. The bispecific antibody of any one of embodiments 69 to 133, wherein the antibody binds human KLK7 with a $K_D$ of less than 20 pM, or less than 15 pM, or less than 10 pM, less than 5 pM, or less than 3 pM, or less than 2 pM, or less than 1 pM, as measured by surface plasmon resonance; and wherein the antibody inhibits human KLK7 protease activity with an IC50 of less than less than 5 nM, or less than 3 nM, or less than 2 nM, or less than 1 nM.

Embodiment 135. The bispecific antibody of embodiment 133 or embodiment 134, wherein inhibition of human KLK7 protease activity is inhibition of human KLK7-mediated cleavage of a substrate comprising the amino acid sequence RPKPVE-Nval-WRK (SEQ ID NO: 121), wherein Nval is norvaline.

Embodiment 136. The bispecific antibody of any one of embodiments 69 to 135, wherein the $K_D$ of the bispecific antibody for human KLK5 and the $K_D$ of the antibody for human KLK7 are within 3-fold, or within 2.5-fold, or within 2-fold, or within 1.5-fold of one another.

Embodiment 137. An isolated nucleic acid encoding the bispecific antibody of any one of embodiments 69 to 136.

Embodiment 138. An isolated nucleic acid encoding the first binding domain of the bispecific antibody of any one of embodiments 69 to 136.

Embodiment 139. An isolated nucleic acid encoding the second binding domain of the bispecific antibody of any one of embodiments 69 to 136.

Embodiment 140. An isolated host cell comprising the isolated nucleic acid of embodiment 137.

Embodiment 141. An isolated host cell comprising the isolated nucleic acid of embodiment 138.

Embodiment 142. An isolated host cell comprising the isolated nucleic acid of embodiment 139.

Embodiment 143. An isolated host cell that expresses the bispecific antibody of any one of embodiments 69 to 136.

Embodiment 144. An isolated host cell that expresses the first binding domain of the bispecific antibody of any one of embodiments 69 to 136.

Embodiment 145. An isolated host cell that expresses the second binding domain of the bispecific antibody of any one of embodiments 69 to 136.

Embodiment 146. A method of producing a bispecific antibody that binds to human KLK5 and human KLK7, comprising culturing the host cell of embodiment 140 or embodiment 143 under conditions suitable for the expression of the antibody.

Embodiment 147. The method of embodiment 146, further comprising recovering the antibody from the host cell.

Embodiment 148. A method of producing a bispecific antibody that binds to human KLK5 and human KLK7, comprising (i) culturing the host cell of embodiment 141 or embodiment 144 under conditions suitable for the expression of the first binding domain; and (ii) culturing the host cell of embodiment 142 or embodiment 145 under conditions suitable for expression of the second binding domain.

Embodiment 149. The method of embodiment 148, further comprising recovering the first binding domain and the second binding domain and assembling the bispecific antibody.

Embodiment 150. A pharmaceutical composition comprising the antibody of any of embodiments 1 to 27 and a pharmaceutically acceptable carrier.

Embodiment 151. The pharmaceutical composition of embodiment 150, further comprising an additional therapeutic agent.

Embodiment 152. The pharmaceutical composition of embodiment 151, wherein the additional therapeutic agent is a KLK5 inhibitor.

Embodiment 153. The pharmaceutical composition of embodiment 152, wherein the KLK5 inhibitor is an anti-KLK5 antibody.

Embodiment 154. The pharmaceutical composition of embodiment 153, wherein the anti-KLK5 antibody comprises:
  a) a heavy chain variable domain (VH) comprising (a) CDR-H1 comprising an amino acid sequence selected from SEQ ID NOs: 39 and 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 46-49; or
  b) a heavy chain variable domain (VH) comprising (a) CDR-H1 comprising the amino acid sequence of SEQ ID NO: 68, (b) CDR-H2 comprising an amino acid sequence selected from SEQ ID NOs: 69 and 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78.

Embodiment 155. The pharmaceutical composition of embodiment 153 or embodiment 154, wherein the anti-KLK5 antibody comprises a heavy chain variable domain (VH) comprising (a) CDR-H1 comprising the amino acid sequence of SEQ ID NO: 39, (b) CDR-H2 comprising the amino acid sequence of SEQ ID NO: 41, and (c) CDR-H3 comprising the amino acid sequence of SEQ ID NO: 42, and a light chain variable domain (VL) comprising (d) CDR-L1 comprising the amino acid sequence of SEQ ID NOs: 43, (e) CDR-L2 comprising the amino acid sequence of SEQ ID NO: 45, and (f) CDR-L3 comprising the amino acid sequence of SEQ ID NO: 47.

Embodiment 156. The pharmaceutical composition of embodiment 153 or embodiment 154, wherein the anti-KLK5 antibody comprises a heavy chain variable domain (VH) comprising (a) CDR-H1 comprising the amino acid sequence of SEQ ID NO: 68, (b) CDR-H2 comprising the amino acid sequence of SEQ ID NO: 70, and (c) CDR-H3 comprising the amino acid sequence of SEQ ID NO: 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 76.

Embodiment 157. The pharmaceutical composition of any one of embodiments 153 to 156, wherein the anti-KLK5 antibody is a monoclonal antibody.

Embodiment 158. The pharmaceutical composition of any one of embodiments 153 to 157, wherein the anti-KLK5 antibody is a humanized, or chimeric antibody.

Embodiment 159. The pharmaceutical composition of any one of embodiments 153 to 158, wherein the anti-KLK5 antibody is an antibody fragment that binds human KLK5.

Embodiment 160. The pharmaceutical composition of any one of embodiments 153-159, wherein the anti-KLK5 antibody comprises a sequence selected from:
  a) a VH sequence having at least 95% sequence identity to an amino acid sequence selected from SEQ ID NOs: 50, 52, 53, 105 and 106;
  b) a VL sequence having at least 95% sequence identity to an amino acid sequence selected from SEQ ID NOs: 51 and 54-67; and
  c) a VH sequence as defined in (a) and a VL sequence as defined in (b);
  d) a VH sequence having at least 95% sequence identity to an amino acid sequence selected from SEQ ID NOs: 79 and 81-87;
  e) a VL sequence having at least 95% sequence identity to an amino acid sequence selected from SEQ ID NOs: 80 and 88-94; and
  f) a VH sequence as defined in (d) and a VL sequence as defined in (e).

Embodiment 161. The pharmaceutical composition of any one of embodiments 153-159, wherein the anti-KLK5 antibody comprises a sequence selected from:
  a) a VH sequence having at least 95% sequence identity to an amino acid sequence selected from SEQ ID NOs: 52, 53, 105 and 106;

b) a VL sequence having at least 95% sequence identity to an amino acid sequence selected from SEQ ID NOs: 54-67; and
c) a VH sequence as defined in (a) and a VL sequence as defined in (b);
d) a VH sequence having at least 95% sequence identity to an amino acid sequence selected from SEQ ID NOs: 81-87;
e) a VL sequence having at least 95% sequence identity to an amino acid sequence selected from SEQ ID NOs: 88-94; and
f) a VH sequence as defined in (d) and a VL sequence as defined in (e).

Embodiment 162. The pharmaceutical composition of any one of embodiments 153-159, wherein the anti-KLK5 antibody comprises a sequence selected from:
a) a VH sequence comprising an amino acid sequence selected from SEQ ID NOs: 50, 52, 53, 105, and 106;
b) a VL sequence comprising an amino acid sequence selected from SEQ ID NOs: 51 and 54-67; and
c) a VH sequence as defined in (a) and a VL sequence as defined in (b);
d) a VH sequence comprising an amino acid sequence selected from SEQ ID NOs: 79 and 81-87;
e) a VL sequence comprising an amino acid sequence selected from SEQ ID NOs: 80 and 88-94; and
f) a VH sequence as defined in (d) and a VL sequence as defined in (e).

Embodiment 163. The pharmaceutical composition of any one of embodiments 153-159, wherein the anti-KLK5 antibody comprises a sequence selected from:
a) a VH sequence comprising an amino acid sequence selected from SEQ ID NOs: 52, 53, 105, and 106;
b) a VL sequence comprising an amino acid sequence selected from SEQ ID NOs: 54-67; and
c) a VH sequence as defined in (a) and a VL sequence as defined in (b);
d) a VH sequence comprising an amino acid sequence selected from SEQ ID NOs: 81-87; e) a VL sequence comprising an amino acid sequence selected from SEQ ID NOs: 88-94; and
f) a VH sequence as defined in (d) and a VL sequence as defined in (e).

Embodiment 164. The pharmaceutical composition of embodiment 153, wherein the anti-KLK5 antibody is an antibody of any one of embodiments 34 to 62.

Embodiment 165. The pharmaceutical composition of embodiment 153, wherein the anti-KLK5 antibody is an antibody of any one of embodiments 47, 48, 51, and 52.

Embodiment 166. A pharmaceutical composition comprising the antibody of any of embodiments 34 to 62 and a pharmaceutically acceptable carrier.

Embodiment 167. The pharmaceutical composition of embodiment 166, further comprising an additional therapeutic agent.

Embodiment 168. The pharmaceutical composition of embodiment 167, wherein the additional therapeutic agent is a KLK7 inhibitor.

Embodiment 169. The pharmaceutical composition of embodiment 168, wherein the KLK7 inhibitor is an anti-KLK7 antibody.

Embodiment 170. The pharmaceutical composition of embodiment 169, wherein the anti-KLK7 antibody is an antibody of any one of embodiments 1 to 27.

Embodiment 171. A pharmaceutical composition comprising the antibody of any of embodiments 1 to 27 and an antibody of any one of embodiments 34 to 62, and a pharmaceutically acceptable carrier.

Embodiment 172. The pharmaceutical composition of any one of embodiments 150 to 171, comprising an additional therapeutic agent selected from an anti-inflammatory agent and an antibiotic.

Embodiment 173. A pharmaceutical composition comprising the bispecific antibody of any one of embodiments 69 to 136.

Embodiment 174. The pharmaceutical composition of embodiment 173, further comprising an additional therapeutic agent.

Embodiment 175. The pharmaceutical composition of embodiment 174, wherein the additional therapeutic agent is an anti-inflammatory agent.

Embodiment 176. The pharmaceutical composition of any one of embodiments 150 to 175, wherein the pharmaceutical composition is for topical administration.

Embodiment 177. The pharmaceutical composition of any one of embodiments 150 to 175, wherein the pharmaceutical composition is for subcutaneous or intravenous administration.

Embodiment 178. The antibody of any one of embodiments 1 to 27 and 34 to 62, the bispecific antibody of any one of embodiments 69 to 136, or the pharmaceutical composition of any one of embodiments 150 to 177 for use as a medicament.

Embodiment 179. The antibody of any one of embodiments 1 to 27 and 34 to 62, the bispecific antibody of any one of embodiments 69 to 136, or the pharmaceutical composition of any one of embodiments 150 to 177 for use in treating disease selected from Netherton Syndrome, asthma, atopic dermatitis, psoriasis, eosinophilic esophagitis, and rosacea.

Embodiment 180. The antibody, bispecific antibody, or pharmaceutical composition for use of embodiment 179, wherein the asthma is selected from atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma.

Embodiment 181. The antibody, bispecific antibody, or pharmaceutical composition for use of embodiment 180, wherein the asthma is eosinophil-low asthma.

Embodiment 182. A combination of an antibody of any one of embodiments 1 to 27 and an antibody of any one of embodiments 34 to 62, for use as a medicament.

Embodiment 183. A combination of an antibody of any one of embodiments 1 to 27 and an antibody of any one of embodiments 34 to 62, for use in treating disease selected from Netherton Syndrome, asthma, atopic dermatitis, psoriasis, eosinophilic esophagitis, and rosacea.

Embodiment 184. The combination of embodiment 183, wherein the asthma is selected from atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma.

Embodiment 185. The combination of embodiment 184, wherein the asthma is eosinophil-low asthma.

Embodiment 186. Use of the antibody of any one of embodiments 1 to 27 and 34 to 62, the bispecific antibody of any one of embodiments 69 to 136, or the pharmaceutical composition of any one of embodiments 150 to 177 in the manufacture of a medicament for treating disease selected from Netherton Syndrome, asthma, atopic dermatitis, psoriasis, eosinophilic esophagitis, and rosacea.

Embodiment 187. The use of embodiment 186, wherein the asthma is selected from atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma.

Embodiment 188. The use of embodiment 187, wherein the asthma is eosinophil-low asthma.

Embodiment 189. Use of a combination of the antibody of any one of embodiments 1 to 27 and the antibody of any one of embodiments 34 to 62 in the manufacture of a medicament for treating disease selected from Netherton Syndrome, asthma, atopic dermatitis, psoriasis, eosinophilic esophagitis, and rosacea.

Embodiment 190. The use of embodiment 189, wherein the asthma is selected from atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma.

Embodiment 191. The use of embodiment 190, wherein the asthma is eosinophil-low asthma.

Embodiment 192. Use of the antibody of any one of embodiments 1 to 27 and 34 to 62, the bispecific antibody of any one of embodiments 69 to 136, or the pharmaceutical composition of any one of embodiments 150 to 177 in the manufacture of a medicament for reducing epithelium inflammation, reducing epithelium permeability, reducing transepidermal water loss, reducing dermal infiltrates, reducing parakeratosis, restoring the epithelial barrier, and/or reducing skin inflammatory cytokines.

Embodiment 193. Use of a combination of the antibody of any one of embodiments 1 to 27 and the antibody of any one of embodiments 34 to 62 in the manufacture of a medicament for reducing epithelium inflammation, reducing epithelium permeability, reducing transepidermal water loss, reducing dermal infiltrates, reducing parakeratosis, restoring the epithelial barrier, and/or reducing skin inflammatory cytokines.

Embodiment 194. A method of treating an individual having a disease selected from Netherton Syndrome, asthma, atopic dermatitis, psoriasis, eosinophilic esophagitis, and rosacea, comprising administering to the individual an effective amount of the antibody of any one of embodiments 1 to 27 and 34 to 62, the bispecific antibody of any one of embodiments 69 to 136, or the pharmaceutical composition of any one of embodiments 150 to 177.

Embodiment 195. A method of treating an individual having a disease selected from Netherton Syndrome, asthma, atopic dermatitis, psoriasis, eosinophilic esophagitis, and rosacea, comprising administering to the individual a) an effective amount of the antibody of any one of embodiments 1 to 27; and b) an effective amount of the antibody of any one of embodiments 34 to 62.

Embodiment 196. The method of embodiment 195, wherein the antibody of (a) and the antibody of (b) are administered simultaneously.

Embodiment 197. The method of embodiment 195, wherein the antibody of (a) and the antibody of (b) are administered sequentially.

Embodiment 198. A method of treating an individual having a disease selected from Netherton Syndrome, asthma, atopic dermatitis, psoriasis, eosinophilic esophagitis, and rosacea, comprising administering to the individual an effective amount of the bispecific antibody of any one of embodiments 69 to 136, or an effective amount of the pharmaceutical composition of any one of embodiments 150 to 177.

Embodiment 199. The method of any one of embodiments 194 to 198, wherein the asthma is selected from atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma.

Embodiment 200. The method of embodiment 199, wherein the asthma is eosinophil-low asthma.

Embodiment 201. The method of any one of embodiments 194 to 198, wherein the individual has Netherton Syndrome.

Embodiment 202. The method of any one of embodiments 194 to 198, wherein the individual has rosacea.

Embodiment 203. The method of any one of embodiments 194 to 202, further comprising administering an additional therapeutic agent to the individual.

Embodiment 204. The method of embodiment 203 wherein the additional therapeutic agent is an anti-inflammatory agent.

Embodiment 205. A method of reducing epithelium inflammation, reducing epithelium permeability, reducing transepidermal water loss, reducing dermal infiltrates, reducing parakeratosis, restoring the epithelial barrier, and/or reducing skin inflammatory cytokines in an individual comprising administering to the individual an effective amount of the antibody of any one of embodiments 1 to 27 and 34 to 62, the bispecific antibody of any one of embodiments 69 to 136, or the pharmaceutical composition of any one of embodiments 150 to 177 to reduce epithelium inflammation, reduce epithelium permeability, reduce transepidermal water loss, reduce dermal infiltrates, reduce parakeratosis, and/or restore the epithelial barrier.

Embodiment 206. A method of reducing epithelium inflammation, reducing epithelium permeability, reducing transepidermal water loss, reducing dermal infiltrates, reducing parakeratosis, restoring the epithelial barrier, and/or reducing skin inflammatory cytokines in an individual comprising administering to the individual a) an effective amount of the antibody of any one of embodiments 1 to 27; and b) an effective amount of the antibody of any one of embodiments 34 to 62, to reduce epithelium inflammation, reduce epithelium permeability, reduce transepidermal water loss, reduce dermal infiltrates, reduce parakeratosis, and/or restore the epithelial barrier.

Embodiment 207. The method of embodiment 206, wherein the antibody of (a) and the antibody of (b) are administered simultaneously.

Embodiment 208. The method of embodiment 206, wherein the antibody of (a) and the antibody of (b) are administered sequentially.

Embodiment 209. A method of reducing epithelium inflammation, reducing epithelium permeability, reducing transepidermal water loss, reducing dermal infiltrates, reducing parakeratosis, restoring the epithelial barrier, and/or reducing skin inflammatory cytokines in an individual comprising administering to the individual the bispecific antibody of any one of embodiments 69 to 136, or an effective amount of the pharmaceutical composition of any one of embodiments 150 to 177, to reduce epithelium inflammation, reduce epithelium permeability, reduce transepidermal water loss, reduce dermal infiltrates, reduce parakeratosis, and/or restore the epithelial barrier.

Embodiment 210. The method of any one of embodiments 194 to 209, wherein the administering is subcutaneous or intravenous administration.

Embodiment 211. The method of any one of embodiments 194 to 209, wherein the administering is topical administration.

Embodiment 212. The method of any one of embodiments 194 to 209, wherein the administering is intravenous administration.

Embodiment 213. An isolated antibody that binds human KLK7, wherein when bound to human KLK7 results in a conformational change of human KLK7, wherein the conformational change allosterically results in the disruption of the substrate binding site and/or the active site of human KLK7.

Embodiment 214. The isolated antibody of embodiment 213, which is a bispecific antibody.

Embodiment 215. The isolated antibody of embodiment 214, wherein the bispecific antibody binds human KLK7 and human KLK5.

Embodiment 216. The isolated antibody of embodiment 215, wherein when bound to human KLK5 results in a conformational change of human KLK5, wherein the conformational change allosterically results in the disruption of the substrate binding site and/or the active site of human KLK5.

Embodiment 217. The isolated antibody of embodiment 216, wherein the antibody binds to an epitope on human KLK5 comprising one or more amino acid residues selected from Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, Asp178, Gly184, Asp185, Lys186, Ala186A, Arg188, Asn223, Arg224, Pro225, and Lys233 according to standard protease numbering.

Embodiment 218. The isolated antibody of embodiment 217, wherein the antibody binds to an epitope on human KLK5 comprising one or more amino acid residues selected from the group consisting of Pro130, Ser131, Ala132, Val162, Leu163, Ser164, Gln165, Lys166, Arg167, Glu169, Asp170, Ala171, Tyr172, Pro173, Arg174, Gln174A, Ile176, Asp177, Asp178, Arg224, and Lys233 according to standard protease numbering.

Embodiment 219. The isolated antibody of embodiment 217, wherein the antibody binds to an epitope on human KLK5 comprising one or more amino acid residues selected from Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, and Lys233 according to standard protease numbering.

Embodiment 220. The isolated antibody of embodiment 217, wherein the antibody binds to an epitope on human KLK5 comprising one or more amino acid residues selected from Ser131, Ala132, Gly133, Leu163, Ser164, Gln165, Lys166, Arg167, Glu169, Asp170, Ala171, Pro173, Arg174, Gly184, Asp185, Lys186, Ala186A, Arg188, Asn223, Arg224, and Pro225 according to standard protease numbering.

Embodiment 221. The isolated antibody of any one of embodiments 213 to 220, wherein the antibody binds an epitope within amino acids R71-N82, K152-S158, and/or Q211-K222 of KLK7 (SEQ ID NO: 4).

Embodiment 222. The isolated antibody of any one of embodiments 213 to 221, wherein the antibody binds an epitope comprising one or more of amino acids H72, P73, G74, 576, Q78, N82, N157, K211, and/or T213 of KLK7 (SEQ ID NO: 4).

Embodiment 223. A bispecific antibody comprising a first binding domain and a second binding domain, wherein the first binding domain binds human KLK7 and the second binding domain binds human KLK5, wherein when bound to human KLK7 results in a conformational change of human KLK7, wherein the conformational change allosterically results in the disruption of the substrate binding site and/or the active site of human KLK7.

Embodiment 224. The bispecific antibody of embodiment 223, wherein when bound to human KLK5 results in a conformational change of human KLK5, wherein the conformational change allosterically results in the disruption of the substrate binding site and/or the active site of human KLK5.

Embodiment 225. A bispecific antibody comprising a first binding domain and a second binding domain, wherein the first binding domain binds human KLK7 and the second binding domain binds human KLK5, wherein when bound to human KLK5 results in a conformational change of human KLK5, wherein the conformational change allosterically results in the disruption of the substrate binding site and/or the active site of human KLK5.

Embodiment 226. The bispecific antibody of embodiment 224 or embodiment 225, wherein the antibody binds to an epitope on human KLK5 comprising one or more amino acid residues selected from Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, Asp178, Gly184, Asp185, Lys186, Ala186A, Arg188, Asn223, Arg224, Pro225, and Lys233 according to standard protease numbering.

Embodiment 227. The isolated antibody of embodiment 226, wherein the antibody binds to an epitope on human KLK5 comprising one or more amino acid residues selected from the group consisting of Pro130, Ser131, Ala132, Val162, Leu163, Ser164, Gln165, Lys166, Arg167, Glu169, Asp170, Ala171, Tyr172, Pro173, Arg174, Gln174A, Ile176, Asp177, Asp178, Arg224, and Lys233 according to standard protease numbering.

Embodiment 228. The isolated antibody of embodiment 226, wherein the antibody binds to an epitope on human KLK5 comprising one or more amino acid residues selected from Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, and Lys233 according to standard protease numbering.

Embodiment 229. The isolated antibody of embodiment 226, wherein the antibody binds to an epitope on human KLK5 comprising one or more amino acid residues selected from Ser131, Ala132, Gly133, Leu163, Ser164, Gln165, Lys166, Arg167, Glu169, Asp170, Ala171, Pro173, Arg174, Gly184, Asp185, Lys186, Ala186A, Arg188, Asn223, Arg224, and Pro225 according to standard protease numbering.

Embodiment 230. The bispecific antibody of any one of embodiments 223 to 229, wherein the antibody binds an epitope within amino acids R71-N82, K152-S158, and/or Q211-K222 of KLK7 (SEQ ID NO: 4).

Embodiment 231. The bispecific antibody of any one of embodiments 223 to 230, wherein the antibody binds an epitope comprising one or more of amino acids H72, P73, G74, S76, Q78, N82, N157, K211, and/or T213 of KLK7 (SEQ ID NO: 4).

Embodiment 232. A pharmaceutical composition comprising the antibody of any one of embodiments 213 to 222 and a pharmaceutically acceptable carrier.

Embodiment 233. A pharmaceutical composition comprising the bispecific antibody of any one of embodiments 223 to 231 and a pharmaceutically acceptable carrier.

Embodiment 234. The antibody of any one of embodiments 213 to 222, the bispecific antibody of any one of embodiments 223 to 231, or the pharmaceutical composition of embodiment 232 or embodiment 233 for use as a medicament.

Embodiment 235. The antibody of any one of embodiments 213 to 222, the bispecific antibody of any one of embodiments 223 to 231, or the pharmaceutical composition of embodiment 232 or embodiment 233 for use in treating disease selected from Netherton Syndrome, asthma, atopic dermatitis, psoriasis, eosinophilic esophagitis, and rosacea.

Embodiment 236. The antibody, bispecific antibody, or pharmaceutical composition for use of embodiment 235, wherein the asthma is selected from atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma.

Embodiment 237. The antibody of any one of embodiments 213 to 222, the bispecific antibody of any one of embodiments 223 to 231, or the pharmaceutical composition of embodiment 232 or embodiment 233 for use in reducing epithelium inflammation, reducing epithelium permeability, reducing transepidermal water loss, reducing dermal infiltrates, reducing parakeratosis, restoring the epithelial barrier, and/or reducing skin inflammatory cytokines.

Embodiment 238. Use of the antibody of any one of embodiments 213 to 222, the bispecific antibody of any one of embodiments 223 to 231, or the pharmaceutical composition of embodiment 232 or embodiment 233 in the manufacture of a medicament for treating disease selected from Netherton Syndrome, asthma, atopic dermatitis, psoriasis, eosinophilic esophagitis, and rosacea.

Embodiment 239. The use of embodiment 238, wherein the asthma is selected from atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma.

Embodiment 240. Use of the antibody of any one of embodiments 213 to 222, the bispecific antibody of any one of embodiments 223 to 231, or the pharmaceutical composition of embodiment 232 or embodiment 233 in the manufacture of a medicament for reducing epithelium inflammation, reducing epithelium permeability, reducing transepidermal water loss, reducing dermal infiltrates, reducing parakeratosis, restoring the epithelial barrier, and/or reducing skin inflammatory cytokines.

Embodiment 241. A method of treating an individual having a disease selected from Netherton Syndrome, asthma, atopic dermatitis, psoriasis, eosinophilic esophagitis, and rosacea, comprising administering to the individual an effective amount of the antibody of any one of 213 to 222, the bispecific antibody of any one of embodiments 223 to 231, or the pharmaceutical composition of embodiment 232 or embodiment 233.

Embodiment 242. The method of embodiment 241, wherein the asthma is selected from atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma.

Embodiment 243. A method of reducing epithelium inflammation, reducing epithelium permeability, reducing transepidermal water loss, reducing dermal infiltrates, reducing parakeratosis, restoring the epithelial barrier, and/or reducing skin inflammatory cytokines in an individual comprising administering to the individual an effective amount of the antibody of any one of 213 to 222, the bispecific antibody of any one of embodiments 223 to 231, or the pharmaceutical composition of embodiment 232 or embodiment 233 to reduce epithelium inflammation, reduce epithelium permeability, reduce transepidermal water loss, reduce dermal infiltrates, reduce parakeratosis, and/or restore the epithelial barrier.

Embodiment 244. The antibody, bispecific antibody, or pharmaceutical composition for use of embodiment 179 or embodiment 235, wherein the disease is Netherton Syndrome.

Embodiment 245. The combination for use of embodiment 183, wherein the disease is Netherton Syndrome.

Embodiment 246. The use of any one of embodiments 186, 189, and 238, wherein the disease is Netherton Syndrome.

Embodiment 247. The use of any one of embodiments 192, 193, and 240, wherein the medicament is for reducing epithelium inflammation, reducing epithelium permeability, reducing transepidermal water loss, reducing dermal infiltrates, reducing parakeratosis, restoring the epithelial barrier, and/or reducing skin inflammatory cytokines in an individual with Netherton Syndrome.

Embodiment 248. A bispecific antibody for use in treating Netherton Syndrome, wherein the bispecific antibody comprises a first binding domain and a second binding domain, wherein the first binding domain binds human KLK7 and the second binding domain binds human KLK5, wherein the first binding domain comprises a heavy chain amino acid sequence of SEQ ID NO: 112 or 194, and a light chain amino acid sequence of SEQ ID NO: 113, and the second binding domain comprises a heavy chain amino acid sequence of SEQ ID NO: 114 or 195, and a light chain amino acid sequence of SEQ ID NO: 115.

Embodiment 249. An anti-KLK5 antibody for use in treating Netherton Syndrome, wherein the anti-KLK5 antibody comprises (a) a VH sequence of SEQ ID NO: 52 and a VL sequence of SEQ ID NO: 55; or (b) a VH sequence of SEQ ID NO: 53 and a VL sequence of SEQ ID NO: 62.

Embodiment 250. An anti-KLK7 antibody for use in treating Netherton Syndrome, wherein the anti-KLK7 antibody comprises (a) a VH sequence of SEQ ID NO: 29 and a VL sequence of SEQ ID NO: 32; or (b) a VH sequence of SEQ ID NO: 30 and a VL sequence of SEQ ID NO: 38.

Embodiment 251. An antibody combination for use in treating Netherton Syndrome, wherein the antibody combination comprises an anti-KLK5 antibody and an anti-KLK7 antibody, wherein the anti-KLK5 antibody comprises a VH sequence of SEQ ID NO: 52 and a VL sequence of SEQ ID NO: 55, or a VH sequence of SEQ ID NO: 53 and a VL sequence of SEQ ID NO: 62; and wherein the anti-KLK7 antibody comprises a VH sequence of SEQ ID NO: 29 and a VL sequence of SEQ ID NO: 32, or a VH sequence of SEQ ID NO: 30 and a VL sequence of SEQ ID NO: 38.

Embodiment 252. A method of treating an individual having a disease selected from Netherton Syndrome, asthma, atopic dermatitis, psoriasis, eosinophilic esophagitis, and rosacea, comprising administering to the individual an effective amount of the bispecific antibody, wherein the bispecific antibody comprises a first binding domain and second binding domain, wherein the first binding domain binds human KLK7 and inhibits KLK7 protease activity and the second binding domain binds human KLK5 and inhibits KLK5 protease activity.

Embodiment 253. A method of treating an individual having a disease selected from Netherton Syndrome, asthma, atopic dermatitis, psoriasis, eosinophilic esophagitis, and rosacea, comprising administering to the individual an anti-KLK5 antibody and an anti-KLK7 antibody, wherein the anti-KLK5 antibody inhibits KLK5 protease activity, and wherein the anti-KLK7 antibody inhibits KLK7 protease activity.

Embodiment 254. A method of reducing epithelium inflammation, reducing epithelium permeability, reducing transepidermal water loss, reducing dermal infiltrates, reducing parakeratosis, restoring the epithelial barrier and/or reducing skin inflammatory cytokines in an individual comprising administering to the individual a KLK5 antagonist and a KLK7 antagonist.

Embodiment 255. The method of embodiment 254, wherein the KLK5 antagonist is an anti-KLK5 antibody and/or the KLK7 antagonist is an anti-KLK7 antibody.

Embodiment 256. A method of reducing epithelium inflammation, reducing epithelium permeability, reducing transepidermal water loss, reducing dermal infiltrates, reducing parakeratosis, restoring the epithelial barrier and/or reducing skin inflammatory cytokines in an individual comprising administering to the individual an effective amount of the bispecific antibody, wherein the bispecific antibody comprises a first binding domain and second binding domain, wherein the first binding domain binds human KLK7 and inhibits KLK7 protease activity and the second binding domain binds human KLK5 and inhibits KLK5 protease activity.

Embodiment 257. A method of reducing epithelium inflammation, reducing epithelium permeability, reducing transepidermal water loss, reducing dermal infiltrates, reducing parakeratosis, restoring the epithelial barrier and/or reducing skin inflammatory cytokines in an individual comprising administering to the individual an anti-KLK5 antibody and an anti-KLK7 antibody, wherein the anti-KLK5 antibody inhibits KLK5 protease activity, and wherein the anti-KLK7 antibody inhibits KLK7 protease activity.

Embodiment 258. A method of ameliorating skin rash and/or scaling in an individual with Netherton Syndrome comprising administering to the individual an effective amount of the bispecific antibody, wherein the bispecific antibody comprises a first binding domain and second binding domain, wherein the first binding domain binds human KLK7 and inhibits KLK7 protease activity and the second binding domain binds human KLK5 and inhibits KLK5 protease activity.

Embodiment 259. A method of ameliorating skin rash and/or scaling in an individual with Netherton Syndrome comprising administering to the individual an anti-KLK5 antibody and an anti-KLK7 antibody, wherein the anti-KLK5 antibody inhibits KLK5 protease activity, and wherein the anti-KLK7 antibody inhibits KLK7 protease activity.

Embodiment 260. The use of any one of embodiments 192, 193, 240, or 247 or the method of any one of embodiments 205, 206, 209, 243, or 254-257, or the antibody, bispecific antibody, or pharmaceutical composition for use of embodiment 237, wherein the skin inflammatory cytokines are one or more of IL-8, TNFα, IL-6, IL-4, and/or G-CSF.

Embodiment 261. A bispecific antibody comprising a first binding domain and a second binding domain, wherein the first binding domain binds human KLK7 and the second binding domain binds human KLK5, wherein the first binding domain comprises a heavy chain amino acid sequence of SEQ ID NO: 194, and a light chain amino acid sequence of SEQ ID NO: 113, and the second binding domain comprises a heavy chain amino acid sequence of SEQ ID NO: 195, and a light chain amino acid sequence of SEQ ID NO: 115.

Embodiment 262. A bispecific antibody comprising a first binding domain and a second binding domain, wherein the first binding domain binds human KLK7 and the second binding domain binds human KLK5, wherein the first binding domain comprises a heavy chain amino acid sequence of SEQ ID NO: 112, and a light chain amino acid sequence of SEQ ID NO: 113, and the second binding domain comprises a heavy chain amino acid sequence of SEQ ID NO: 195, and a light chain amino acid sequence of SEQ ID NO: 115.

Embodiment 263. A bispecific antibody comprising a first binding domain and a second binding domain, wherein the first binding domain binds human KLK7 and the second binding domain binds human KLK5, wherein the first binding domain comprises a heavy chain amino acid sequence of SEQ ID NO: 194, and a light chain amino acid sequence of SEQ ID NO: 113, and the second binding domain comprises a heavy chain amino acid sequence of SEQ ID NO: 114, and a light chain amino acid sequence of SEQ ID NO: 115.

BRIEF DESCRIPTION OF THE FIGURES

FIGS. 1A-1B show an alignment of anti-KLK7 antibody rb.14H11c-LC light chain variable region with certain humanized versions of the light chain variable regions (1A) and anti-KLK7 antibody rb.14H11c-HC heavy chain variable region with certain humanized versions of the heavy chain variable regions (1B). CDRs according to Chothia, Kabat, and contact residues are indicated. Differences in the humanized versions relative to the rabbit parental variable regions are shown in white with a black background.

FIGS. 2A-2B show an alignment of humanized anti-KLK5 antibody hu.10C5-H28L5 light chain variable region with certain modified humanized versions of the light chain variable regions (2A) and humanized anti-KLK5 antibody hu.10C5-H28L5 heavy chain variable region with certain modified humanized versions of the heavy chain variable regions (2B). CDRs according to Chothia, Kabat, and contact residues are indicated. Differences in the humanized versions relative to the parental variable regions are shown in white with a black background.

FIGS. 3A-3B show an alignment of humanized anti-KLK5 antibody hu.9H5-H14L4 light chain variable region with certain modified humanized versions of the light chain variable regions (3A) and humanized anti-KLK5 antibody hu.9H5-H14L4 heavy chain variable region with certain modified humanized versions of the heavy chain variable regions (3B).

CDRs according to Chothia, Kabat, and contact residues are indicated. Differences in the humanized versions relative to the parental variable regions are shown in white with a black background.

Figure 4:
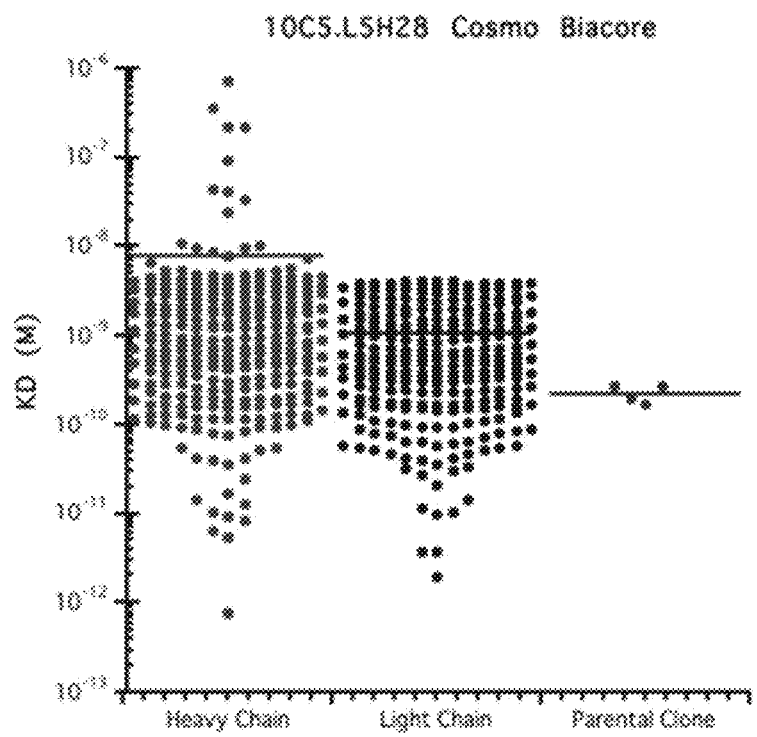

FIG. 4 shows the affinity of humanized anti-KLK5 antibody hu. 10C5.L5H28 heavy chain and light chain variants and parental hu.10C5.L5H28.

Figure 5:
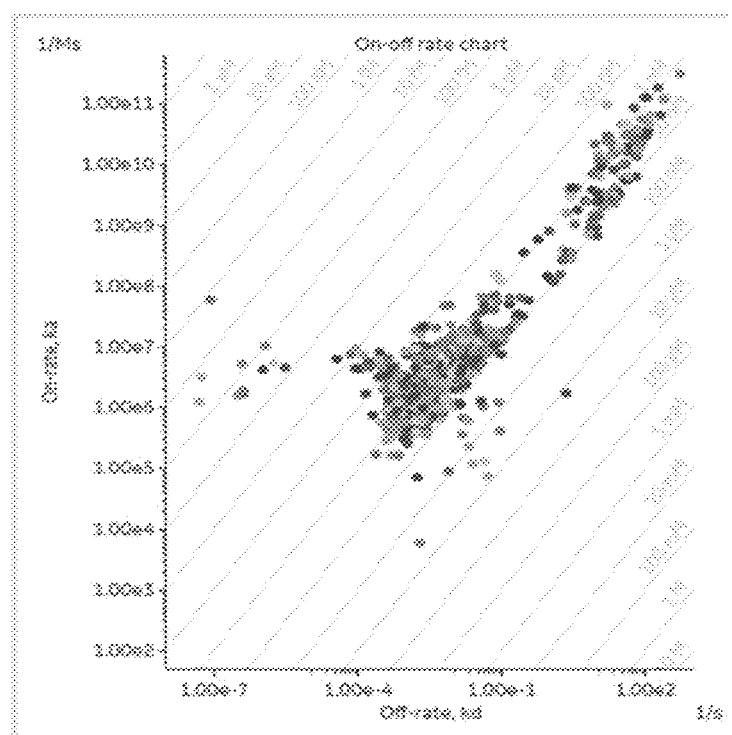

FIG. 5 shows a scatter plot of the on rates (ka) and off-rates (kd) of humanized anti-KLK5 antibody hu.9H5.L4H14 heavy chain and light chain variants.

Figure 6A:
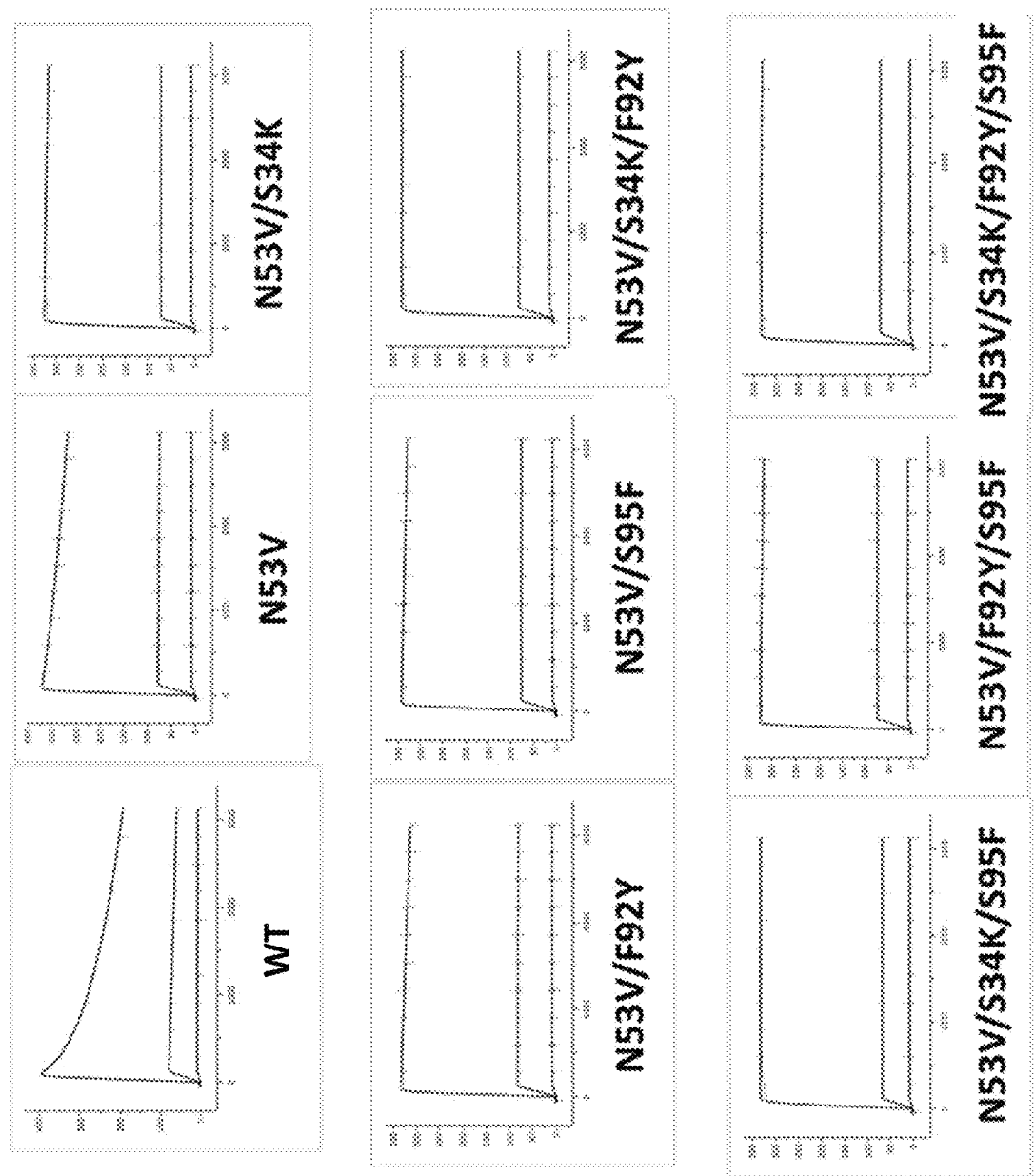
Figure 6B:
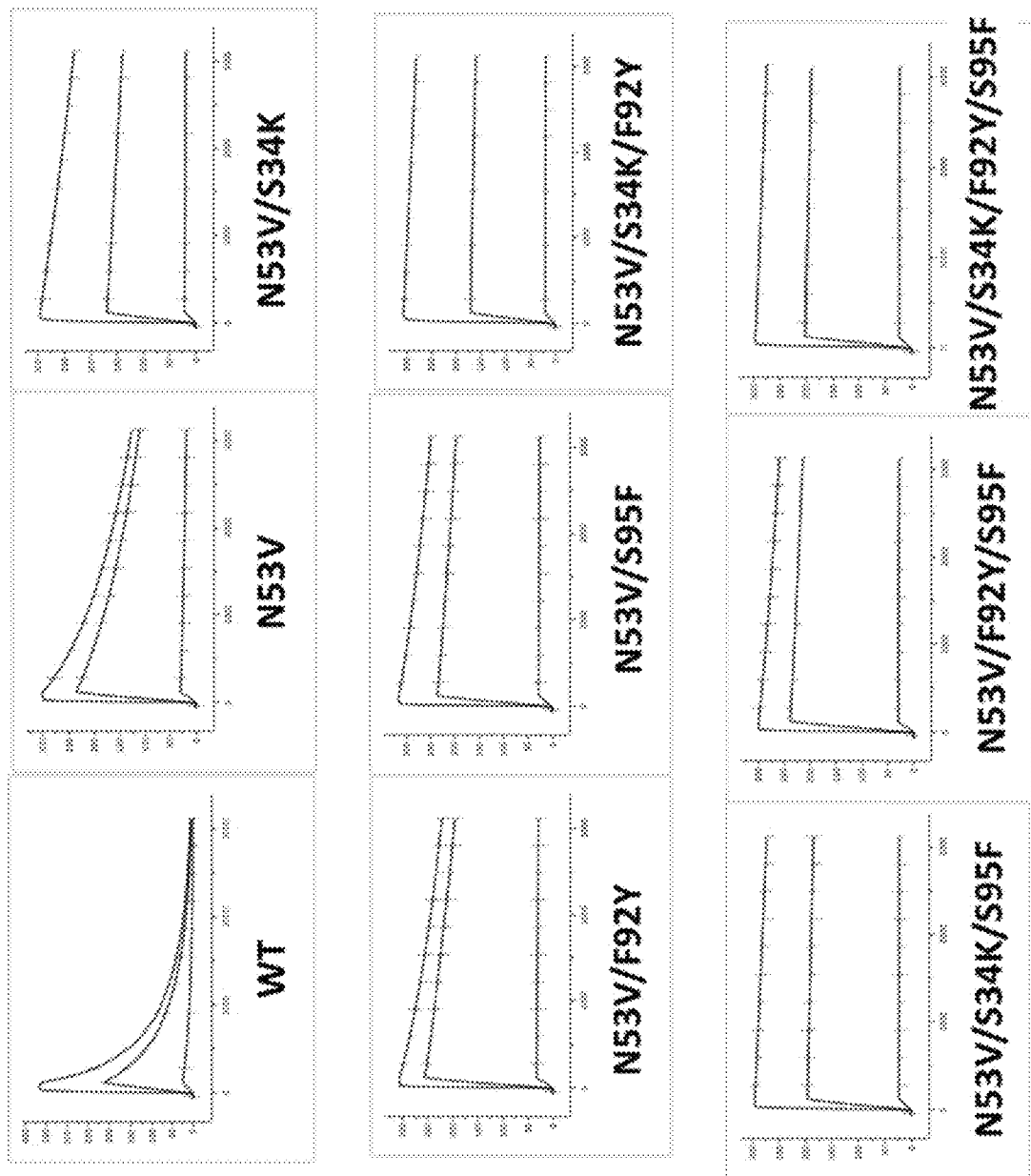

FIGS. 6A-6B show surface plasmon resonance traces for the indicated hu.10C5.L5H28 variants for human KLK5 (FIG. 6A) and cynomolgus monkey KLK5 (FIG. 6B).

Figure 7A:
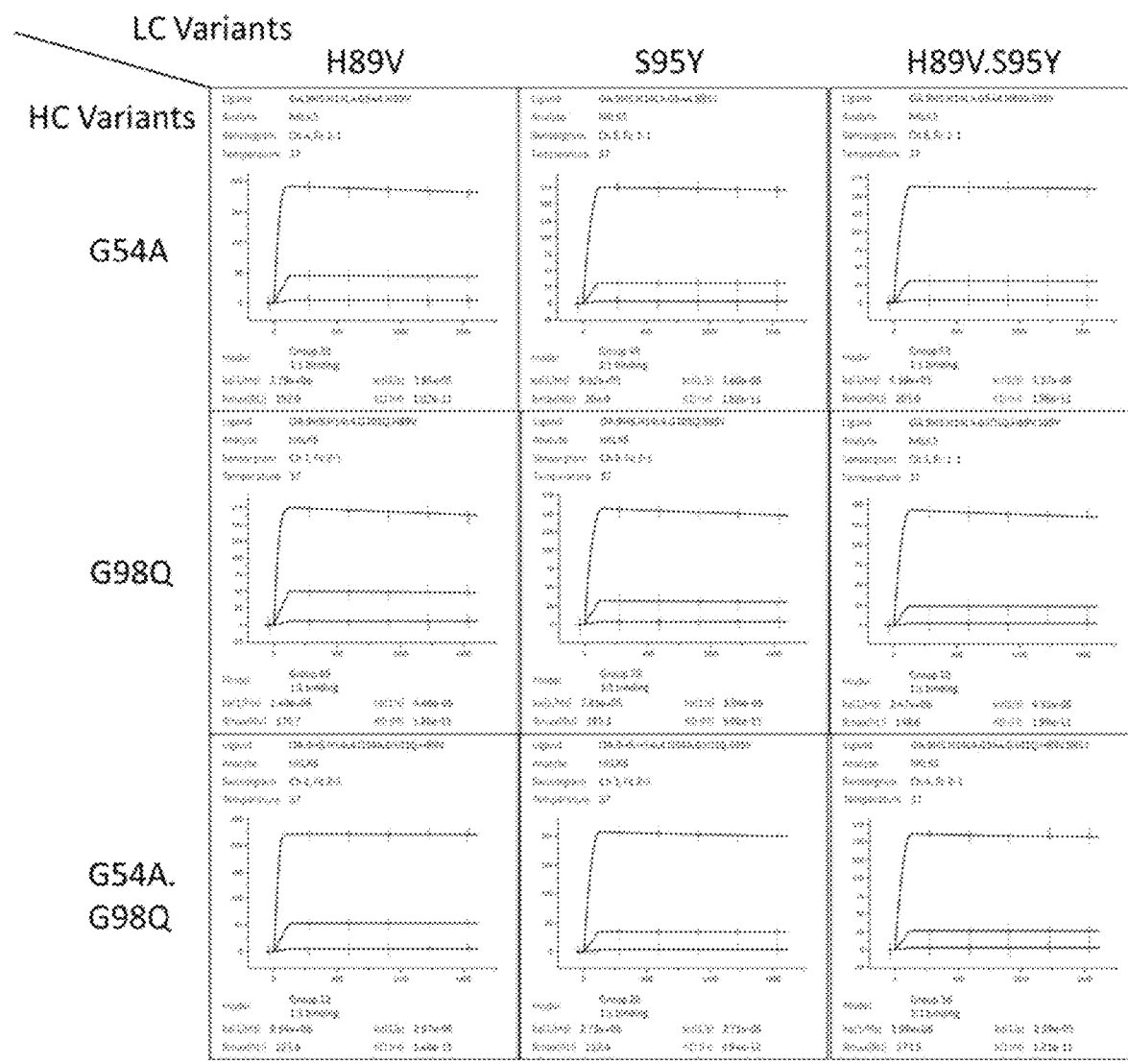
Figure 7A:
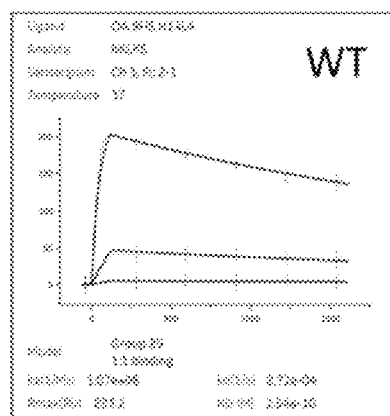
Figure 7B:
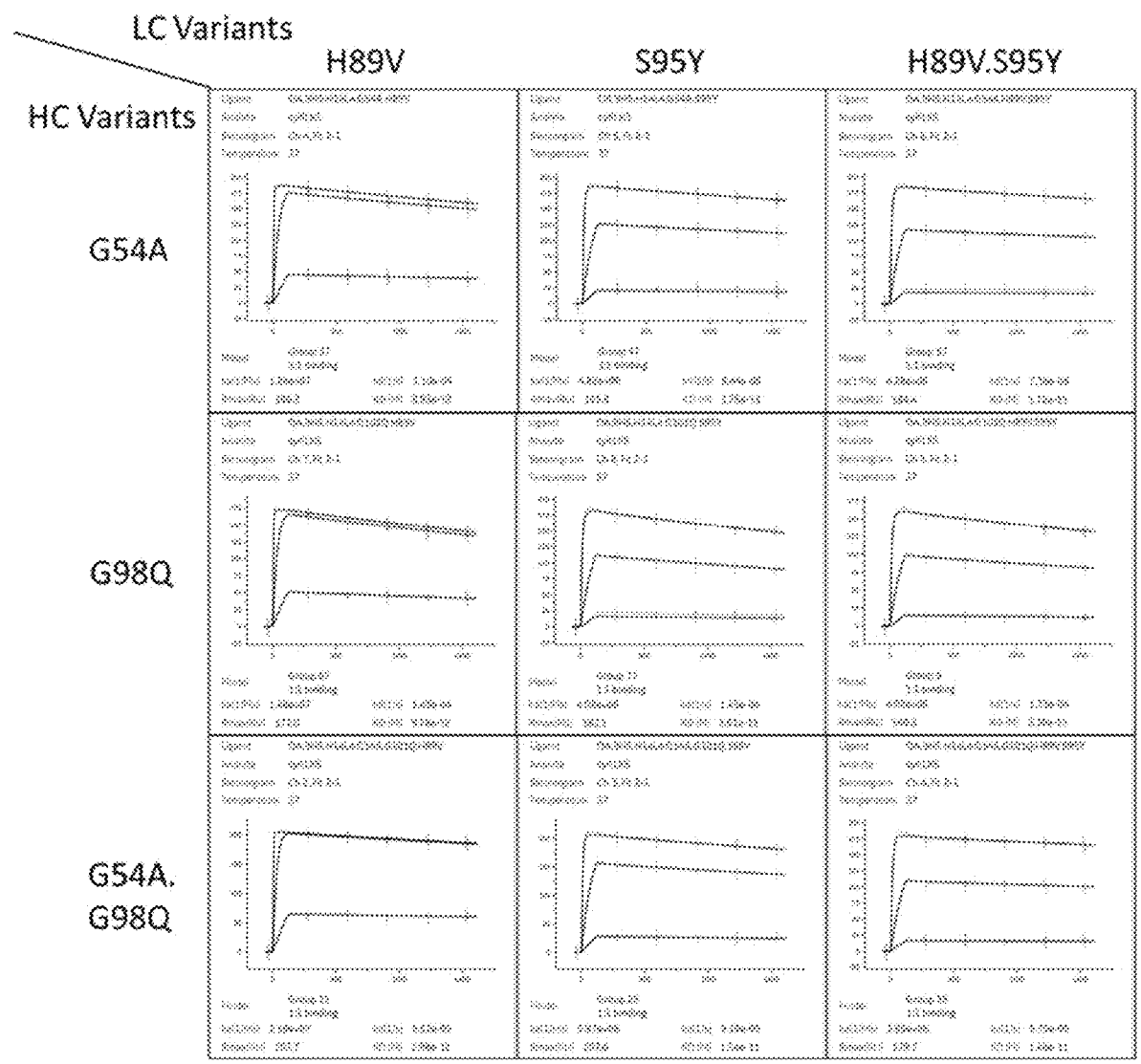
Figure 7B:
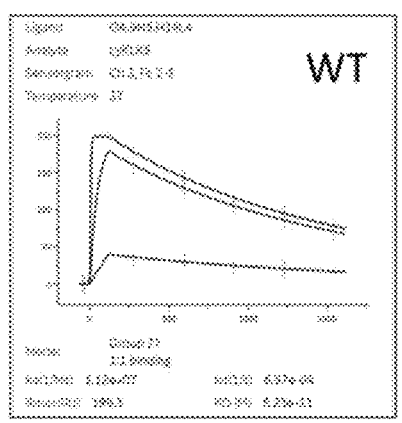

FIGS. 7A-7B show surface plasmon resonance traces for the indicated hu.9H5.L4H14 variants for human KLK5 (FIG. 7A) and cynomolgus monkey KLK5 (FIG. 7B).

Figure 8:
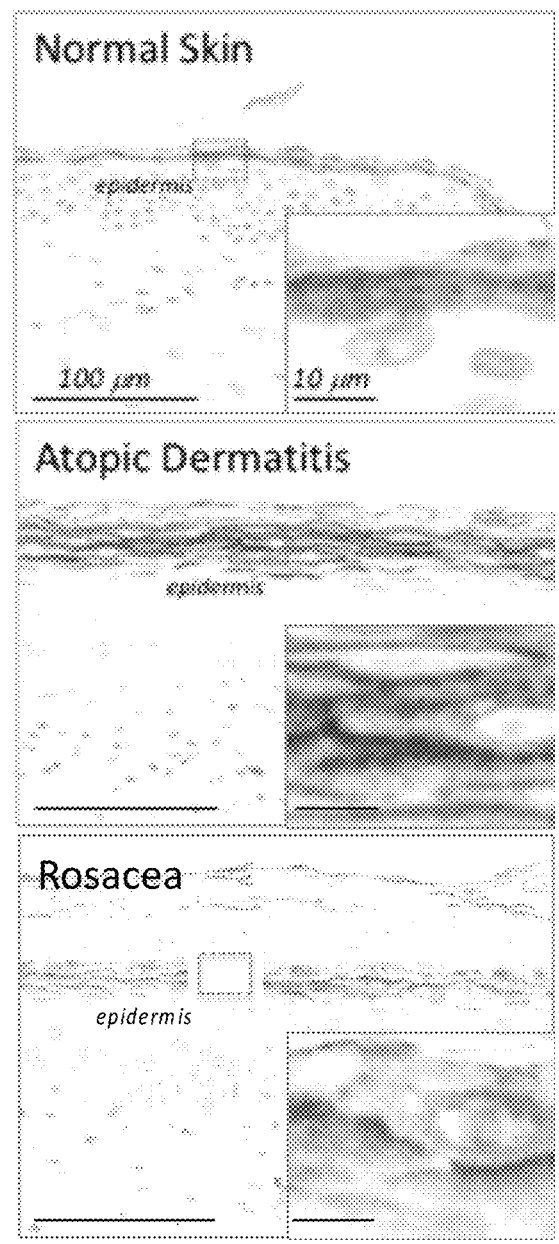

FIG. 8 shows representative KLK5 protein expression in human normal skin, atopic dermatitis, and rosacea.

Figure 9:
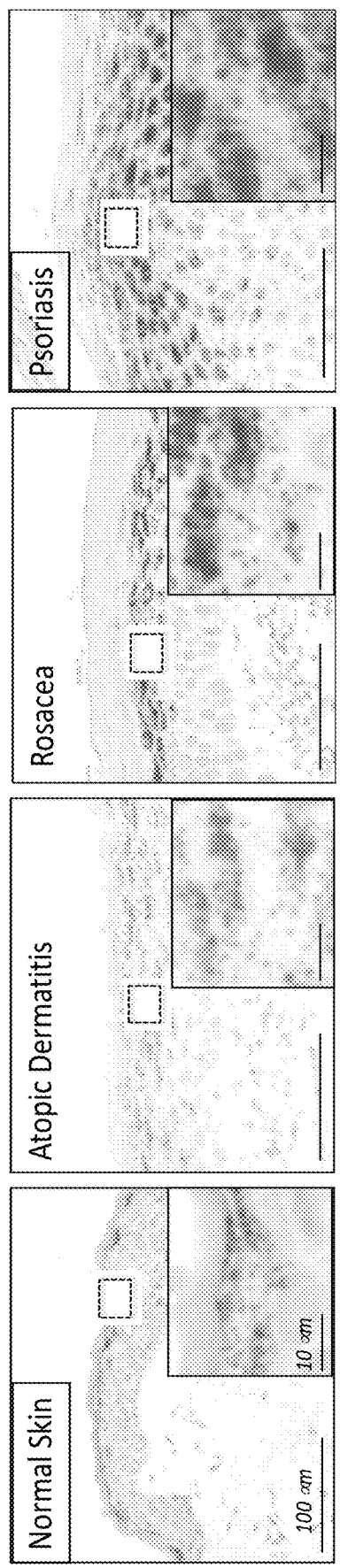

FIG. 9 shows representative KLK7 mRNA staining in human normal skin, atopic dermatitis, rosacea, and psoriasis.

Figure 10A:
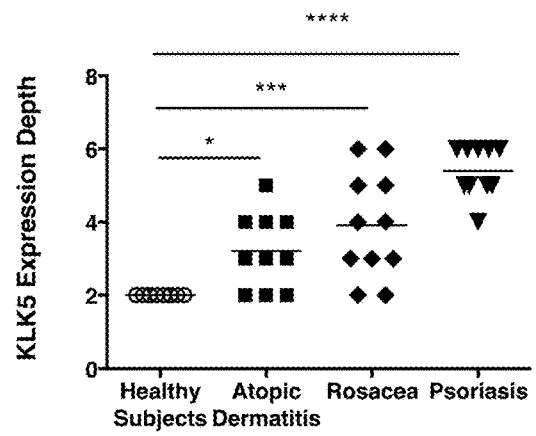
Figure 10B:
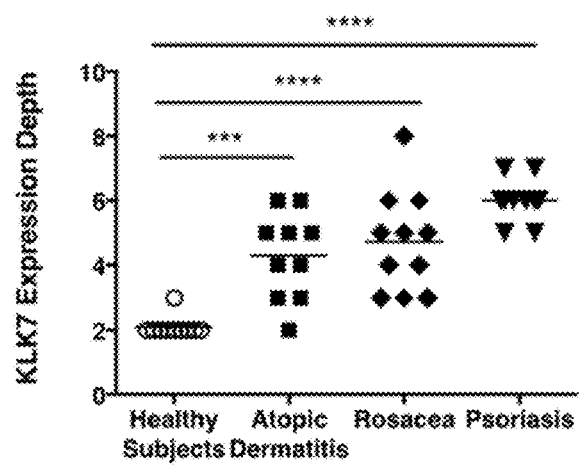
Figure 10C:
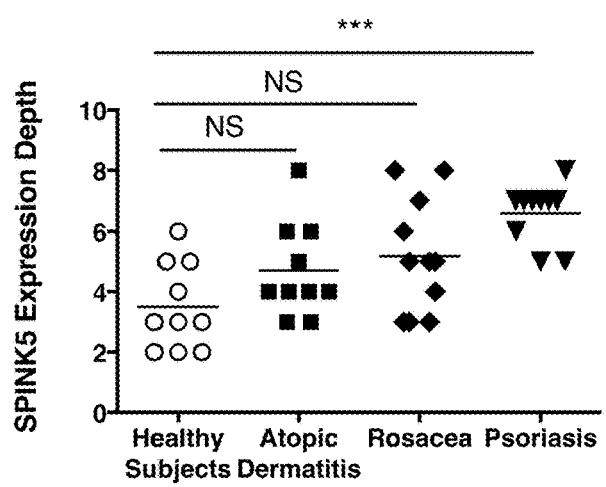

FIGS. 10A-10C show KLK5 expression depth (10A), KLK7 expression depth (10B), and SPINK5 expression depth (10C) in human normal skin, topic dermatitis, rosacea, and psoriasis.

Figure 11:
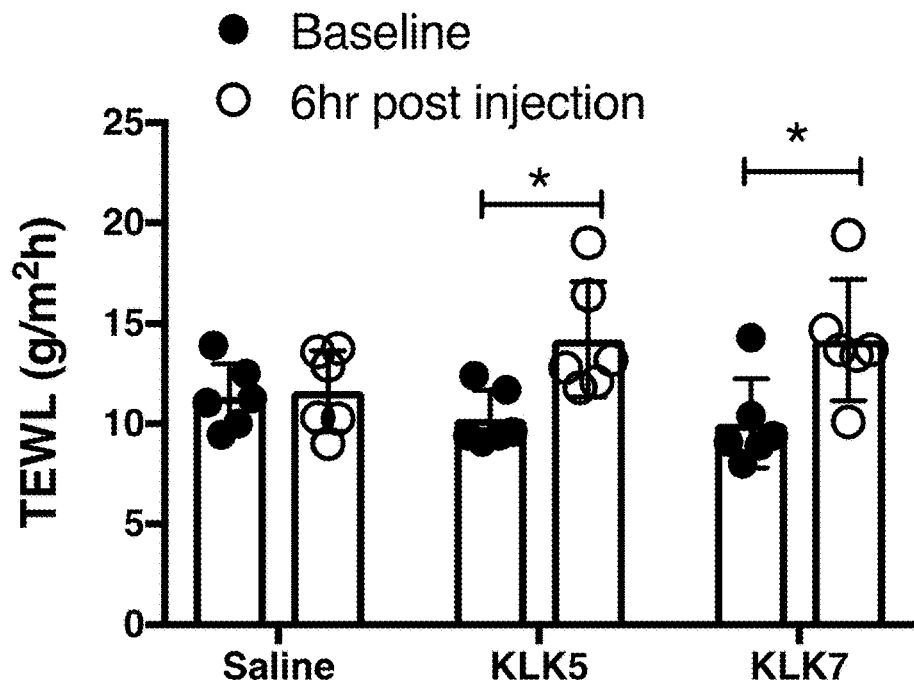

FIG. 11 shows transepidermal water loss in mice administered saline, KLK5, or KLK7.

Figure 12A:
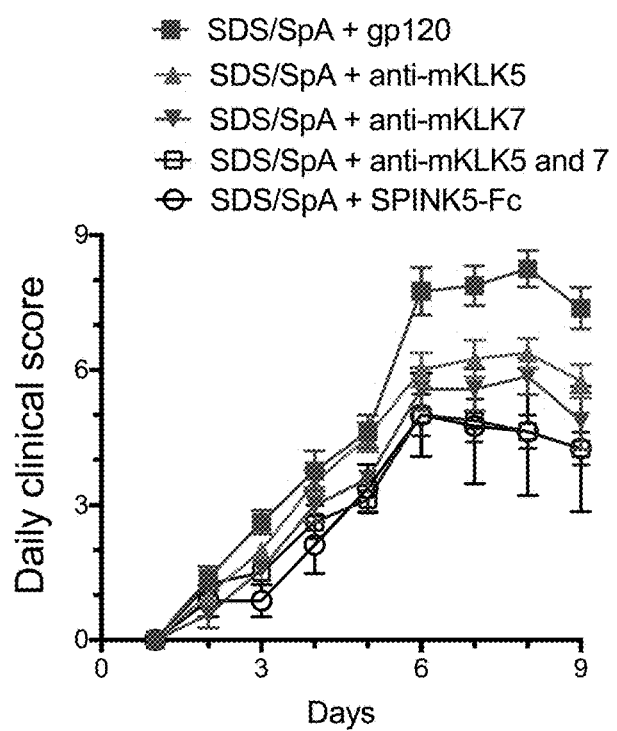
Figure 12B:
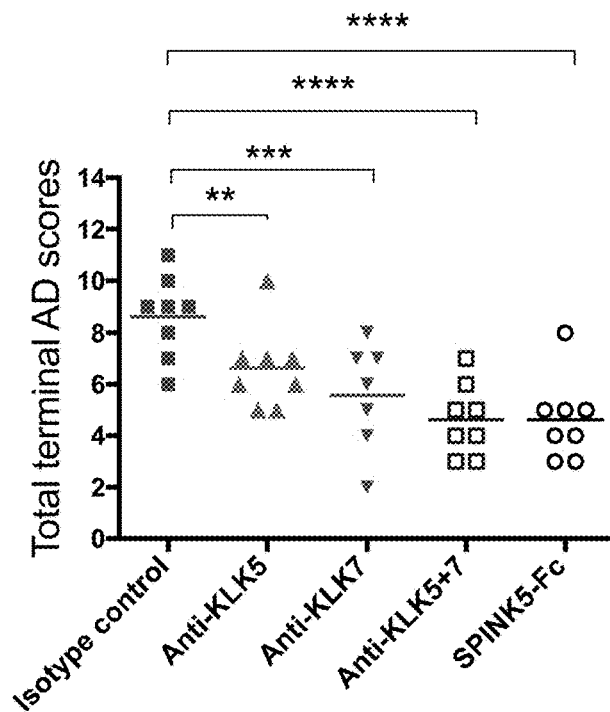
Figure 12C:
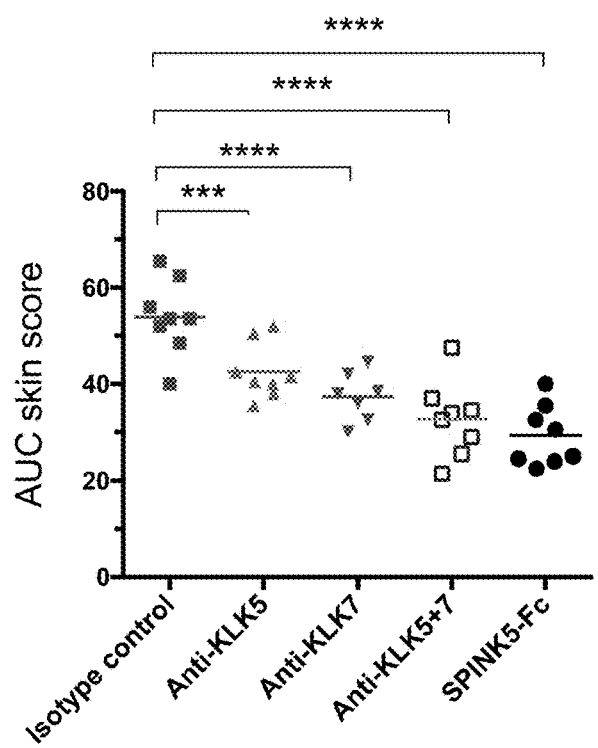

FIGS. 12A-12C show daily clinical score (12A), total terminal atopic dermatitis score (12B), and AUC skin score (12C) in SDS/S. *Aureus* protein A atopic dermatitis model mice administered isotype control antibody, anti-murine KLK5 antibody, anti-murine KLK7 antibody, a combination of anti-KLK5 and anti-KLK7 antibodies, or SPINK5-Fc.

Figure 13:
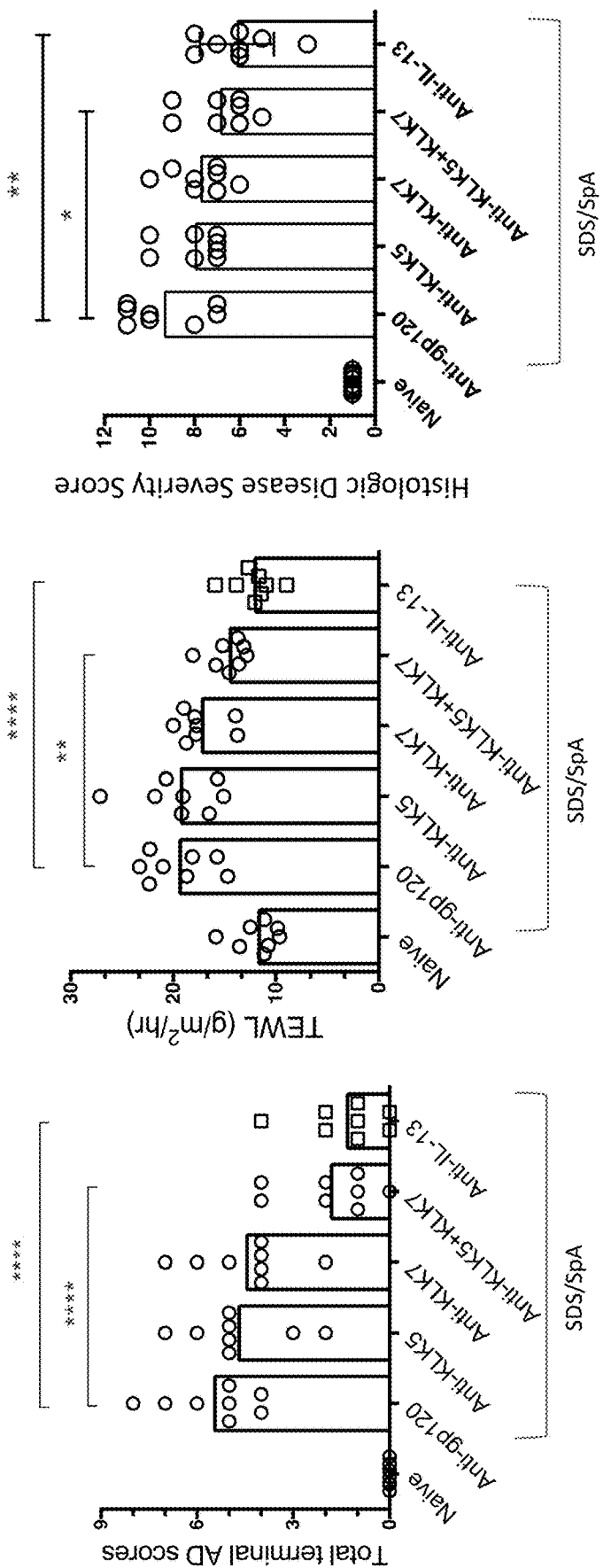

FIG. 13 shows total terminal atopic dermatitis score, transepidermal water loss, and histological disease severity score in SDS/S. *Aureus* protein A atopic dermatitis model mice administered isotype control antibody, anti-murine KLK5 antibody, anti-murine KLK7 antibody, a combination of anti-KLK5 and anti-KLK7 antibodies, or anti-IL-13 antibody.

Figure 14:
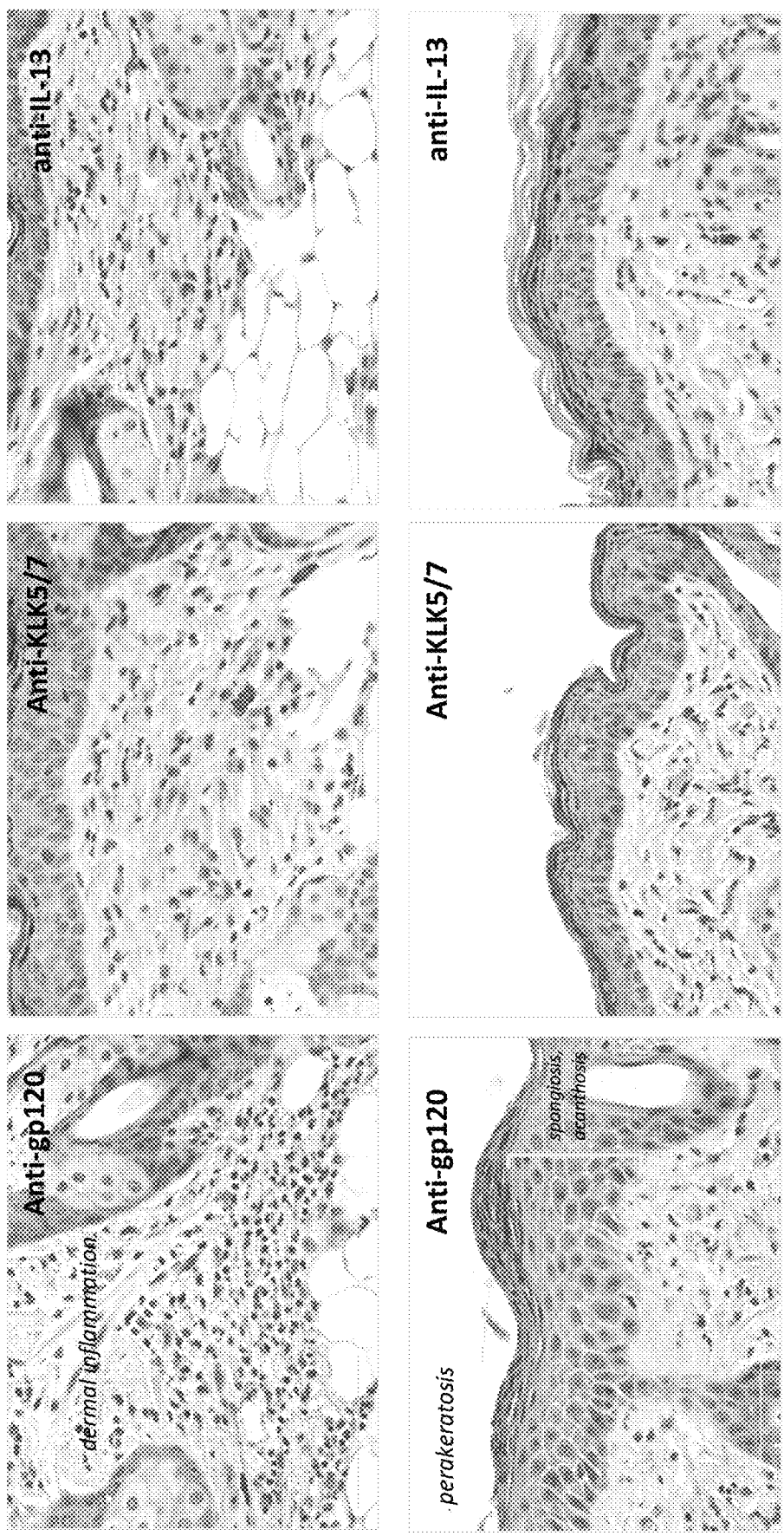

FIG. 14 shows representative hematoxylin and eosin staining of skin from SDS/S. *Aureus* protein A atopic dermatitis model mice administered isotype control antibody, a combination of anti-KLK5 and anti-KLK7 antibodies, or anti-IL-13 antibody.

Figure 15:
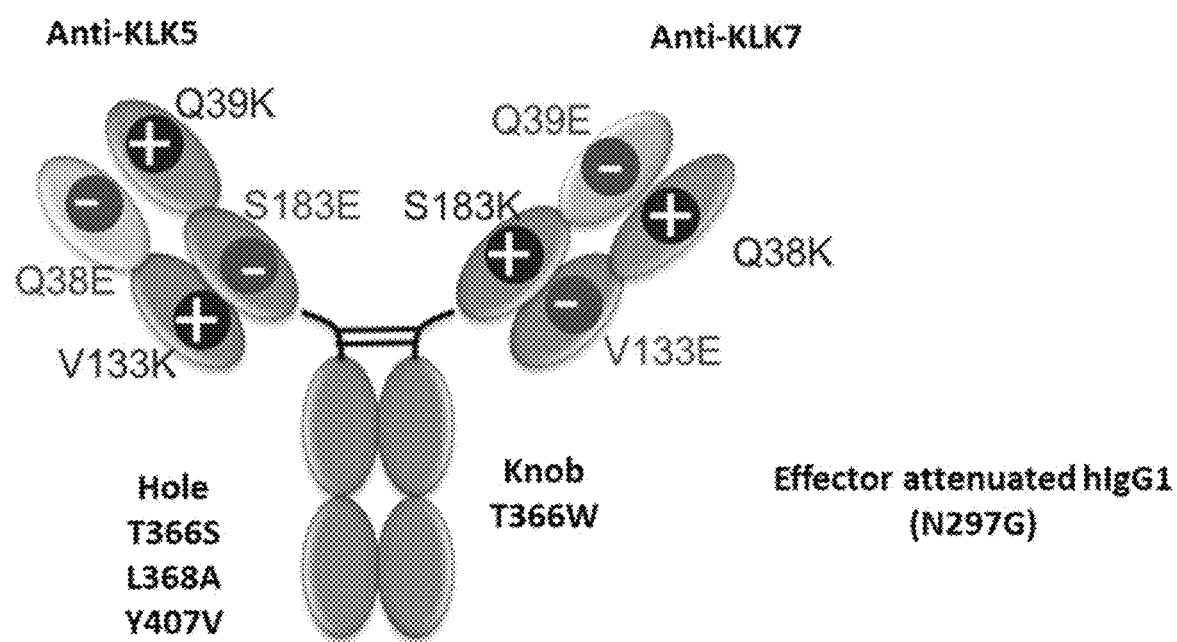
Figure 16B:
Figure 16D:
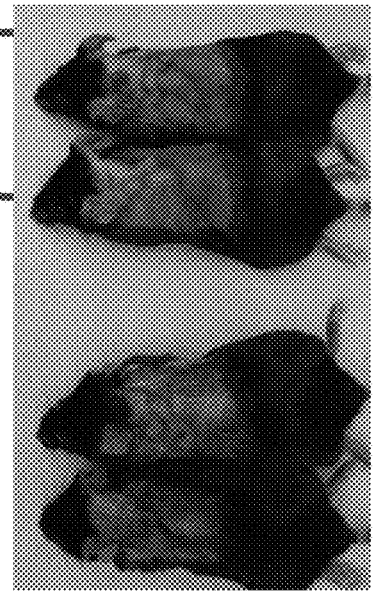
Figure 16A:
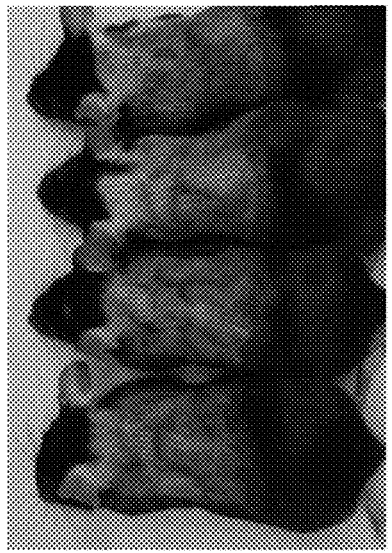
Figure 16C:
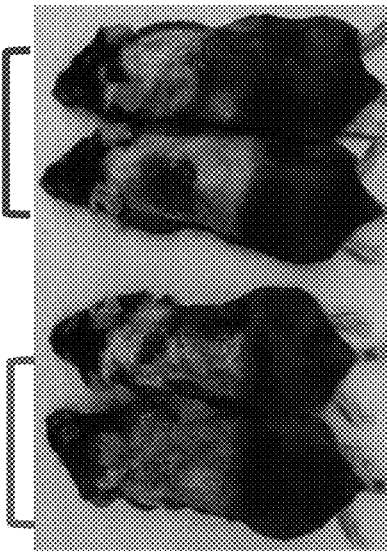
Figures 17A, 17B, 17C, 17D, 17E:
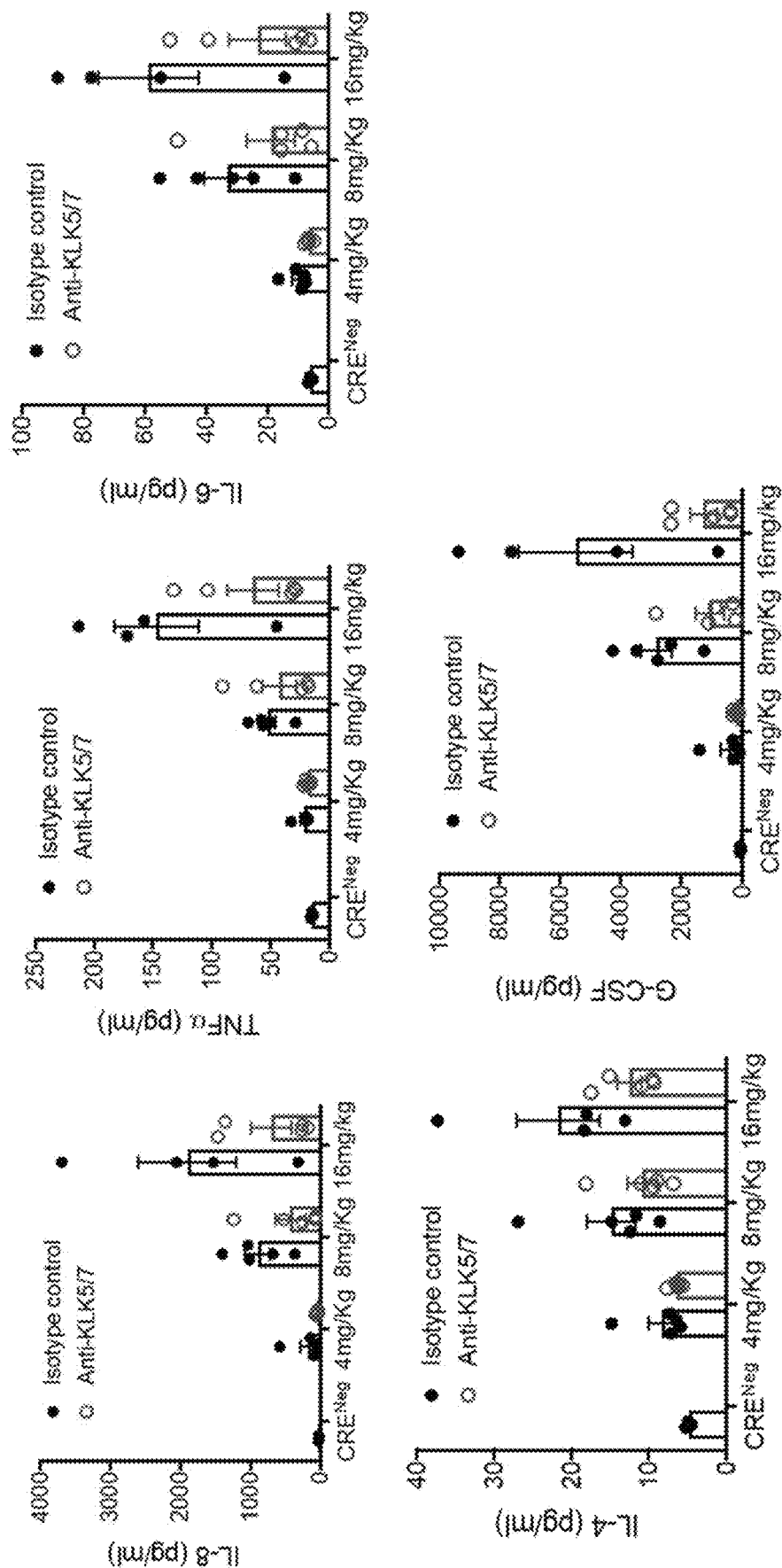

FIG. 15 shows a schematic of an exemplary bispecific anti-KLK5/KLK7 antibody provided herein, including substitutions to promote proper heavy chain/light chain pairing and/or substitutions to reduce effector functions. In an alternative format, the knob may be present on the anti-KLK5 arm, and the hole may be present on the anti-KLK7 arm.

FIGS. 16A-16D show reduction of skin rash and scaling in Spink5 deficient mice treated with anti-mKLK5/mKLK7 bispecific antibody. Spink5 f/f Cre-ERT2-negative control mice were treated with 16 mg/kg tamoxifen (16A), and Spink5 f/f Cre-ERT2+ mice were injected with 16 mg/kg (16B), 8 mg/kg (16C), or 4 mg/kg (16D) tamoxifen, then treated with 2.5 mg anti-gp120 isotype control antibody or 2.5 mg anti-mKLK5/mKLK7 bispecific antibody every other day. Back skin was analyzed 6 days post-injection.

FIGS. 17A-17E show reduction of cytokines IL-8 (17A), TNF-α (17B), IL-6 (17C), IL-4 (17D), and G-CSF (17E) in lysates prepared from back skin of Spink5 deficient mice following anti-mKLK5/mKLK7 bispecific antibody treatment compared to isotype control antibody treatment.

Figure 18:
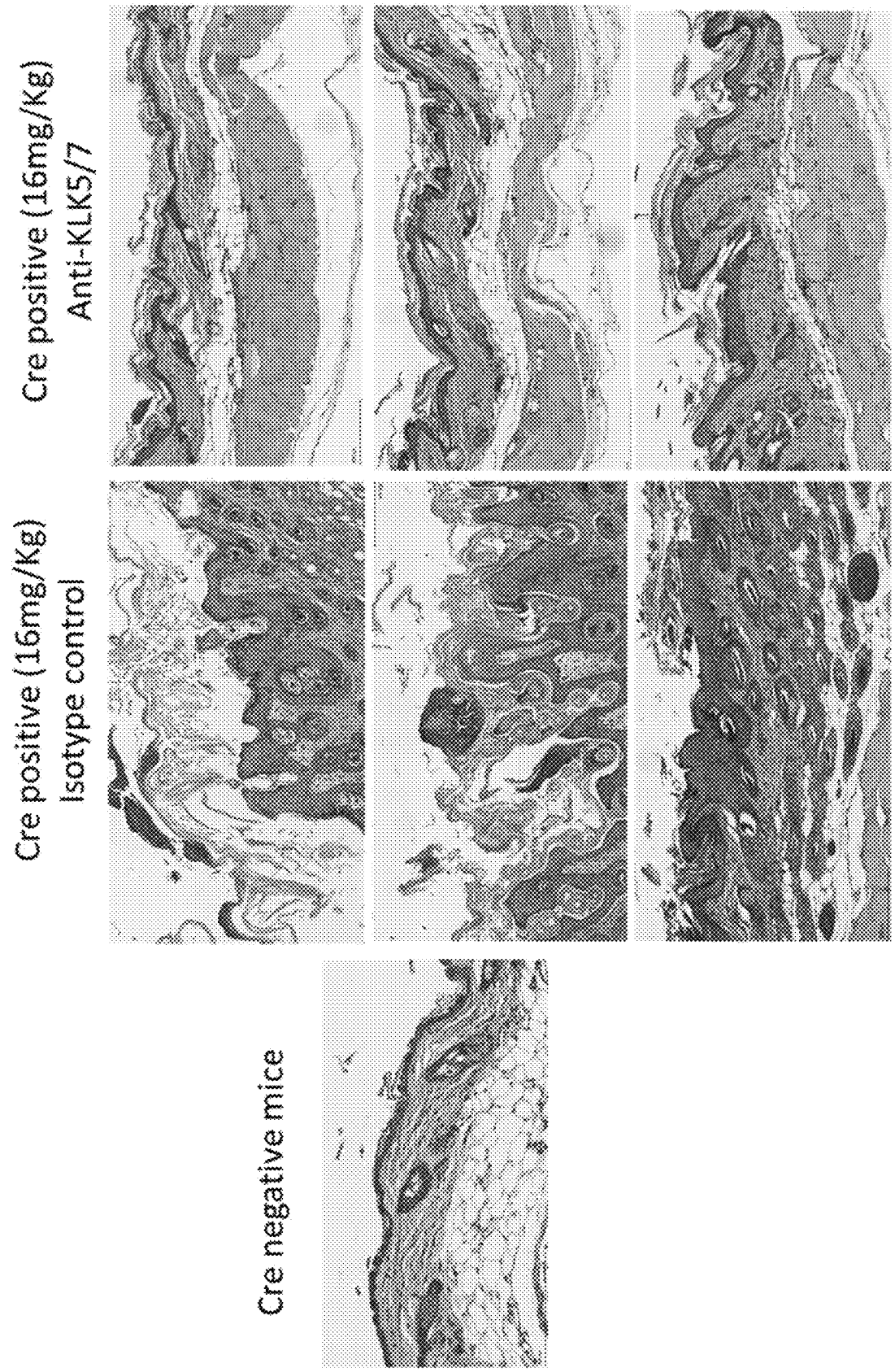

FIG. 18 shows representative cross-sections of hematoxylin and eosin stained skin from Spink5 f/f Cre-ERT2-negative control mice treated with 16 mg/kg tamoxifen and Spink5 f/f Cre-ERT2+ mice treated with 16 mg/kg tamoxifen and isotype control antibody or anti-mKLK5/mKLK7 bispecific antibody.

Figure 19A:
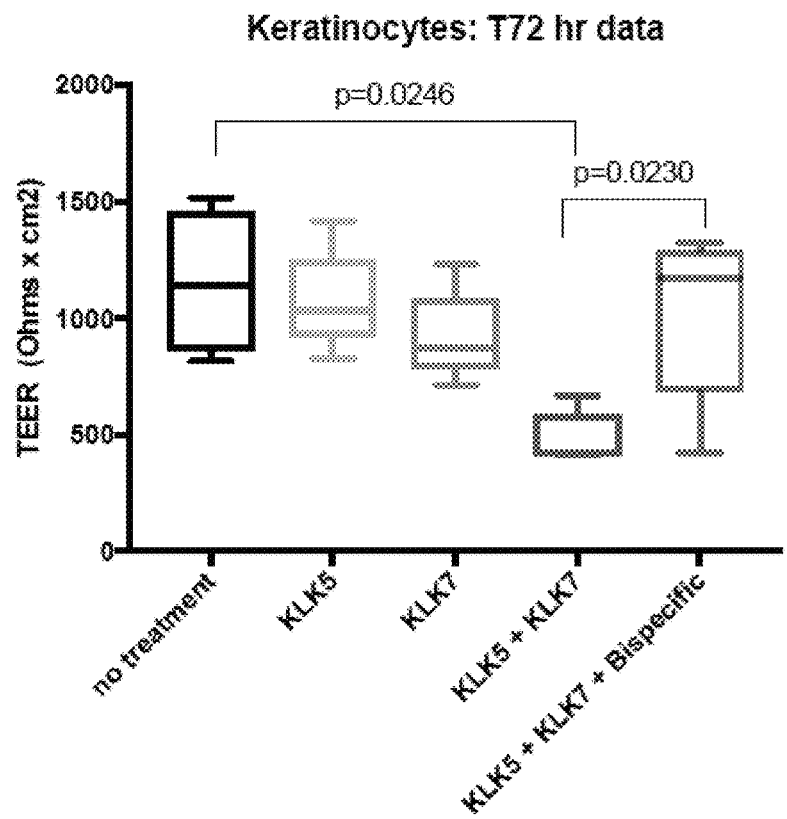
Figure 19B:
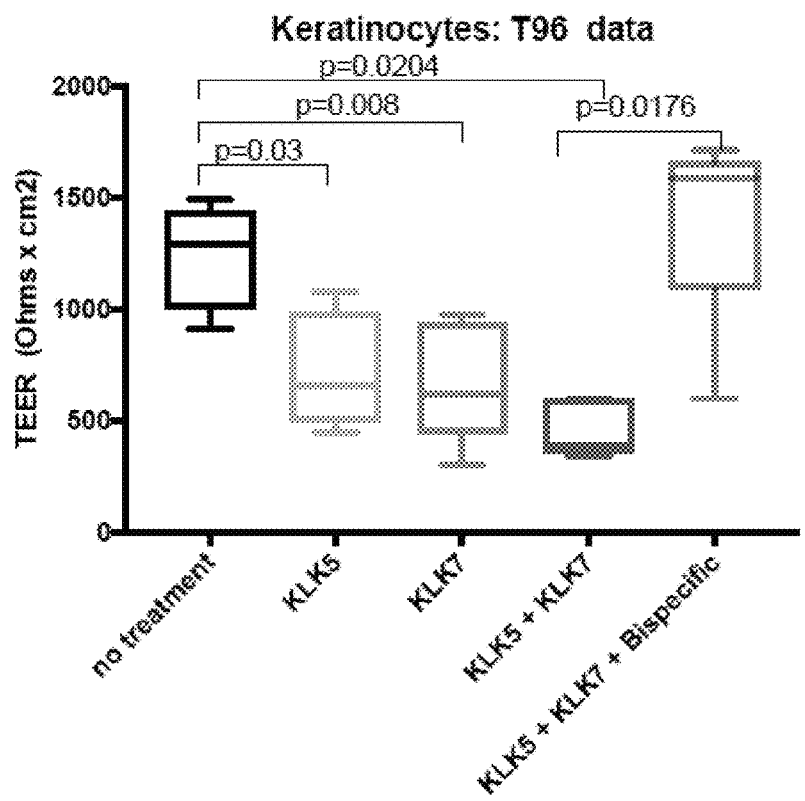

FIGS. 19A-19B show epithelial permeability as measured by trans-epithelial electrical resistance (TEER) in human epidermal keratinocytes treated with KLK5, KLK7, KLK5+KLK7, and KLK5+KLK7+anti-KLK5/KLK7 bispecific antibody.

Figure 20A:
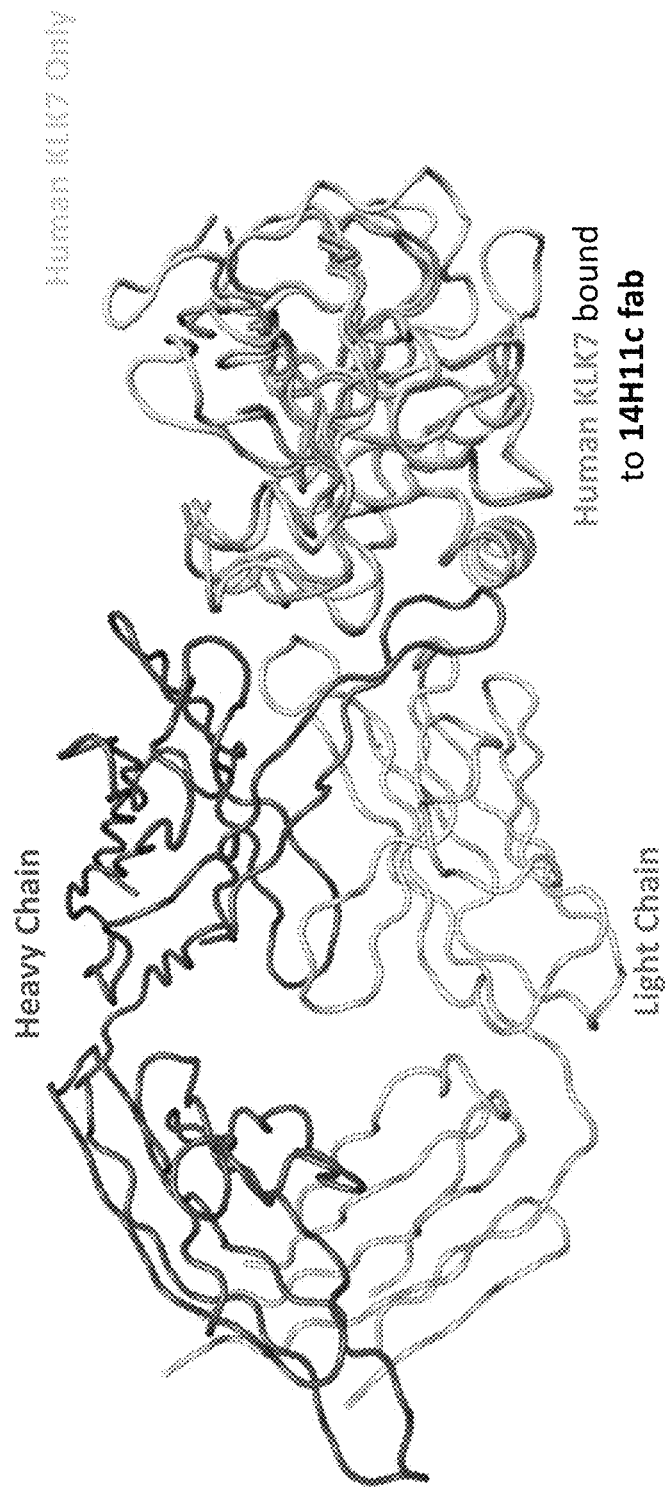
Figure 20B:
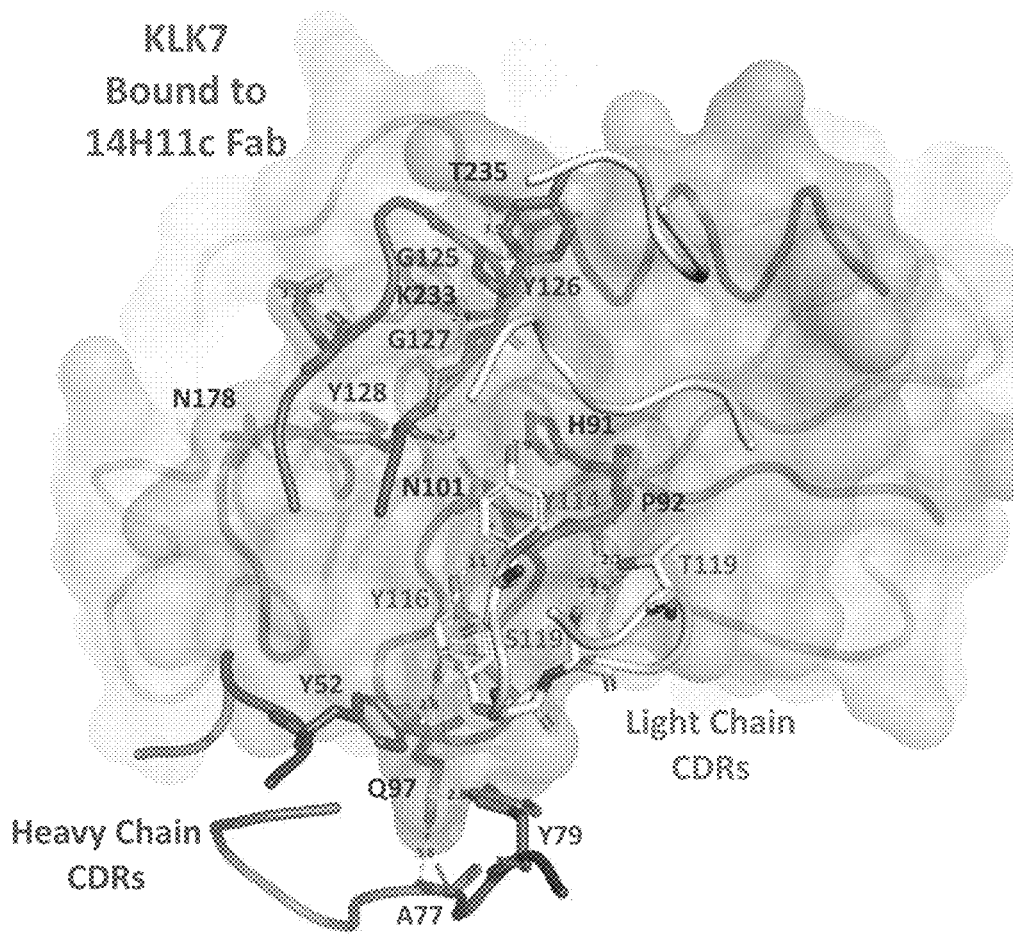
Figure 20C:
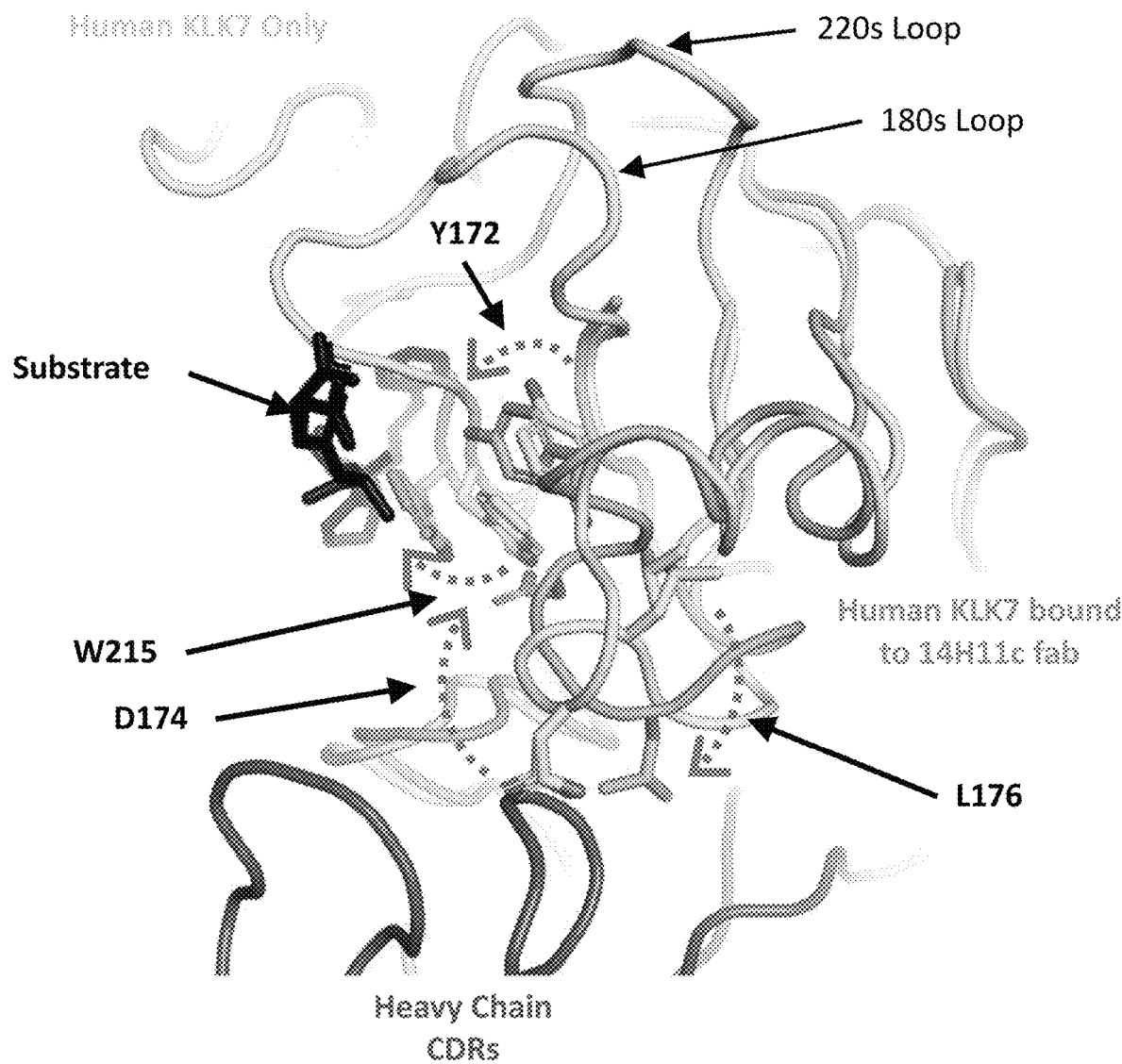

FIGS. 20A-20C show the crystal structure of anti-KLK7 rb.14H11c Fab bound to KLK7. The complete Fab bound to KLK7 is shown in FIG. 20A, with an overlay of KLK7 alone. FIG. 20B shows the KLK7-Fab interface. FIG. 20C shows an overlay of KLK7 in its native conformation (yellow) and KLK7 bound to rb.14H11c Fab (cyan). Portions of the rb14H11c heavy chain are shown in dark blue.

DETAILED DESCRIPTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes.

In some aspects, the number of amino acid changes are 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary methods for measuring binding affinity are described in the following.

An "affinity matured" antibody refers to an antibody with one or more alterations in one or more complementary determining regions (CDRs), compared to a parent antibody which does not possess such alterations, such alterations resulting in an improvement in the affinity of the antibody for antigen.

The terms "anti-KLK7 antibody" and "an antibody that binds to KLK7" refer to an antibody that is capable of binding KLK7, such as human KLK7, with sufficient affinity such that the antibody is useful as a diagnostic and/or therapeutic agent in targeting KLK7. In one aspect, the extent of binding of an anti-KLK7 antibody to an unrelated, non-KLK7 protein is less than about 10% of the binding of the antibody to KLK7 as measured, e.g., by surface plasmon resonance (SPR). In certain aspects, an antibody that binds to KLK7 has a dissociation constant ($K_D$) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). An antibody is said to "specifically bind" to KLK7 when the antibody has a $K_D$ of 1 μM or less. In certain aspects, an anti-KLK7 antibody binds to an epitope of KLK7 that is conserved among KLK7 from different species.

The terms "anti-KLK5 antibody" and "an antibody that binds to KLK5" refer to an antibody that is capable of binding KLK5, such as human KLK5, with sufficient affinity such that the antibody is useful as a diagnostic and/or therapeutic agent in targeting KLK5. In one aspect, the extent of binding of an anti-KLK5 antibody to an unrelated, non-KLK5 protein is less than about 10% of the binding of the antibody to KLK5 as measured, e.g., by surface plasmon resonance (SPR). In certain aspects, an antibody that binds to KLK5 has a dissociation constant ($K_D$) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). An antibody is said to "specifically bind" to KLK5 when the antibody has a $K_D$ of 1 μM or less. In certain aspects, an anti-KLK5 antibody binds to an epitope of KLK5 that is conserved among KLK5 from different species.

The terms "anti-KLK5/KLK7 antibody" and "an antibody that binds to KLK5 and KLK7" refer to a multispecific antibody that is capable of binding KLK7 and KLK5 with sufficient affinity such that the antibody is useful as a diagnostic and/or therapeutic agent in targeting KLK7 and/or KLK5. In one aspect, the extent of binding of an anti-KLK5/KLK7 antibody to an unrelated, non-KLK7/non-KLK5 protein is less than about 10% of the binding of the antibody to KLK7 or KLK5 as measured, e.g., by surface plasmon resonance (SPR). In certain aspects, a multispecific antibody that binds to KLK7 and KLK5 has a dissociation constant ($K_D$) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M) for each of KLK5 and KLK7. An antibody is said to "specifically bind" to a target protein when the antibody has a $K_D$ of 1 μM or less. In certain aspects, an anti-KLK5/KLK7 antibody binds to an epitope of KLK7 that is conserved among KLK7 from different species. In certain aspects, an anti-KLK5/KLK7 antibody binds to an epitope of KLK5 that is conserved among KLK5 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

A "binding domain" of an antibody, as used herein, refers to a portion of a variable domain that is sufficient to bind antigen. In some embodiments, a binding domain comprises heavy chain (HC) CDR1, CDR2, and CDR3 and light chain (LC) CDR1, CDR2, and CDR3. In some embodiments, a binding domain comprises heavy chain (HC) CDR1, FR2, CDR2, FR3, and CDR3 and light chain (LC) CDR1, FR2, CDR2, FR3, and CDR3.

The term "epitope" denotes the site on an antigen, either proteinaceous or non-proteinaceous, to which an anti-KLK7 antibody or anti-KLK5 antibody binds. Epitopes can be formed both from contiguous amino acid stretches (linear epitope) or comprise non-contiguous amino acids (conformational epitope), e.g., coming in spatial proximity due to the folding of the antigen, i.e. by the tertiary folding of a proteinaceous antigen. Linear epitopes are typically still bound by an antibody after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation.

Screening for antibodies binding to a particular epitope (i.e., those binding to the same epitope) can be done using methods routine in the art such as, e.g., without limitation, alanine scanning, peptide blots (see Meth. Mol. Biol. 248 (2004) 443-463), peptide cleavage analysis, epitope excision, epitope extraction, chemical modification of antigens (see Prot. Sci. 9 (2000) 487-496), and cross-blocking (see "Antibodies", Harlow and Lane (Cold Spring Harbor Press, Cold Spring Harb., NY).

Antigen Structure-based Antibody Profiling (ASAP), also known as Modification-Assisted Profiling (MAP), allows to bin a multitude of monoclonal antibodies specifically binding to KLK7 or KLK5 based on the binding profile of each of the antibodies from the multitude to chemically or enzymatically modified antigen surfaces (see, e.g., US 2004/0101920). The antibodies in each bin bind to the same epitope which may be a unique epitope either distinctly different from or partially overlapping with epitope represented by another bin.

Also competitive binding can be used to easily determine whether an antibody binds to the same epitope of KLK7 as, or competes for binding with, an anti-KLK7 antibody. For example, an "antibody that binds to the same epitope" as a reference anti-KLK7 antibody refers to an antibody that blocks binding of the reference anti-KLK7 antibody, respectively, to its antigen in a competition assay by 50% or more, and conversely, the reference antibody blocks binding of the antibody to its antigen in a competition assay by 50% or more. Also for example, to determine if an antibody binds to the same epitope as a reference anti-KLK7 antibody, the reference antibody is allowed to bind to KLK7 under saturating conditions. After removal of the excess of the reference anti-KLK7 antibody, the ability of an anti-KLK7 antibody in question to bind to KLK7 is assessed. If the anti-KLK7 antibody is able to bind to KLK7 after saturation binding of the reference anti-KLK7 antibody, it can be concluded that the anti-KLK7 antibody in question binds to a different epitope than the reference anti-KLK7 antibody. But, if the anti-KLK7 antibody in question is not able to bind to KLK7 after saturation binding of the reference anti-KLK7 antibody, then the anti-KLK7 antibody in question may bind to the same epitope as the epitope bound by the reference anti-KLK7 antibody. To confirm whether the antibody in question binds to the same epitope or is just hampered from binding by steric reasons routine experimentation can be used (e.g., peptide mutation and binding analyses using ELISA, RIA, surface plasmon resonance, flow cytometry or any other quantitative or qualitative antibody-binding assay available in the art). This assay should be carried out in two set-ups, i.e. with both of the antibodies being the saturating antibody. If, in both set-ups, only the first (saturating) antibody is capable of binding to KLK7, then it can be concluded that the anti-KLK7 antibody in question and the reference anti-KLK7 antibody compete for binding to KLK7.

Similarly, competitive binding can be used to easily determine whether an antibody binds to the same epitope of KLK5 as, or competes for binding with, an anti-KLK5 antibody. For example, an "antibody that binds to the same epitope" as a reference anti-KLK5 antibody refers to an antibody that blocks binding of the reference anti-KLK5 antibody, respectively, to its antigen in a competition assay by 50% or more, and conversely, the reference antibody blocks binding of the antibody to its antigen in a competition assay by 50% or more. Also for example, to determine if an antibody binds to the same epitope as a reference anti-KLK5 antibody, the reference antibody is allowed to bind to KLK5 under saturating conditions. After removal of the excess of the reference anti-KLK5 antibody, the ability of an anti-KLK5 antibody in question to bind to KLK5 is assessed. If the anti-KLK5 antibody is able to bind to KLK5 after saturation binding of the reference anti-KLK5 antibody, it can be concluded that the anti-KLK5 antibody in question binds to a different epitope than the reference anti-KLK5 antibody. But, if the anti-KLK5 antibody in question is not able to bind to KLK5 after saturation binding of the reference anti-KLK5 antibody, then the anti-KLK5 antibody in question may bind to the same epitope as the epitope bound by the reference anti-KLK5 antibody. To confirm whether the antibody in question binds to the same epitope or is just hampered from binding by steric reasons routine experimentation can be used (e.g., peptide mutation and binding analyses using ELISA, RIA, surface plasmon resonance, flow cytometry or any other quantitative or qualitative antibody-binding assay available in the art). This assay should be carried out in two set-ups, i.e. with both of the antibodies being the saturating antibody. If, in both set-ups, only the first (saturating) antibody is capable of binding to KLK5, then it can be concluded that the anti-KLK5 antibody in question and the reference anti-KLK5 antibody compete for binding to KLK5.

In some aspects, two antibodies are deemed to bind to the same or an overlapping epitope if a 1-, 5-, 10-, 20- or 100-fold excess of one antibody inhibits binding of the other by at least 50%, at least 75%, at least 90% or even 99% or more as measured in a competitive binding assay (see, e.g., Junghans et al., Cancer Res. 50 (1990) 1495-1502).

In some aspects, two antibodies are deemed to bind to the same epitope if essentially all amino acid mutations in the antigen that reduce or eliminate binding of one antibody also reduce or eliminate binding of the other. Two antibodies are deemed to have "overlapping epitopes" if only a subset of the amino acid mutations that reduce or eliminate binding of one antibody reduce or eliminate binding of the other.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. In certain aspects, the antibody is of the $IgG_1$ isotype. In certain aspects, the antibody is of the $IgG_1$ isotype with the P329G, L234A and L235A mutation to reduce Fc-region effector function. In other aspects, the antibody is of the $IgG_2$ isotype. In certain aspects, the antibody is of the $IgG_4$ isotype with the S228P mutation in the hinge region to improve stability of $IgG_4$ antibody. The heavy chain constant domains that correspond to the different classes of immunoglobulins are called $\alpha$, $\delta$, $\epsilon$, $\gamma$, and $\mu$, respectively. The light chain of an antibody may be assigned to one of two types, called kappa ($\kappa$) and lambda ($\lambda$), based on the amino acid sequence of its constant domain.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of an agent, e.g., a pharmaceutical composition, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to EU index). Therefore, the C-terminal lysine (Lys447), or the C-terminal glycine (Gly446) and lysine (Lys447), of the Fc region may or may not be present. Thus, a "full-length IgG1" for example, includes an IgG1 with Gly446 and Lys447, or without Lys447, or without both Gly446 and Lys447. Amino acid sequences of heavy chains including an Fc region are denoted herein without C-terminal glycine-lysine dipeptide if not indicated otherwise. In one aspect, a heavy chain including an Fc region as specified herein, comprised in an antibody according to the invention, may comprise Gly446 and Lys447 (numbering according to EU index). In one aspect, a heavy chain including an Fc region as specified herein, comprised in an antibody according to the invention, may comprise Gly446 (numbering according to EU index).

Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, M D, 1991.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The terms "full length antibody", "intact antibody", and "whole antibody" are used herein interchangeably to refer to an antibody having a structure substantially similar to a native antibody structure or having heavy chains that contain an Fc region as defined herein.

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one aspect, for the VL, the subgroup is subgroup kappa I as in Kabat et al., supra. In one aspect, for the VH, the subgroup is subgroup III as in Kabat et al., supra.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and which determine antigen binding specificity, for example "complementarity determining regions" ("CDRs").

Generally, antibodies comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Figure 2A:
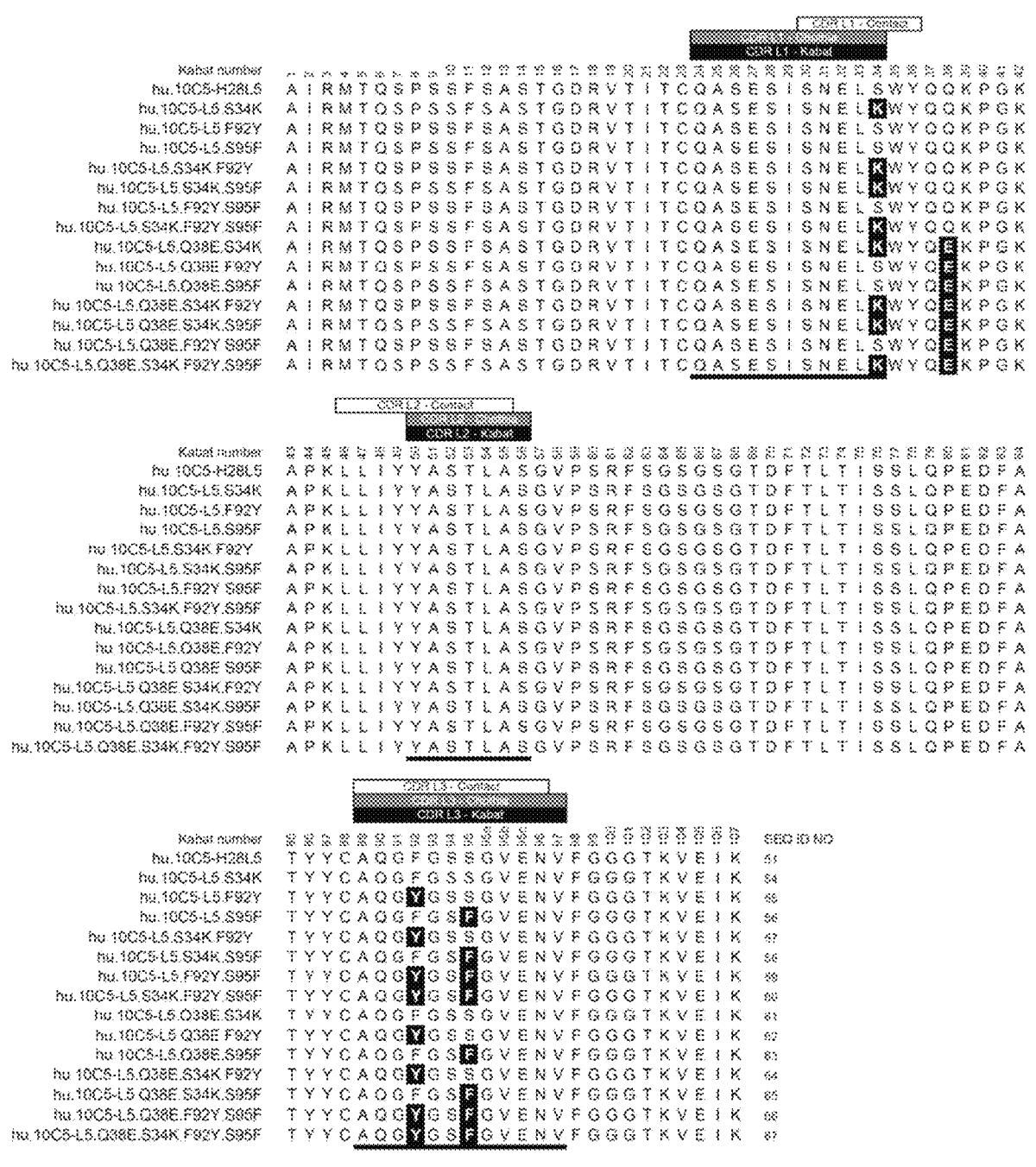
Figure 3A:
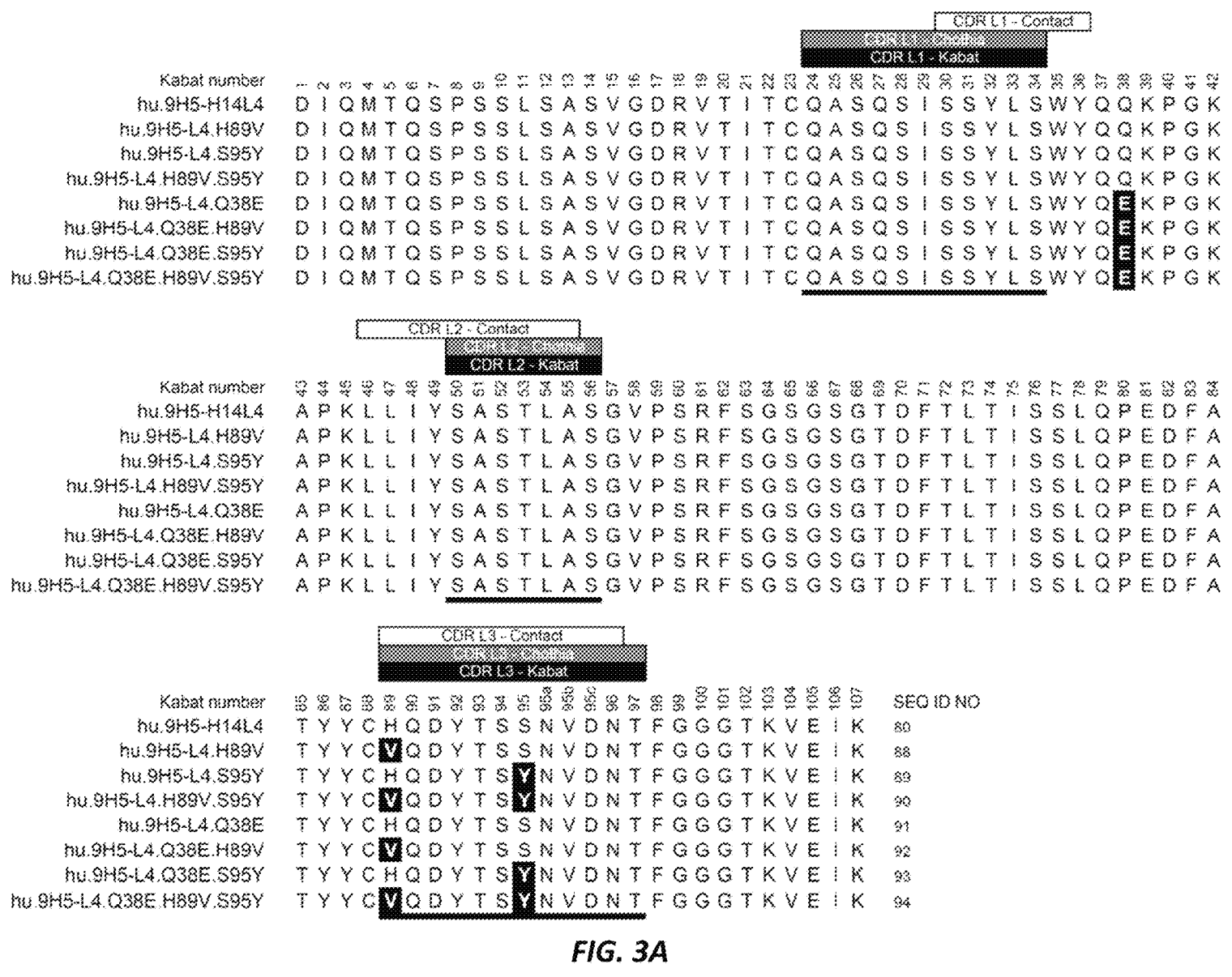
Figure 3B:
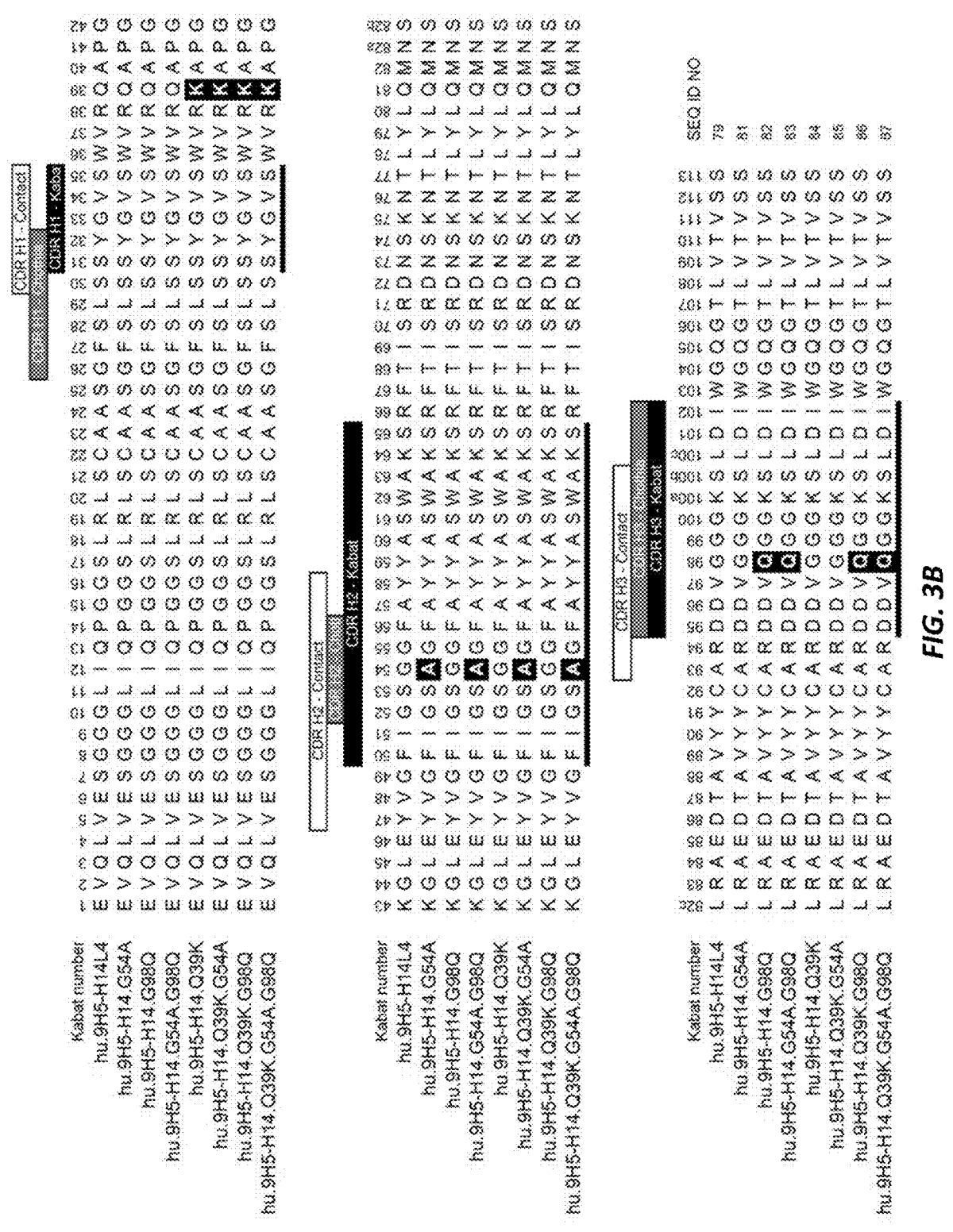

Unless otherwise indicated, the CDRs are determined according to Kabat et al., supra. One of skill in the art will understand that the CDR designations can also be determined according to Chothia, supra, McCallum, supra, or any other scientifically accepted nomenclature system. In one aspect, CDR residues comprise those identified in FIGS. 1-3, or elsewhere in the specification.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the individual or subject is a human.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IF), capillary electrophoresis) or chromatographic (e.g., ion exchange or reverse phase HPLC) methods. For a review of methods for assessment of antibody purity, see, e.g., Flatman et al., *J. Chromatogr. B* 848:79-87 (2007).

The term "linked" when used in the context of two polypeptides, means that the polypeptides are part of the same sequence of amino acids. Two polypeptides that are linked may be separated by additional amino acid sequence; that is, they need not be contiguous or directly linked to one another.

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi:10.1038/nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-KLK7 antibody" refers to one or more nucleic acid molecules encoding anti-KLK7 antibody heavy and light chains (or fragments thereof), including such nucleic acid molecule(s) in a single vector or separate vectors, and such nucleic acid molecule(s) present at one or more locations in a host cell.

"Isolated nucleic acid encoding an anti-KLK5 antibody" refers to one or more nucleic acid molecules encoding anti-KLK5 antibody heavy and light chains (or fragments thereof), including such nucleic acid molecule(s) in a single vector or separate vectors, and such nucleic acid molecule(s) present at one or more locations in a host cell.

"Isolated nucleic acid encoding an anti-KLK5/KLK7 bispecific antibody" refers to one or more nucleic acid molecules encoding anti-KLK5/KLK7 bispecific antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical composition.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable domain (VH), also called a variable heavy domain or a heavy chain variable region, followed by three constant heavy domains (CH1, CH2, and CH3). Similarly, from N- to C-terminus, each light chain has a variable domain (VL), also called a variable light domain or a light chain variable region, followed by a constant light (CL) domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNAS-TAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, percent amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from www.fasta.bioch.virginia.edu/fasta_www2/fasta_down.shtml or www.ebi.ac.uk/Tools/sss/fasta. Alternatively, a public server accessible at fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

The terms "KLK5" and "kallikrein related peptidase 5," as used herein, refer to any native KLK5 from any vertebrate source, including mammals such as primates (e.g., humans) and rodents (e.g., mice and rats), unless otherwise indicated. The term encompasses "full-length", unprocessed KLK5 as well as any form of KLK5 that results from processing in the cell. The term also encompasses naturally occurring variants of KLK5, e.g., splice variants or allelic variants. The amino acid sequence of an exemplary human precursor KLK5 protein is shown in SEQ ID NO: 1 (UniProtKB/Swiss-Prot: Q9Y337.3). The amino acid sequence of an exemplary human mature KLK5 protein, which lacks the signal peptide (amino acids 1-22) and propeptide (amino acids 23-66) is shown in SEQ ID NO: 2. The amino acid sequence of an exemplary cynomolgus monkey precursor KLK5 protein is shown in SEQ ID NO: 100 (UniProtKB: A0A2K5W0T6). The amino acid sequence of an exemplary cynomolgus monkey mature KLK5 protein, which lacks the signal peptide (amino acids 1-22) and propeptide (amino acids 23-64) is shown in SEQ ID NO: 101.

The terms "KLK7" and "kallikrein related peptidase 7," as used herein, refer to any native KLK7 from any vertebrate source, including mammals such as primates (e.g., humans) and rodents (e.g., mice and rats), unless otherwise indicated. The term encompasses "full-length", unprocessed KLK7 as well as any form of KLK7 that results from processing in the cell. The term also encompasses naturally occurring variants of KLK7, e.g., splice variants or allelic variants. The amino acid sequence of an exemplary human precursor KLK7 protein is shown in SEQ ID NO: 3 (UniProtKB/Swiss-Prot: P49862.1). The amino acid sequence of an exemplary human mature KLK7 protein, which lacks the signal peptide (amino acids 1-22) and propeptide (amino acids 23-29) is shown in SEQ ID NO: 4. The amino acid sequence of an exemplary cynomolgus monkey precursor KLK7 protein is shown in SEQ ID NO: 5 (UniProtKB: G7PYG2). The amino acid sequence of an exemplary cynomolgus monkey mature KLK7 protein, which lacks the signal peptide (amino acids 1-21) and propeptide (amino acids 22-29) is shown in SEQ ID NO: 6.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). See, e.g., Kindt et al. *Kuby Immunology*, 6$^{th}$ ed., W.H. Freeman and Co., page 91 (2007). A variable domain may comprise heavy chain (HC) CDR1-FR2-CDR2-FR3-CDR3 with or without all or a portion of FR1 and/or FR4; and light chain (LC) CDR1-FR2-CDR2-FR3-CDR3 with or without all or a portion of FR1 and/or FR4. That is, a variable domain may lack a portion of FR1 and/or FR4 so long as it retains antigen-binding activity. A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on the finding that KLK5 and KLK7 may both play a role in epithelial barrier permeability. Inhibiting both KLK5 and KLK7 may therefore show improved efficacy in treating conditions associated with excessive epithelial barrier permeability. In certain aspects, antibodies that bind to KLK5 are provided. In certain aspects, antibodies that bind to KLK7 are provided. In certain aspects, multispecific antibodies that bind to KLK5 and KLK7 are provided. Antibodies of the invention are useful, e.g., for the diagnosis or treatment of Netherton Syndrome, asthma, atopic dermatitis, psoriasis, eosinophilic esophagitis, and rosacea.

A. Exemplary Anti-KLK7 Antibodies

In one aspect, the invention provides antibodies that bind to KLK7. In one aspect, provided are isolated antibodies that bind to KLK7. In one aspect, the invention provides antibodies that specifically bind to KLK7. In certain aspects, an anti-KLK7 antibody inhibits KLK7 protease activity. In some embodiments, an anti-KLK7 antibody inhibits human KLK7-mediated cleavage of a substrate comprising the amino acid sequence RPKPVE-Nval-WRK (SEQ ID NO: 121), wherein Nval is norvaline. In some embodiments, an anti-KLK7 antibody inhibits human KLK7-mediated cleavage of a substrate comprising the amino acid sequence RPKPVE-Nval-WRK (SEQ ID NO: 121), wherein Nval is norvaline, with an IC50 of less than 5 nM, or less than 3 nM, or less than 2 nM, or less than 1 nM. In some embodiments, an anti-KLK7 antibody inhibits human KLK7-mediated cleavage of a substrate comprising the amino acid sequence RPKPVE-Nval-WRK (SEQ ID NO: 121), wherein Nval is norvaline, with an IC50 of no greater than 5 nM, or no greater than 3 nM, or no greater than 2 nM, or no greater than 1 nM. In some embodiments, an anti-KLK7 antibody binds human KLK7 with a $K_D$ of less than 20 pM, less than 10 pM, or less than 9 pM, or less than 8 pM, or less than 7 pM, or less than 6 pM, or less than 5 pM, or less than 3 pM, or less than 2 pM, or less than 1 pM, as measured by surface plasmon resonance. In some embodiments, an anti-KLK7 antibody binds human KLK7 with a $K_D$ of no greater than 20 pM, no greater than 10 pM, or no greater than 9 pM, or no greater than 8 pM, or no greater than 7 pM, or no greater than 6 pM, or no greater than 5 pM, or no greater than 3 pM, or no greater than 2 pM, or no greater than 1 pM, as measured by surface plasmon resonance.

In some embodiments, an anti-KLK7 antibody binds an epitope within amino acids R71-N82, K152-S158, and/or Q211-K222 of KLK7, wherein the amino acids are numbered according to SEQ ID NO: 4. In some embodiments, the anti-KLK7 antibody contacts at least one amino acid within amino acids R71-N82, contact at least one amino acid within amino acids K152-S158, and contacts at least one amino acid within amino acids Q211-K222 of KLK7, as numbered according to SEQ ID NO: 4. In some embodiments, an anti-KLK7 antibody binds an epitope comprising one or more of amino acids H72, P73, G74, S76, Q78, N82, N157, K211, and/or T213 of KLK7, as numbered according to SEQ ID NO: 4. In some embodiments, an anti-KLK7 antibody binds an epitope comprising one or more of amino acids H91, P92, G93, S95, Q97, N101, N178, K233, and/or T235 of KLK7, by chymotrypsin numbering. In some embodiments, an anti-KLK7 antibody binds an epitope comprising amino acids H72, P73, G74, S76, Q78, N82, N157, K211, and T213 of KLK7, as numbered according to SEQ ID NO: 4. In some embodiments, an anti-KLK7 antibody binds an epitope comprising amino acids H91, P92, G93, S95, Q97, N101, N178, K233, and T235 of KLK7, by chymotrypsin numbering.

In some embodiments, an anti-KLK7 antibody, when bound to KLK7, results in a conformational change of human KLK7, wherein the conformational change allosterically results in the disruption of the substrate binding site and/or the active site of human KLK7.

In some embodiments, the anti-KLK7 antibody does not bind to KLK5. In some embodiments, the anti-KLK7 antibody does not bind to KLK1, KLK4, KLK5, KLK11, and KLK14. In some embodiments, the anti-KLK7 antibody binds to human KLK7 and cynomolgus monkey KLK7.

In one aspect, the invention provides an anti-KLK7 antibody comprising at least one, at least two, at least three, at least four, at least five, or all six CDRs selected from (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12.

In one aspect, the invention provides an antibody comprising at least one, at least two, or all three VH CDR sequences selected from (a) CDR-H1 comprising the amino acid sequence of SEQ ID NO: 7; (b) CDR-H2 comprising the amino acid sequence of SEQ ID NO: 8; and (c) CDR-H3 comprising the amino acid sequence of SEQ ID NO: 9. In one aspect, the antibody comprises CDR-H3 comprising the amino acid sequence of SEQ ID NO: 9. In another aspect, the antibody comprises CDR-H3 comprising the amino acid sequence of SEQ ID NO: 9 and CDR-L3 comprising the amino acid sequence of SEQ ID NO: 12. In a further aspect, the antibody comprises CDR-H3 comprising the amino acid sequence of SEQ ID NO: 9, CDR-L3 comprising the amino acid sequence of SEQ ID NO: 12, and CDR-H2 comprising the amino acid sequence of SEQ ID NO: 8. In a further aspect, the antibody comprises (a) CDR-H1 comprising the amino acid sequence of SEQ ID NO: 7; (b) CDR-H2 comprising the amino acid sequence of SEQ ID NO: 8; and (c) CDR-H3 comprising the amino acid sequence of SEQ ID NO: 9.

In another aspect, the invention provides an antibody comprising at least one, at least two, or all three VL CDR sequences selected from (a) CDR-L1 comprising the amino acid sequence of SEQ ID NO: 10; (b) CDR-L2 comprising the amino acid sequence of SEQ ID NO: 11; and (c) CDR-L3 comprising the amino acid sequence of SEQ ID NO: 12. In one aspect, the antibody comprises (a) CDR-L1 comprising the amino acid sequence of SEQ ID NO: 10; (b) CDR-L2 comprising the amino acid sequence of SEQ ID NO: 11; and (c) CDR-L3 comprising the amino acid sequence of SEQ ID NO: 12.

In another aspect, an antibody of the invention comprises (a) a VH domain comprising at least one, at least two, or all three VH CDR sequences selected from (i) CDR-H1 comprising the amino acid sequence of SEQ ID NO: 7, (ii) CDR-H2 comprising the amino acid sequence of SEQ ID NO: 8, and (iii) CDR-H3 comprising the amino acid sequence of SEQ ID NO: 9; and (b) a VL domain comprising at least one, at least two, or all three VL CDR sequences selected from (i) CDR-L1 comprising the amino acid sequence of SEQ ID NO: 10, (ii) CDR-L2 comprising the amino acid sequence of SEQ ID NO: 11, and (c) CDR-L3 comprising the amino acid sequence of SEQ ID NO: 12.

In another aspect, the invention provides an antibody comprising (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12.

In any of the aspects provided herein, an anti-KLK7 antibody is humanized. In one aspect, an anti-KLK7 antibody further comprises an acceptor human framework, e.g. a human immunoglobulin framework or a human consensus framework.

In one aspect, an anti-KLK7 antibody comprises a VH domain comprising one or more heavy chain framework sequences selected from (a) a heavy chain frame work region 1 (HC-FR1) of SEQ ID NO: 123-128, (b) a heavy chain frame work region 2 (HC-FR2) of SEQ ID NO:130-133, (c) a heavy chain frame work region 3 (HC-FR3) of SEQ ID NO:135-143, and (d) a heavy chain frame work region 4 (HC-FR4) of SEQ ID NO: 144-145.

In another aspect, an anti-KLK7 antibody comprises a VH domain comprising a HC-FR1 of SEQ ID NO: 123-128. In another aspect, an anti-KLK7 antibody comprises a VH domain comprising a HC-FR2 of SEQ ID NO:130-133. In another aspect, an anti-KLK7 antibody comprises a VH domain comprising a HC-FR3 of SEQ ID NO:135-143. In another aspect, an anti-KLK7 antibody comprises a VH domain comprising a HC-FR4 of SEQ ID NO: 144-145.

In another aspect, an anti-KLK7 antibody comprises a VH domain comprising a HC-FR1 of at least 85%, 86%, 87%, 88%, 89%, 90%, 91%, 92%, 93%, 94%, 95%, 96%, 97%, 98% or 99% sequence identity with SEQ ID NO:123-128. In one aspect, the VH domain comprises a HC-FR1 of at least 95% sequence identity with SEQ ID NO:123-128. In another aspect, the VH domain comprises a HC-FR1 of at least 98% sequence identity with SEQ ID NO: 123-128.

In another aspect, an anti-KLK7 antibody comprises a VH domain comprising a HC-FR2 of at least 85%, 86%, 87%, 88%, 89%, 90%, 91%, 92%, 93%, 94%, 95%, 96%, 97%, 98% or 99% sequence identity to SEQ ID NO:130-133. In one aspect, the VH domain comprises a HC-FR2 of at least 95% sequence identity with SEQ ID NO:130-133. In another aspect, the VH domain comprises a HC-FR2 of at least 98% sequence identity with SEQ ID NO:130-133.

In another aspect, an anti-KLK7 antibody comprises a VH domain comprising a HC-FR3 of at least 85%, 86%, 87%, 88%, 89%, 90%, 91%, 92%, 93%, 94%, 95%, 96%, 97%, 98% or 99% sequence identity to SEQ ID NO:135-143. In one aspect, the VH domain comprises a HC-FR3 of at least 95% sequence identity with SEQ ID NO:135-143. In another aspect, the VH domain comprises a HC-FR3 of at least 98% sequence identity with SEQ ID NO:135-143.

In another aspect, an anti-KLK7 antibody comprises a VH domain comprising a HC-FR4 of at least 85%, 86%, 87%, 88%, 89%, 90%, 91%, 92%, 93%, 94%, 95%, 96%, 97%, 98% or 99% sequence identity to SEQ ID NO:144-145. In one aspect, the VH domain comprises a HC-FR4 of at least 95% sequence identity with SEQ ID NO:144-145. In another aspect, the VH domain comprises a HC-FR4 of at least 98% sequence identity with SEQ ID NO:144-145.

In one aspect, an anti-KLK7 antibody comprises a VL domain comprising one or more light chain framework sequences selected from (a) a light chain frame work region 1 (LC-FR1) of SEQ ID NO:147-150, (b) a light chain frame work region 2 (LC-FR2) of SEQ ID NO: 152-154, (c) a light chain frame work region 3 (LC-FR3) of SEQ ID NO:156-158, and (d) a light chain frame work region 4 (LC-FR4) of SEQ ID NO:160.

In another aspect, an anti-KLK7 antibody comprises a VL domain comprising a LC-FR1 of SEQ ID NO:147-150. In another aspect, an anti-KLK7 antibody comprises a VL domain comprising a LC-FR2 of SEQ ID NO:152-154. In another aspect, an anti-KLK7 antibody comprises a VL domain comprising a LC-FR3 of SEQ ID NO:156-158. In another aspect, an anti-KLK7 antibody comprises a VL domain comprising a LC-FR4 of SEQ ID NO: 160.

In another aspect, an anti-KLK7 antibody comprises a VL domain comprising a LC-FR1 of at least 85%, 86%, 87%, 88%, 89%, 90%, 91%, 92%, 93%, 94%, 95%, 96%, 97%, 98% or 99% sequence identity to SEQ ID NO:147-150. In one aspect, the VL domain comprises a LC-FR1 of at least 95% sequence identity with SEQ ID NO:147-150. In another aspect, the VL domain comprises a LC-FR1 of at least 98% sequence identity with SEQ ID NO: 147-150.

In another aspect, an anti-KLK7 antibody comprises a VL domain comprising a LC-FR2 of at least 85%, 86%, 87%, 88%, 89%, 90%, 91%, 92%, 93%, 94%, 95%, 96%, 97%, 98% or 99% sequence identity to SEQ ID NO:152-154. In one aspect, the VL domain comprises a LC-FR2 of at least 95% sequence identity with SEQ ID NO:152-154. In another aspect, the VL domain comprises a LC-FR2 of at least 98% sequence identity with SEQ ID NO:152-154.

In another aspect, an anti-KLK7 antibody comprises a VL domain comprising a LC-FR3 of at least 85%, 86%, 87%, 88%, 89%, 90%, 91%, 92%, 93%, 94%, 95%, 96%, 97%, 98% or 99% sequence identity to SEQ ID NO: 156-158. In one aspect, the VL domain comprises a LC-FR3 of at least 95% sequence identity with SEQ ID NO:156-158. In another aspect, the VL domain comprises a LC-FR3 of at least 98% sequence identity with SEQ ID NO: 156-158.

In another aspect, an anti-KLK7 antibody comprises a VL domain comprising a LC-FR4 of at least 85%, 86%, 87%, 88%, 89%, 90%, 91%, 92%, 93%, 94%, 95%, 96%, 97%, 98% or 99% sequence identity to SEQ ID NO: 160. In one aspect, the VL domain comprises a LC-FR1 of at least 95% sequence identity with SEQ ID NO: 160. In another aspect, the VL domain comprises a LC-FR1 of at least 98% sequence identity with SEQ ID NO:160.

In another aspect, an anti-KLK7 antibody comprises one or more of the CDR sequences of a VH selected from SEQ ID NOs: 13 and 15-30. In another embodiment, an anti-KLK7 antibody comprises one or more of the CDR sequences of a VL selected from SEQ ID NOs: 14 and 31-38. In another embodiment, an anti-KLK7 antibody comprises the CDR sequences of a VH selected from SEQ ID NOs: 13 and 15-30 and the CDR sequences of a VL selected from SEQ ID NOs: 14 and 31-38.

In a further aspect, an anti-KLK7 antibody comprises the CDR-H1, CDR-H2 and CDR-H3 amino acid sequences of a VH selected from SEQ ID NOs: 13 and 15-30 and the CDR-L1, CDR-L2 and CDR-L3 amino acid sequences of a VL selected from SEQ ID NOs: 14 and 31-38.

In one aspect, an anti-KLK7 antibody comprises one or more of the heavy chain CDR amino acid sequences of a VH selected from SEQ ID NOs: 13 and 15-30 and a framework of at least 85%, 86%, 87%, 88%, 89%, 90%, 91%, 92%, 93%, 94%, 95%, 96%, 97%, 98%, 99% sequence identity to the framework amino acid sequence of a VH selected from SEQ ID NOs: 13 and 15-30. In one aspect, the anti-KLK7 antibody comprises the three heavy chain CDR amino acid sequences of a VH selected from SEQ ID NOs: 13 and 15-30 and a framework of at least 85%, 86%, 87%, 88%, 89%, 90%, 91%, 92%, 93%, 94%, 95%, 96%, 97%, 98%, 99% sequence identity to the framework amino acid sequence of a VH selected from SEQ ID NOs: 13 and 15-30. In one aspect, the anti-KLK7 antibody comprises the three heavy chain CDR amino acid sequences of a VH selected from SEQ ID NOs: 13 and 15-30 and a framework of at least 95% sequence identity to the framework amino acid sequence of a VH selected from SEQ ID NOs: 13 and 15-30. In another aspect, the anti-KLK7 antibody comprises the three heavy chain CDR amino acid sequences of a VH selected from SEQ ID NOs: 13 and 15-30 and a framework of at least of at least 98% sequence identity to the framework amino acid sequence of a VH selected from SEQ ID NOs: 13 and 15-30.

In one aspect, an anti-KLK7 antibody comprises one or more of the light chain CDR amino acid sequences of a VL selected from SEQ ID NOs: 14 and 31-38 and a framework of at least 85%, 86%, 87%, 88%, 89%, 90%, 91%, 92%, 93%, 94%, 95%, 96%, 97%, 98%, 99% sequence identity to the framework amino acid sequence of a VL selected from SEQ ID NOs: 14 and 31-38. In one aspect, the anti-KLK7 antibody comprises the three light chain CDR amino acid sequences of a VL selected from SEQ ID NOs: 14 and 31-38 and a framework of at least 85%, 86%, 87%, 88%, 89%, 90%, 91%, 92%, 93%, 94%, 95%, 96%, 97%, 98%, 99% sequence identity to the framework amino acid sequence of a VL selected from SEQ ID NOs: 14 and 31-38. In one aspect, the anti-KLK7 antibody comprises the three light chain CDR amino acid sequences of a VL selected from SEQ ID NOs: 14 and 31-38 and a framework of at least 95% sequence identity to the framework amino acid sequence of a VL selected from SEQ ID NOs: 14 and 31-38. In another aspect, the anti-KLK7 antibody comprises the three light chain CDR amino acid sequences of a VL selected from SEQ ID NOs: 14 and 31-38 and a framework of at least particularly of at least 98% sequence identity to the framework amino acid sequence of a VL selected from SEQ ID NOs: 14 and 31-38.

In one aspect, the anti-KLK7 antibody comprises (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12, and a VH domain having at least 90%, 91%, 92%, 93%, 94%, 95%, 96%, 97%, 98%, 99%, or 100% sequence identity to an amino acid sequence selected from SEQ ID NOs: 13 and 15-30, and a VL domain having at least 90%, 91%, 92%, 93%, 94%, 95%, 96%, 97%, 98%, 99%, or 100% sequence identity to an amino acid sequence selected from SEQ ID NOs: 14 and 31-38. In one aspect, the VH domain has at least 95% sequence identity to an amino acid sequence selected from SEQ ID NOs: 13 and 15-30. In one aspect, the VL domain has at least 95% sequence identity to an amino acid sequence selected from SEQ ID NOs: 14 and 31-38.

In one aspect, the anti-KLK7 antibody comprises (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12, and a VH domain having at least 90%, 91%, 92%, 93%, 94%, 95%, 96%, 97%, 98%, 99%, or 100% sequence identity to an amino acid sequence selected from SEQ ID NOs: 13 and 15-30, and a VL domain having at least 90%, 91%, 92%, 93%, 94%, 95%, 96%, 97%, 98%, 99%, or 100% sequence identity to an amino acid sequence selected from SEQ ID NOs: 14 and 31-38; wherein the antibody specifically binds to KLK7. In one aspect, the VH domain has at least 95% sequence identity to an amino acid sequence selected from SEQ ID NOs: 13 and 15-30. In one aspect, the VL domain has at least 95% sequence identity to an amino acid sequence selected from SEQ ID NOs: 14 and 31-38. In one aspect, the antibody binds to KLK7 having a dissociation constant ($K_D$) of less than 10 pM, or less than 9 pM, or less than 8 pM, or less than 7 pM, or less than 6 pM, or less than 5 pM as measured by surface plasmon resonance. In one aspect, the antibody binds to KLK7 having a dissociation constant ($K_D$) of no greater than 10 pM, or no greater than 9 pM, or no greater than 8 pM, or no greater than 7 pM, or no greater than 6 pM, or no greater than 5 pM as measured by surface plasmon resonance.

In another aspect, an anti-KLK7 antibody comprises a heavy chain variable domain (VH) sequence having at least 90%, 91%, 92%, 93%, 94%, 95%, 96%, 97%, 98%, 99%, or 100% sequence identity to an amino acid sequence selected from SEQ ID NOs: 13 and 15-30. In one aspect, an anti-KLK7 antibody comprises a heavy chain variable domain (VH) sequence having at least 95%, sequence identity to an amino acid sequence selected from SEQ ID NOs: 13 and 15-30. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK7 antibody comprising that sequence retains the ability to bind to KLK7. In certain aspects, a total of 1 to 10 amino acids have been substituted, inserted and/or deleted in an amino acid sequence selected from SEQ ID NOs: 13 and 15-30. In certain aspects, substitutions, insertions, or deletions occur in regions outside the CDRs (i.e., in the FRs). Optionally, the anti-KLK7 antibody comprises the VH sequence in an amino acid sequence selected from SEQ ID NOs: 13 and 15-30, including post-translational modifications of the sequence. Optionally, the anti-KLK7 antibody comprises the VH sequence in SEQ ID NO: 29 or 30, including post-translational modifications of the sequence. In a particular aspect, the VH comprises one, two or three CDRs selected from: (a) CDR-H1, comprising the amino acid sequence of SEQ ID NO: 7, (b) CDR-H2, comprising the amino acid sequence of SEQ ID NO: 8, and (c) CDR-H3, comprising the amino acid sequence of SEQ ID NO: 9. In another aspect, an anti-KLK7 antibody is provided, wherein the antibody comprises a light chain variable domain (VL) sequence having at least 90%, 91%, 92%, 93%, 94%, 95%, 96%, 97%, 98%, 99%, or 100% sequence identity to an amino acid sequence selected from SEQ ID NOs: 14 and 31-38. In one aspect, an anti-KLK7 antibody comprises a light chain variable domain (VL) sequence having at least 95% sequence identity to an amino acid sequence selected from SEQ ID NOs: 14 and 31-38. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK7 antibody comprising that sequence retains the ability to bind to KLK7. In certain aspects, a total of 1 to 10 amino acids have been substituted, inserted and/or deleted in an amino acid sequence selected from SEQ ID NOs: 14 and 31-38. In certain aspects, the substitutions, insertions, or deletions occur in regions outside the CDRs (i.e., in the FRs). Optionally, the anti-KLK7 antibody comprises the VL sequence in an amino acid sequence selected from SEQ ID NOs: 14 and 31-38, including post-translational modifications of that sequence. Optionally, the anti-KLK7 antibody comprises the VL sequence in SEQ ID NO: 32 or 38, including post-translational modifications of that sequence. In a particular aspect, the VL comprises one, two or three CDRs selected from: (a) CDR-L1, comprising the amino acid sequence of SEQ ID NO: 10, (b) CDR-L2, comprising the amino acid sequence of SEQ ID NO: 11, and (c) CDR-L3, comprising the amino acid sequence of SEQ ID NO: 12.

In another aspect, an anti-KLK7 antibody is provided, wherein the antibody comprises a VH sequence as in any of the aspects provided above, and a VL sequence as in any of the aspects provided above. In one aspect, the antibody comprises the VH and VL sequences in SEQ ID NO: 29 and SEQ ID NO: 32, respectively, including post-translational modifications of those sequences. In one aspect, the antibody comprises the VH and VL sequences in SEQ ID NO: 30 and SEQ ID NO: 38, respectively, including post-translational modifications of those sequences.

In a further aspect, the invention provides an antibody that binds to the same epitope as an anti-KLK7 antibody provided herein. For example, in certain aspects, an antibody is provided that binds to the same epitope as an anti-KLK7 antibody comprising a VH sequence of SEQ ID NO: 29 and a VL sequence of SEQ ID NO: 32.

In a further aspect, the invention provides an antibody that competes for binding to KLK7 with an anti-KLK7 antibody provided herein.

In a further aspect of the invention, an anti-KLK7 antibody according to any of the above aspects is a monoclonal antibody, including a chimeric, humanized or human antibody. In one aspect, an anti-KLK7 antibody is an antibody fragment, e.g., a Fv, Fab, Fab', scFv, diabody, or F(ab')$_2$ fragment. In another aspect, the antibody is a full-length antibody, e.g., an intact IgG1 antibody or other antibody class or isotype as defined herein.

In a further aspect, an anti-KLK7 antibody according to any of the above aspects may incorporate any of the features, singly or in combination, as described in Sections 1-8, below B. Exemplary Anti-KLK5 Antibodies In one aspect, the invention provides antibodies that bind to KLK5. In one aspect, provided are isolated antibodies that bind to KLK5. In one aspect, the invention provides antibodies that specifically bind to KLK5. In certain aspects, an anti-KLK5 antibody inhibits KLK5 protease activity. In some embodiments, an anti-KLK5 antibody inhibits human KLK5-mediated cleavage of the substrate Boc-Val-Pro-Arg-AMC. In some embodiments, an anti-KLK5 antibody inhibits human KLK5-mediated cleavage of the substrate Boc-Val-Pro-Arg-AMC with an IC50 of less than 5 nM, or less than 3 nM, or less than 2 nM, or less than 1 nM.

In some embodiments, an anti-KLK5 antibody inhibits human KLK5-mediated cleavage of the substrate Boc-Val-Pro-Arg-AMC with an IC50 of no greater than 5 nM, or no greater than 3 nM, or no greater than 2 nM, or no greater than 1 nM. In some embodiments, an anti-KLK5 antibody binds KLK5 with a $K_D$ of less than 60 pM, less than 30 pM, less than 20 pM, less than 10 pM, or less than 5 pM, as measured by surface plasmon resonance. In some embodiments, an anti-KLK5 antibody binds KLK5 with a $K_D$ of no greater than 60 pM, no greater than 30 pM, no greater than 20 pM, no greater than 10 pM, or no greater than 5 pM, as measured by surface plasmon resonance.

In some embodiments, an anti-KLK5 antibody, when bound to human KLK5 results in a conformational change of human KLK5, wherein the conformational change allosterically results in the disruption of the substrate binding site and/or the active site of human KLK5.

In some embodiments, an anti-KLK5 antibody binds to an epitope on human KLK5 comprising one or more amino acid residues selected from Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, Asp178, Gly184, Asp185, Lys186, Ala186A, Arg188, Asn223, Arg224, Pro225, and Lys233 according to standard protease numbering (P113, S114, A115, G116, V145, L146, S147, Q148, K149, R150, E152, D153, A154, Y155, P156, R157, Q158, I159, D160, D161, G167, D168, K169, A170, R172, N204, R205, P206, and K214 by sequential numbering of SEQ ID NO: 2). See, e.g., PCT Publication No. WO 2019/178316 A1. In some embodiments, an anti-KLK5 antibody binds to an epitope on human KLK5 comprising one or more amino acid residues selected from the group consisting of Pro130, Ser131, Ala132, Val162, Leu163, Ser164, Gln165, Lys166, Arg167, Glu169, Asp170, Ala171, Tyr172, Pro173, Arg174, Gln174A, Ile176, Asp177, Asp178, Arg224, and Lys233 according to standard protease numbering. In some embodiments, an anti-KLK5 antibody binds to an epitope on human KLK5 comprising one or more amino acid residues selected from Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, and Lys233 according to standard protease numbering. In some embodiments, an anti-KLK5 antibody binds to an epitope on human KLK5 comprising one or more amino acid residues selected from Ser131, Ala132, Gly133, Leu163, Ser164, Gln165, Lys166, Arg167, Glu169, Asp170, Ala171, Pro173, Arg174, Gly184, Asp185, Lys186, Ala186A, Arg188, Asn223, Arg224, and Pro225 according to standard protease numbering.

In some embodiments, the anti-KLK5 antibody does not bind to KLK7. In some embodiments, the anti-KLK5 antibody does not bind to KLK1, KLK4, KLK7, KLK11, or KLK14. In some embodiments, the anti-KLK5 antibody binds to human KLK5 and cynomolgus monkey KLK5.

Antibody hu.10C5-H28L5 and Variants

In one aspect, the invention provides an anti-KLK5 antibody comprising at least one, at least two, at least three, at least four, at least five, or all six CDRs selected from (a) CDR-H1 comprising the amino acid sequence of SEQ ID NO: 39 and 107; (b) CDR-H2 comprising the amino acid sequence of SEQ ID NO: 40 and 41; (c) CDR-H3 comprising the amino acid sequence of SEQ ID NO: 42; (d) CDR-L1 comprising the amino acid sequence of SEQ ID NO: 43 and 44; (e) CDR-L2 comprising the amino acid sequence of SEQ ID NO: 45; and (f) CDR-L3 comprising the amino acid sequence of SEQ ID NO: 46-49.

In one aspect, the invention provides an antibody comprising at least one, at least two, or all three VH CDR sequences selected from (a) CDR-H1 comprising the amino acid sequence of SEQ ID NO: 39; (b) CDR-H2 comprising the amino acid sequence of SEQ ID NO: 41; and (c) CDR-H3 comprising the amino acid sequence of SEQ ID NO:42. In a further aspect, the antibody comprises (a) CDR-H1 comprising the amino acid sequence of SEQ ID NO: 39; (b) CDR-H2 comprising the amino acid sequence of SEQ ID NO: 41; and (c) CDR-H3 comprising the amino acid sequence of SEQ ID NO:42.

In another aspect, the invention provides an antibody comprising at least one, at least two, or all three VL CDR sequences selected from (a) CDR-L1 comprising the amino acid sequence of SEQ ID NO: 43; (b) CDR-L2 comprising the amino acid sequence of SEQ ID NO: 45; and (c) CDR-L3 comprising the amino acid sequence of SEQ ID NO: 47. In one aspect, the antibody comprises (a) CDR-L1 comprising the amino acid sequence of SEQ ID NO: 43; (b) CDR-L2 comprising the amino acid sequence of SEQ ID NO: 45; and (c) CDR-L3 comprising the amino acid sequence of SEQ ID NO: 47.

In one aspect, the invention provides an antibody comprising at least one, at least two, or all three VH CDR sequences selected from (a) CDR-H1 comprising the amino acid sequence of SEQ ID NO: 39 and 107; (b) CDR-H2 comprising the amino acid sequence of SEQ ID NO: 40 and 41; and (c) CDR-H3 comprising the amino acid sequence of SEQ ID NO: 42. In another aspect, the antibody comprises CDR-H1 comprising the amino acid sequence of SEQ ID NO: 39, CDR-H2 comprising the amino acid sequence of SEQ ID NO: 41, and CDR-H3 comprising the amino acid sequence of SEQ ID NO:42.

In another aspect, the invention provides an antibody comprising at least one, at least two, or all three VL CDR sequences selected from (a) CDR-L1 comprising the amino acid sequence of SEQ ID NO: 43 and 44; (b) CDR-L2 comprising the amino acid sequence of SEQ ID NO: 45; and (c) CDR-L3 comprising the amino acid sequence of SEQ ID NO: 46-49. In one aspect, the antibody comprises (a) CDR-L1 comprising the amino acid sequence of SEQ ID NO: 43; (b) CDR-L2 comprising the amino acid sequence of SEQ ID NO: 45; and (c) CDR-L3 comprising the amino acid sequence of SEQ ID NO: 47.

In another aspect, an antibody of the invention comprises (a) a VH domain comprising at least one, at least two, or all three VH CDR sequences selected from (i) CDR-H1 comprising the amino acid sequence of SEQ ID NO: 39 and 107, (ii) CDR-H2 comprising the amino acid sequence of SEQ ID NO: 40 and 41, and (iii) CDR-H3 comprising the amino acid sequence of SEQ ID NO: 42; and (b) a VL domain comprising at least one, at least two, or all three VL CDR sequences selected from (i) CDR-L1 comprising the amino acid sequence of SEQ ID NO: 43 and 44, (ii) CDR-L2 comprising the amino acid sequence of SEQ ID NO: 45, and (c) CDR-L3 comprising the amino acid sequence of SEQ ID NO: 46-49.

In another aspect, the invention provides an antibody comprising (a) CDR-H1 comprising the amino acid sequence of SEQ ID NO: 39; (b) CDR-H2 comprising the amino acid sequence of SEQ ID NO: 41; (c) CDR-H3 comprising the amino acid sequence of SEQ ID NO: 42; (d) CDR-L1 comprising the amino acid sequence of SEQ ID NO: 43; (e) CDR-L2 comprising the amino acid sequence of SEQ ID NO: 45; and (f) CDR-L3 comprising the amino acid sequence of SEQ ID NO: 47.

In any of the aspects provided herein, an anti-KLK5 antibody is humanized. In one aspect, an anti-KLK5 antibody further comprises an acceptor human framework, e.g. a human immunoglobulin framework or a human consensus framework.

In one aspect, an anti-KLK5 antibody comprises a VH domain comprising one or more heavy chain framework sequences selected from (a) a heavy chain frame work region 1 (HC-FR1) of SEQ ID NO:161, (b) a heavy chain frame work region 2 (HC-FR2) of SEQ ID NO: 162-163, (c) a heavy chain frame work region 3 (HC-FR3) of SEQ ID NO:164, and (d) a heavy chain frame work region 4 (HC-FR4) of SEQ ID NO:165.

In another aspect, an anti-KLK5 antibody comprises a VH domain comprising a HC-FR1 of SEQ ID NO:161. In another aspect, an anti-KLK5 antibody comprises a VH domain comprising a HC-FR2 of SEQ ID NO: 162-163. In another aspect, an anti-KLK5 antibody comprises a VH domain comprising a HC-FR3 of SEQ ID NO: 164. In another aspect, an anti-KLK5 antibody comprises a VH domain comprising a HC-FR4 of SEQ ID NO: 165.

In another aspect, an anti-KLK5 antibody comprises a VH domain comprising a HC-FR1 of at least 85%, 86%, 87%, 88%, 89%, 90%, 91%, 92%, 93%, 94%, 95%, 96%, 97%, 98% or 99% sequence identity with SEQ ID NO:161. In one aspect, the VH domain comprises a HC-FR1 of at least 95% sequence identity with SEQ ID NO: 161. In another aspect, the VH domain comprises a HC-FR1 of at least 98% sequence identity with SEQ ID NO: 161.

In another aspect, an anti-KLK5 antibody comprises a VH domain comprising a HC-FR2 of at least 85%, 86%, 87%, 88%, 89%, 90%, 91%, 92%, 93%, 94%, 95%, 96%, 97%, 98% or 99% sequence identity to SEQ ID NO: 162-163. In one aspect, the VH domain comprises a HC-FR2 of at least 95% sequence identity with SEQ ID NO: 162-163. In another aspect, the VH domain comprises a HC-FR2 of at least 98% sequence identity with SEQ ID NO: 162-163.

In another aspect, an anti-KLK5 antibody comprises a VH domain comprising a HC-FR3 of at least 85%, 86%, 87%, 88%, 89%, 90%, 91%, 92%, 93%, 94%, 95%, 96%, 97%, 98% or 99% sequence identity to SEQ ID NO: 164. In one aspect, the VH domain comprises a HC-FR3 of at least 95% sequence identity with SEQ ID NO: 164. In another aspect, the VH domain comprises a HC-FR3 of at least 98% sequence identity with SEQ ID NO: 164.

In another aspect, an anti-KLK5 antibody comprises a VH domain comprising a HC-FR4 of at least 85%, 86%, 87%, 88%, 89%, 90%, 91%, 92%, 93%, 94%, 95%, 96%, 97%, 98% or 99% sequence identity to SEQ ID NO: 165. In one aspect, the VH domain comprises a HC-FR4 of at least 95% sequence identity with SEQ ID NO: 165. In another aspect, the VH domain comprises a HC-FR4 of at least 98% sequence identity with SEQ ID NO: 165.

In one aspect, an anti-KLK5 antibody comprises a VL domain comprising one or more light chain framework sequences selected from (a) a light chain frame work region 1 (LC-FR1) of SEQ ID NO: 166, (b) a light chain frame work region 2 (LC-FR2) of SEQ ID NO: 167-168, (c) a light chain frame work region 3 (LC-FR3) of SEQ ID NO: 169, and (d) a light chain frame work region 4 (LC-FR4) of SEQ ID NO: 170.

In another aspect, an anti-KLK5 antibody comprises a VL domain comprising a LC-FR1 of SEQ ID NO: 166. In another aspect, an anti-KLK5 antibody comprises a VL domain comprising a LC-FR2 of SEQ ID NO: 167-168. In another aspect, an anti-KLK5 antibody comprises a VL domain comprising a LC-FR3 of SEQ ID NO: 169. In another aspect, an anti-KLK5 antibody comprises a VL domain comprising a LC-FR4 of SEQ ID NO: 170.

In another aspect, an anti-KLK5 antibody comprises a VL domain comprising a LC-FR1 of at least 85%, 86%, 87%, 88%, 89%, 90%, 91%, 92%, 93%, 94%, 95%, 96%, 97%, 98% or 99% sequence identity to SEQ ID NO: 166. In one aspect, the VL domain comprises a LC-FR1 of at least 95% sequence identity with SEQ ID NO: 166. In another aspect, the VL domain comprises a LC-FR1 of at least 98% sequence identity with SEQ ID NO: 166.

In another aspect, an anti-KLK5 antibody comprises a VL domain comprising a LC-FR2 of at least 85%, 86%, 87%, 88%, 89%, 90%, 91%, 92%, 93%, 94%, 95%, 96%, 97%, 98% or 99% sequence identity to SEQ ID NO: 167-168. In one aspect, the VL domain comprises a LC-FR2 of at least 95% sequence identity with SEQ ID NO: 167-168. In another aspect, the VL domain comprises a LC-FR2 of at least 98% sequence identity with SEQ ID NO: 167-168.

In another aspect, an anti-KLK5 antibody comprises a VL domain comprising a LC-FR3 of at least 85%, 86%, 87%, 88%, 89%, 90%, 91%, 92%, 93%, 94%, 95%, 96%, 97%, 98% or 99% sequence identity to SEQ ID NO: 169. In one aspect, the VL domain comprises a LC-FR3 of at least 95% sequence identity with SEQ ID NO: 169. In another aspect, the VL domain comprises a LC-FR3 of at least 98% sequence identity with SEQ ID NO: 169.

In another aspect, an anti-KLK5 antibody comprises a VL domain comprising a LC-FR4 of at least 85%, 86%, 87%, 88%, 89%, 90%, 91%, 92%, 93%, 94%, 95%, 96%, 97%, 98% or 99% sequence identity to SEQ ID NO: 170. In one aspect, the VL domain comprises a LC-FR4 of at least 95% sequence identity with SEQ ID NO: 170. In another aspect, the VL domain comprises a LC-FR4 of at least 98% sequence identity with SEQ ID NO: 170.

In another aspect, an anti-KLK5 antibody comprises one or more of the CDR sequences of the VH of SEQ ID NO: 50, 52, 53, 105, or 106. In another embodiment, an anti-KLK5 antibody comprises one or more of the CDR sequences of the VL of SEQ ID NO: 51 or 54-57. In another embodiment, an anti-KLK5 antibody comprises the CDR sequences of the VH of SEQ ID NO: 50, 52, 53, 105, or 106 and the CDR sequences of the VL of SEQ ID NO: 51 or 54-57.

In a further aspect, an anti-KLK5 antibody comprises the CDR-H1, CDR-H2 and CDR-H3 amino acid sequences of the VH domain of SEQ ID NO: 50, 52, 53, 105, or 106 and the CDR-L1, CDR-L2 and CDR-L3 amino acid sequences of the VL domain of SEQ ID NO: 51 or 54-57.

In one aspect, an anti-KLK5 antibody comprises one or more of the heavy chain CDR amino acid sequences of the VH domain of SEQ ID NO: 50, 52, 53, 105, or 106 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 50, 52, 53, 105, or 106. In one aspect, the anti-KLK5 antibody comprises the three heavy chain CDR amino acid sequences of the VH domain of SEQ ID NO: 50, 52, 53, 105, or 106 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 50, 52, 53, 105, or 106. In one aspect, the anti-KLK5 antibody comprises the three heavy chain CDR amino acid sequences of the VH domain of SEQ ID NO: 50, 52, 53, 105, or 106 and a framework of at least 95% sequence identity to the framework amino acid sequence of the VH domain of SEQ ID NO: 50, 52, 53, 105, or 106. In another aspect, the anti-KLK5 antibody comprises the three heavy chain CDR amino acid sequences of the VH domain of SEQ ID NO: 50, 52, 53, 105, or 106 and a framework of at least of at least 98% sequence identity to the framework amino acid sequence of the VH domain of SEQ ID NO: 50, 52, 53, 105, or 106.

In one aspect, an anti-KLK5 antibody comprises one or more of the light chain CDR amino acid sequences of the VL domain of SEQ ID NO: 51 or 54-57 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 51 or 54-57. In one aspect, the anti-KLK5 antibody comprises the three light chain CDR amino acid sequences of the VL domain of SEQ ID NO: 51 or 54-57 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 51 or 54-57. In one aspect, the anti-KLK5 antibody comprises the three light chain CDR amino acid sequences of the VL domain of SEQ ID NO: 51 or 54-57 and a framework of at least 95% sequence identity to the framework amino acid sequence of the VL domain of SEQ ID NO: 51 or 54-57. In another aspect, the anti-KLK5 antibody comprises the three light chain CDR amino acid sequences of the VL domain of SEQ ID NO: 51 or 54-57 and a framework of at least particularly of at least 98% sequence identity to the framework amino acid sequence of the VH domain of SEQ ID NO: 50, 52, 53, 105, and 106.

In one aspect, the anti-KLK5 antibody comprises (a) CDR-H1 comprising the amino acid sequence of SEQ ID NO:39 or 107; (b) CDR-H2 comprising the amino acid sequence of SEQ ID NO: 40 or 41; (c) CDR-H3 comprising the amino acid sequence of SEQ ID NO: 42; (d) CDR-L1 comprising the amino acid sequence of SEQ ID NO: 43 or 44; (e) CDR-L2 comprising the amino acid sequence of SEQ ID NO: 45; and (f) CDR-L3 comprising the amino acid sequence of SEQ ID NO: 46-49, and a VH domain having at least 90%, 91%, 92%, 93%, 94%, 95%, 96%, 97%, 98%, 99%, or 100% sequence identity to the amino acid sequence of SEQ ID NO: 50, 52, 53, 105, and 106, and a VL domain having at least 90%, 91%, 92%, 93%, 94%, 95%, 96%, 97%, 98%, 99%, or 100% sequence identity to the amino acid sequence of SEQ ID NO: 51 and 54-67. In one aspect, the VH domain has at least 95% sequence identity to the amino acid sequence of SEQ ID NO: 50, 52, 53, 105, and 106. In one aspect, the VL domain has at least 95% sequence identity to the amino acid sequence of SEQ ID NO: 51 and 54-67.

In one aspect, the anti-KLK5 antibody comprises (a) CDR-H1 comprising the amino acid sequence of SEQ ID NO:39 or 107; (b) CDR-H2 comprising the amino acid sequence of SEQ ID NO:40 or 41; (c) CDR-H3 comprising the amino acid sequence of SEQ ID NO: 42; (d) CDR-L1 comprising the amino acid sequence of SEQ ID NO: 43 or 44; (e) CDR-L2 comprising the amino acid sequence of SEQ ID NO: 45; and (f) CDR-L3 comprising the amino acid sequence of SEQ ID NO: 46-49, and a VH domain having at least 90%, 91%, 92%, 93%, 94%, 95%, 96%, 97%, 98%, 99%, or 100% sequence identity to the amino acid sequence of SEQ ID NO: 50, 52, 53, 105, and 106, and a VL domain having at least 90%, 91%, 92%, 93%, 94%, 95%, 96%, 97%, 98%, 99%, or 100% sequence identity to the amino acid sequence of SEQ ID NO: 51 and 54-67; wherein the antibody specifically binds to KLK5. In one aspect, the VH domain has at least 95% sequence identity to the amino acid sequence of SEQ ID NO: 50, 52, 53, 105, and 106. In one aspect, the VL domain has at least 95% sequence identity to the amino acid sequence of SEQ ID NO: 51 and 54-67. In one aspect, the antibody binds to KLK5 having a dissociation constant ($K_D$) that is up to 10 fold reduced or up to 10 fold increase when compared to the dissociation constant ($K_D$) of an antibody comprising a VH sequence of SEQ ID NO: 50, 52, 53, 105, and 106 and a VL sequence of SEQ ID NO: 51 and 54-67.

In another aspect, an anti-KLK5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 50, 52, 53, 105, and 106. In one aspect, an anti-KLK5 antibody comprises a heavy chain variable domain (VH) sequence having at least 95%, sequence identity to the amino acid sequence of SEQ ID NO: 50, 52, 53, 105, and 106. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain aspects, a total of 1 to 10 amino acids have been substituted, inserted and/or deleted in SEQ ID NO: 50, 52, 53, 105, and 106. In certain aspects, substitutions, insertions, or deletions occur in regions outside the CDRs (i.e., in the FRs). Optionally, the anti-KLK5 antibody comprises the VH sequence in SEQ ID NO: 50, 52, 53, 105, and 106, including post-translational modifications of that sequence. In a particular aspect, the VH comprises one, two or three CDRs selected from: (a) CDR-H1, comprising the amino acid sequence of SEQ ID NO: 39 or 107, (b) CDR-H2, comprising the amino acid sequence of SEQ ID NO:40 or 41, and (c) CDR-H3, comprising the amino acid sequence of SEQ ID NO: 42. In another aspect, an anti-KLK5 antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 51 and 54-67. In one aspect, an anti-KLK5 antibody comprises a light chain variable domain (VL) sequence having at least 95% sequence identity to the amino acid sequence of SEQ ID NO: 51 and 54-67. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain aspects, a total of 1 to 10 amino acids have been substituted, inserted and/or deleted in SEQ ID NO: 51 and 54-67. In certain aspects, the substitutions, insertions, or deletions occur in regions outside the CDRs (i.e., in the FRs). Optionally, the anti-KLK5 antibody comprises the VL sequence in SEQ ID NO: 51 and 54-67, including post-translational modifications of that sequence. In a particular aspect, the VL comprises one, two or three CDRs selected from: (a) CDR-L1, comprising the amino acid sequence of SEQ ID NO: 43 or 44, (b) CDR-L2, comprising the amino acid sequence of SEQ ID NO: 45, and (c) CDR-L3, comprising the amino acid sequence of SEQ ID NO: 46-49.

In another aspect, an anti-KLK5 antibody is provided, wherein the antibody comprises a VH sequence as in any of the aspects provided above, and a VL sequence as in any of the aspects provided above. In one aspect, the antibody comprises the VH and VL sequences in SEQ ID NO: 50, 52, 53, 105, and 106 and SEQ ID NO: 51 and 54-67, respectively, including post-translational modifications of those sequences.

In a further aspect, the invention provides an antibody that binds to the same epitope as an anti-KLK5 antibody provided herein. For example, in certain aspects, an antibody is provided that binds to the same epitope as an anti-KLK5 antibody comprising a VH sequence of SEQ ID NO: 50, 52, 53, 105, and 106 and a VL sequence of SEQ ID NO: 51 and 54-67.

In a further aspect of the invention, an anti-KLK5 antibody according to any of the above aspects is a monoclonal antibody, including a chimeric, humanized or human antibody. In one aspect, an anti-KLK5 antibody is an antibody fragment, e.g., a Fv, Fab, Fab', scFv, diabody, or F(ab')$_2$ fragment. In another aspect, the antibody is a full-length antibody, e.g., an intact IgG1 antibody or other antibody class or isotype as defined herein.

In a further aspect, an anti-KLK5 antibody according to any of the above aspects may incorporate any of the features, singly or in combination, as described in Sections 1-8 below.

Antibody Hu.9H5-H14L4 and Variants

In one aspect, the invention provides an anti-KLK5 antibody comprising at least one, at least two, at least three, at least four, at least five, or all six CDRs selected from (a) CDR-H1 comprising the amino acid sequence of SEQ ID NO:68; (b) CDR-H2 comprising the amino acid sequence of SEQ ID NO: 69 and 70; (c) CDR-H3 comprising the amino acid sequence of SEQ ID NO: 71 and 72; (d) CDR-L1 comprising the amino acid sequence of SEQ ID NO: 73; (e) CDR-L2 comprising the amino acid sequence of SEQ ID NO: 74; and (f) CDR-L3 comprising the amino acid sequence of SEQ ID NO:75-78.

In one aspect, the invention provides an antibody comprising at least one, at least two, or all three VH CDR sequences selected from (a) CDR-H1 comprising the amino acid sequence of SEQ ID NO: 68; (b) CDR-H2 comprising the amino acid sequence of SEQ ID NO: 70; and (c) CDR-H3 comprising the amino acid sequence of SEQ ID NO:72. In a further aspect, the antibody comprises (a) CDR-H1 comprising the amino acid sequence of SEQ ID NO: 68; (b) CDR-H2 comprising the amino acid sequence of SEQ ID NO: 70; and (c) CDR-H3 comprising the amino acid sequence of SEQ ID NO:72.

In another aspect, the invention provides an antibody comprising at least one, at least two, or all three VL CDR sequences selected from (a) CDR-L1 comprising the amino acid sequence of SEQ ID NO: 73; (b) CDR-L2 comprising the amino acid sequence of SEQ ID NO: 74; and (c) CDR-L3 comprising the amino acid sequence of SEQ ID NO: 76. In one aspect, the antibody comprises (a) CDR-L1 comprising the amino acid sequence of SEQ ID NO: 73; (b) CDR-L2 comprising the amino acid sequence of SEQ ID NO: 74; and (c) CDR-L3 comprising the amino acid sequence of SEQ ID NO: 76.

In another aspect, an antibody of the invention comprises (a) a VH domain comprising at least one, at least two, or all three VH CDR sequences selected from (i) CDR-H1 comprising the amino acid sequence of SEQ ID NO: 68, (ii) CDR-H2 comprising the amino acid sequence of SEQ ID NO: 69 and 70, and (iii) CDR-H3 comprising the amino acid sequence of SEQ ID NO: 71 and 72; and (b) a VL domain comprising at least one, at least two, or all three VL CDR sequences selected from (i) CDR-L1 comprising the amino acid sequence of SEQ ID NO: 73, (ii) CDR-L2 comprising the amino acid sequence of SEQ ID NO: 74, and (c) CDR-L3 comprising the amino acid sequence of SEQ ID NO: 75-78.

In another aspect, the invention provides an antibody comprising (a) CDR-H1 comprising the amino acid sequence of SEQ ID NO: 68; (b) CDR-H2 comprising the amino acid sequence of SEQ ID NO: 70; (c) CDR-H3 comprising the amino acid sequence of SEQ ID NO: 72; (d) CDR-L1 comprising the amino acid sequence of SEQ ID NO: 73; (e) CDR-L2 comprising the amino acid sequence of SEQ ID NO: 74; and (f) CDR-L3 comprising the amino acid sequence of SEQ ID NO: 76.

In any of the aspects provided herein, an anti-KLK5 antibody is humanized. In one aspect, an anti-KLK5 antibody further comprises an acceptor human framework, e.g. a human immunoglobulin framework or a human consensus framework.

In one aspect, an anti-KLK5 antibody comprises a VH domain comprising one or more heavy chain framework sequences selected from (a) a heavy chain frame work region 1 (HC-FR1) of SEQ ID NO: 171, (b) a heavy chain frame work region 2 (HC-FR2) of SEQ ID NO: 172-173, (c) a heavy chain frame work region 3 (HC-FR3) of SEQ ID NO: 174, and (d) a heavy chain frame work region 4 (HC-FR4) of SEQ ID NO: 175.

In another aspect, an anti-KLK5 antibody comprises a VH domain comprising a HC-FR1 of SEQ ID NO:171. In another aspect, an anti-KLK5 antibody comprises a VH domain comprising a HC-FR2 of SEQ ID NO: 172 or 173. In another aspect, an anti-KLK5 antibody comprises a VH domain comprising a HC-FR3 of SEQ ID NO: 174. In another aspect, an anti-KLK5 antibody comprises a VH domain comprising a HC-FR4 of SEQ ID NO: 175.

In another aspect, an anti-KLK5 antibody comprises a VH domain comprising a HC-FR1 of at least 85%, 86%, 87%, 88%, 89%, 90%, 91%, 92%, 93%, 94%, 95%, 96%, 97%, 98% or 99% sequence identity with SEQ ID NO: 171. In one aspect, the VH domain comprises a HC-FR1 of at least 95% sequence identity with SEQ ID NO: 171. In another aspect, the VH domain comprises a HC-FR1 of at least 98% sequence identity with SEQ ID NO: 171.

In another aspect, an anti-KLK5 antibody comprises a VH domain comprising a HC-FR2 of at least 85%, 86%, 87%, 88%, 89%, 90%, 91%, 92%, 93%, 94%, 95%, 96%, 97%, 98% or 99% sequence identity to SEQ ID NO: 172 or 173. In one aspect, the VH domain comprises a HC-FR2 of at least 95% sequence identity with SEQ ID NO: 172 or 173. In another aspect, the VH domain comprises a HC-FR2 of at least 98% sequence identity with SEQ ID NO: 172 or 173.

In another aspect, an anti-KLK5 antibody comprises a VH domain comprising a HC-FR3 of at least 85%, 86%, 87%, 88%, 89%, 90%, 91%, 92%, 93%, 94%, 95%, 96%, 97%, 98% or 99% sequence identity to SEQ ID NO: 174. In one aspect, the VH domain comprises a HC-FR3 of at least 95% sequence identity with SEQ ID NO: 174. In another aspect, the VH domain comprises a HC-FR3 of at least 98% sequence identity with SEQ ID NO: 174.

In another aspect, an anti-KLK5 antibody comprises a VH domain comprising a HC-FR4 of at least 85%, 86%, 87%, 88%, 89%, 90%, 91%, 92%, 93%, 94%, 95%, 96%, 97%, 98% or 99% sequence identity to SEQ ID NO: 175. In one aspect, the VH domain comprises a HC-FR4 of at least 95% sequence identity with SEQ ID NO: 175. In another aspect, the VH domain comprises a HC-FR4 of at least 98% sequence identity with SEQ ID NO: 175.

In one aspect, an anti-KLK5 antibody comprises a VL domain comprising one or more light chain framework sequences selected from (a) a light chain frame work region 1 (LC-FR1) of SEQ ID NO: 176, (b) a light chain frame work region 2 (LC-FR2) of SEQ ID NO: 177-178, (c) a light chain frame work region 3 (LC-FR3) of SEQ ID NO: 179, and (d) a light chain frame work region 4 (LC-FR4) of SEQ ID NO: 180.

In another aspect, an anti-KLK5 antibody comprises a VL domain comprising a LC-FR1 of SEQ ID NO: 176. In another aspect, an anti-KLK5 antibody comprises a VL domain comprising a LC-FR2 of SEQ ID NO: 177-178. In another aspect, an anti-KLK5 antibody comprises a VL domain comprising a LC-FR3 of SEQ ID NO: 179. In another aspect, an anti-KLK5 antibody comprises a VL domain comprising a LC-FR4 of SEQ ID NO: 180.

In another aspect, an anti-KLK5 antibody comprises a VL domain comprising a LC-FR1 of at least 85%, 86%, 87%, 88%, 89%, 90%, 91%, 92%, 93%, 94%, 95%, 96%, 97%, 98% or 99% sequence identity to SEQ ID NO: 176. In one aspect, the VL domain comprises a LC-FR1 of at least 95% sequence identity with SEQ ID NO: 176. In another aspect, the VL domain comprises a LC-FR1 of at least 98% sequence identity with SEQ ID NO:176.

In another aspect, an anti-KLK5 antibody comprises a VL domain comprising a LC-FR2 of at least 85%, 86%, 87%, 88%, 89%, 90%, 91%, 92%, 93%, 94%, 95%, 96%, 97%, 98% or 99% sequence identity to SEQ ID NO: 177 or 178. In one aspect, the VL domain comprises a LC-FR2 of at least 95% sequence identity with SEQ ID NO: 177 or 178. In another aspect, the VL domain comprises a LC-FR2 of at least 98% sequence identity with SEQ ID NO: 177 or 178.

In another aspect, an anti-KLK5 antibody comprises a VL domain comprising a LC-FR3 of at least 85%, 86%, 87%, 88%, 89%, 90%, 91%, 92%, 93%, 94%, 95%, 96%, 97%, 98% or 99% sequence identity to SEQ ID NO: 179. In one aspect, the VL domain comprises a LC-FR3 of at least 95% sequence identity with SEQ ID NO: 179. In another aspect, the VL domain comprises a LC-FR3 of at least 98% sequence identity with SEQ ID NO: 179.

In another aspect, an anti-KLK5 antibody comprises a VL domain comprising a LC-FR4 of at least 85%, 86%, 87%, 88%, 89%, 90%, 91%, 92%, 93%, 94%, 95%, 96%, 97%, 98% or 99% sequence identity to SEQ ID NO: 180. In one aspect, the VL domain comprises a LC-FR1 of at least 95% sequence identity with SEQ ID NO: 180. In another aspect, the VL domain comprises a LC-FR1 of at least 98% sequence identity with SEQ ID NO: 180.

In another aspect, an anti-KLK5 antibody comprises one or more of the CDR sequences of the VH of SEQ ID NO: 79 or 81-87. In another embodiment, an anti-KLK5 antibody comprises one or more of the CDR sequences of the VL of SEQ ID NO: 80 or 88-94.

In another embodiment, an anti-KLK5 antibody comprises the CDR sequences of the VH of SEQ ID NO: 79 or 81-87 and the CDR sequences of the VL of SEQ ID NO: 80 or 88-94.

In a further aspect, an anti-KLK5 antibody comprises the CDR-H1, CDR-H2 and CDR-H3 amino acid sequences of the VH domain of SEQ ID NO: 79 or 81-87 and the CDR-L1, CDR-L2 and CDR-L3 amino acid sequences of the VL domain of SEQ ID NO: 80 or 88-94.

In one aspect, an anti-KLK5 antibody comprises one or more of the heavy chain CDR amino acid sequences of the VH domain of SEQ ID NO: 79 or 81-87 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 79 or 81-87. In one aspect, the anti-KLK5 antibody comprises the three heavy chain CDR amino acid sequences of the VH domain of SEQ ID NO: 79 or 81-87 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 79 or 81-87. In one aspect, the anti-KLK5 antibody comprises the three heavy chain CDR amino acid sequences of the VH domain of SEQ ID NO: 79 or 81-87 and a framework of at least 95% sequence identity to the framework amino acid sequence of the VH domain of SEQ ID NO: 79 or 81-87. In another aspect, the anti-KLK5 antibody comprises the three heavy chain CDR amino acid sequences of the VH domain of SEQ ID NO: 79 or 81-87 and a framework of at least of at least 98% sequence identity to the framework amino acid sequence of the VH domain of SEQ ID NO: 79 or 81-87.

In one aspect, an anti-KLK5 antibody comprises one or more of the light chain CDR amino acid sequences of the VL domain of SEQ ID NO: 80 or 88-94 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 80 or 88-94. In one aspect, the anti-KLK5 antibody comprises the three light chain CDR amino acid sequences of the VL domain of SEQ ID NO: 80 or 88-94 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 80 or 88-94. In one aspect, the anti-KLK5 antibody comprises the three light chain CDR amino acid sequences of the VL domain of SEQ ID NO: 80 or 88-94 and a framework of at least 95% sequence identity to the framework amino acid sequence of the VL domain of SEQ ID NO: 80 or 88-94. In another aspect, the anti-KLK5 antibody comprises the three light chain CDR amino acid sequences of the VL domain of SEQ ID NO: 80 or 88-94 and a framework of at least particularly of at least 98% sequence identity to the framework amino acid sequence of the VH domain of SEQ ID NO: 80 or 88-94.

In one aspect, the anti-KLK5 antibody comprises (a) CDR-H1 comprising the amino acid sequence of SEQ ID NO: 68; (b) CDR-H2 comprising the amino acid sequence of SEQ ID NO: 69-70; (c) CDR-H3 comprising the amino acid sequence of SEQ ID NO: 71-72; (d) CDR-L1 comprising the amino acid sequence of SEQ ID NO: 73; (e) CDR-L2 comprising the amino acid sequence of SEQ ID NO: 74; and (f) CDR-L3 comprising the amino acid sequence of SEQ ID NO: 75-78, and a VH domain having at least 90%, 91%, 92%, 93%, 94%, 95%, 96%, 97%, 98%, 99%, or 100% sequence identity to the amino acid sequence of SEQ ID NO: 79 or 81-87, and a VL domain having at least 90%, 91%, 92%, 93%, 94%, 95%, 96%, 97%, 98%, 99%, or 100% sequence identity to the amino acid sequence of SEQ ID NO: 80 or 88-94. In one aspect, the VH domain has at least 95% sequence identity to the amino acid sequence of SEQ ID NO: 79 or 81-87. In one aspect, the VL domain has at least 95% sequence identity to the amino acid sequence of SEQ ID NO: 80 or 88-94.

In one aspect, the anti-KLK5 antibody comprises (a) CDR-H1 comprising the amino acid sequence of SEQ ID NO: 68; (b) CDR-H2 comprising the amino acid sequence of SEQ ID NO: 69-70; (c) CDR-H3 comprising the amino acid sequence of SEQ ID NO: 71-72; (d) CDR-L1 comprising the amino acid sequence of SEQ ID NO: 73; (e) CDR-L2 comprising the amino acid sequence of SEQ ID NO: 74; and (f) CDR-L3 comprising the amino acid sequence of SEQ ID NO: 75-78, and a VH domain having at least 90%, 91%, 92%, 93%, 94%, 95%, 96%, 97%, 98%, 99%, or 100% sequence identity to the amino acid sequence of SEQ ID NO: 79 or 81-87, and a VL domain having at least 90%, 91%, 92%, 93%, 94%, 95%, 96%, 97%, 98%, 99%, or 100% sequence identity to the amino acid sequence of SEQ ID NO: 80 or 88-94; wherein the antibody specifically binds to KLK5. In one aspect, the VH domain has at least 95% sequence identity to the amino acid sequence of SEQ ID NO: 79 or 81-87. In one aspect, the VL domain has at least 95% sequence identity to the amino acid sequence of SEQ ID NO: 80 or 88-94. In one aspect, the antibody binds to KLK5 having a dissociation constant ($K_D$) that is up to 10 fold reduced or up to 10 fold increase when compared to the dissociation constant ($K_D$) of an antibody comprising a VH sequence of SEQ ID NO: 79 or 81-87 and a VL sequence of SEQ ID NO: 80 or 88-94.

In another aspect, an anti-KLK5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 79 or 81-87. In one aspect, an anti-KLK5 antibody comprises a heavy chain variable domain (VH) sequence having at least 95%, sequence identity to the amino acid sequence of SEQ ID NO: 79 or 81-87. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain aspects, a total of 1 to 10 amino acids have been substituted, inserted and/or deleted in SEQ ID NO: 79 or 81-87. In certain aspects, substitutions, insertions, or deletions occur in regions outside the CDRs (i.e., in the FRs). Optionally, the anti-KLK5 antibody comprises the VH sequence in SEQ ID NO: 79 or 81-87, including post-translational modifications of that sequence. In a particular aspect, the VH comprises one, two or three CDRs selected from: (a) CDR-H1, comprising the amino acid sequence of SEQ ID NO: 68, (b) CDR-H2, comprising the amino acid sequence of SEQ ID NO: 69-70, and (c) CDR-H3, comprising the amino acid sequence of SEQ ID NO: 71-72. In another aspect, an anti-KLK5 antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 80 or 88-94. In one aspect, an anti-KLK5 antibody comprises a light chain variable domain (VL) sequence having at least 95% sequence identity to the amino acid sequence of SEQ ID NO: 80 or 88-94. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain aspects, a total of 1 to 10 amino acids have been substituted, inserted and/or deleted in SEQ ID NO: 80 or 88-94. In certain aspects, the substitutions, insertions, or deletions occur in regions outside the CDRs (i.e., in the FRs). Optionally, the anti-KLK5 antibody comprises the VL sequence in SEQ ID NO: 80 or 88-94, including post-translational modifications of that sequence. In a particular aspect, the VL comprises one, two or three CDRs selected from: (a) CDR-L1, comprising the amino acid sequence of SEQ ID NO: 73, (b) CDR-L2, comprising the amino acid sequence of SEQ ID NO: 74, and (c) CDR-L3, comprising the amino acid sequence of SEQ ID NO: 75-78.

In another aspect, an anti-KLK5 antibody is provided, wherein the antibody comprises a VH sequence as in any of the aspects provided above, and a VL sequence as in any of the aspects provided above. In one aspect, the antibody comprises the VH and VL sequences in SEQ ID NO: 79 or 81-87 and SEQ ID NO: 80 or 88-94, respectively, including post-translational modifications of those sequences.

In a further aspect, the invention provides an antibody that binds to the same epitope as an anti-KLK5 antibody provided herein. For example, in certain aspects, an antibody is provided that binds to the same epitope as an anti-KLK5 antibody comprising a VH sequence of SEQ ID NO: 79 or 81-87 and a VL sequence of SEQ ID NO: 80 or 88-94.

In a further aspect of the invention, an anti-KLK5 antibody according to any of the above aspects is a monoclonal antibody, including a chimeric, humanized or human antibody. In one aspect, an anti-KLK5 antibody is an antibody fragment, e.g., a Fv, Fab, Fab', scFv, diabody, or F(ab')$_2$ fragment. In another aspect, the antibody is a full-length antibody, e.g., an intact IgG1 antibody or other antibody class or isotype as defined herein.

In a further aspect, an anti-KLK5 antibody according to any of the above aspects may incorporate any of the features, singly or in combination, as described in Sections 1-8 below.

C. Exemplary Anti-KLK5/KLK7 Multispecific Antibodies

In one aspect, the invention provides multispecific antibodies that bind to both KLK5 and KLK7. In some embodiments, bispecific antibodies are provided that bind to both KLK5 and KLK7. In some embodiments, the multispecific (such as bispecific) antibodies inhibit both KLK5 protease activity and KLK7 protease activity. In some embodiments, the multispecific (such as bispecific) antibodies bind KLK5 with a $K_D$ of less than 60 pM, less than 30 pM, less than 20 pM, less than 10 pM, or less than 5 pM, as measured by surface plasmon resonance. In some embodiments, the multispecific (such as bispecific) antibodies bind to KLK7 with a $K_D$ of less than 20 pM, less than 10 pM, or less than 9 pM, or less than 8 pM, or less than 7 pM, or less than 6 pM, or less than 5 pM, or less than 3 pM, or less than 2 pM, or less than 1 pM, as measured by surface plasmon resonance. In some embodiments, the multispecific (such as bispecific) antibodies bind KLK5 with a $K_D$ of no greater than 60 pM, no greater than 30 pM, no greater than 20 pM, no greater than 10 pM, or no greater than 5 pM, as measured by surface plasmon resonance. In some embodiments, the multispecific (such as bispecific) antibodies bind to KLK7 with a $K_D$ of no greater than 20 pM, no greater than 10 pM, or no greater than 9 pM, or no greater than 8 pM, or no greater than 7 pM, or no greater than 6 pM, or no greater than 5 pM, or no greater than 3 pM, or no greater than 2 pM, or no greater than 1 pM, as measured by surface plasmon resonance.

In some embodiments, an anti-KLK5/KLK7 multispecific antibody inhibits human KLK7 protease activity and inhibits human KLK5 protease activity. In some embodiments, an anti-KLK5/KLK7 multispecific antibody inhibits human KLK7-mediated cleavage of a substrate comprising the amino acid sequence RPKPVE-Nval-WRK (SEQ ID NO: 121), wherein Nval is norvaline, with an IC50 of less than 5 nM, or less than 3 nM, or less than 2 nM, or less than 1 nM. In some embodiments, an anti-KLK5/KLK7 multispecific antibody inhibits human KLK5-mediated cleavage of the substrate Boc-Val-Pro-Arg-AMC with an IC50 of less than 5 nM, or less than 3 nM, or less than 2 nM, or less than 1 nM. In some embodiments, an anti-KLK5/KLK7 multispecific antibody inhibits human KLK7-mediated cleavage of a substrate comprising the amino acid sequence RPKPVE-Nval-WRK (SEQ ID NO: 121), wherein Nval is norvaline, with an IC50 of no greater than 5 nM, or no greater than 3 nM, or no greater than 2 nM, or no greater than 1 nM. In some embodiments, an anti-KLK5/KLK7 multispecific antibody inhibits human KLK5-mediated cleavage of the substrate Boc-Val-Pro-Arg-AMC with an IC50 of no greater than 5 nM, or no greater than 3 nM, or no greater than 2 nM, or no greater than 1 nM. In some embodiments, the $K_D$ of the multispecific antibody for human KLK5 and the $K_D$ of the antibody for human KLK7 are within 3-fold, or within 2.5-fold, or within 2-fold, or within 1.5-fold of one another.

In some aspects, a multispecific antibody that binds to both KLK5 and KLK7 comprises a first binding domain that binds to KLK7 and a second binding domain that binds KLK5.

In some embodiments, a multispecific antibody that binds to both KLK5 and KLK7, when bound to human KLK5, results in a conformational change of human KLK5, wherein the conformational change allosterically results in the disruption of the substrate binding site and/or the active site of human KLK5. In some embodiments, a multispecific antibody that binds to both KLK5 and KLK7, when bound to human KLK7, results in a conformational change of human KLK7, wherein the conformational change allosterically results in the disruption of the substrate binding site and/or the active site of human KLK7.

In some embodiments, the first binding domain comprises an anti-KLK7 antibody binding domain described herein. For example, in some such embodiments, the first binding domain comprises (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12. As a further nonlimiting example, in some embodiments, the first binding domain comprises (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12, and a VH domain having at least 90%, 91%, 92%, 93%, 94%, 95%, 96%, 97%, 98%, 99%, or 100% sequence identity to an amino acid sequence selected from SEQ ID NOs: 13 and 15-30, and a VL domain having at least 90%, 91%, 92%, 93%, 94%, 95%, 96%, 97%, 98%, 99%, or 100% sequence identity to an amino acid sequence selected from SEQ ID NOs: 14 and 31-38. In some embodiments, the first binding domain comprises the VH and VL sequences in SEQ ID NO: 29 and SEQ ID NO: 32, respectively, including post-translational modifications of those sequences. In some embodiments, the first binding domain comprises the VH and VL sequences in SEQ ID NO: 30 and SEQ ID NO: 38, respectively, including post-translational modifications of those sequences.

In some embodiments, the second binding domain comprises an anti-KLK5 antibody binding domain described herein. For example, in some such embodiments, the second binding domain comprises (a) CDR-H1 comprising an amino acid sequence selected from SEQ ID NOs: 39 and 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 46-49. As a further nonlimiting example, in some embodiments, the second binding domain comprises (a) CDR-H1 comprising an amino acid sequence selected from SEQ ID NOs: 39 and 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 46-49, and a VH domain having at least 90%, 91%, 92%, 93%, 94%, 95%, 96%, 97%, 98%, 99%, or 100% sequence identity to an amino acid sequence selected from SEQ ID NOs: 50, 52, 53, 105, and 106, and a VL domain having at least 90%, 91%, 92%, 93%, 94%, 95%, 96%, 97%, 98%, 99%, or 100% sequence identity to an amino acid sequence selected from SEQ ID NOs: 51 and 54-67. In some embodiments, the second binding domain comprises the VH and VL sequences in SEQ ID NO: 52 and SEQ ID NO: 55, respectively, including post-translational modifications of those sequences. In some embodiments, the second binding domain comprises the VH and VL sequences in SEQ ID NO: 53 and SEQ ID NO: 62, respectively, including post-translational modifications of those sequences.

In some embodiments, the second binding domain comprises (a) CDR-H1 comprising the amino acid sequence of SEQ ID NO: 68, (b) CDR-H2 comprising an amino acid sequence selected from SEQ ID NOs: 69 and 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78. As a further nonlimiting example, in some embodiments, the second binding domain comprises (a) CDR-H1 comprising the amino acid sequence of SEQ ID NO: 68, (b) CDR-H2 comprising an amino acid sequence selected from SEQ ID NOs: 69 and 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78, and a VH domain having at least 90%, 91%, 92%, 93%, 94%, 95%, 96%, 97%, 98%, 99%, or 100% sequence identity to an amino acid sequence selected from SEQ ID NOs: 79 and 81-87, and a VL domain having at least 90%, 91%, 92%, 93%, 94%, 95%, 96%, 97%, 98%, 99%, or 100% sequence identity to an amino acid sequence selected from SEQ ID NOs: 80 and 88-94. In some embodiments, the second binding domain comprises the VH and VL sequences in SEQ ID NO: 83 and SEQ ID NO: 88, respectively, including post-translational modifications of those sequences. In some embodiments, the second binding domain comprises the VH and VL sequences in SEQ ID NO: 87 and SEQ ID NO: 92, respectively, including post-translational modifications of those sequences.

In some embodiments, a multispecific antibody (such as a bispecific antibody) is provided, wherein the first binding domain binds KLK7 and the second binding domain binds KLK5, wherein the first binding domain is an anti-KLK7 antibody binding domain provided herein and the second binding domain is an anti-KLK5 binding domain provided herein. In some such embodiments, the first binding domain In some embodiments, the first binding domain comprises (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12; and the second binding domain comprises (a) CDR-H1 comprising an amino acid sequence selected from SEQ ID NOs: 39 and 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 46-49. In some embodiments, the first binding domain comprises (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12; and the second binding domain comprises (a) CDR-H1 comprising an amino acid sequence of SEQ ID NO: 68, (b) CDR-H2 comprising an amino acid sequence selected from SEQ ID NOs: 69 and 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78.

In some embodiments, the first binding domain comprises (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12, and a VH domain having at least 90%, 91%, 92%, 93%, 94%, 95%, 96%, 97%, 98%, 99%, or 100% sequence identity to an amino acid sequence selected from SEQ ID NOs: 13 and 15-30, and a VL domain having at least 90%, 91%, 92%, 93%, 94%, 95%, 96%, 97%, 98%, 99%, or 100% sequence identity to an amino acid sequence selected from SEQ ID NOs: 14 and 31-38; and the second binding domain comprises (a) CDR-H1 comprising an amino acid sequence selected from SEQ ID NOs: 39 and 107, (b) CDR-H2 comprising an amino acid sequence selected from SEQ ID NOs: 40 and 41, and (c) CDR-H3 comprising the amino acid sequence of SEQ ID NO: 42, and a light chain variable domain (VL) comprising (d) CDR-L1 comprising an amino acid sequence selected from SEQ ID NOs: 43 and 44, (e) CDR-L2 comprising the amino acid sequence of SEQ ID NO: 45, and (f) CDR-L3 comprising an amino acid sequence selected from SEQ ID NOs: 46-49, and a VH domain having at least 90%, 91%, 92%, 93%, 94%, 95%, 96%, 97%, 98%, 99%, or 100% sequence identity to an amino acid sequence selected from SEQ ID NOs: 50, 52, 53, 105, and 106, and a VL domain having at least 90%, 91%, 92%, 93%, 94%, 95%, 96%, 97%, 98%, 99%, or 100% sequence identity to an amino acid sequence selected from SEQ ID NOs: 51 and 54-67.

In some embodiments, the first binding domain comprises (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 10; (e) CDR-L2 comprising the amino acid sequence of SEQ ID NO: 11; and (f) CDR-L3 comprising the amino acid sequence of SEQ ID NO: 12, and a VH domain having at least 90%, 91%, 92%, 93%, 94%, 95%, 96%, 97%, 98%, 99%, or 100% sequence identity to an amino acid sequence selected from SEQ ID NOs: 13 and 15-30, and a VL domain having at least 90%, 91%, 92%, 93%, 94%, 95%, 96%, 97%, 98%, 99%, or 100% sequence identity to an amino acid sequence selected from SEQ ID NOs: 14 and 31-38; and the second binding domain comprises (a) CDR-H1 comprising the amino acid sequence of SEQ ID NO: 68, (b) CDR-H2 comprising an amino acid sequence selected from SEQ ID NOs: 69 and 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78, and a VH domain having at least 90%, 91%, 92%, 93%, 94%, 95%, 96%, 97%, 98%, 99%, or 100% sequence identity to an amino acid sequence selected from SEQ ID NOs: 79 and 81-87, and a VL domain having at least 90%, 91%, 92%, 93%, 94%, 95%, 96%, 97%, 98%, 99%, or 100% sequence identity to an amino acid sequence selected from SEQ ID NOs: 80 and 88-94.

In some embodiments, a bispecific anti-KLK5/KLK7 antibody comprises a first binding domain and a second binding domain, wherein the first binding domain binds human KLK7 and the second binding domain binds human KLK5, wherein the first binding domain comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12; and the second binding domain comprises a heavy chain variable domain (VH) comprising (a) CDR-H1 comprising the amino acid sequence of SEQ ID NO: 39, (b) CDR-H2 comprising the amino acid sequence of SEQ ID NO: 41, and (c) CDR-H3 comprising the amino acid sequence of SEQ ID NO: 42, and a light chain variable domain (VL) comprising (d) CDR-L1 comprising the amino acid sequence of SEQ ID NOs: 43, (e) CDR-L2 comprising the amino acid sequence of SEQ ID NO: 45, and (f) CDR-L3 comprising the amino acid sequence of SEQ ID NO: 47.

In some embodiments, a bispecific anti-KLK5/KLK7 antibody comprises a first binding domain and a second binding domain, wherein the first binding domain binds human KLK7 and the second binding domain binds human KLK5, wherein the first binding domain comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12; and the second binding domain comprises a heavy chain variable domain (VH) comprising (a) CDR-H1 comprising the amino acid sequence of SEQ ID NO: 68, (b) CDR-H2 comprising the amino acid sequence of SEQ ID NO: 70, and (c) CDR-H3 comprising the amino acid sequence of SEQ ID NO: 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 76.

In some embodiments, a bispecific anti-KLK5/KLK7 antibody comprises a first binding domain and a second binding domain, wherein the first binding domain binds human KLK7 and the second binding domain binds human KLK5, wherein (i) the first binding domain comprises a VH amino acid sequence of SEQ ID NO: 29 and a VL amino acid sequence of SEQ ID NO: 32, or a VH amino acid sequence of SEQ ID NO: 30 and a VL amino acid sequence of SEQ ID NO: 38; and (ii) the second binding domain comprises a VH sequence of SEQ ID NO: 52 and a VL amino acid sequence of SEQ ID NO: 55; or a VH sequence of SEQ ID NO: 53 and a VL amino acid sequence of SEQ ID NO: 62. In some embodiments, the first binding domain comprises a VH sequence of SEQ ID NO: 30 and a VL sequence of SEQ ID NO: 38, and the second binding domain comprises a VH sequence of SEQ ID NO: 53 and a VL sequence of SEQ ID NO: 62.

In some embodiments, a bispecific anti-KLK5/KLK7 antibody comprises a first binding domain and a second binding domain, wherein the first binding domain binds human KLK7 and the second binding domain binds human KLK5, wherein (i) the first binding domain comprises a VH amino acid sequence of SEQ ID NO: 29 and a VL amino acid sequence of SEQ ID NO: 32, or a VH amino acid sequence of SEQ ID NO: 30 and a VL amino acid sequence of SEQ ID NO: 38; and (ii) the second binding domain comprises a VH sequence of SEQ ID NO: 83 and a VL amino acid sequence of SEQ ID NO: 88; or a VH sequence of SEQ ID NO: 87 and a VL amino acid sequence of SEQ ID NO: 92. In some embodiments, the first binding domain comprises a VH sequence of SEQ ID NO: 30 and a VL sequence of SEQ ID NO: 38, and the second binding domain comprises a VH sequence of SEQ ID NO: 87 and a VL sequence of SEQ ID NO: 92.

In some embodiments, a bispecific anti-KLK5/KLK7 antibody comprises a first binding domain that binds KLK7 and a second binding domain that binds KLK5, wherein the first binding domain comprises a first heavy chain variable region and a first light chain variable region, and the second binding domain comprises a second heavy chain variable region and a second light chain variable region. In some such embodiments, the first heavy chain variable region comprises a Q39E substitution (Kabat numbering) and the first light chain variable region comprises a Q38K substitution (Kabat numbering); and the second heavy chain variable region comprises a Q39K substitution (Kabat numbering) and the second light chain variable region comprises a Q38E substitution (Kabat numbering). In some embodiments, the first heavy chain variable region comprises a Q39K substitution (Kabat numbering) and the first light chain variable region comprises a Q38E substitution (Kabat numbering); and the second heavy chain variable region comprises a Q39E substitution (Kabat numbering) and the second light chain variable region comprises a Q38K substitution (Kabat numbering). In some embodiments, the Q39E/Q38K and Q39K/Q38E substitutions reduce mispairing of the heavy and light chains of the bispecific antibody.

In some embodiments, the first binding domain comprises a first heavy chain variable domain linked to a first heavy chain constant region and a first light chain variable domain linked to a first light chain constant region; and the second binding domain comprises a second heavy chain variable domain linked to a second heavy chain constant region and a second light chain variable domain linked to a second light chain constant region. In some such embodiments, the first heavy chain constant region comprises a S183K substitution (EU numbering) and the first light chain constant region comprises a V133E substitution (EU numbering), and the second heavy chain constant region comprises a S183E substitution (EU numbering) and the second light chain constant region comprises a V133K substitution (EU numbering). In some embodiments, the first heavy chain constant region comprises a S183E substitution (EU numbering) and the first light chain constant region comprises a V133K substitution (EU numbering), and the second heavy chain constant region comprises a S183K substitution (EU numbering) and the second light chain constant region comprises a V133E substitution (EU numbering). In some embodiments, the S183K/V133E and S183E/V133K substitutions reduce mispairing of the heavy and light chains of the bispecific antibody.

In some embodiments, a bispecific anti-KLK5/KLK7 antibody comprises Q39E/Q38K and Q39K/Q38E substitutions in the binding domains and S183K/V133E and S183E/V133K substitutions in the constant regions. See, e.g., WO 2016/172485, which is incorporated by reference here in its entirety for any purpose. A nonlimiting exemplary schematic of a bispecific antibody is shown in FIG. 15.

In some embodiments, a bispecific anti-KLK5/KLK7 antibody is provided, wherein the bispecific antibody comprises a first binding domain and a second binding domain, wherein the first binding domain binds human KLK7 and the second binding domain binds human KLK5, wherein the first binding domain comprises a heavy chain amino acid sequence of SEQ ID NO: 108 or 192, and a light chain amino acid sequence of SEQ ID NO: 109, and the second binding domain comprises a heavy chain amino acid sequence of SEQ ID NO: 110 or 193 and a light chain amino acid sequence of SEQ ID NO: 111. In some embodiments, a bispecific anti-KLK5/KLK7 antibody is provided, wherein the bispecific antibody comprises a first binding domain and a second binding domain, wherein the first binding domain binds human KLK7 and the second binding domain binds human KLK5, wherein the first binding domain comprises a heavy chain amino acid sequence of SEQ ID NO: 112 or 194, and a light chain amino acid sequence of SEQ ID NO: 113, and the second binding domain comprises a heavy chain amino acid sequence of SEQ ID NO: 114 or 195 and a light chain amino acid sequence of SEQ ID NO: 115.

In some embodiments, a bispecific anti-KLK5/KLK7 antibody is provided, wherein the bispecific antibody comprises a first binding domain and a second binding domain, wherein the first binding domain binds human KLK7 and the second binding domain binds human KLK5, wherein the first binding domain comprises a heavy chain amino acid sequence of SEQ ID NO: 108 or 192, and a light chain amino acid sequence of SEQ ID NO: 109, and the second binding domain comprises a heavy chain amino acid sequence of SEQ ID NO: 114 or 195 and a light chain amino acid sequence of SEQ ID NO: 111. In some embodiments, a bispecific anti-KLK5/KLK7 antibody is provided, wherein the bispecific antibody comprises a first binding domain and a second binding domain, wherein the first binding domain binds human KLK7 and the second binding domain binds human KLK5, wherein the first binding domain comprises a heavy chain amino acid sequence of SEQ ID NO: 112 or 194, and a light chain amino acid sequence of SEQ ID NO: 113, and the second binding domain comprises a heavy chain amino acid sequence of SEQ ID NO: 110 or 193 and a light chain amino acid sequence of SEQ ID NO: 115.

In some embodiments, a bispecific anti-KLK5/KLK7 antibody is provided, wherein the bispecific antibody comprises a first binding domain and a second binding domain, wherein the first binding domain binds human KLK7 and the second binding domain binds human KLK5, wherein the first binding domain comprises a heavy chain amino acid sequence of SEQ ID NO: 194, and a light chain amino acid sequence of SEQ ID NO: 113, and the second binding domain comprises a heavy chain amino acid sequence of SEQ ID NO: 195, and a light chain amino acid sequence of SEQ ID NO: 115.

In some embodiments, a bispecific anti-KLK5/KLK7 antibody is provided, wherein the bispecific antibody comprises a first binding domain and a second binding domain, wherein the first binding domain binds human KLK7 and the second binding domain binds human KLK5, wherein the first binding domain comprises a heavy chain amino acid sequence of SEQ ID NO: 112, and a light chain amino acid sequence of SEQ ID NO: 113, and the second binding domain comprises a heavy chain amino acid sequence of SEQ ID NO: 195, and a light chain amino acid sequence of SEQ ID NO: 115.

In some embodiments, a bispecific anti-KLK5/KLK7 antibody is provided, wherein the bispecific antibody comprises a first binding domain and a second binding domain, wherein the first binding domain binds human KLK7 and the second binding domain binds human KLK5, wherein the first binding domain comprises a heavy chain amino acid sequence of SEQ ID NO: 194, and a light chain amino acid sequence of SEQ ID NO: 113, and the second binding domain comprises a heavy chain amino acid sequence of SEQ ID NO: 114, and a light chain amino acid sequence of SEQ ID NO: 115.

In a further aspect, a multispecific antibody according to any of the above aspects may incorporate any of the features, singly or in combination, as described in Sections 1-8 below.

1. Antibody Affinity

In certain aspects, an antibody provided herein has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$M or less, e.g., from $10^{-8}$ M to $10^{-13}$ M, e.g., from $10^{-9}$ M to $10^{-13}$ M).

In one aspect, $K_D$ is measured using surface plasmon resonance. In one aspect, $K_D$ is measured using a BIACORE® surface plasmon resonance assay, such as a BIAcore™ T200 or BIAcore™ 8K assay. For example, an assay using a BIAcore™ 8K (BIAcore, Inc., Piscataway, NJ) is performed at 25° C. or 37° C. with immobilized antibody on a protein A chip at ~300 response units (RU). Ten-fold serial dilutions of antigen (such as human KLK7 or human KLK5) are injected in HBS-P buffer at 37° C. with a flow rate of 100 µL/min. Alternatively, ten-fold serial dilutions of antigen are injected in HBS-P buffer at 25° C. with a flow rate of 30 µL/min. Association rates (ka) and dissociation rates (kd) are calculated using a 1:1 Langmuir binding model (for example, using BIAcore Insight Evaluation Software version 2.0). The equilibrium dissociation constant ($K_D$) are calculated as the ratio kd/ka.

In an alternative method, $K_D$ is measured by a radiolabeled antigen binding assay (RIA). In one aspect, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 pg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed, and the plate washed eight times with 0.1% polysorbate 20 (TWEEN-20®) in PBS. When the plates have dried, 150 µl/well of scintillant (MICROSCINT-20™, Packard) is added, and the plates are counted on a TOPCOUNT™ gamma counter (Packard) for ten minutes. Concentrations of each Fab that give less than or equal to 20% of maximal binding are chosen for use in competitive binding assays.

2. Antibody Fragments

In certain aspects, an antibody provided herein is an antibody fragment.

In one aspect, the antibody fragment is a Fab, Fab', Fab'-SH, or F(ab')$_2$ fragment, in particular a Fab fragment. Papain digestion of intact antibodies produces two identical antigen-binding fragments, called "Fab" fragments containing each the heavy- and light-chain variable domains (VH and VL, respectively) and also the constant domain of the light chain (CL) and the first constant domain of the heavy chain (CH1). The term "Fab fragment" thus refers to an antibody fragment comprising a light chain comprising a VL domain and a CL domain, and a heavy chain fragment comprising a VH domain and a CH1 domain. "Fab' fragments" differ from Fab fragments by the addition of residues at the carboxy terminus of the CH1 domain including one or more cysteines from the antibody hinge region. Fab'-SH are Fab' fragments in which the cysteine residue(s) of the constant domains bear a free thiol group. Pepsin treatment yields an F(ab')$_2$ fragment that has two antigen-binding sites (two Fab fragments) and a part of the Fc region. For discussion of Fab and F(ab')$_2$ fragments comprising salvage receptor binding epitope residues and having increased in vivo half-life, see U.S. Pat. No. 5,869,046.

In another aspect, the antibody fragment is a diabody, a triabody or a tetrabody. "Diabodies" are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

In a further aspect, the antibody fragment is a single chain Fab fragment. A "single chain Fab fragment" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CHT-linker-VL-CL, b) VL-CL-linker-VH-CHT, c) VH-CL-linker-VL-CH1 or d) VL-CHT-linker-VH-CL. In particular, said linker is a polypeptide of at least 30 amino acids, preferably between 32 and 50 amino acids. Said single chain Fab fragments are stabilized via the natural disulfide bond between the CL domain and the CH1 domain. In addition, these single chain Fab fragments might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Plückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as recombinant production by recombinant host cells (e.g., E. coli), as described herein.

3. Chimeric and Humanized Antibodies

In certain aspects, an antibody provided herein is a chimeric antibody. Certain chimeric antibodies are described, e.g., in U.S. Pat. No. 4,816,567; and Morrison et al., Proc. Nat. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain aspects, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In some aspects, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain aspects, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating variable domain sequences selected from human-derived phage display libraries. Such variable domain sequences may then be combined with a desired human constant domain. Techniques for selecting human antibodies from antibody libraries are described below.

5. Library-Derived Antibodies

In certain aspects, an antibody provided herein is derived from a library. Antibodies of the invention may be isolated by screening combinatorial libraries for antibodies with the desired activity or activities. Methods for screening combinatorial libraries are reviewed, e.g., in Lerner et al. in *Nature Reviews* 16:498-508 (2016). For example, a variety of methods are known in the art for generating phage display libraries and screening such libraries for antibodies possessing the desired binding characteristics. Such methods are reviewed, e.g., in Frenzel et al. in *mAbs* 8:1177-1194 (2016); Bazan et al. in *Human Vaccines and Immunotherapeutics* 8:1817-1828 (2012) and Zhao et al. in *Critical Reviews in Biotechnology* 36:276-289 (2016) as well as in Hoogenboom et al. in *Methods in Molecular Biology* 178:1-37 (O'Brien et al., ed., Human Press, Totowa, N J, 2001) and in Marks and Bradbury in *Methods in Molecular Biology* 248:161-175 (Lo, ed., Human Press, Totowa, N J, 2003).

In certain phage display methods, repertoires of VH and VL genes are separately cloned by polymerase chain reaction (PCR) and recombined randomly in phage libraries, which can then be screened for antigen-binding phage as described in Winter et al. in *Annual Review of Immunology* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self antigens without any immunization as described by Griffiths et al. in *EMBO Journal* 12: 725-734 (1993). Furthermore, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in *Journal of Molecular Biology* 227: 381-388 (1992). Patent publications describing human antibody phage libraries include, for example: U.S. Pat. Nos. 5,750,373; 7,985, 840; 7,785,903 and 8,679,490 as well as US Patent Publication Nos. 2005/0079574, 2007/0117126, 2007/0237764 and 2007/0292936.

Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in *Methods in Molecular Biology* 503:135-56 (2012) and in Cherf et al. in *Methods in Molecular biology* 1319: 155-175 (2015) as well as in Zhao et al. in *Methods in Molecular Biology* 889:73-84 (2012). Methods for ribosome display are described, e.g., in He et al. in *Nucleic Acids Research* 25:5132-5134 (1997) and in Hanes et al. in *PNAS* 94:4937-4942 (1997).

Antibodies or antibody fragments isolated from human antibody libraries are considered human antibodies or human antibody fragments herein.

6. Multispecific Antibodies

In certain aspects, an antibody provided herein is a multispecific antibody, e.g., a bispecific antibody. "Multispecific antibodies" are monoclonal antibodies that have binding specificities for at least two different sites, i.e., different epitopes on different antigens or different epitopes on the same antigen. In certain aspects, the multispecific antibody has three or more binding specificities. In certain aspects, one of the binding specificities is for KLK7 and the other specificity is for any other antigen. In certain aspects, one of the binding specificities is for KLK7 and the other specificity is for KLK5. In certain aspects, bispecific antibodies may bind to two (or more) different epitopes of an antigen. Multispecific antibodies may be prepared as full-length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see, e.g., U.S. Pat. No. 5,731,168, and Atwell et al., J. Mol. Biol. 270:26 (1997)). Nonlimiting exemplary knob-in-hole substitutions include T366W (knob) and T366S/L368A/Y407V (hole). In some embodiments, the knob-in-hole substitutions are in IgG1 constant domains.

Multi-specific antibodies may also be made by engineering electrostatic steering effects for making antibody Fc-heterodimeric molecules. See, e.g., WO 2009/089004; Dillon et al., Mabs 9(2): 213-230 (2017). As a nonlimiting example, in a bispecific antibody comprising two heavy chain variable regions and two light chain variable regions, a first heavy chain variable region may comprise a Q39E substitution (Kabat numbering) and a first light chain variable region may comprise a Q38K substitution (Kabat numbering); and a second heavy chain variable region may comprise a Q39K substitution (Kabat numbering) and a second light chain variable region may comprise a Q38E substitution (Kabat numbering). In some embodiments, the Q39E/Q38K and Q39K/Q38E substitutions reduce mispairing of the heavy and light chains of the bispecific antibody. Similarly, a first heavy chain constant region may comprise a S183K substitution (EU numbering) and a first light chain constant region may comprise a V133E substitution (EU numbering), and the a second heavy chain constant region may comprise a S183E substitution (EU numbering) and a second light chain constant region may comprise a V133K substitution (EU numbering). In some embodiments, the S183K/V133E and S183E/V133K substitutions reduce mispairing of the heavy and light chains of the bispecific antibody.

In some embodiments, a bispecific antibody comprises Q39E/Q38K and Q39K/Q38E substitutions in the binding domains and S183K/V133E and S183E/V133K substitutions in the constant regions. In some embodiments, a bispecific antibody comprises both knob-in-hole substitutions and electrostatic substitutions. See, e.g., WO 2016/172485, which is incorporated by reference here in its entirety for any purpose. A nonlimiting exemplary schematic of a bispecific antibody is shown in FIG. 15.

Accordingly, in some embodiments, a multispecific antibody is provided, which comprises a) a first heavy chain/light chain pair binding to a first antigen which comprises a first heavy chain polypeptide (H1) and a first light chain polypeptide (L1), and b) a second heavy chain/light chain pair binding to a second antigen which comprises a second heavy chain polypeptide (H2) and a second light chain polypeptide (L2), wherein each H1 and H2 comprises a heavy chain variable domain (VH) and a heavy chain constant domain (CH1), and each L1 and L2 comprises a light chain variable domain (VL) and a light chain constant domain (CL); wherein the CH1 domain of H1 comprises an amino acid substitution at S183 (EU numbering) and the CL domain of L1 comprises an amino acid substitution at V133 (EU numbering); and wherein the VH domain of H1 comprises an amino acid substitution at position Q39 and the VL domain of L1 comprises an amino acid substitutions at position Q38 and/or the VH domain of H2 comprises an amino acid substitutions at position Q39 and the VL domain of L2 comprises an amino acid substitution at position Q38 (all Kabat numbering). In some embodiments, the VH domain of H1 comprises an amino acid substitution at Q39 (Kabat numbering) and the VL domain of L1 comprises an amino acid substitution at Q38 (Kabat numbering). In some embodiments, the CH1 domain of H2 comprises an amino acid substitution at S183 (EU numbering) and the CL domain of L2 comprises an amino acid substitution at V133 (EU numbering). In some embodiments, the VH domain of H2 further comprises an amino acid substitution at position Q39 and the VL domain of L2 further comprises an amino acid substitution at position Q38 (Kabat numbering). In some embodiments, the CH1 domain of H1 comprises a S183K mutation and CL of L1 comprises a V133E mutation, and CH1 of H2 comprises a S183E mutation and the CL domain of L2 comprises the V133K mutation. In some embodiments, the VH domain of H1 comprises a Q39E mutation, the VL domain of L1 comprises a Q38K mutation, the VH domain of H2 comprises a Q39K mutation and the VL domain of L2 comprises a Q38E mutation (all Kabat numbering).

Multi-specific antibodies may also be made by cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992) and WO 2011/034605); using the common light chain technology for circumventing the light chain mispairing problem (see, e.g., WO 98/50431); using "diabody" technology for making bispecific antibody fragments (see, e.g., Hollinger et al., *Proc. Nat. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991).

Engineered antibodies with three or more antigen binding sites, including for example, "Octopus antibodies", or DVD-Ig are also included herein (see, e.g., WO 2001/77342 and WO 2008/024715). Other examples of multispecific antibodies with three or more antigen binding sites can be found in WO 2010/115589, WO 2010/112193, WO 2010/136172, WO 2010/145792, and WO 2013/026831. The bispecific antibody or antigen binding fragment thereof also includes a "Dual Acting FAb" or "DAF" comprising an antigen binding site that binds to KLK7 as well as another different antigen, such as KLK5 (see, e.g., US 2008/0069820 and WO 2015/095539).

Multi-specific antibodies may also be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). In one aspect, the multispecific antibody comprises a cross-Fab fragment. The term "cross-Fab fragment" or "xFab fragment" or "crossover Fab fragment" refers to a Fab fragment, wherein either the variable regions or the constant regions of the heavy and light chain are exchanged. A cross-Fab fragment comprises a polypeptide chain composed of the light chain variable region (VL) and the heavy chain constant region 1 (CH1), and a polypeptide chain composed of the heavy chain variable region (VH) and the light chain constant region (CL). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

Examples of bispecific antibody formats that may be useful for this purpose include, but are not limited to, the so-called "BiTE" (bispecific T cell engager) molecules wherein two scFv molecules are fused by a flexible linker (see, e.g., WO 2004/106381, WO 2005/061547, WO 2007/042261, and WO 2008/119567, Nagorsen and Bäuerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO 2013/026839, WO 2016/020309; Bacac et al., Oncoimmunology 5(8) (2016) e1203498.

7. Antibody Variants

In certain aspects, amino acid sequence variants of the antibodies provided herein are contemplated. For example, it may be desirable to alter the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain aspects, antibody variants having one or more amino acid substitutions are provided. Sites of interest for substitutional mutagenesis include the CDRs and FRs. Conservative substitutions are shown in Table 1 under the heading of "preferred substitutions". More substantial changes are provided in Table 1 under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |

TABLE 1-continued

| Original Residue | Exemplary Substitutions | Preferred Substitutions |
| --- | --- | --- |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for a member of another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, e.g., to improve antibody affinity. Such alterations may be made in CDR "hotspots", i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some aspects of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain aspects, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in the CDRs. Such alterations may, for example, be outside of antigen contacting residues in the CDRs. In certain variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT (antibody directed enzyme prodrug therapy)) or a polypeptide which increases the serum half-life of the antibody.

b) Glycosylation Variants

In certain aspects, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.,* 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain aspects, one or more amino acid modifications may be introduced into the Fc region of an antibody provided herein, thereby generating an Fc region variant. The Fc region variant may comprise a human Fc region sequence (e.g., a human $IgG_1$, IgG2, IgG3 or IgG4 Fc region) comprising an amino acid modification (e.g., a substitution) at one or more amino acid positions.

In certain aspects, the invention contemplates an antibody variant that possesses some but not all effector functions, which make it a desirable candidate for applications in which the half-life of the antibody in vivo is important yet certain effector functions (such as complement-dependent cytotoxicity (CDC) and antibody-dependent cell-mediated cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991).

Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M.S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006); WO 2013/120929 A1).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain aspects, an antibody variant comprises an Fc region with one or more amino acid substitutions which improve ADCC, e.g., substitutions at positions 298, 333, and/or 334 of the Fc region (EU numbering of residues).

In certain aspects, an antibody variant comprises an Fc region with one or more amino acid substitutions which diminish FcγR binding, e.g., substitutions at positions 234 and 235 of the Fc region (EU numbering of residues). In one aspect, the substitutions are L234A and L235A (LALA). In certain aspects, the antibody variant further comprises D265A and/or P329G in an Fc region derived from a human IgG$_1$ Fc region. In one aspect, the substitutions are L234A, L235A and P329G (LALA-PG) in an Fc region derived from a human IgG$_1$ Fc region. (See, e.g., WO 2012/130831). In another aspect, the substitutions are L234A, L235A and D265A (LALA-DA) in an Fc region derived from a human IgG$_1$ Fc region.

In some aspects, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424, 428 or 434, e.g., substitution of Fc region residue 434 (See, e.g., U.S. Pat. No. 7,371,826; Dall'Acqua, W. F., et al. J. Biol. Chem. 281 (2006) 23514-23524). In some embodiments, an antibody provided herein comprises substitutions M428L and/or N434S, such as M428L and N434S ("LS").

Fc region residues critical to the mouse Fc-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU index numbering) are involved in the interaction (Medesan, C., et al., Eur. J. Immunol. 26 (1996) 2533; Firan, M., et al., Int. Immunol. 13 (2001) 993; Kim, J. K., et al., Eur. J. Immunol. 24 (1994) 542). Residues I253, H310, and H435 were found to be critical for the interaction of human Fc with murine FcRn (Kim, J. K., et al., Eur. J. Immunol. 29 (1999) 2819). Studies of the human Fc-human FcRn complex have shown that residues I253, S254, H435, and Y436 are crucial for the interaction (Firan, M., et al., Int. Immunol. 13 (2001) 993; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

In certain aspects, an antibody variant comprises an Fc region with one or more amino acid substitutions, which reduce FcRn binding, e.g., substitutions at positions 253, and/or 310, and/or 435 of the Fc-region (EU numbering of residues). In certain aspects, the antibody variant comprises an Fc region with the amino acid substitutions at positions 253, 310 and 435. In one aspect, the substitutions are I253A, H310A and H435A in an Fc region derived from a human IgG1 Fc-region. See, e.g., Grevys, A., et al., J. Immunol. 194 (2015) 5497-5508.

In certain aspects, an antibody variant comprises an Fc region with one or more amino acid substitutions, which reduce FcRn binding, e.g., substitutions at positions 310, and/or 433, and/or 436 of the Fc region (EU numbering of residues). In certain aspects, the antibody variant comprises an Fc region with the amino acid substitutions at positions 310, 433 and 436. In one aspect, the substitutions are H310A, H433A and Y436A in an Fc region derived from a human IgG1 Fc-region. (See, e.g., WO 2014/177460 A1).

In certain aspects, an antibody variant comprises an Fc region with one or more amino acid substitutions which increase FcRn binding, e.g., substitutions at positions 252, and/or 254, and/or 256 of the Fc region (EU numbering of residues). In certain aspects, the antibody variant comprises an Fc region with amino acid substitutions at positions 252, 254, and 256. In one aspect, the substitutions are M252Y, S254T and T256E in an Fc region derived from a human IgG$_1$ Fc-region. See also Duncan & Winter, *Nature* 322:738-40 (1988); U.S. Pat. Nos. 5,648,260; 5,624,821; and WO 94/29351 concerning other examples of Fc region variants.

The C-terminus of the heavy chain of the antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, an antibody comprising a heavy chain including a C-terminal CH3 domain as specified herein, comprises the C-terminal glycine-lysine dipeptide (G446 and K447, EU index numbering of amino acid positions). In one aspect of all aspects as reported herein, an antibody comprising a heavy chain including a C-terminal CH3 domain, as specified herein, comprises a C-terminal glycine residue (G446, EU index numbering of amino acid positions).

d) Cysteine Engineered Antibody Variants

In certain aspects, it may be desirable to create cysteine engineered antibodies, e.g., THIOMAB™ antibodies, in which one or more residues of an antibody are substituted with cysteine residues. In particular aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,30,930, 7,855,275, 9,000,130, or WO 2016040856.

e) Antibody Derivatives

In certain aspects, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

8. Immunoconjugates

The invention also provides immunoconjugates comprising an antibody herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in *Pharmacol Review* 68:3-19 (2016).

In another aspect, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another aspect, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

D. Recombinant Methods and Compositions

Antibodies may be produced using recombinant methods and compositions, e.g., as described in U.S. Pat. No. 4,816, 567. For these methods one or more isolated nucleic acid(s) encoding an antibody are provided.

In case of a native antibody or native antibody fragment two nucleic acids are required, one for the light chain or a fragment thereof and one for the heavy chain or a fragment thereof. Such nucleic acid(s) encode an amino acid sequence comprising the VL and/or an amino acid sequence comprising the VH of the antibody (e.g., the light and/or heavy chain(s) of the antibody). These nucleic acids can be on the same expression vector or on different expression vectors.

In case of a bispecific antibody with heterodimeric heavy chains four nucleic acids are required, one for the first light chain, one for the first heavy chain comprising the first heteromonomeric Fc-region polypeptide, one for the second light chain, and one for the second heavy chain comprising the second heteromonomeric Fc-region polypeptide. The four nucleic acids can be comprised in one or more nucleic acid molecules or expression vectors. Such nucleic acid(s) encode an amino acid sequence comprising the first VL and/or an amino acid sequence comprising the first VH including the first heteromonomeric Fc-region and/or an amino acid sequence comprising the second VL and/or an amino acid sequence comprising the second VH including the second heteromonomeric Fc-region of the antibody (e.g., the first and/or second light and/or the first and/or second heavy chains of the antibody). These nucleic acids can be on the same expression vector or on different expression vectors, normally these nucleic acids are located on two or three expression vectors, i.e. one vector can comprise more than one of these nucleic acids. Examples of these bispecific antibodies are CrossMabs (see, e.g., Schaefer, W. et al, PNAS, 108 (2011) 11187-1191). For example, one of the heteromonomeric heavy chain comprises the so-called "knob mutations" (T366W and optionally one of S354C or Y349C) and the other comprises the so-called "hole mutations" (T366S, L368A and Y407V and optionally Y349C or S354C) (see, e.g., Carter, P. et al., Immunotechnol. 2 (1996) 73) according to EU index numbering.

In one aspect, isolated nucleic acids encoding an antibody as used in the methods as reported herein are provided.

In one aspect, a method of making an antibody is provided, wherein the method comprises culturing a host cell comprising nucleic acid(s) encoding the antibody, as provided above, under conditions suitable for expression of the antibody, and optionally recovering the antibody from the host cell (or host cell culture medium).

For recombinant production of an antibody, nucleic acids encoding the antibody, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of (glycosylated) antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as YO, NSO and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

In one aspect, the host cell is eukaryotic, e.g., a Chinese Hamster Ovary (CHO) cell or lymphoid cell (e.g., YO, NSO, Sp20 cell).

E. Assays

Anti-KLK7 antibodies and anti-KLK5 provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with an antibody provided herein, such as hu.1411c-H11L2, for binding to KLK7. In certain aspects, such a competing antibody binds to the same epitope (e.g., a linear or a conformational epitope) that is bound by hu.1411c-H11L2. In certain aspects, such a competing antibody binds to the same epitope (e.g., a linear or a conformational epitope) that is bound by hu.1411c-H11L2. In some embodiments, competition assays may be used to identify an antibody that competes with an antibody provided herein, such as hu.10C5-H28L5 or hu.9H5-H14L4, for binding to KLK5. In certain aspects, such a competing antibody binds to the same epitope (e.g., a linear or a conformational epitope) that is bound by hu.10C5-H28L5 or hu.9H5-H14L4. Detailed exemplary methods for mapping an epitope to which an antibody binds are provided in Morris (1996) "Epitope Mapping Protocols", in *Methods in Molecular Biology* vol. 66 (Humana Press, Totowa, NJ).

In an exemplary competition assay, immobilized antigen (such as KLK5 or KLK7) is incubated in a solution comprising a first labeled antibody that binds to the antigen (e.g., hu.1411c-H11L2, hu.10C5-H28L5 or hu.9H5-H14L4) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to antigen. See Harlow and Lane (1988) *Antibodies: A Laboratory Manual* ch.14 (Cold Spring Harbor Laboratory, Cold Spring Harbor, NY).

2. Activity Assays

KLK7 is a chymotrypsin-like serine protease. In some embodiments, KLK7 cleaves polypeptides after aromatic and/or hydrophobic amino acids, such as after tyrosine, phenylalanine, and/or leucine. In one aspect, assays are provided for identifying anti-KLK7 antibodies that inhibit human KLK7 activity. Biological activity may include, e.g., KLK7 protease activity. Antibodies having such biological activity in vivo and/or in vitro are also provided.

In certain aspects, an antibody of the invention is tested for such biological activity. Assays for determining KLK7 protease activity are known in the art, and typically include incubating KLK7 in the presence of substrate and a test molecule (such as an anti-KLK7 antibody). A nonlimiting assay for testing whether an anti-KLK7 antibody (or a multispecific antibody comprising an anti-KLK7 binding arm) inhibits KLK7 protease activity follows: A KLK7 direct functional assay may be performed at room temperature in a 384-well plate at a final reaction volume of 15 µL. Inhibitor samples are diluted to 3× final concentration in assay buffer (75 mM Tris, pH 8.0, 150 mM NaCl, 0.01% Tween 20). Inhibitor (e.g., anti-KLK7 antibody) or control samples (5 µL) are added to the plate, followed by 5 µL human KLK7 (SEQ ID NO: 4) in assay buffer at a final concentration of 0.5 nM After 40 min, 5 µL Mca-RPKPVE-Nval-WRK(Dnp) (SEQ ID NO: 121; Bachem M-2110, 4.3 mM stock solution in DMSO) at a final concentration of 10 pM in assay buffer is added. After addition of substrate, the plate is read in PHERAstar® microplate reader (BMG Labtech) using optic module FI 320 405 with the gain set to 0%. Measurements are taken every 100 s for ~1.5 h. Reaction rates (expressed as RFU/s) are calculated by linear regression in the linear range. Reaction rates may be normalized to the values of 0% and 100% activity controls, and fit with a 4-parameter equation to calculate IC50 values. For bivalent inhibitors, the raw IC50 may be multiplied by two.

KLK5 is a trypsin-like serine protease. In one aspect, assays are provided for identifying anti-KLK5 antibodies that inhibit human KLK5 activity. Biological activity may include, e.g., KLK5 protease activity. In one embodiment, the anti-KLK5 antibodies inhibit the serine protease activity of KLK5. Antibodies having such biological activity in vivo and/or in vitro are also provided.

In certain aspects, an antibody of the invention is tested for such biological activity. Assays for determining KLK5 protease activity are known in the art, and may include, for example, incubating KLK5 in the presence of substrate and a test molecule (such as an anti-KLK5 antibody). In some embodiments, the biological activity of an anti-KLK5 antibody is tested by one or more methods selected from a direct activity assay, fluorescent peptide assay, an LC/MS assay, and a Ki(app) assay. In some embodiments, the biological activity is measured by one or more methods selected from a recombinant KLK5 direct activity assay, coupled pro-KLK1 fluorescent peptide assay, a coupled pro-KLK7 fluorescent peptide assay, a pro-KLK1 LC/MS assay, a pro-KLK7 LC/MS assay, and a Ki(app) assay. In some embodiments, the IC50 values are measured by the assays described herein. In some embodiments, an anti-KLK5 antibody of the invention inhibits the biological activity of KLK5 by at least 50% as measured by one or more methods selected from a recombinant KLK5 direct activity assay, coupled pro-KLK1 fluorescent peptide assay, a coupled pro-KLK7 fluorescent peptide assay, a pro-KLK1 LC/MS assay, a pro-KLK7 LC/MS assay, and a Ki(app) assay. In some embodiments, the biological activity is the serine protease activity of KLK5. In some embodiments, the IC50 values are measured by the assays described herein.

A nonlimiting assay for testing whether an anti-KLK5 antibody (or a multispecific antibody comprising an anti-KLK5 binding arm) inhibits KLK5 protease activity follows: A KLK5 direct functional assay may be performed at room temperature in a 384-well plate at a final reaction volume of 15 µL. Inhibitor samples are diluted to 3× final concentration in assay buffer (75 mM Tris, pH 8.0, 150 mM NaCl, 0.01% Tween 20). Inhibitor (e.g., anti-KLK5 antibody) or control samples (5 µL) are added to the plate, followed by 5 µL human KLK5 (SEQ ID NO: 2) in assay buffer at a final concentration of 0.5 nM After 40 min, 5 µL Boc-Val-Pro-Arg-AMC (Bachem 1-1120, 31.3 mM stock solution in water) at a final concentration of 50 pM in assay buffer is added. After addition of substrate, the plate is read in PHERAstar® microplate reader (BMG Labtech) using optic module FI 320 405 with the gain set to 0%. Measurements are taken every 100 s for ~1.5 h. Reaction rates (expressed as RFU/s) are calculated by linear regression in the linear range. Reaction rates may be normalized to the values of 0% and 100% activity controls, and fit with a 4-parameter equation to calculate IC50 values. For bivalent inhibitors, the raw IC50 may be multiplied by two.

F. Methods and Compositions for Diagnostics and Detection

In certain aspects, any of the antibodies provided herein is useful for detecting the presence of antigen in a biological sample. The term "detecting" as used herein encompasses quantitative or qualitative detection. In certain aspects, a biological sample comprises a cell or tissue, such as a skin sample.

In one aspect, an antibody for use in a method of diagnosis or detection is provided. In a further aspect, a method of detecting the presence of KLK5 and/or KLK7 in a biological sample is provided. In certain aspects, the method comprises contacting the biological sample with an anti-KLK5 antibody or anti-KLK7 antibody as described herein under conditions permissive for binding of the antibody to its antigen, and detecting whether a complex is formed between the antibody and the antigen. Such method may be an in vitro or in vivo method. In some embodiments, methods of selecting patients for treatment with an antibody provided herein comprise determining KLK5 and/or KLK7 expression in a sample from the patient.

In certain aspects, labeled anti-KLK7 antibodies are provided. In certain aspects, labeled anti-KLK5 antibodies are provided. In certain aspects, labeled multispecific anti-KLK5/KLK7 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

G. Pharmaceutical Compositions

In a further aspect, provided are pharmaceutical compositions comprising any of the antibodies provided herein, e.g., for use in any of the below therapeutic methods. In one aspect, a pharmaceutical composition comprises any of the antibodies provided herein and a pharmaceutically acceptable carrier. In another aspect, a pharmaceutical composition comprises any of the antibodies provided herein and at least one additional therapeutic agent, e.g., as described below.

Pharmaceutical compositions of an anti-KLK7 antibody and/or anti-KLK5 antibody and/or anti-KLK5/KLK7 antibody as described herein are prepared by mixing such antibody or antibodies having the desired degree of purity with one or more optional pharmaceutically acceptable carriers (*Remington's Pharmaceutical Sciences* 16th edition, Osol, A. Ed. (1980)), in the form of lyophilized compositions or aqueous solutions. Pharmaceutically acceptable carriers are generally nontoxic to recipients at the dosages and concentrations employed, and include, but are not limited to: buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Halozyme, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

In some embodiments, an antibody or antibodies provided herein are formulated for subcutaneous administration. In some embodiments, an antibody or antibodies provided herein are formulated for intravenous administration. In some embodiments, an antibody or antibodies provided herein are formulated for topical administration.

Exemplary lyophilized antibody compositions are described in U.S. Pat. No. 6,267,958. Aqueous antibody compositions include those described in U.S. Pat. No. 6,171,586 and WO 2006/044908, the latter compositions including a histidine-acetate buffer.

The pharmaceutical composition herein may also contain more than one active ingredients as necessary for the particular indication being treated, preferably those with complementary activities that do not adversely affect each other. For example, in some embodiments, a pharmaceutical composition comprises an anti-KLK7 antibody in combination with an anti-KLK5 antibody. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Pharmaceutical compositions for sustained release may be prepared. Suitable examples of sustained-release preparations include semipermeable matrices of solid hydrophobic polymers containing the antibody, which matrices are in the form of shaped articles, e.g., films, or microcapsules.

The pharmaceutical compositions to be used for in vivo administration are generally sterile. Sterility may be readily accomplished, e.g., by filtration through sterile filtration membranes.

H. Therapeutic Methods and Routes of Administration

Any of the antibodies provided herein may be used in therapeutic methods, alone or in combination.

In one aspect, an anti-KLK7 antibody for use as a medicament is provided. In one aspect, an anti-KLK5 antibody for use as a medicament is provided. In one aspect, a multispecific anti-KLK5/KLK7 antibody for use as a medicament is provided. In one aspect, a combination of an anti-KLK7 antibody and an anti-KLK5 antibody for use as a medicament is provided. In further aspects, such antibodies for use in treating Netherton Syndrome, asthma, atopic dermatitis, psoriasis, eosinophilic esophagitis, and/or rosacea are provided. In certain aspects, an anti-KLK7 antibody for use in a method of treatment is provided. In certain aspects, an anti-KLK5 antibody for use in a method of treatment is provided. In certain aspects, a multispecific anti-KLK5/KLK7 antibody for use in a method of treatment is provided. In certain aspects, a combination of an anti-KLK7 antibody and anti-KLK5 antibody for use in a method of treatment is provided. In certain aspects, the invention provides such antibodies for use in a method of treating an individual having Netherton Syndrome, asthma, atopic dermatitis, psoriasis, eosinophilic esophagitis, and/or rosacea comprising administering to the individual an effective amount of the antibody or antibodies. In one such aspect, the method further comprises administering to the individual an effective amount of at least one additional therapeutic agent (e.g., one, two, three, four, five, or six additional therapeutic agents), e.g., as described below.

In further aspects, the invention provides an anti-KLK7 antibody and/or an anti-KLK5 antibody and/or a multispecific anti-KLK5/KLK5 antibody for use in reducing epithelium inflammation, reducing epithelium permeability, reducing transepidermal water loss, reducing dermal infiltrates, reducing parakeratosis, restoring the epithelial barrier, and/or reducing skin inflammatory cytokines. In certain aspects, the invention provides an anti-KLK7 antibody and/or an anti-KLK5 antibody and/or a multispecific anti-KLK5/KLK5 antibody for use in a method of reducing epithelium inflammation, reducing epithelium permeability, reducing transepidermal water loss, reducing dermal infiltrates, reducing parakeratosis, restoring the epithelial barrier, and/or reducing skin inflammatory cytokines in an individual comprising administering to the individual an effective amount of the antibody or antibodies to reduce epithelium inflammation, reduce epithelium permeability, reduce transepidermal water loss, reduce dermal infiltrates, reduce parakeratosis, and/or restore the epithelial barrier. An "individual" according to any of the above aspects is preferably a human.

In a further aspect, the invention provides for the use of an anti-KLK7 antibody and/or an anti-KLK5 antibody and/or a multispecific anti-KLK5/KLK5 antibody in the manufacture or preparation of a medicament. In one aspect, the medicament is for treatment of Netherton Syndrome, asthma, atopic dermatitis, psoriasis, eosinophilic esophagitis, and/or rosacea. In a further aspect, the medicament is for use in a method of treating Netherton Syndrome, asthma, atopic dermatitis, psoriasis, eosinophilic esophagitis, and/or rosacea comprising administering to an individual having Netherton Syndrome, asthma, atopic dermatitis, psoriasis, eosinophilic esophagitis, and/or rosacea an effective amount of the medicament. In one such aspect, the method further comprises administering to the individual an effective amount of at least one additional therapeutic agent, e.g., as described below. In a further aspect, the medicament is for reducing epithelium inflammation, reducing epithelium permeability, reducing transepidermal water loss, reducing dermal infiltrates, reducing parakeratosis, restoring the epithelial barrier, and/or reducing skin inflammatory cytokines. In a further aspect, the medicament is for use in a method of reducing epithelium inflammation, reducing epithelium permeability, reducing transepidermal water loss, reducing dermal infiltrates, reducing parakeratosis, restoring the epithelial barrier, and/or reducing skin inflammatory cytokines in an individual comprising administering to the individual an effective amount of the medicament to reduce epithelium inflammation, reduce epithelium permeability, reduce transepidermal water loss, reduce dermal infiltrates, reduce parakeratosis, and/or restore the epithelial barrier. An "individual" according to any of the above aspects may be a human.

In a further aspect, the invention provides a method for treating Netherton Syndrome, asthma, atopic dermatitis, psoriasis, eosinophilic esophagitis, and/or rosacea. In one aspect, the method comprises administering to an individual having Netherton Syndrome, asthma, atopic dermatitis, psoriasis, eosinophilic esophagitis, and/or rosacea an effective amount of an anti-KLK7 antibody and/or an anti-KLK5 antibody and/or a multispecific anti-KLK5/KLK5 antibody. In one such aspect, the method further comprises administering to the individual an effective amount of at least one additional therapeutic agent, as described below.

In some embodiments, methods of ameliorating skin rash and/or scaling in an individual with Netherton Syndrome are provided, comprising administering to the individual an effective amount of an anti-KLK7 antibody and/or an anti-KLK5 antibody and/or a multispecific anti-KLK5/KLK5 antibody.

An "individual" according to any of the above aspects may be a human.

In a further aspect, the invention provides a method for reducing epithelium inflammation, reducing epithelium permeability, reducing transepidermal water loss, reducing dermal infiltrates, reducing parakeratosis, restoring the epithelial barrier, and/or reducing skin inflammatory cytokines in an individual. In one aspect, the method comprises administering to the individual an effective amount of an anti-KLK7 antibody and/or an anti-KLK5 antibody and/or a multispecific anti-KLK5/KLK5 antibody to reduce epithelium inflammation, reduce epithelium permeability, reduce transepidermal water loss, reduce dermal infiltrates, reduce parakeratosis, restore the epithelial barrier, and/or reduce skin inflammatory cytokines. Nonlimiting exemplary skin inflammatory cytokines include IL-8, TNFα, IL-6, IL-4, and G-CSF. In one aspect, an "individual" is a human.

In a further aspect, the invention provides pharmaceutical compositions comprising any of the antibodies provided herein, e.g., for use in any of the above therapeutic methods. In one aspect, a pharmaceutical composition comprises any of the antibodies provided herein and a pharmaceutically acceptable carrier. In another aspect, a pharmaceutical composition comprises any of the antibodies provided herein and at least one additional therapeutic agent, e.g., as described below.

Antibodies of the invention can be administered alone or used in a combination therapy. For instance, the combination therapy includes administering an antibody of the invention and administering at least one additional therapeutic agent (e.g. one, two, three, four, five, or six additional therapeutic agents). In certain aspects, the combination therapy comprises administering an antibody of the invention and administering at least one additional therapeutic agent, such as an anti-inflammatory agent. In some embodiments, the anti-inflammatory agent is administered orally. In some embodiments, the anti-inflammatory agent is administered topically. Anti-inflammatory agents include, but are not limited to, low-dose antibiotics, steroids, corticosteroids, tacrolimus, anti-IL4R antibodies, TNF inhibitors, IL-12/23 inhibitors, IL-17 inhibitors, and IL-4 receptor inhibitors. Nonlimiting exemplary anti-inflammatory agents include doxycycline, methotrexate, prednisone, cyclosporine, mycophenolate mofetil, dupilumab, certolizumab pegol, etanercept, adalimumab, infliximab, golimumab, ustekinumab, secukinumab, ixekizumab, brodalumab, abatacept, tidrakizumab-asmn, risankisumab-rzaa, and guselkumab.

In some embodiments, for example, in the treatment of rosacea, the additional therapeutic is doxycycline administered orally. In some embodiments, for example in the treatment of atopic dermatitis, the additional therapeutic is dupilumab administered subcutaneously; and/or a steroid administered topically. In some embodiments, for example, in the treatment of rosacea, the additional therapeutic is selected from a steroid administered topically; methotrexate administered orally; cyclosporine administered orally; and a TNF inhibitor, typically administered subcutaneously.

Such combination therapies noted above encompass combined administration (where two or more therapeutic agents are included in the same or separate pharmaceutical compositions), and separate administration, in which case, administration of the antibody of the invention can occur prior to, simultaneously, and/or following, administration of the additional therapeutic agent or agents. In one aspect, administration of the antibody or antibodies of the invention and administration of an additional therapeutic agent occur within about one month, or within about one, two or three weeks, or within about one, two, three, four, five, or six days, of each other. In one aspect, the antibody and additional therapeutic agent are administered to the patient on Day 1 of the treatment.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

In some embodiments, an antibody of the invention is administered subcutaneously. In some embodiments, the antibody is administered every four weeks or every month. In some embodiments, an antibody of the invention is administered intravenously. In some embodiments, the antibody is administered every four weeks or every month. In some embodiments, for example, when the antibody comprises half-life extending substitutions such as M428L (EU numbering) and N434S (EU numbering), the antibody is administered every eight weeks.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the pharmaceutical composition, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 pg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 pg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. However, other dosage regimens may be useful. The progress of this therapy is easily monitored by conventional techniques and assays.

In various embodiments, an anti-KLK5 antibody used in a method herein may be replaced with a KLK5 antagonist, wherein the KLK5 antagonist inhibits KLK5 protease activity. In various embodiments, an anti-KLK7 antibody used in a method herein may be replaced with a KLK7 antagonist, wherein the KLK7 antagonist inhibits KLK5 protease activity. In various embodiments, a bispecific anti-KLK5. KLK7 antibody used in a method herein may be replaced with a KLK5/KLK7 antagonist, wherein the KLK5/KLK7 antagonist inhibits KLK5 protease activity and KLK7 protease activity.

I. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

III. EXAMPLES

The following are examples of methods and compositions of the invention. It is understood that various other embodiments may be practiced, given the general description provided above.

Example 1: Generation of Anti-KLK7 Antibodies

New Zealand White rabbits were immunized with human KLK7 (SEQ ID NO: 4) and single B cells were isolated using a modified protocol related to published literature. See, e.g., Offner et al., PLoS ONE 9(2), 2014. This modified workflow included direct FACS sorting of IgG+huKLK7+B cells into single wells. The B cell culture supernatants were assayed by ELISA for binding to human KLK7 and an irrelevant control protein. KLK7 specific B cells were lysed and immediately frozen in −80° C. for storage until molecular cloning. Variable regions (VH and VL) of each monoclonal antibody from rabbit B cells were cloned into expression vectors from extracted mRNA as previously described. See id. Individual recombinant rabbit antibodies were expressed in Expi293 cells and subsequently purified with protein A. ~244 anti-KLK7 antibodies were obtained that bound to both human and cyno KLK7. 171 antibodies were cloned and expressed for further characterization. Purified anti-KLK7 antibodies were screened for binding affinity to huKLK7, selectivity to huKLK7, and functional activity.

The binding affinity of the antibodies was determined by BIAcore™ T200 machine. Rabbit antibodies were recombinantly expressed. For kinetics measurements, antibodies were captured on research grade protein A chip (GE Healthcare, USA) to achieve approximately 300 RU. Ten-fold serial dilutions of human and cyno KLK7 were injected in HBS-P buffer at 25° C. with a flow rate of 30 μL/min. Association rates (ka) and dissociation rates (kd) were calculated using a 1:1 Langmuir binding model (BIAcore™ T200 Evaluation Software version 2.0). The equilibrium dissociation constant (KD) was calculated as the ratio kd/ka.

The results of the off-rates against human KLK7 and cynomolgus monkey KLK7 for a subset of the most potent antibodies are shown in Table 1 No binding was observed to huKLK1, huKLK4, huKLK5, or huKLK11, confirming that these antibodies are specific.

TABLE 1

| Clone ID | hu KLK7 kd (1/s) | Cy KLK7 kd (1/s) |
|---|---|---|
| 5D10 | <1E−6 | <1E−6 |
| 7C7(14D10) | <1E−6 | 2.08E−5 |
| 9C7 | <1E−6 | 3.66E−5 |
| 11D11 | <1E−6 | 1.06E−4 |

TABLE 1-continued

| Clone ID | hu KLK7 kd (1/s) | Cy KLK7 kd (1/s) |
|---|---|---|
| 15A2 | <1E−6 | 3.90E−4 |
| 14H11 | <1E−6 | <1E−6 |
| 12F11 | 2.84E−5 | 4.95E−4 |
| 13A4 | <1E−6 | <1E−6 |
| 13C10 | <1E−6 | 1.78E−4 |
| 15E6 | <1E−6 | 7.65E−5 |
| 10C8 | <1E−6 | 1.97E−4 |
| 11H7 | 3.51E−4 | 1.53E−4 |
| 27E9 | 4.02E−3 | 3.06E−4 |
| 17B9 | 1.25E−3 | 6.96E−4 |
| 25B8 | 2.87E−5 | 4.01E−4 |
| 27D10 | 4.34E−4 | 9.75E−4 |
| 2-18D4 | 1e−5 | 1e−5 |

A KLK7 direct functional assay was performed at room temperature in a 384-well plate (black, low-volume round bottom, Corning #4514) with a final reaction volume of 15 μL. Inhibitor samples were diluted to 3× final concentration in assay buffer (75 mM Tris, pH 8.0, 150 mM NaCl, 0.01% Tween 20). Reactions lacking inhibitor and reactions with 200 nM final SFTI 21705 (Genentech, 10 mM stock in DMSO; also referred to as SFTI-KLK7; sequence GKCLFSNPPICFPN (SEQ ID NO: 196); see, e.g., de Veer et al., 2017, J. Investig. Dermatol., 137: 430-439) were used as 100% and 0% activity controls, respectively. Inhibitor or control samples (5 μL) were added to the plate, followed by 5 μL human KLK7 (SEQ ID NO: 4 plus a C-terminal FLAG tag; Genentech) or 5 μL cyno KLK7 (SEQ ID NO: 6 plus a C-terminal FLAG tag; Genentech) in assay buffer at a final concentration of 0.5 nM (Mca substrate assay). After 40 min, 5 μL Mca-RPKPVE-Nval-WRK(Dnp) (SEQ ID NO: 121; Bachem M-2110, 4.3 mM stock solution in DMSO) at a final concentration of 10 μM substrate in assay buffer were added. After addition of substrate, the plate was read in PHERAstar® microplate reader (BMG Labtech) using optic module FI 320 405 with the gain set to 0%. Measurements were taken every 100 s for ~1.5 h. Reaction rates (expressed as RFU/s) were calculated by linear regression in the linear range. Reaction rates were normalized to the values of the 0% and 100% activity controls and fit with a 4-parameter equation to calculate IC50 values. For certain data relating to bivalent inhibitors, the raw IC50 was multiplied by two, as noted below.

Initial rates were calculated for each assay well by linear regression of the relative fluorescence units (RFU) measured at each time point. The first two time points were typically ignored. Percent control activities were calculated relative to the average of the No Inhibition and Full Inhibition controls. These percent control activities were plotted versus inhibitor concentration and fit using a 4-parameter equation to determine IC50 values. Table 2 shows the results of the human KLK7 and cynomolgus monkey KLK7 inhibition assays for certain antibody clones. In Table 2, the IC50s are not corrected for bivalency because all clones are bivalent.

TABLE 2

Figure 1A:
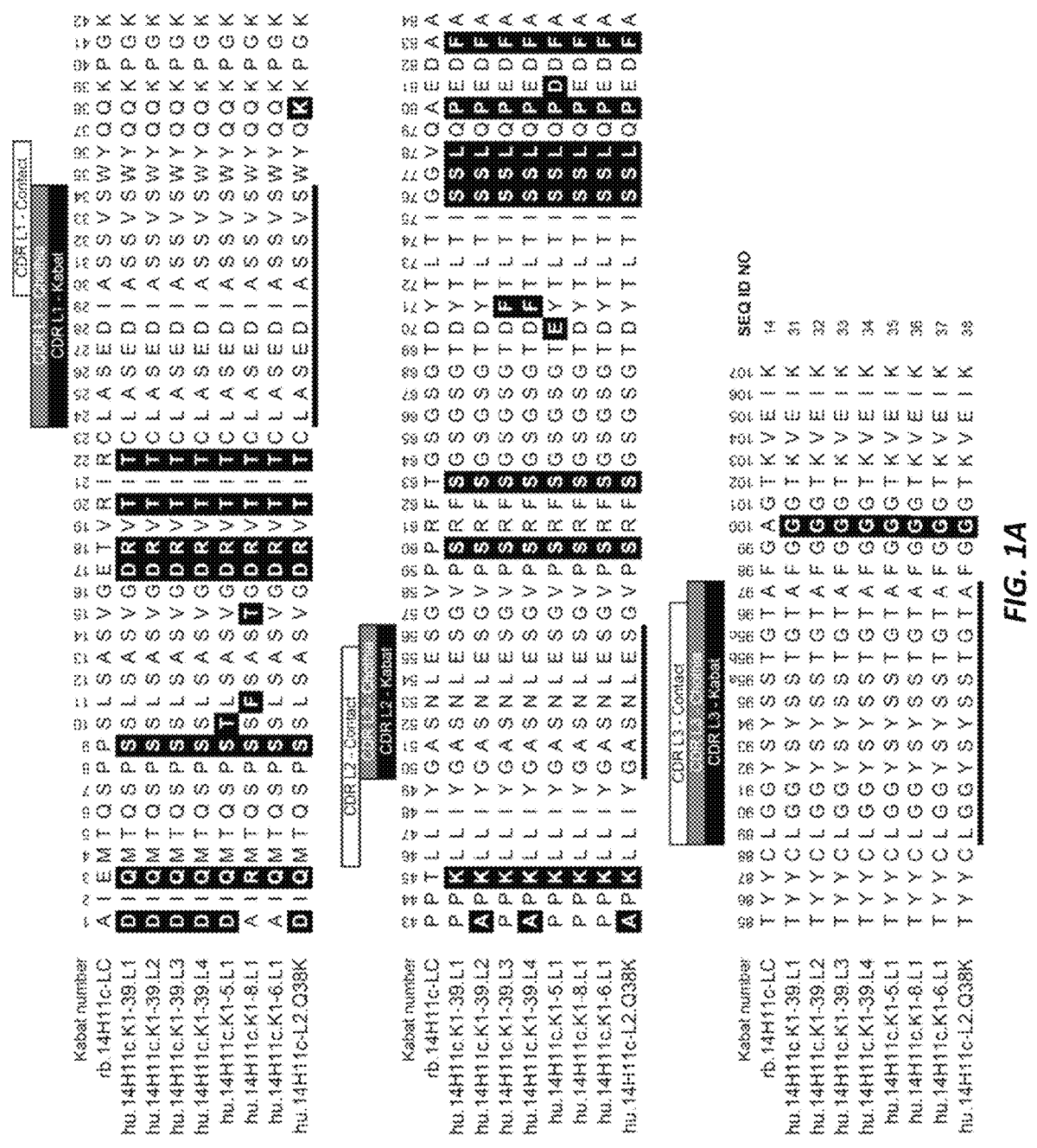
Figure 1B:
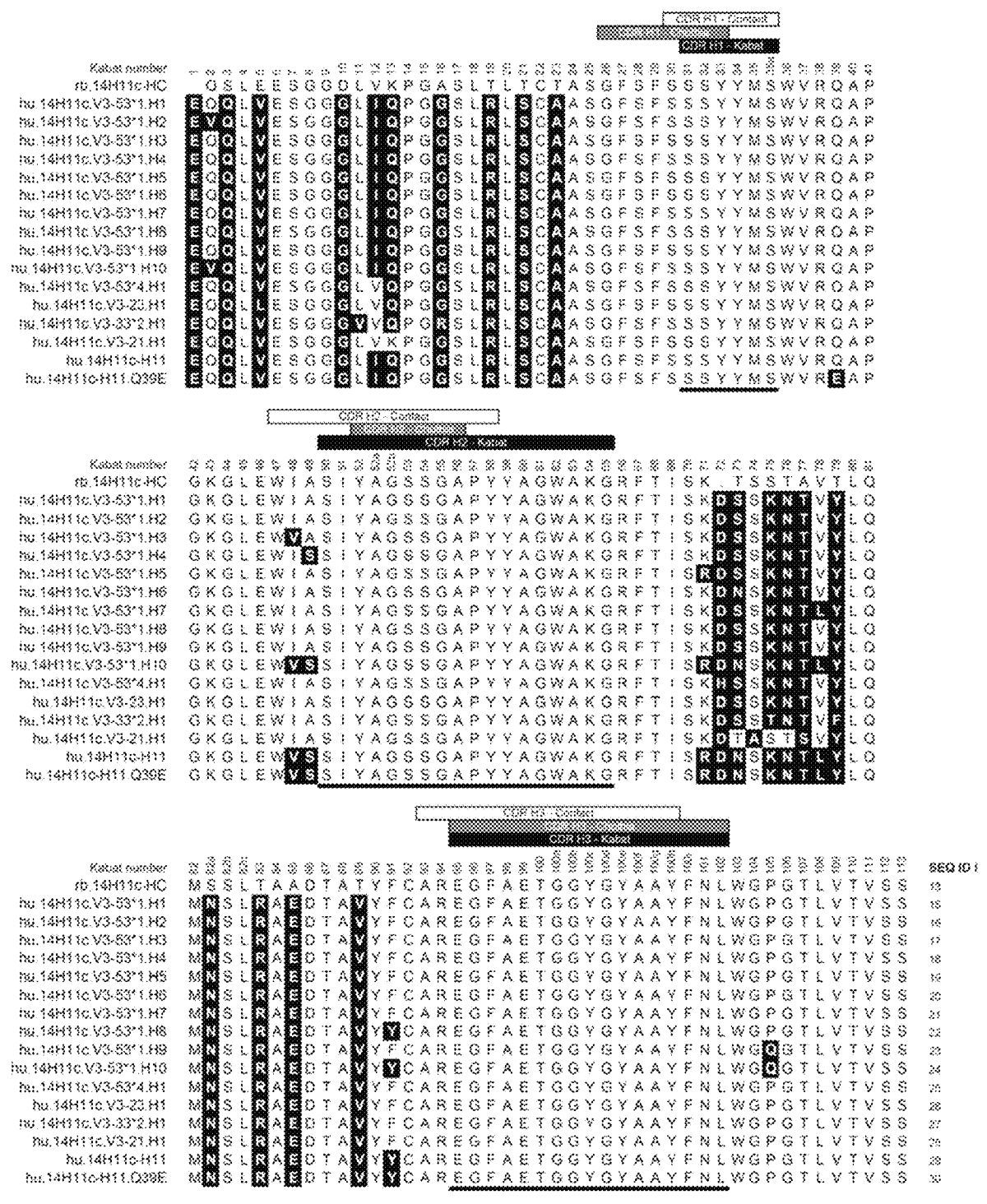

IC50 for anti-KLK7 antibodies using MCA peptide substrate, bivalency not accounted for in IC50 (FIG. 1a and b)

| Clone ID | Hu KLK7 (0.5 nM) IC50 (nM) | Cy KLK7 (0.3125 nM) IC50 (nM) |
|---|---|---|
| 5D10 | 0.15 ± 0.01 | 0.18 ± 0.009 |
| 7C7(14D10) | 0.11 ± 0.004 | 0.07 ± 0.006 |
| 9C7 | 1.19 ± 0.04 | 0.47 ± 0.016 |

TABLE 2-continued

IC50 for anti-KLK7 antibodies using MCA peptide substrate, bivalency not accounted for in IC50 (FIG. 1a and b)

| Clone ID | Hu KLK7 (0.5 nM) IC50 (nM) | Cy KLK7 (0.3125 nM) IC50 (nM) |
|---|---|---|
| 11D11 | 0.12 ± 0.004 | 0.09 ± 0.004 |
| 15A2 | 0.2 ± 0.01 | 0.90 ± 0.088 |
| 14H11 | 0.11 ± 0.004 | 0.15 ± 0.004 |
| 12F11 | 0.31 ± 0.013 | 1.58 ± 0.18 |
| 13A4 | 0.79 ± 0.02 | 0.51 ± 0.046 |
| 13C10 | 0.12 ± 0.005 | 0.51 ± 0.023 |
| 15E6 | 0.1 ± 0.01 | 0.25 ± 0.008 |
| 10C8 | 0.28 ± 0.02 | 0.21 ± 0.009 |
| 11H7 | 0.12 ± 0.01 | 0.13 ± 0.005 |
| 27E9 | 0.28 ± 0.02 | 0.18 ± 0.006 |
| 17B9 | 1.59 ± 0.18 | 3.37 ± 1.26 |
| 25B8 | 0.24 ± 0.01 | 0.17 ± 0.011 |
| 27D10 | 0.43 ± 0.05 | 2.98 ± 0.565 |

Example 2: Humanization of Anti-KLK7 Antibodies

After screening as described in Example 1, 17 antibodies with the best inhibitory activities were chosen for further characterization. The antibody with the strongest binding affinity, inhibitory activity, and fewest manufacturing issues (14H11) was selected for humanization. Antibody 14H11 heavy chain variable region (SEQ ID NO: 116) was first modified by substituting C35a with S to eliminate an unpaired cysteine, resulting in antibody 14H11c (VH, SEQ ID NO: 13; VL SEQ ID NO: 14).

Rabbit monoclonal antibody 14H11c was humanized as follows. Residue numbers are according to Kabat et al., Sequences of proteins of immunological interest, 5$^{th}$ Ed., Public Health Service, National Institutes of Health, Bethesda, Md. (1991).

Variants constructed during the humanization of 14H11c were assessed in the form of human IgG1. Hypervariable regions from the rabbit antibody, positions 24-34 (Li; SEQ ID NO: 10), 50-56 (L2; SEQ ID NO: 11) and 89-97 (L3; SEQ ID NO: 12) in VL domain were grafted into human KV1D-39*01 framework; and 31-35b (H1; SEQ ID NO: 7), 50-65 (H2; SEQ ID NO: 8) and 95-102 (H3; SEQ ID NO: 9) in VH domain were grafted into human HV3-53*01 framework. All VL and VH Vernier positions from rabbit antibodies were also grafted into their respective human germline frameworks. The grafts with all rabbit amino acids in Vernier positions are referred to as L1H1 (hu.14H11c.L1H1; SEQ ID NOs: 15 (VH) and 31 (VL)).

The binding affinity of the humanized antibodies was determined by BIAcore™ 8K SPR system. For kinetics measurements, antibodies were captured on research grade protein A chip (GE Healthcare) to achieve approximately 300 RU. Ten-fold serial dilutions of human KLK7 were injected in HBS-P buffer at 37° C. with a flow rate of 100 L/min. Association rates (ka) and dissociation rates (kd) were calculated using a 1:1 Langmuir binding model (BIAcore Insight Evaluation Software version 2.0). The equilibrium dissociation constant (KD) was calculated as the ratio kd/ka.

The binding affinity of hu.14H11c.L1H1 antibody was compared to its chimeric parental clone. Rabbit Vernier positions of hu.14H11c.L1H1 antibodies were converted back to human residues to evaluate the contribution of each rabbit Vernier positions to binding affinity to hKLK7. Three additional light chains (L2: L1+Ala43 (SEQ ID NO: 32), L3: L1+Phe71 (SEQ ID NO: 33), and L4: L1+Ala43+Phe71 (SEQ ID NO: 34)) and nine additional heavy chains (H2: H1+Val2 (SEQ ID NO: 16), H3: H1+Val48 (SEQ ID NO: 17), H4: H1+Ser49 (SEQ ID NO: 18), H5: H1+Arg71 (SEQ ID NO: 19), H6: H1+Asn73 (SEQ ID NO: 20), H7: H1+Leu78 (SEQ ID NO: 21), H8: H1+Tyr91 (SEQ ID NO: 22), H9: H1+Gln105 (SEQ ID NO: 23), H10: no rabbit residues in Vernier positions (SEQ ID NO: 24)) were made. See FIGS. 1A-1B. Tyr71 on light chain (L2; SEQ ID NO: 32), and Gln2 and Pro105 on the heavy chain (H11; SEQ ID NO: 29) were determined to be important rabbit Vernier residues based on binding affinity evaluation of the variant antibodies described above (data not shown). Chimeric 14H11c bound with a KD of ≤1 pM, while hu.14H11c.L2H11, bound with a KD of 0.4 pM.

TABLE 3

Affinities of humanized anti-KLK7 antibody

| Ligand | Sample | ka (1/Ms) | kd (1/s) | KD (M) |
|---|---|---|---|---|
| human KLK7 | chimeric rb.14H11c-hIgG1 | 2.16E+07 | <1E−06 | <1E−12 |
| | hu.14H11c.L2H11-hIgG1 (VH/VL; SEQ. ID NOs: 29, 32) | 3.43E+07 | 1.22E−05 | 3.56E−13 |
| | One-armed hu.14H11c.L2H11-hIgG1 knob-in-hole (VH/VL; SEQ. ID NOs: 30, 38; IgG1 knob SEQ. ID NOs: 96 linked to VH; paired with "dummy" IgG1 hole SEQ. ID NO: 182) | 2.82E+07 | 2.52E−05 | 8.94E−13 |

Example 3: Affinity Optimization of Anti-KLK5 Antibodies

To increase the affinity of anti-KLK5 antibodies hu.9H5.L4H14 and hu.10C5.L5H28, 544 and 576 single point mutation variants were generated, respectively. The resulting antibodies were screened by surface plasmon resonance and ranked according to off-rates. See FIG. 4 (hu.10C5.L5H28 variants) and FIG. 5 (hu.9H5.L4H14 variants). There were only five mutations in hu.10C5.L5H28 that resulted in a significantly slower off-rate. These were LC.S34K (SEQ ID NO: 54), LC.F92Y (SEQ ID NO: 55), LC.S95F (SEQ ID NO: 56), HC.G33P (SEQ ID NO: 105), and HC.N53V (SEQ ID NO: 52). See FIGS. 2A-2B. For hu.9H5.L4H14, there were only four mutations with slower off-rates than the parental antibody: LC.H89V (SEQ ID NO: 88), LC.S95Y (SEQ ID NO: 89), HC.G54A (SEQ ID NO: 81), and HC.G98Q (SEQ ID NO: 82). See FIGS. 3A-3B.

To identify good combinations of variants, we generated one-armed (OA) monovalent antibodies with a human IgG1 Fc with both individual and combined sets of mutations. Good combinations were identified by surface plasmon resonance characterization. Tables 4-7 show the kinetic properties of the one-armed (OA) monovalent antibodies.

TABLE 4

Affinities of hu.9H5.L4H14 variants for human KLK5

| antibody variant (all with Q38E/Q39K) | ka (1/Ms) | kd (1/s) | KD (M) | VH/VL SEQ IDs |
|---|---|---|---|---|
| OA.hu.9H5.H14L4 | 1.07E+06 | 2.72E-04 | 2.54E-10 | 84/91 |
| OA.hu.9H5.H14L4.G54A.H89V | 3.79E+06 | 3.85E-05 | 1.02E-11 | 85/92 |
| OA.hu.9H5.H14L4.G54A.S95Y | 9.92E+05 | 1.60E-05 | 1.62E-11 | 85/93 |
| OA.hu.9H5.H14L4.G54A.H89V.S95Y | 6.99E+05 | 1.37E-05 | 1.96E-11 | 85/94 |
| OA.hu.9H5.H14L4.G98Q.H89V | 2.40E+06 | 4.46E-05 | 1.86E-11 | 86/92 |
| OA.hu.9H5.H14L4.G98Q.S95Y | 7.85E+05 | 3.94E-05 | 5.02E-11 | 86/93 |
| OA.hu.9H5.H14L4.G98Q.H89V.S95Y | 2.47E+06 | 4.91E-05 | 1.99E-11 | 86/94 |
| OA.hu.9H5.H14L4.G54A.G98Q.H89V | 8.54E+06 | 2.97E-06 | 3.48E-13 | 87/92 |
| OA.hu.9H5.H14L4.G54A.G98Q.S95Y | 2.73E+06 | 2.71E-05 | 9.94E-12 | 87/93 |
| OA.hu.9H5.H14L4.G54A.G98Q.H89V.S95Y | 1.98E+06 | 2.39E-05 | 1.21E-11 | 87/94 |

TABLE 5

Affinities of hu9H5.L4H14 variants for cyno KLK5

| antibody variant (all with Q38E/Q39K) | ka (1/Ms) | kd (1/s) | KD (M) | VH/VL SEQ IDs |
|---|---|---|---|---|
| OA.hu.9H5.H14L4 | 1.12E+07 | 6.97E-04 | 6.23E-11 | 84/91 |
| OA.hu.9H5.H14L4.G54A.H89V | 1.24E+07 | 1.10E-04 | 8.93E-12 | 85/92 |
| OA.hu.9H5.H14L4.G54A.S95Y | 4.82E+06 | 8.44E-05 | 1.75E-11 | 85/93 |
| OA.hu.9H5.H14L4.G54A.H89V.S95Y | 4.28E+06 | 7.36E-05 | 1.72E-11 | 85/94 |
| OA.hu.9H5.H14L4.G98Q.H89V | 1.48E+07 | 1.45E-04 | 9.78E-12 | 86/92 |
| OA.hu.9H5.H14L4.G98Q.S95Y | 4.02E+06 | 1.45E-04 | 3.61E-11 | 86/93 |
| OA.hu.9H5.H14L4.G98Q.H89V.S95Y | 4.02E+06 | 1.33E-04 | 3.30E-11 | 86/94 |
| OA.hu.9H5.H14L4.G54A.G98Q.H89V | 2.19E+07 | 6.52E-05 | 2.98E-12 | 87/92 |
| OA.hu.9H5.H14L4.G54A.G98Q.S95Y | 5.97E+06 | 9.18E-05 | 1.54E-11 | 87/93 |
| OA.hu.9H5.H14L4.G54A.G98Q.H89V.S95Y | 3.95E+06 | 5.75E-05 | 1.46E-11 | 87/94 |

TABLE 6

Affinities of hu10C5.L5H28 variants for human KLK5

| antibody variant (all except OA.hu.10C5.L5H28.WT and OA.hu.10C5.N53V with Q38E/Q39K) | ka (1/Ms) | kd (1/s) | KD (pM) | VH/VL SEQ IDs |
|---|---|---|---|---|
| OA.hu.10C5.L5H28.WT | 1.25E+07 | 1.28E-03 | 102.417 | 50/51 |
| OA.hu.10C5.N53V | 6.84E+06 | 9.23E-05 | 13.497 | 52/51 |
| OA.hu.10C5.N53V.S34K | 3.42E+06 | 9.88E-06 | 2.887 | 53/61 |
| OA.hu.10C5.N53V.F92Y | 6.41E+06 | 2.45E-05 | 3.817 | 53/62 |
| OA.hu.10C5.N53V.S95F | 5.82E+06 | 1.51E-05 | 2.587 | 53/63 |
| OA.hu.10C5.N53V.S34K.F92Y | 3.00E+06 | <1E-06 * | <0.334 | 53/64 |
| OA.hu.10C5.N53V.S34K.S95F | 4.25E+06 | <1E-06 * | <0.235 | 53/65 |
| OA.hu.10C5.N53V.F92Y.S95F | 1.01E+07 | 8.65E-06 | 0.853 | 53/66 |
| OA.hu.10C5.N53V.S34K.F92Y.S95F | 5.13E+06 | 1.88E-06 | 0.367 | 53/67 |

TABLE 7

Affinities of hu10C5.L5H28 variants for cyno KLK5

| antibody variant (all except OA.hu.10C5.L5H28.WT and OA.hu.10C5.N53V with Q38E/Q39K) | ka (1/Ms) | kd (1/s) | KD (pM) | VH/VL SEQ IDs |
|---|---|---|---|---|
| OA.hu.10C5.L5H28.WT | 1.14E+07 | 4.24E-03 | 371.354 | 50/51 |
| OA.hu.10C5.N53V | 1.46E+07 | 5.20E-04 | 35.520 | 52/51 |
| OA.hu.10C5.N53V.S34K | 5.48E+06 | 8.88E-05 | 16.218 | 53/61 |
| OA.hu.10C5.N53V.F92Y | 1.82E+07 | 1.61E-04 | 8.846 | 53/62 |

TABLE 7-continued

Affinities of hu10C5.L5H28 variants for cyno KLK5

| antibody variant (all except OA.hu.10C5.L5H28.WT and OA.hu.10C5.N53V with Q38E/Q39K) | ka (1/Ms) | kd (1/s) | KD (pM) | VH/VL SEQ IDs |
|---|---|---|---|---|
| OA.hu.10C5.N53V.S95F | 1.35E+07 | 1.00E−04 | 7.444 | 53/63 |
| OA.hu.10C5.N53V.S34K.F92Y | 5.90E+06 | 3.08E−05 | 5.220 | 53/64 |
| OA.hu.10C5.N53V.S34K.S95F | 9.41E+06 | 2.86E−05 | 3.034 | 53/65 |
| OA.hu.10C5.N53V.F92Y.S95F | 1.52E+07 | 5.72E−05 | 3.764 | 53/66 |
| OA.hu.10C5.N53V.S34K.F92Y.S95F | 1.06E+07 | 2.81E−05 | 2.646 | 53/67 |

FIG. 6 shows surface plasmon resonance traces for the indicated hu.10C5. L5H28 variants for human KLK15 (FIG. 6A) and cynomolgus monkey KLK5 (FIG. 6B). FIG. 7 shows surface plasmon resonance traces for the indicated hu.9H5.L4H14 variants for human KLK5 (FIG. 7A) and cynomolgus monkey KLK5 (FIG. 7B).

Example 4: Generation and Characterization of Anti-KLK5/KLK7 Bispecific Antibodies To choose good combinations of 10C5.L5H28 variants to pair with the anti-KLK7 arm in a bispecific antibody, we evaluated each variant for KLK5 inhibitory activity, non-specific binding in a baculovirus binding assay, and correct bispecific generation upon co-expression with the anti-KLK7 arm in a single cell. Each variant was constructed with mutations previously described to enhance correct chain pairing for single cell bispecific assembly. See Dillon et al., Mabs 9(2): 213-230 (2017). The anti-KLK5 LC contained Q38E and V133K and the HC contained Q39K and S183E. The anti-KLK7 LC contained Q38K and V133E and the HC contained Q39E and S183K.

All one-armed anti-KLK5 antibody variants exhibited similar potencies in the KLK5 inhibition assay, with IC50s ranging from 1.14 nM to 2.30 nM (data not shown).

Non-specific binding of each anti-KLK5 antibody variant was measured in an ELISA using baculovirus particles, substantially as described in Hotzel et al., Mabs 4(6): 753-760 (2012).

Two variants (N53V/S34K and N53V/S34K/F92Y/S95F) were eliminated following the baculovirus binding assay because of higher nonspecific binding, which can lead to poor pharmacokinetic properties. See Tables 8 and 9.

TABLE 8

Baculovirus binding ELISA for hu10C5.L5H28 variants

| Sample | BV ELISA | VH/VL SEQ IDs |
|---|---|---|
| hu.10C5.L5H28.WT | 0.22 | 50/51 |
| hu.10C5.N53V | 0.38 | 52/51 |
| hu.10C5.N53V.S34K | 1.81 | 52/54 |
| hu.10C5.N53V.F92Y | 0.19 | 52/55 |
| hu.10C5.N53V.S95F | 0.28 | 52/56 |
| hu.10C5.N53V.S34K.F92Y | 0.29 | 52/57 |
| hu.10C5.N53V.S34K.S95F | 0.29 | 52/58 |
| hu.10C5.N53V.F92Y.S95F | n.d. | 52/59 |
| hu.10C5.N53V.S34K.F92Y.S95F | 0.46 | 52/60 |

TABLE 9

Baculovirus binding ELISA for hu.9H5.L4H14 variants

| xKLK5 variant (all with Q38E/Q39K) | BV ELISA | VH/VL SEQ IDs |
|---|---|---|
| OA.hu.9H5.H14L4 | 0.02 | 84/91 |
| OA.hu.9H5.H14L4.G54A.H89V | 0.30 | 85/92 |
| OA.hu.9H5.H14L4.G54A.S95Y | 0.17 | 85/93 |
| OA.hu.9H5.H14L4.G54A.H89V.S95Y | 0.34 | 85/94 |
| OA.hu.9H5.H14L4.G98Q.H89V | 0.32 | 86/92 |
| OA.hu.9H5.H14L4.G98Q.S95Y | 0.12 | 86/93 |
| OA.hu.9H5.H14L4.G98Q.H89V.S95Y | 0.33 | 86/94 |
| OA.hu.9H5.H14L4.G54A.G98Q.H89V | 0.27 | 87/92 |
| OA.hu.9H5.H14L4.G54A.G98Q.S95Y | 0.12 | 87/93 |
| OA.hu.9H5.H14L4.G54A.G98Q.H89V.S95Y | 0.20 | 87/94 |

The ability of each variant to pair correctly with the anti-KLK7 arm upon co-expression in HEK293 cells was evaluated. As shown in Table 10, all variants with LC. S34K exhibited poor assembly properties.

TABLE 10

Mass spectrometry measurement of % correct bispecific upon single cell production

| Clone (hu.10C5 VH/VL; hu.14H11 VH/VL) | Correct (%) | 2xHoleLC (%) | 2xKnobLC (%) |
|---|---|---|---|
| hu.10C5VKYF.hu14H11c.L2H11 1:1 (53/67; 30/38) | 58.5 | 0.0 | 41.5 |
| hu.10C5VK.hu14H11c.L2H11 1:1 (53/61; 30/38) | 67.9 | 1.5 | 30.6 |
| hu.10C5VY.hu14H11c.L2H11 1:1 (53/62; 30/38) | 89.0 | 0.0 | 11.0 |
| hu.10C5VF.hu14H11c.L2H11 1:1 (53/63; 30/38) | 84.9 | 1.3 | 13.8 |
| hu.10C5VKY.hu14H11c.L2H11 1:1 (53/64; 30/38) | 63.4 | 1.9 | 34.7 |
| hu.10C5VKF.hu14H11c.L2H11 1:1 (53/65; 30/38) | 55.3 | 0.0 | 44.7 |

Based on the combined properties, hu.10C5.L5H28.N53V.F92Y with Q39K/Q38E mutations (VH, SEQ ID NO: 53; VL, SEQ ID NO: 62) was chosen as the anti-KLK5 arm to pair with the hu14H11c.L2H11 with Q39E/Q38K mutations (VH, SEQ ID NO: 30; VL, SEQ ID NO: 38) anti-KLK7 arm. Two versions of the bispecific antibody were generated with hIgG1 N297G, which has attenuated effector function. One of the versions contained two mutations (M428L/N434S) that have been shown to enhance antibody half-life in vivo. See Zalevsky et al. Nature Biotech, 2010, 28: 157-9; Ko et al. Nature, 2014, 514: 642-5; Gaudinski et al. PLOS Medicine, 2018, 15:e1002493.

The affinities of the anti-KLK5/KLK7 bispecific antibodies, with and without the M428L/N434S ("LS") mutations, was determined for human and cynomolgus monkey KLK5 and KLK7.

TABLE 11

Affinities of bispecific antibodies for human and cyno KLK5

| | Human KLK5 | | | Cyno KLK5 | | |
|---|---|---|---|---|---|---|
| | ka (1/Ms) | kd (1/s) | KD (pM) | ka (1/Ms) | kd (1/s) | KD (pM) |
| hu.10C5VY.hu14H11c.L2H11 WT (SEQ ID NOs: 108/109 and 110/111) | (2.1 ± 0.9)E+7 | (1.5 ± 0.6)E−5 | 0.8 ± 0.2 | (1.0 ± 0.2) E+7 | (1.9 ± 0.1)E−4 | 19 ± 1 |
| hu.10C5VY.hu14H11c.L2H11 LS (SEQ ID NOs: 112/113 and 114/115) | (1.5 ± 0.7) E+7 | (1.97 ± 0.09)E−5 | 1.5 ± 0.6 | (1.11 ± 0.03) E+7 | (1.8 ± 0.5)E−4 | 16 ± 4 |

TABLE 12

Affinities of bispecific antibodies for human and cyno KLK7

| | Human KLK7 | | | Cyno KLK7 | | |
|---|---|---|---|---|---|---|
| | ka (1/Ms) | kd (1/s) | KD (pM) | ka (1/Ms) | kd (1/s) | KD (pM) |
| hu.10C5VY.hu14H11c.L2H11 WT (SEQ ID NOs: 108/109 and 110/111) | (5.8 ± 0.1) E+7 | <1E−6 | <1 | (4 ± 1) E+7 | (9 ± 5)E−5 | 2.3 ± 0.6 |
| hu.10C5VY.hu14H11c.L2H11 LS (SEQ ID NOs: 112/113 and 114/115) | (5.7 ± 0.5)E+7 | (1.4 ± 0.1)E−5 | 0.24 ± 0.9 | (3 ± 1)E+7 | (7 ± 3)E−5 | 3 ± 2 |

Activity of the bispecific antibodies was assayed using KLK7 and KLK5 direct functional assays, substantially as described in Example 1. For KLK5 functional assays, the assay in Example 1 was modified to use human or cynomolgus monkey KLK5 (SEQ ID NOs: 2 and 101, respectively) in place of KLK7, and substrate Boc-Val-Pro-Arg-AMC (Bachem 1-1120, 31.3 mMv stock solution in water) at a final concentration of 50 μM. 200 nM SPINK9.SRE.Fc (SEQ ID NO: 197; Genentech; see, e.g., Brannstrom et al., 2012, *Biol. Chem.* 393: 369-377) was used as a 000 activity control. The results are shown in Tables 13 and 14.

TABLE 13

IC50 for the anti-KLK5/KLK7 bispecific antibodies and parental monospecific antibodies against human KLK5 and KLK7, bivalency corrected in IC50s (AMC = Boc-Val-Pro-Arg-AMC; MCA = Mca-RPKPVE-Nval-WRK(Dnp))

| | IC50 (nM) | |
|---|---|---|
| Antibody | KLK5 AMC | KLK7 MCA |
| hu.10C5VY.hu14H11c.L2H11 WT (SEQ ID NOs: 108/109 and 110/111) | 0.67 ± 0.06 | 0.37 ± 0.08 |
| hu.10C5VY.hu14H11c.L2H11 LS (SEQ ID NOs: 112/113 and 114/115) | 0.54 ± 0.04 | 0.34 ± 0.07 |
| hu14H11c.L2H11 (SEQ ID NOs: 29/32) | >10 | 0.29 ± 0.06 |
| hu10C5VY (SEQ ID NOs: 52/55) | 0.46 ± 0.04 | >10 |

TABLE 14

IC50 for the anti-KLK5/KLK7 bispecific antibodies and parental monospecific antibodies against cynomolgus monkey KLK5 and KLK7, bivalency corrected in IC50s (AMC = Boc-Val-Pro-Arg-AMC; MCA = Mca-RPKPVE-Nval-WRK(Dnp))

| | IC50 (nM) | |
|---|---|---|
| Antibody | KLK5 AMC | KLK7 MCA |
| hu.10C5VY.hu14H11c.L2H11 WT (SEQ ID NOs: 108/109 and 110/111) | 0.73 ± 0.04 | 0.37 ± 0.05 |
| hu.10C5VY.hu14H11c.L2H11 LS (SEQ ID NOs: 112/113 and 114/115) | 0.58 ± 0.02 | 0.36 ± 0.05 |
| hu14H11c.L2H11 (SEQ ID NOs: 29/32) | >10 | 0.29 ± 0.06 |
| hu10C5VY (SEQ ID NOs: 52/55) | 0.56 ± 0.03 | >10 |

Example 5: Expression of KLK5 and KLK7 in Atopic Dermatitis, Rosacea, and Psoriasis Immunochemistry was used to determine the expression of KLK5 in human rosacea and atopic dermatitis samples. As shown in FIG. 8, KLK5 protein is elevated in human rosacea and atopic dermatitis, compared to normal skin.

To determine whether KLK7 is also expressed in human dermatitis conditions, an antisense RNA probe was used for in situ hybridization to visualize KLK5 and KLK7 expression. FIG. 9 show representative KLK7 mRNA staining in atopic dermatitis, rosacea, and psoriasis, compared to normal skin. FIG. 10 shows that KLK5 (10A) and KLK7 (10B) mRNA show similar anatomic expression in human skin and are both upregulated in atopic dermatitis, rosacea, and psoriasis. The increase in SPINK5 expression was not significant in atopic dermatitis or rosacea, but was significant in psoriasis. The data in FIG. 10 shows double-blinded quantification by a pathologist.

Example 6: Intradermal Injection of KLK5 or KLK7 Increases Transepidermal Water Loss To test whether KLK5 or KLK7 directly promotes epithelial barrier dysregulation and increases transepidermal water loss, 2 pg recombinant KLK5 or KLK7 was intradermally injected into dorsal skin of Balb/c mice.

As shown in FIG. 11, 6 hours after injection, both KLK5 and KLK7 injected animals have increased transepidermal water loss, as measured by a portable skin Vapometer (Delfin technologies). These data suggested that KLK5 and KLK7 may each promote increased epithelial permeability.

Example 7: Inhibition of KLK5 and KLK7 Ameliorates Murine Inflammatory Dermatitis Surrogate anti-murine KLK5 and anti-murine KLK7 inhibitory antibodies were generated to test the therapeutic efficacy of inhibiting KLK5 and KLK7 in murine atopic dermatitis. Murine atopic dermatitis was induced by topical treatment with SDS and *Staphylococcus aureus* protein A. Mice with inflammatory dermatitis then received an intraperitoneal injection of 250 pg isotype control (anti-gp120), anti-murine KLK5 antibody, anti-murine KLK7 antibody, or a combination of anti-KLK5 and anti-KLK7 antibodies. Murine SPINK5-Fc fusion protein was used here as a non-specific inhibitor for multiple KLKs (including KLK5, KLK7, and KLK14).

As shown in FIG. 12, while inhibition of KLK5 or KLK7 alone provides moderate protection in daily dermatitis clinical score (12A), total terminal atopic dermatitis score (12B), and AUC skin score (12C), co-inhibition of KLK5 and KLK7 provides a superior therapeutic efficacy, similar to SPINK5-Fc. Since SPINK5 inhibits other KLKs in addition to KLK5 and KLK7, this data suggests that inhibition of KLK5 and KLK7 is sufficient for therapeutic efficacy.

Inflammatory atopic dermatitis is associated with T cell infiltration and IL-13 production. Neutralizing IL-13 improves atopic dermatitis in murine animal models and human atopic dermatitis patients. In a second experiment, an anti-IL-13 antibody was used as a positive control in the SDS/*S. aureus* protein A atopic dermatitis model. As shown in FIG. 13, the combination of anti-KLK5 and anti-KLK7 antibodies reduced total terminal AD scores, reduced transepidermal water loss (TEWL), and reduced histologic disease severity scores, to a similar extent as anti-IL-13 antibody. FIG. 14 shows representative hematoxylin and eosin staining, demonstrating that combined anti-KLK5 and KLK7 antibodies reduced dermal inflammation and parakeratosis to a similar extent as anti-IL-13 antibody.

Taken together, these results suggest a redundant role for KLK5 and KLK7 in promoting epithelial barrier permeability. Combined inhibition of KLK5 and KLK7 is therefore expected to result in improved dermatitis clinical scores, skin barrier function, and histopathology manifestation, compared to inhibition of KLK5 or KLK7 alone.

Example 8: Skin Rash and Scaling in Spink5 Deficient Mice Improves with Anti-mKLK5/mKLK7 Bispecific Antibody Treatment or Anti-mKLK5 Antibody/Anti-mKLK7 Antibody Combination Treatment Spink5 f/f Cre-ERT2+ mice were intraperitoneally injected with 16 mg/kg, 8 mg/kg, or 4 mg/kg tamoxifen to delete the Spink5 gene. One day before tamoxifen treatment, anti-murine KLK5 antibody (2.5 mg per mouse) and anti-murine KLK7 antibody (0.5 mg per mouse) or an isotype control antibody (2.5 mg per mouse). An excess of anti-mKLK5 antibody compared to anti-mKLK7 antibody was used because the anti-mKLK5 antibody was determined to be 100-fold less potent than the anti-mKLK7 antibody, with an $IC_{50}$ of 4.78 nM compared to an $IC_{50}$ of 0.48 nM for the anti-mKLK7 antibody. Back skin was analyzed 6 days post injection of tamoxifen. Spink5 f/f Cre-ERT2-negative mice were also treated with 16 mg/kg tamoxifen as a control.

The back skin of the mice 6 days post infection is shown in FIGS. 16A-16D. Skins of the Spink5 deficient mice treated with an isotype control became dry, scaly, inflamed, and reddened. These exterior Netherton Syndrome-like symptoms were significantly improved by combined injection of anti-mKLK5 antibody and anti-mKLK7 antibody across different tamoxifen dose.

Back skin of the mice were homogenized in phosphate-buffered saline to produce skin lysates. The lysates were analyzed for cytokine levels using Bio-Plex Multiplex Immunoassays (BioRad).

The results of the cytokine assays are shown in FIG. 17A-17E. Levels of cytokines IL-8 (17A), TNF-α (17B), IL-6 (17C), IL-4 (17D), and G-CSF (17E) were reduced by anti-mKLK5/mKLK7 bispecific antibody treatment compared to isotype control antibody treatment.

FIG. 18 shows representative cross-sections of hematoxylin and eosin stained skin from Spink5 deficient mice treated with 16 mg/kg tamoxifen and isotype control antibody or combined anti-mKLK5 antibody/anti-mKLK7 antibody. While the skin from Spink5 deficient mice treated with isotype control antibody shows significant leukocyte infiltration, thickening of epidermis layers, and epidermis desquamation, a combined blockade of mKLK5 and mKLK7 significantly reduced the pathological manifestation.

Example 9: Anti-KLK5/KLK7 Bispecific Antibody Inhibits KLK5- and KLK7-Induced Epithelial Permeability Human epidermal keratinocytes were seeded into a tissue culture trans-well plate coated with collagen and differentiated with 1.5 mM $CaCl_2$ for 2 days. After differentiation, $CaCl_2$ was reduced to 0.1 mM. The top apical side of the monolayer was treated with KLK5 (5 pg/ml), KLK7 (5 pg/ml), KLK5+KLK7 (5 pg/ml each), or KLK5+KLK7 (5 pg/ml each)+100 pg/ml anti-KLK5/KLK7 bispecific antibody (hu.10C5VY.hu14H11c.L2H11 LS) for 72h or 96h. Trans-epithelial electrical resistance (TEER) was measured with a volt/ohm meter at each time point.

The results are shown in FIGS. 22A-22B. Addition of recombinant KLK5, KLK7, or KLK5/KLK7 together induced epithelial permeability as quantified by trans-epithelial electrical resistance. Anti-KLK5/KLK7 bispecific antibody significantly reduced the KLK5- and KLK7-induced epithelial permeability.

Example 10: Structural Determination of Anti-KLK7 Antibody 14H11c Bound to KLK7

Recombinant KLK7 residues I30-R253 (SEQ ID NO: 4) was expressed in a mammalian expression system (CHO cells), with a His-tag at the N-terminus, followed by an enterokinase cleavage site engineered between the His-tag and KLK7. The CHO cells were co-expressed with EndoH with 1 mg/mL of Kifunensine. The expression media was harvested and purified with Ni-NTA as the first step. Protein eluted from the Ni-NTA column was further purified on a Superdex 200 (S200) size-exclusion column. The His tag on KLK7 was removed by treating with enterokinase overnight, and KLK7 was further purified on a SP HP cation exchange column with 25 mM Hepes pH7.8 and a gradient of 0-800 mM NaCl.

Fab fragments including heavy and light chains of anti-KLK7 antibody rb.14H11c were expressed in HEK293 cells. A His-tag was added at the C-terminus of the heavy chain for ease of purification using a Ni-NTA resin, followed by size exclusion chromatography in PBS. The sequences of the heavy and light chain are shown in SEQ ID NOs: 198 and 199, respectively. For the purposes of this example, the sequences were numbered beginning with the signal sequence. The numbering of the Fab heavy chain shown in SEQ ID NO: 198 therefore begins with 20 (amino acids 20-256) and the numbering of the Fab light chain shown in SEQ ID NO: 199 therefore begins with 23 (amino acids 23-237).

KLK7 was mixed with the 14H11c Fab, at a molar ratio of 1:1.5 KLK7:Fab and the complex was purified by size-exclusion chromatography in 25 mM HEPES pH 7.8, 150 mM NaCl. The peak containing the KLK7:Fab complex was methylated on the lysines (*Methods in Structure*, 2006, 14, 1617-1622) and further purified on an S200 column using 25 mM TRIS pH 7.8 and 150 mM NaCl. The complex was concentrated to 10 mg/mL and crystals were grown by hanging drop with 1 μL protein and 1 μL of 10% PEG 4K and 0.2M ammonium sulfate. Crystals appeared after 3 days and matured over an additional 2-3 days. Crystals were then harvested for data collection.

X-ray diffraction data was collected under cryocooled conditions at 100 Kelvin using various synchrotron X-ray radiation at the Advanced Light Source (Berkeley, CA) according to standard methods. Diffraction images were processed and reduced using the data processing software XDS (Kabsch, W. *XDS. Acta Cryst.* D66, 125-132 (2010)). Models were generated using the molecular replacement technique with the program PHASER. The structure of human KLK7 (*Proc Natl Acad Sci USA* 104: 16086-16091 (2007)) and Fab antibody model were used as search models. The structures underwent iterative rounds of model adjustment using the program COOT and refinement using the PHENIX. Models were refined to acceptable R and R free values and Ramachandran statistics (calculated by Molprobity). Amino acid residue numbering for KLK7 was based on the chymotrypsin numbering system (*Proc Natl Acad Sci USA* 104: 16086-16091 (2007) for KLK7, PDB code 2QXI for reference; also referred to as "standard protease numbering").

The structure of the 14H11c Fab bound to human KLK7 is shown in FIGS. 20A-20B. The complete Fab bound to KLK7 is shown in FIG. 20A, with an overlay of KLK7 alone. FIG. 20B shows the KLK7-Fab interface.

Table 15 lists the 14H11c heavy chain amino acids and KLK7 amino acids involved in the Fab-KLK7 interface.

TABLE 15

Interface residues between 14H11c heavy chain and KLK7

| Interface residues in 14H11c Heavy Chain | Interface residues in KLK7 (Chymotrypsin numbering system) | Interface residues in KLK7 (sequential numbering of SEQ ID NO: 4) |
|---|---|---|
| Ser 49 | His 91 | His72 |
| Ser 50 | Ser 95 | Ser76 |
| Tyr 51 | Thr 96 | Thr77 |
| Tyr 52 | Gln 97 | Gln78 |
| Tyr 71 | Thr 98 | Thr79 |
| Ser 74 | Val 100 | Val81 |
| Ser 75 | Asn 101 | Asn82 |
| Ala 77 | Lys 173 | Lys152 |
| Tyr 79 | Leu 175 | Leu154 |
| Phe 120 | Leu 176 | Leu 155 |
| Glu 122 | Glu 177 | Glu156 |
| Thr 123 | Asn 178 | Asn157 |
| Gly 124 | Ser 179 | Ser158 |
| Gly 125 | Gln 230 | Gln209 |
| Tyr 126 | Cys 232 | Cys210 |
| Gly 127 | Lys 233 | Lys211 |
| Tyr 128 | Phe 234 | Phe212 |
|  | Thr 235 | Thr213 |
|  | Lys 236 | Lys214 |
|  | Trp 237 | Trp215 |
|  | Asp 240 | Asp218 |

Table 16 lists the 14H11c light chain amino acids and KLK7 amino acids involved in the Fab-KLK7 interface.

TABLE 16

Interface residues between 14H11c light chain and KLK7

| Interface residues in 14H11c Light Chain | Interface residues in KLK7 (Chymotrypsin numbering system) | Interface residues in KLK7 (sequential numbering of SEQ ID NO: 4) |
|---|---|---|
| Glu 49 | Arg 90 | Arg71 |
| Asp 50 | His 91 | His72 |
| Ile 51 | Pro 92 | Pro73 |
| Ala 52 | Gly 93 | Gly74 |
| Tyr 114 | Tyr 94 | Tyr75 |
| Tyr 116 | Ser 95 | Ser76 |
| Ser 117 | Thr 96 | Thr77 |
| Ser 118 | Gln 97 | Gln78 |
| Thr 119 | Val 100 | Val81 |
|  | Asn 101 | Asn82 |
|  | Trp 237 | Trp215 |
|  | Thr 241 | Thr219 |
|  | Lys 244 | Lys222 |

Table 17 lists the 14H11c heavy chain amino acids and KLK7 amino acids that form hydrogen bonds in the structure, and Table 18 lists the 14H11c heavy chain amino acids and KLK17 amino acids that form salt bridges.

TABLE 17

Hydrogen bonds between 14H11c heavy chain and KLK7

| Heavy Chain Residue | Bond Length (Angstrom) | KLK7 residue (Chymotrypsin numbering system) | KLK7 residue (sequential numbering of SEQ ID NO: 4) |
|---|---|---|---|
| Tyr 52 [OH] | 2.8 | Ser 95 [OG] | Ser76 [OG] |
| Ser 95 [O] | 3.8 | Gln 97 [NE2] | Gln78 [NE2] |
| Gly 125 [O] | 3.1 | Thr 235 [N] | Thr213 [N] |
| Gly 125 [O] | 3.9 | Thr 235 [OG1] | Thr213 [OG1] |

TABLE 17-continued

Hydrogen bonds between 14H11c heavy chain and KLK7

| Heavy Chain Residue | Bond Length (Angstrom) | KLK7 residue (Chymotrypsin numbering system) | KLK7 residue (sequential numbering of SEQ ID NO: 4) |
|---|---|---|---|
| Tyr 128 [O] | 3.7 | Asn 101 [ND2] | Asn82 [ND2] |
| Tyr 52 [OH] | 3.0 | Gln 97 [OE1] | Gln78 [OE1] |
| Ala 77 [N] | 3.7 | Gln 97 [OE1] | Gln78 [OE1] |
| Tyr 79 [OH] | 2.8 | Gln 97 [OE1] | Gln78 [OE1] |
| Tyr 126 [N] | 3.2 | Lys 233 [O] | Lys211 [O] |
| Gly 127 [N] | 2.9 | Lys 233 [O] | Lys211 [O] |
| Tyr 128 [N] | 2.9 | Asn 101 [OD1] | Asn82 [OD1] |
| Tyr 128 [OH] | 2.9 | Asn 178 [OD1] | Asn157 [OD1] |

TABLE 18

Salt bridges between 14H11c heavy chain and KLK7

| Heavy Chain Residue | Bond Length (Angstrom) | KLK7 residue (Chymotrypsin numbering system) | KLK7 residue (sequential numbering of SEQ ID NO: 4) |
|---|---|---|---|
| Glu 122 [OE1] | 3.2 | Lys 233 [NZ] | Lys211 [NZ] |
| Glu 122 [OE2] | 3.8 | Lys 233 [NZ] | Lys211 [NZ] |

Table 19 lists the 14H11c heavy chain amino acids and KLK7 amino acids that form hydrogen bonds in the structure.

TABLE 19

Hydrogen bonds between 14H11c light chain and KLK7

| Light Chain Residue | Bond Length (Angstrom) | KLK7 residue (Chymotrypsin numbering system) | KLK7 residue (sequential numbering of SEQ ID NO: 4) |
|---|---|---|---|
| Tyr 114 [OH] | 2.9 | His 91 [NE2] | His72 [NE2] |
| Tyr 116 [OH] | 3.1 | Gly 93 [O] | Gly74 [O] |
| Ser 117 [OG] | 2.9 | Pro 92 [O] | Pro73 [O] |
| Thr 119 [OG1] | 2.7 | Pro 92 [O] | Pro73 [O] |

Based on the crystal structure, anti-KLK7 antibody rb.14H11c binds a discontinuous epitope of KLK7, with an interface comprising regions R71-N82, K152-S158, and Q211-K222 of KLK7 (SEQ ID NO: 4). rb.14H11c forms hydrogen bonds and/or salt bridges with amino acids H72, P73, G74, S76, Q78, N82, N157, K211, and T213 of KLK7, as numbered according to SEQ ID NO: 4 (H91, P92, G93, S95, Q97, N101, N178, K233, and T235, by chymotrypsin numbering).

As shown in FIG. 20C, 14H11c Fab binding to the 170s loop of KLK7 (chymotrypsin numbering) results in concerted conformational changes in 170s loop, with most significant changes in the conformations of L176 (L155 in SEQ ID NO: 4) and D174 (D153 in SEQ ID NO: 4). L176, which is in a hydrophobic core of KLK7 in the native state, is facing the Fab (and is stabilized by interactions with Fab). Due to steric clash with the Fab, D174 moves into the region closer to substrate binding region, resulting in movement of Y172 (Y151 in SEQ ID NO: 4) and W215 (W192 in SEQ ID NO: 4), clashing with the 180s loop, resulting in unfolding of both 180s and 220s loops and a constriction of the substrate binding site. It is believed that these conformational changes results in inactivation of the KLK7 enzyme.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

IV. Table of Certain Sequences

| SEQ ID NO | Description | Sequence |
|---|---|---|
| 1 | Human KLK5 amino acid sequence (UniProtKB/Swiss-Prot: Q9Y337.3) | MATARPPWMW VLCALITALL LGVTEHVLAN NDVSCDHPSN TVPSGSNQDL GAGAGEDARS DDSSSRIING SDCDMHTQPW QAALLLRPNQ LYCGAVLVHP QWLLTAAHCR KKVFRVRLGH YSLSPVYESG QQMFQGVKSI PHPGYSHPGH SNDLMLIKLN RRIRPTKDVR PINVSSHCPS AGTKCLVSGW GTTKSPQVHF PKVLQCLNIS VLSQKRCEDA YPRQIDDTMF CAGDKAGRDS CQGDSGGPVV CNGSLQGLVS WGDYPCARPN RPGVYTNLCK FTKWIQETIQ ANS |
| 2 | Human mature KLK5 amino acid sequence (amino acids 67-293 of UniProtKB/Swiss-Prot: Q9Y337.3; signal is 1-22, propeptide is 23-66) | IINGSD CDMHTQPWQA ALLLRPNQLY CGAVLVHPQW LLTAAHCRKK VFRVRLGHYS LSPVYESGQQ MFQGVKSIPH PGYSHPGHSN DLMLIKLNRR IRPTKDVRPI NVSSHCPSAG TKCLVSGWGT TKSPQVHFPK VLQCLNISVL SQKRCEDAYP RQIDDTMFCA GDKAGRDSCQ GDSGGPVVCN GSLQGLVSWG DYPCARPNRP GVYTNLCKFT KWIQETIQAN S |
| 100 | Cynomolgus monkey KLK5 amino acid sequence (UniProtKB: A0A2K5W0T6) | MATARTPWMW VLCALITALL LGVTEHVLAN DDVSCDNPSN TVPSGSNRDV GAGDDARSDD SSSRIINGSD CDEHTQPWQA ALLLGPNQLY CGGVLVHPQW LLTAAHCRKK VFRVRLGHYS LSPVYESGQQ MFQGIKSIPH PGYSHPGHSN DLMLIKLNRR IHSTKDVRPI NVSSHCPSAG TKCLVSGWGT TRSPQVHFPK VLQCLNISVL SQKRCEDAYP RQIDDTMFCA GDEAGRDSCQ GDSGGPVVCN GSLQGLVSWG DYPCAKPNRP GVYTNLCKFT KWIQETIQAN S |

IV. Table of Certain Sequences

| SEQ ID NO | Description | Sequence |
|---|---|---|
| 101 | Cynomolgus monkey mature KLK5 amino acid sequence (amino acids 1-22 of UniProtKB: A0A2K5W0T6; signal is, propeptide is 23-64) | IINGSDCDEH TQPWQAALLL GPNQLYCGGV LVHPQWLLTA AHCRKKVFRV RLGHYSLSPV YESGQQMFQG IKSIPHPGYS HPGHSNDLML IKLNRRIHST KDVRPINVSS HCPSAGTKCL VSGWGTTRSP QVHFPKVLQC LNISVLSQKR CEDAYPRQID DTMFCAGDEA GRDSCQGDSG GPVVCNGSLQ GLVSWGDYPC AKPNRPGVYT NLCKFTKWIQ ETIQANS |
| 3 | Human KLK7 amino acid sequence (UniProtKB/Swiss-Prot: P49862.1) | MARSLLLPLQ ILLLSLALET AGEEAQGDKI IDGAPCARGS HPWQVALLSG NQLHCGGVLV NERWVLTAAH CKMNEYTVHL GSDTLGDRRA QRIKASKSFR HPGYSTQTHV NDLMLVKLNS QARLSSMVKK VRLPSRCEPP GTTCTVSGWG TTTSPDVTFP SDLMCVDVKL ISPQDCTKVY KDLLENSMLC AGIPDSKKNA CNGDSGGPLV CRGTLQGLVS WGTFPCGQPN DPGVYTQVCK FTKWINDTMK KHR |
| 4 | Human mature KLK7 amino acid sequence (amino acids 30-253 of UniProtKB/Swiss-Prot: P49862.1; signal is 1-22, propeptide is 23-29) | IIDGAPCARG SHPWQVALLS GNQLHCGGVL VNERWVLTAA HCKMNEYTVH LGSDTLGDRR AQRIKASKSF RHPGYSTQTH VNDLMLVKLN SQARLSSMVK KVRLPSRCEP PGTTCTVSGW GTTTSPDVTF PSDLMCVDVK LISPQDCTKV YKDLLENSML CAGIPDSKKN ACNGDSGGPL VCRGTLQGLV SWGTFPCGQP NDPGVYTQVC KFTKWINDTM KKHR |
| 5 | Cynomolgus monkey KLK7 amino acid sequence (UniProtKB: G7PYG2) | MAGSLLLPLQ ILLLSLALGT AGQEAQGDKI IDGAPCTRGS HPWQVALLSG NQLHCGGVLV NERWVLTAAH CKMNDYTVHL GSDTLGDRKA QRIKASRSFR HPGYSTQTHV NDLMLVKLNS PARLSSTVKK VRLPSRCEPP GTTCTVSGWG TTTSPDVTFP SDLMCVDVKL ISSQDCTKVY KDLMGNSMLC AGIPNSKKNA CNGDSGGPLV CRGTLQGLVS WGTFPCGQPN DPGVYTQVCK FTKWINDTIK KHR |
| 6 | Cynomolgus monkey mature KLK7 amino acid sequence (amino acids 30-253 of UniProtKB: G7PYG2; signal is 1-21, propeptide is 22-29) | I IDGAPCTRGS HPWQVALLSG NQLHCGGVLV NERWVLTAAH CKMNDYTVHL GSDTLGDRKA QRIKASRSFR HPGYSTQTHV NDLMLVKLNS PARLSSTVKK VRLPSRCEPP GTTCTVSGWG TTTSPDVTFP SDLMCVDVKL ISSQDCTKVY KDLMGNSMLC AGIPNSKKNA CNGDSGGPLV CRGTLQGLVS WGTFPCGQPN DPGVYTQVCK FTKWINDTIK KHR |
| 7 | rb.14H11c CDRH1 hu.14H11c.V3-53*1.H1 CDRH1 hu.14H11c.V3-53*1.H2 CDRH1 hu.14H11c.V3-53*1.H3 CDRH1 hu.14H11c.V3-53*1.H4 CDRH1 hu.14H11c.V3-53*1.H5 CDRH1 hu.14H11c.V3-53*1.H6 CDRH1 hu.14H11c.V3-53*1.H7 CDRH1 hu.14H11c.V3-53*1.H8 CDRH1 hu.14H11c.V3-53*1.H9 CDRH1 hu.14H11c.V3-53*1.H10 CDRH1 hu.14H11c.V3-53*4.H1 CDRH1 hu.14H11c.V3-23.H1 CDRH1 hu.14H11c.V3-33*2.H1 CDRH1 hu.14H11c.V3-21.H1 CDRH1 hu.14H11c-H11 CDRH1 hu.14H11c-H11.Q39E CDRH1 | SSYYMS |
| 8 | rb.14H11c CDRH2 hu.14H11c.V3-53*1.H1 CDRH2 hu.14H11c.V3-53*1.H2 CDRH2 hu.14H11c.V3-53*1.H3 | SIYAGSSGAPYYAGWAKG |

IV. Table of Certain Sequences

| SEQ ID NO | Description | Sequence |
|---|---|---|
| | CDRH2 hu.14H11c.V3-53*1.H4 | |
| | CDRH2 hu.14H11c.V3-53*1.H5 | |
| | CDRH2 hu.14H11c.V3-53*1.H6 | |
| | CDRH2 hu.14H11c.V3-53*1.H7 | |
| | CDRH2 hu.14H11c.V3-53*1.H8 | |
| | CDRH2 hu.14H11c.V3-53*1.H9 | |
| | CDRH2 hu.14H11c.V3-53*1.H10 | |
| | CDRH2 hu.14H11c.V3-53*4.H1 | |
| | CDRH2 hu.14H11c.V3-23.H1 CDRH2 | |
| | hu.14H11c.V3-33*2.H1 CDRH2 | |
| | hu.14H11c.V3-21.H1 CDRH2 | |
| | hu.14H11c-H11 CDRH2 | |
| | hu.14H11c-H11.Q39E CDRH2 | |
| 9 | rb.14H11c CDRH3 hu.14H11c.V3-53*1.H1 CDRH3 hu.14H11c.V3-53*1.H2 CDRH3 hu.14H11c.V3-53*1.H3 CDRH3 hu.14H11c.V3-53*1.H4 CDRH3 hu.14H11c.V3-53*1.H5 CDRH3 hu.14H11c.V3-53*1.H6 CDRH3 hu.14H11c.V3-53*1.H7 CDRH3 hu.14H11c.V3-53*1.H8 CDRH3 hu.14H11c.V3-53*1.H9 CDRH3 hu.14H11c.V3-53*1.H10 CDRH3 hu.14H11c.V3-53*4.H1 CDRH3 hu.14H11c.V3-23.H1 CDRH3 hu.14H11c.V3-33*2.H1 CDRH3 hu.14H11c.V3-21.H1 CDRH3 hu.14H11c-H11 CDRH3 hu.14H11c-H11.Q39E CDRH3 | EGFAETGGYGYAAYFNL |
| 10 | rb.14H11c CDRL1 hu.14H11c.K1-39.L1 CDRL1 hu.14H11c.K1-39.L2 CDRL1 hu.14H11c.K1-39.L3 CDRL1 hu.14H11c.K1-39.L4 CDRL1 hu.14H11c.K1-5.L1 CDRL1 hu.14H11c.K1-8.L1 CDRL1 hu.14H11c.K1-6.L1 CDRL1 hu.14H11c-L2.Q38K CDRL1 | LASEDIASSVS |
| 11 | rb.14H11c CDRL2 hu.14H11c.K1-39.L1 CDRL2 hu.14H11c.K1-39.L2 CDRL2 hu.14H11c.K1-39.L3 CDRL2 hu.14H11c.K1-39.L4 CDRL2 hu.14H11c.K1-5.L1 CDRL2 hu.14H11c.K1-8.L1 CDRL2 hu.14H11c.K1-6.L1 CDRL2 hu.14H11c-L2.Q38K CDRL2 | GASNLES |

IV. Table of Certain Sequences

| SEQ ID NO | Description | Sequence |
|---|---|---|
| 12 | rb.14H11c CDRL3<br>hu.14H11c.K1-39.L1 CDRL3<br>hu.14H11c.K1-39.L2 CDRL3<br>hu.14H11c.K1-39.L3 CDRL3<br>hu.14H11c.K1-39.L4 CDRL3<br>hu.14H11c.K1-5.L1 CDRL3<br>hu.14H11c.K1-8.L1 CDRL3<br>hu.14H11c.K1-6.L1 CDRL3<br>hu.14H11c-L2.Q38K CDRL3 | LGGYSYSSTGTA |
| 122 | rb.14H11c VH FR1 | QSLEESGGDLVKPGASLTLTCTASGFSFS |
| 123 | hu.14H11c.V3-53*1.H1 VH FR1<br>hu.14H11c.V3-53*1.H3 VH FR1<br>hu.14H11c.V3-53*1.H4 VH FR1<br>hu.14H11c.V3-53*1.H5 VH FR1<br>hu.14H11c.V3-53*1.H6 VH FR1<br>hu.14H11c.V3-53*1.H7 VH FR1<br>hu.14H11c.V3-53*1.H8 VH FR1<br>hu.14H11c.V3-53*1.H9 VH FR1<br>hu.14H11c-H11 VH FR1<br>hu.14H11c-H11.Q39E VH FR1 | EQQLVESGGGLIQPGGSLRLSCAASGFSFS |
| 124 | hu.14H11c.V3-53*1.H2 VH FR1<br>hu.14H11c.V3-53*1.H10 VH FR1 | EVQLVESGGGLIQPGGSLRLSCAASGFSFS |
| 125 | hu.14H11c.V3-53*4.H1 VH FR1 | EQQLVESGGGLVQPGGSLRLSCAASGFSFS |
| 126 | hu.14H11c.V3-23.H1 VH FR1 | EQQLLESGGGLVQPGGSLRLSCAASGFSFS |
| 127 | hu.14H11c.V3-33*2.H1 VH FR1 | EQQLVESGGGVVQPGRSLRLSCAASGFSFS |
| 128 | hu.14H11c.V3-21.H1 VH FR1 | EQQLVESGGGLVKPGGSLRLSCAASGFSFS |
| 129 | rb.14H11c VH FR2<br>hu.14H11c.V3-53*1.H1 VH FR2<br>hu.14H11c.V3-53*1.H2 VH FR2<br>hu.14H11c.V3-53*1.H5 VH FR2<br>hu.14H11c.V3-53*1.H6 VH FR2<br>hu.14H11c.V3-53*1.H7 VH FR2<br>hu.14H11c.V3-53*1.H8 VH FR2<br>hu.14H11c.V3-53*1.H9 VH FR2<br>hu.14H11c.V3-53*4.H1 VH FR2<br>hu.14H11c.V3-23.H1 VH FR2<br>hu.14H11c.V3-33*2.H1 VH FR2<br>hu.14H11c.V3-21.H1 VH FR2 | WVRQAPGKGLEWIA |
| 130 | hu.14H11c.V3-53*1.H3 VH FR2 | WVRQAPGKGLEWVA |
| 131 | hu.14H11c.V3-53*1.H4 VH FR2 | WVRQAPGKGLEWIS |
| 132 | hu.14H11c.V3-53*1.H10 VH FR2<br>hu.14H11c-H11 VH FR2 | WVRQAPGKGLEWVS |
| 133 | hu.14H11c-H11.Q39E VH FR2 | WVREAPGKGLEWVS |
| 134 | rb.14H11c VH FR3 | RFTISKTSSTAVTLQMSSLTAADTATYFCAR |
| 135 | hu.14H11c.V3-53*1.H1 VH FR3<br>hu.14H11c.V3-53*1.H2 VH FR3<br>hu.14H11c.V3-53*1.H3 VH FR3<br>hu.14H11c.V3-53*1.H4 VH FR3<br>hu.14H11c.V3-53*1.H9 VH FR3 | RFTISKDSSKNTVYLQMNSLRAEDTAVYFCAR |

| | IV. Table of Certain Sequences | |
|---|---|---|
| SEQ ID NO | Description | Sequence |
| | hu.14H11c.V3-23.H1 VH FR3 | |
| 136 | hu.14H11c.V3-53*1.H5 VH FR3 | RFTISRDSSKNTVYLQMNSLRAEDTAVYFCAR |
| 137 | hu.14H11c.V3-53*1.H6 VH FR3 | RFTISKDNSKNTVYLQMNSLRAEDTAVYFCAR |
| 138 | hu.14H11c.V3-53*1.H7 VH FR3 | RFTISKDSSKNTLYLQMNSLRAEDTAVYFCAR |
| 139 | hu.14H11c.V3-53*1.H8 VH FR3 | RFTISKDSSKNTVYLQMNSLRAEDTAVYYCAR |
| 140 | hu.14H11c.V3-53*1.H10 VH FR3<br>hu.14H11c-H11 VH FR3<br>hu.14H11c-H11.Q39E VH FR3 | RFTISRDNSKNTLYLQMNSLRAEDTAVYYCAR |
| 141 | hu.14H11c.V3-53*4.H1 VH FR3 | RFTISKHSSKNTVYLQMNSLRAEDTAVYFCAR |
| 142 | hu.14H11c.V3-33*2.H1 VH FR3 | RFTISKDSSTNTVFLQMNSLRAEDTAVYFCAR |
| 143 | hu.14H11c.V3-21.H1 VH FR3 | RFTISKDTASTSVYLQMNSLRAEDTAVYFCAR |
| 144 | rb.14H11c VH FR4<br>hu.14H11c.V3-53*1.H1 VH FR4<br>hu.14H11c.V3-53*1.H2 VH FR4<br>hu.14H11c.V3-53*1.H3 VH FR4<br>hu.14H11c.V3-53*1.H4 VH FR4<br>hu.14H11c.V3-53*1.H5 VH FR4<br>hu.14H11c.V3-53*1.H6 VH FR4<br>hu.14H11c.V3-53*1.H7 VH FR4<br>hu.14H11c.V3-53*1.H8 VH FR4<br>hu.14H11c.V3-53*4.H1 VH FR4<br>hu.14H11c.V3-23.H1 VH FR4<br>hu.14H11c.V3-33*2.H1 VH FR4<br>hu.14H11c.V3-21.H1 VH FR4<br>hu.14H11c-H11 VH FR4<br>hu.14H11c-H11.Q39E VH FR4 | WGPGTLVTVSS |
| 145 | hu.14H11c.V3-53*1.H9 VH FR4<br>hu.14H11c.V3-53*1.H10 VH FR4 | WGQGTLVTVSS |
| 146 | rb.14H11c VL FR1 | AIEMTQSPPSLSASVGETVRIRC |
| 147 | hu.14H11c.K1-39.L1 VL FR1<br>hu.14H11c.K1-39.L2 VL FR1<br>hu.14H11c.K1-39.L3 VL FR1<br>hu.14H11c.K1-39.L4 VL FR1<br>hu.14H11c-L2.Q38K VL FR1 | DIQMTQSPSSLSASVGDRVTITC |
| 148 | hu.14H11c.K1-5.L1 VL FR1 | DIQMTQSPSTLSASVGDRVTITC |
| 149 | hu.14H11c.K1-8.L1 VL FR1 | AIRMTQSPSSFSASTGDRVTITC |
| 150 | hu.14H11c.K1-6.L1 VL FR1 | AIQMTQSPSSLSASVGDRVTITC |
| 151 | rb.14H11c VL FR2 | WYQQKPGKPPTLLIY |
| 152 | hu.14H11c.K1-39.L1 VL FR2<br>hu.14H11c.K1-39.L3 VL FR2<br>hu.14H11c.K1-5.L1 VL FR2<br>hu.14H11c.K1-8.L1 VL FR2<br>hu.14H11c.K1-6.L1 VL FR2 | WYQQKPGKPPKLLIY |
| 153 | hu.14H11c.K1-39.L2 VL FR2<br>hu.14H11c.K1-39.L4 VL FR2 | WYQQKPGKAPKLLIY |
| 154 | hu.14H11c-L2.Q38K VL FR2 | WYQKKPGKAPKLLIY |
| 155 | rb.14H11c VL FR3 | GVPPRFTGSGSGTDYTLTIGGVQAEDAATYYC |
| 156 | hu.14H11c.K1-39.L1 VL FR3<br>hu.14H11c.K1-39.L2 VL FR3<br>hu.14H11c.K1-8.L1 VL FR3<br>hu.14H11c.K1-6.L1 VL FR3<br>hu.14H11c-L2.Q38K VL FR3 | GVPSRFSGSGSGTDYTLTISSLQPEDFATYYC |

-continued

IV. Table of Certain Sequences

| SEQ ID NO | Description | Sequence |
|---|---|---|
| 157 | hu.14H11c.K1-39.L3 VL FR3<br>hu.14H11c.K1-39.L4 VL FR3 | GVPSRFSGSGSGTDFTLTISSLQPEDFATYYC |
| 158 | hu.14H11c.K1-5.L1 VL FR3 | GVPSRFSGSGSGTEYTLTISSLQPDDFATYYC |
| 159 | rb.14H11c VL FR4 | FGAGTKVEIK |
| 160 | hu.14H11c.K1-39.L1 VL FR4<br>hu.14H11c.K1-39.L2 VL FR4<br>hu.14H11c.K1-39.L3 VL FR4<br>hu.14H11c.K1-39.L4 VL FR4<br>hu.14H11c.K1-5.L1 VL FR4<br>hu.14H11c.K1-8.L1 VL FR4<br>hu.14H11c.K1-6.L1 VL FR4<br>hu.14H11c-L2.Q38K VL FR4 | FGGGTKVEIK |
| 116 | rb.14H11 Heavy Chain Variable Region (VH) | QSLEESGGDL VKPGASLTLT CTASGFSFSS SYYMCWVRQA PGKGLEWIAS IYAGSSGAPY YAGWAKGRFT ISKTSSTAVT LQMSSLTAAD TATYFCAREG FAETGGYGYA AYFNLWGPGT LVTVSS |
| 13 | rb.14H11c Heavy Chain Variable Region (VH) | QSLEESGGDL VKPGASLTLT CTASGFSFSS SYYMSWVRQA PGKGLEWIAS IYAGSSGAPY YAGWAKGRFT ISKTSSTAVT LQMSSLTAAD TATYFCAREG FAETGGYGYA AYFNLWGPGT LVTVSS |
| 14 | rb.14H11c Light Chain Variable Region (VL)<br>rb.14H11 VL | AIEMTQSPPS LSASVGETVR IRCLASEDIA SSVSWYQQKP GKPPTLLIYG ASNLESGVPP RFTGSGSGTD YTLTIGGVQA EDAATYYCLG GYSYSSTGTA FGAGTKVEIK |
| 198 | rb.14H11c Heavy Chain Fab (amino acids 20-256, when numbered beginning with signal sequence) | QSLEESGGDL VKPGASLTLT CTASGFSFSS SYYMSWVRQA PGKGLEWIAS IYAGSSGAPY YAGWAKGRFT ISKTSSTAVT LQMSSLTAAD TATYFCAREG FAETGGYGYA AYFNLWGPGT LVTVSSGQPK APSVFPLAPC CGDTPSSTVT LGCLVKGYLP EPVTVTWNSG TLTNGVRTFP SVRQSSGLYS LSSVVSVTSS SQPVTCNVAH PATNTKVDKT VAPSTCSKPT HHHHHHP |
| 199 | rb.14H11c Light Chain Fab (amino acids 23-237, when numbered beginning with signal sequence) | AIEMTQSPPS LSASVGETVR IRCLASEDIA NSVSWYQQKP GKPPTLLIYG ASNLESGVPP RFTGSGSGTD YTLTIGGVQA EDAATYYCLG GYSYSSTGTA FGAGTKVEIN RDPVAPSVLL FPPSKEELTT GTATIVCVAN KFYPSDITVT WKVDGTTQQS GIENSKTPQS PEDNTYNLSS TLTLTSTQYN SHKEYTCKVT QGTTSVVQSF NRGDC |
| 15 | hu.14H11c.V3-53*1.H1 VH | EQQLVESGGG LIQPGGSLRL SCAASGFSFS SSYYMSWVRQ APGKGLEWIA SIYAGSSGAP YYAGWAKGRF TISKDSSKNT VYLQMNSLRA EDTAVYFCAR EGFAETGGYG YAAYFNLWGP GTLVTVSS |
| 16 | hu.14H11c.V3-53*1.H2 VH | EVQLVESGGG LIQPGGSLRL SCAASGFSFS SSYYMSWVRQ APGKGLEWIA SIYAGSSGAP YYAGWAKGRF TISKDSSKNT VYLQMNSLRA EDTAVYFCAR EGFAETGGYG YAAYFNLWGP GTLVTVSS |
| 17 | hu.14H11c.V3-53*1.H3 VH | EQQLVESGGG LIQPGGSLRL SCAASGFSFS SSYYMSWVRQ APGKGLEWVA SIYAGSSGAP YYAGWAKGRF TISKDSSKNT VYLQMNSLRA EDTAVYFCAR EGFAETGGYG YAAYFNLWGP GTLVTVSS |
| 18 | hu.14H11c.V3-53*1.H4 VH | EQQLVESGGG LIQPGGSLRL SCAASGFSFS SSYYMSWVRQ APGKGLEWIS SIYAGSSGAP YYAGWAKGRF TISKDSSKNT VYLQMNSLRA EDTAVYFCAR EGFAETGGYG YAAYFNLWGP GTLVTVSS |
| 19 | hu.14H11c.V3-53*1.H5 VH | EQQLVESGGG LIQPGGSLRL SCAASGFSFS SSYYMSWVRQ APGKGLEWIA SIYAGSSGAP YYAGWAKGRF TISRDSSKNT VYLQMNSLRA EDTAVYFCAR EGFAETGGYG YAAYFNLWGP GTLVTVSS |
| 20 | hu.14H11c.V3-53*1.H6 VH | EQQLVESGGG LIQPGGSLRL SCAASGFSFS SSYYMSWVRQ APGKGLEWIA SIYAGSSGAP YYAGWAKGRF TISKDNSKNT VYLQMNSLRA EDTAVYFCAR EGFAETGGYG YAAYFNLWGP GTLVTVSS |

IV. Table of Certain Sequences

| SEQ ID NO | Description | Sequence |
|---|---|---|
| 21 | hu.14H11c.V3-53*1.H7 VH | EQQLVESGGG LIQPGGSLRL SCAASGFSFS SSYYMSWVRQ APGKGLEWIA SIYAGSSGAP YYAGWAKGRF TISKDSSKNT LYLQMNSLRA EDTAVYFCAR EGFAETGGYG YAAYFNLWGP GTLVTVSS |
| 22 | hu.14H11c.V3-53*1.H8 VH | EQQLVESGGG LIQPGGSLRL SCAASGFSFS SSYYMSWVRQ APGKGLEWIA SIYAGSSGAP YYAGWAKGRF TISKDSSKNT VYLQMNSLRA EDTAVYYCAR EGFAETGGYG YAAYFNLWGP GTLVTVSS |
| 23 | hu.14H11c.V3-53*1.H9 VH | EQQLVESGGG LIQPGGSLRL SCAASGFSFS SSYYMSWVRQ APGKGLEWIA SIYAGSSGAP YYAGWAKGRF TISKDSSKNT VYLQMNSLRA EDTAVYFCAR EGFAETGGYG YAAYFNLWGQ GTLVTVSS |
| 24 | hu.14H11c.V3-53*1.H10 VH | EVQLVESGGG LIQPGGSLRL SCAASGFSFS SSYYMSWVRQ APGKGLEWVS SIYAGSSGAP YYAGWAKGRF TISRDNSKNT LYLQMNSLRA EDTAVYYCAR EGFAETGGYG YAAYFNLWGQ GTLVTVSS |
| 25 | hu.14H11c.V3-53*4.H1 VH | EQQLVESGGG LVQPGGSLRL SCAASGFSFS SSYYMSWVRQ APGKGLEWIA SIYAGSSGAP YYAGWAKGRF TISKHSSKNT VYLQMNSLRA EDTAVYFCAR EGFAETGGYG YAAYFNLWGP GTLVTVSS |
| 26 | hu.14H11c.V3-23.H1 VH | EQQLLESGGG LVQPGGSLRL SCAASGFSFS SSYYMSWVRQ APGKGLEWIA SIYAGSSGAP YYAGWAKGRF TISKDSSKNT VYLQMNSLRA EDTAVYFCAR EGFAETGGYG YAAYFNLWGP GTLVTVSS |
| 27 | hu.14H11c.V3-33*2.H1 VH | EQQLVESGGG VVQPGRSLRL SCAASGFSFS SSYYMSWVRQ APGKGLEWIA SIYAGSSGAP YYAGWAKGRF TISKDSSTNT VFLQMNSLRA EDTAVYFCAR EGFAETGGYG YAAYFNLWGP GTLVTVSS |
| 28 | hu.14H11c.V3-21.H1 VH | EQQLVESGGG LVKPGGSLRL SCAASGFSFS SSYYMSWVRQ APGKGLEWIA SIYAGSSGAP YYAGWAKGRF TISKDTASTS VYLQMNSLRA EDTAVYFCAR EGFAETGGYG YAAYFNLWGP GTLVTVSS |
| 29 | hu.14H11c-H11 VH | EQQLVESGGG LIQPGGSLRL SCAASGFSFS SSYYMSWVRQ APGKGLEWVS SIYAGSSGAP YYAGWAKGRF TISRDNSKNT LYLQMNSLRA EDTAVYYCAR EGFAETGGYG YAAYFNLWGP GTLVTVSS |
| 30 | hu.14H11c-H11.Q39E VH | EQQLVESGGG LIQPGGSLRL SCAASGFSFS SSYYMSWVRE APGKGLEWVS SIYAGSSGAP YYAGWAKGRF TISRDNSKNT LYLQMNSLRA EDTAVYYCAR EGFAETGGYG YAAYFNLWGP GTLVTVSS |
| 31 | hu.14H11c.K1-39.L1 VL | DIQMTQSPSS LSASVGDRVT ITCLASEDIA SSVSWYQQKP GKPPKLLIYG ASNLESGVPS RFSGSGSGTD YTLTISSLQP EDFATYYCLG GYSYSSTGTA FGGGTKVEIK |
| 32 | hu.14H11c.K1-39.L2 VL | DIQMTQSPSS LSASVGDRVT ITCLASEDIA SSVSWYQQKP GKAPKLLIYG ASNLESGVPS RFSGSGSGTD YTLTISSLQP EDFATYYCLG GYSYSSTGTA FGGGTKVEIK |
| 33 | hu.14H11c.K1-39.L3 VL | DIQMTQSPSS LSASVGDRVT ITCLASEDIA SSVSWYQQKP GKPPKLLIYG ASNLESGVPS RFSGSGSGTD FTLTISSLQP EDFATYYCLG GYSYSSTGTA FGGGTKVEIK |
| 34 | hu.14H11c.K1-39.L4 VL | DIQMTQSPSS LSASVGDRVT ITCLASEDIA SSVSWYQQKP GKAPKLLIYG ASNLESGVPS RFSGSGSGTD FTLTISSLQP EDFATYYCLG GYSYSSTGTA FGGGTKVEIK |
| 35 | hu.14H11c.K1-5.L1 VL | DIQMTQSPST LSASVGDRVT ITCLASEDIA SSVSWYQQKP GKPPKLLIYG ASNLESGVPS RFSGSGSGTE YTLTISSLQP DDFATYYCLG GYSYSSTGTA FGGGTKVEIK |
| 36 | hu.14H11c.K1-8.L1 VL | AIRMTQSPSS FSASTGDRVT ITCLASEDIA SSVSWYQQKP GKPPKLLIYG ASNLESGVPS RFSGSGSGTD YTLTISSLQP EDFATYYCLG GYSYSSTGTA FGGGTKVEIK |

-continued

| IV. Table of Certain Sequences | | |
|---|---|---|
| SEQ ID NO | Description | Sequence |
| 37 | hu.14H11c.K1-6.L1 VL | AIQMTQSPSS LSASVGDRVT ITCLASEDIA SSVSWYQQKP GKPPKLLIYG ASNLESGVPS RFSGSGSGTD YTLTISSLQP EDFATYYCLG GYSYSSTGTA FGGGTKVEIK |
| 38 | hu.14H11c-L2.Q38K VL | DIQMTQSPSS LSASVGDRVT ITCLASEDIA SSVSWYQKKP GKAPKLLIYG ASNLESGVPS RFSGSGSGTD YTLTISSLQP EDFATYYCLG GYSYSSTGTA FGGGTKVEIK |
| 39 | hu.10C5-H28L5 CDRH1<br>hu.10C5-H28.N53V CDRH1<br>hu.10C5-H28.Q39K.N53V CDRH1 | SYGVT |
| 107 | hu.10C5-H28.G33P CDRH1<br>hu.10C5-H28.G33P.N53V CDRH1 | SYPVT |
| 40 | hu.10C5-H28L5 CDRH2<br>hu.10C5-H28.G33P CDRH2 | YITSNYGVSYYASWAKS |
| 41 | hu.10C5-H28.N53V CDRH2<br>hu.10C5-H28.Q39K.N53V CDRH2<br>hu.10C5-H28.G33P.N53V CDRH2 | YITSVYGVSYYASWAKS |
| 42 | hu.10C5-H28L5 CDRH3<br>hu.10C5-H28.N53V CDRH3<br>hu.10C5-H28.Q39K.N53V CDRH3<br>hu.10C5-H28.G33P CDRH3<br>hu.10C5-H28.G33P.N53V CDRH3 | ENPDYGYAYDA |
| 43 | hu.10C5-H28L5 CDRL1<br>hu.10C5-L5.F92Y CDRL1<br>hu.10C5-L5.S95F CDRL1<br>hu.10C5-L5.F92Y.S95F CDRL1<br>hu.10C5-L5.Q38E.F92Y CDRL1<br>hu.10C5-L5.Q38E.S95F CDRL1<br>hu.10C5-L5.Q38E.F92Y.S95F CDRL1 | QASESISNELS |
| 44 | hu.10C5-L5.S34K CDRL1<br>hu.10C5-L5.S34K.F92Y CDRL1<br>hu.10C5-L5.S34K.S95F CDRL1<br>hu.10C5-L5.S34K.F92Y.S95F CDRL1<br>hu.10C5-L5.Q38E.S34K CDRL1<br>hu.10C5-L5.Q38E.S34K.F92Y CDRL1<br>hu.10C5-L5.Q38E.S34K.S95F CDRL1<br>hu.10C5-L5.Q38E.S34K.F92Y.S95F CDRL1 | QASESISNELK |
| 45 | hu.10C5-H28L5 CDRL2<br>hu.10C5-L5.S34K CDRL2<br>hu.10C5-L5.F92Y CDRL2<br>hu.10C5-L5.S95F CDRL2<br>hu.10C5-L5.S34K.F92Y CDRL2<br>hu.10C5-L5.S34K.S95F CDRL2<br>hu.10C5-L5.F92Y.S95F CDRL2<br>hu.10C5-L5.S34K.F92Y.S95F CDRL2<br>hu.10C5-L5.Q38E.S34K CDRL2<br>hu.10C5-L5.Q38E.F92Y | YASTLAS |

-continued

| SEQ ID NO | Description | Sequence |
|---|---|---|
| | CDRL2 hu.10C5-L5.Q38E.S95F CDRL2 hu.10C5-L5.Q38E.S34K.F92Y CDRL2 hu.10C5-L5.Q38E.S34K.S95F CDRL2 hu.10C5-L5.Q38E.F92Y.S95F CDRL2 hu.10C5-L5.Q38E.S34K.F92Y.S95F CDRL2 | |
| 46 | hu.10C5-H28L5 CDRL3 hu.10C5-L5.S34K CDRL3 hu.10C5-L5.Q38E.S34K CDRL3 | AQGFGSSGVENV |
| 47 | hu.10C5-L5.F92Y CDRL3 hu.10C5-L5.S34K.F92Y CDRL3 hu.10C5-L5.Q38E.F92Y CDRL3 hu.10C5-L5.Q38E.S34K.F92Y CDRL3 | AQGYGSSGVENV |
| 48 | hu.10C5-L5.S95F CDRL3 hu.10C5-L5.S34K.S95F CDRL3 hu.10C5-L5.Q38E.S95F CDRL3 hu.10C5-L5.Q38E.S34K.S95F CDRL3 | AQGFGSFGVENV |
| 49 | hu.10C5-L5.F92Y.S95F CDRL3 10C5-L5.S34K.F92Y.S95F CDRL3 hu.10C5-L5.Q38E.F92Y.S95F CDRL3 hu.10C5-L5.Q38E.S34K.F92Y.S95F CDRL3 | AQGYGSFGVENV |
| 161 | hu.10C5-H28L5 VH FR1 hu.10C5-H28.G33P VH FR1 hu.10C5-H28.N54V VH FR1 hu.10C5-H28.G33P.N54V VH FR1 hu.10C5-H28.Q39K.N54V VH FR1 | EVQLVESGGGLVQPGGSLRLSCAASGFSLS |
| 162 | hu.10C5-H28L5 VH FR2 hu.10C5-H28.G33P VH FR2 hu.10C5-H28.N54V VH FR2 hu.10C5-H28.G33P.N54V VH FR2 | WVRQAPGKGLEWIG |
| 163 | hu.10C5-H28.Q39K.N54V VH FR2 | WVRKAPGKGLEWIG |
| 164 | hu.10C5-H28L5 VH FR3 hu.10C5-H28.G33P VH FR3 hu.10C5-H28.N54V VH FR3 hu.10C5-H28.G33P.N54V VH FR3 hu.10C5-H28.Q39K.N54V VH FR3 | RSTISRDTSKNTVYLQMGSLRAEDMAVYYCAR |
| 165 | hu.10C5-H28L5 VH FR4 hu.10C5-H28.G33P VH FR4 hu.10C5-H28.N54V VH FR4 hu.10C5-H28.G33P.N54V VH FR4 hu.10C5-H28.Q39K.N54V VH FR4 | WGQGTTVTVSS |

| SEQ ID NO | Description | Sequence |
|---|---|---|
| 166 | hu.10C5-H28L5 VL FR1<br>hu.10C5-L5.S34K VL FR1<br>hu.10C5-L5.F92Y VL FR1<br>hu.10C5-L5.S95F VL FR1<br>hu.10C5-L5.S34.KF92Y VL FR1<br>hu.10C5-L5.S34K.S95F VL FR1<br>hu.10C5-L5.F92Y.S95F VL FR1<br>hu.10C5-L5.S34K.F92Y.S95F VL FR1<br>hu.10C5-L5.Q38E.S34K VL FR1<br>hu.10C5-L5.Q38E.F92Y VL FR1<br>hu.10C5-L5.Q38E.S95F VL FR1<br>hu.10C5-L5.Q38E.S34K.F92Y VL FR1<br>hu.10C5-L5.Q38E.S34K.S95F VL FR1<br>hu.10C5-L5.Q38E.F92Y.S95F VL FR1<br>hu.10C5-L5.Q38E.S34K.F92Y.S95F VL FR1 | AIRMTQSPSSFSASTGDRVTITC |
| 167 | hu.10C5-H28L5 VL FR2<br>hu.10C5-L5.S34K VL FR2<br>hu.10C5-L5.F92Y VL FR2<br>hu.10C5-L5.S95F VL FR2<br>hu.10C5-L5.S34.KF92Y VL FR2<br>hu.10C5-L5.S34K.S95F VL FR2<br>hu.10C5-L5.F92Y.S95F VL FR2<br>hu.10C5-L5.S34K.F92Y.S95F VL FR2 | WYQQKPGKAPKLLIY |
| 168 | hu.10C5-L5.Q38E.S34K VL FR2<br>hu.10C5-L5.Q38E.F92Y VL FR2<br>hu.10C5-L5.Q38E.S95F VL FR2<br>hu.10C5-L5.Q38E.S34K.F92Y VL FR2<br>hu.10C5-L5.Q38E.S34K.S95F VL FR2<br>hu.10C5-L5.Q38E.F92Y.S95F VL FR2<br>hu.10C5-L5.Q38E.S34K.F92Y.S95F VL FR2 | WYQEKPGKAPKLLIY |
| 169 | hu.10C5-H28L5 VL FR3<br>hu.10C5-L5.S34K VL FR3<br>hu.10C5-L5.F92Y VL FR3<br>hu.10C5-L5.S95F VL FR3<br>hu.10C5-L5.S34.KF92Y VL FR3<br>hu.10C5-L5.S34K.S95F VL FR3<br>hu.10C5-L5.F92Y.S95F VL FR3<br>hu.10C5-L5.S34K.F92Y.S95F VL FR3<br>hu.10C5-L5.Q38E.S34K VL FR3<br>hu.10C5-L5.Q38E.F92Y VL FR3<br>hu.10C5-L5.Q38E.S95F VL | GVPSRFSGSGSGTDFTLTISSLQPEDFATYYC |

IV. Table of Certain Sequences

| SEQ ID NO | Description | Sequence |
|---|---|---|
| | FR3 hu.10C5-L5.Q38E.S34K.F92Y VL FR3 hu.10C5-L5.Q38E.S34K.S95F VL FR3 hu.10C5-L5.Q38E.F92Y.S95F VL FR3 hu.10C5-L5.Q38E.S34K.F92Y.S95F VL FR3 | |
| 170 | hu.10C5-H28L5 VL FR4 hu.10C5-L5.S34K VL FR4 hu.10C5-L5.F92Y VL FR4 hu.10C5-L5.S95F VL FR4 hu.10C5-L5.S34.KF92Y VL FR4 hu.10C5-L5.S34K.S95F VL FR4 hu.10C5-L5.F92Y.S95F VL FR4 hu.10C5-L5.S34K.F92Y.S95F VL FR4 hu.10C5-L5.Q38E.S34K VL FR4 hu.10C5-L5.Q38E.F92Y VL FR4 hu.10C5-L5.Q38E.S95F VL FR4 hu.10C5-L5.Q38E.S34K.F92Y VL FR4 hu.10C5-L5.Q38E.S34K.S95F VL FR4 hu.10C5-L5.Q38E.F92Y.S95F VL FR4 hu.10C5-L5.Q38E.S34K.F92Y.S95F VL FR4 | FGGGTKVEIK |
| 50 | hu.10C5-H28L5 VH | EVQLVESGGG LVQPGGSLRL SCAASGFSLS SYGVTWVRQA PGKGLEWIGY ITSNYGVSYY ASWAKSRSTI SRDTSKNTVY LQMGSLRAED MAVYYCAREN PDYGYAYDAW GQGTTVTVSS |
| 51 | hu.10C5-H28L5 VL | AIRMTQSPSS FSASTGDRVT ITCQASESIS NELSWYQQKP GKAPKLLIYY ASTLASGVPS RFSGSGSGTD FTLTISSLQP EDFATYYCAQ GFSSGVENV FGGGTKVEIK |
| 52 | hu.10C5-H28.N53V VH | EVQLVESGGG LVQPGGSLRL SCAASGFSLS SYGVTWVRQA PGKGLEWIGY ITSVYGVSYY ASWAKSRSTI SRDTSKNTVY LQMGSLRAED MAVYYCAREN PDYGYAYDAW GQGTTVTVSS |
| 53 | hu.10C5-H28.Q39K.N53V VH | EVQLVESGGG LVQPGGSLRL SCAASGFSLS SYGVTWVRKA PGKGLEWIGY ITSVYGVSYY ASWAKSRSTI SRDTSKNTVY LQMGSLRAED MAVYYCAREN PDYGYAYDAW GQGTTVTVSS |
| 105 | hu.10C5-H28.G33P VH | EVQLVESGGG LVQPGGSLRL SCAASGFSLS SYPVTWVRQA PGKGLEWIGY ITSNYGVSYY ASWAKSRSTI SRDTSKNTVY LQMGSLRAED MAVYYCAREN PDYGYAYDAW GQGTTVTVSS |
| 106 | hu.10C5-H28.G33P.N53V VH | EVQLVESGGG LVQPGGSLRL SCAASGFSLS SYPVTWVRQA PGKGLEWIGY ITSVYGVSYY ASWAKSRSTI SRDTSKNTVY LQMGSLRAED MAVYYCAREN PDYGYAYDAW GQGTTVTVSS |
| 54 | hu.10C5-L5.S34K VL | AIRMTQSPSS FSASTGDRVT ITCQASESIS NELKWYQQKP GKAPKLLIYY ASTLASGVPS RFSGSGSGTD FTLTISSLQP EDFATYYCAQ GFSSGVENV FGGGTKVEIK |
| 55 | hu.10C5-L5.F92Y VL | AIRMTQSPSS FSASTGDRVT ITCQASESIS NELSWYQQKP GKAPKLLIYY ASTLASGVPS RFSGSGSGTD FTLTISSLQP EDFATYYCAQ GYSSGVENV FGGGTKVEIK |
| 56 | hu.10C5-L5.S95F VL | AIRMTQSPSS FSASTGDRVT ITCQASESIS NELSWYQQKP GKAPKLLIYY ASTLASGVPS RFSGSGSGTD FTLTISSLQP EDFATYYCAQ GFSFGVENV FGGGTKVEIK |

| SEQ ID NO | Description | Sequence |
|---|---|---|
| 57 | hu.10C5-L5.S34K.F92Y VL | AIRMTQSPSS FSASTGDRVT ITCQASESIS NELKWYQQKP GKAPKLLIYY ASTLASGVPS RFSGSGSGTD FTLTISSLQP EDFATYYCAQ GYGSSGVENV FGGGTKVEIK |
| 58 | hu.10C5-L5.S34K.S95F VL | AIRMTQSPSS FSASTGDRVT ITCQASESIS NELKWYQQKP GKAPKLLIYY ASTLASGVPS RFSGSGSGTD FTLTISSLQP EDFATYYCAQ GFGSFGVENV FGGGTKVEIK |
| 59 | hu.10C5-L5.F92Y.S95F VL | AIRMTQSPSS FSASTGDRVT ITCQASESIS NELSWYQQKP GKAPKLLIYY ASTLASGVPS RFSGSGSGTD FTLTISSLQP EDFATYYCAQ GYGSFGVENV FGGGTKVEIK |
| 60 | hu.10C5-L5.S34K.F92Y.S95F VL | AIRMTQSPSS FSASTGDRVT ITCQASESIS NELKWYQQKP GKAPKLLIYY ASTLASGVPS RFSGSGSGTD FTLTISSLQP EDFATYYCAQ GYGSFGVENV FGGGTKVEIK |
| 61 | hu.10C5-L5.Q38E.S34K VL | AIRMTQSPSS FSASTGDRVT ITCQASESIS NELKWYQEKP GKAPKLLIYY ASTLASGVPS RFSGSGSGTD FTLTISSLQP EDFATYYCAQ GFGSSGVENV FGGGTKVEIK |
| 62 | hu.10C5-L5.Q38E.F92Y VL | AIRMTQSPSS FSASTGDRVT ITCQASESIS NELSWYQEKP GKAPKLLIYY ASTLASGVPS RFSGSGSGTD FTLTISSLQP EDFATYYCAQ GYGSSGVENV FGGGTKVEIK |
| 63 | hu.10C5-L5.Q38E.S95F VL | AIRMTQSPSS FSASTGDRVT ITCQASESIS NELSWYQEKP GKAPKLLIYY ASTLASGVPS RFSGSGSGTD FTLTISSLQP EDFATYYCAQ GFGSFGVENV FGGGTKVEIK |
| 64 | hu.10C5-L5.Q38E.S34K.F92Y VL | AIRMTQSPSS FSASTGDRVT ITCQASESIS NELKWYQEKP GKAPKLLIYY ASTLASGVPS RFSGSGSGTD FTLTISSLQP EDFATYYCAQ GYGSSGVENV FGGGTKVEIK |
| 65 | hu.10C5-L5.Q38E.S34K.S95F VL | AIRMTQSPSS FSASTGDRVT ITCQASESIS NELKWYQEKP GKAPKLLIYY ASTLASGVPS RFSGSGSGTD FTLTISSLQP EDFATYYCAQ GFGSFGVENV FGGGTKVEIK |
| 66 | hu.10C5-L5.Q38E.F92Y.S95F VL | AIRMTQSPSS FSASTGDRVT ITCQASESIS NELSWYQEKP GKAPKLLIYY ASTLASGVPS RFSGSGSGTD FTLTISSLQP EDFATYYCAQ GYGSFGVENV FGGGTKVEIK |
| 67 | hu.10C5-L5.Q38E.S34K.F92Y.S95F VL | AIRMTQSPSS FSASTGDRVT ITCQASESIS NELKWYQEKP GKAPKLLIYY ASTLASGVPS RFSGSGSGTD FTLTISSLQP EDFATYYCAQ GYGSFGVENV FGGGTKVEIK |
| 68 | hu.9H5-H14L4 CDRH1 hu.9H5-H14.G54A CDRH1 hu.9H5-H14.G98Q CDRH1 hu.9H5-H14.G54A.G98Q CDRH1 hu.9H5-H14.Q39K CDRH1 hu.9H5-H14.Q39K.G54A CDRH1 hu.9H5-H14.Q39K.G98Q CDRH1 hu.9H5-H14.Q39K.G54A.G98Q CDRH1 | SYGVS |
| 69 | hu.9H5-H14L4 CDRH2 hu.9H5-H14.G98Q CDRH2 hu.9H5-H14.Q39K CDRH2 hu.9H5-H14.Q39K.G98Q CDRH2 | FIGSGGFAYYASWAKS |
| 70 | hu.9H5-H14.G54A CDRH2 hu.9H5-H14.G54A.G98Q CDRH2 hu.9H5-H14.Q39K.G54A CDRH2 hu.9H5-H14.Q39K.G54A.G98Q CDRH2 | FIGSAGFAYYASWAKS |
| 71 | hu.9H5-H14L4 CDRH3 hu.9H5-H14.G54A CDRH3 | DDVGGGKSLDI |

IV. Table of Certain Sequences

| SEQ ID NO | Description | Sequence |
|---|---|---|
|  | hu.9H5-H14.Q39K CDRH3<br>hu.9H5-H14.Q39K.G54A CDRH3 |  |
| 72 | hu.9H5-H14.G98Q CDRH3<br>hu.9H5-H14.G54A.G98Q CDRH3<br>hu.9H5-H14.Q39K.G98Q CDRH3<br>hu.9H5-H14.Q39K.G54A.G98Q CDRH3 | DDVQGGKSLDI |
| 73 | hu.9H5-H14L4 CDRL1<br>hu.9H5-L4.H89V CDRL1<br>hu.9H5-L4.S95Y CDRL1<br>hu.9H5-L4.H89V.S95Y CDRL1<br>hu.9H5-L4.Q38E CDRL1<br>hu.9H5-L4.Q38E.H89V CDRL1<br>hu.9H5-L4.Q38E.S95Y CDRL1<br>hu.9H5-L4.Q38E.H89V.S95Y CDRL1 | QASQSISSYLS |
| 74 | hu.9H5-H14L4 CDRL2<br>hu.9H5-L4.H89V CDRL2<br>hu.9H5-L4.S95Y CDRL2<br>hu.9H5-L4.H89V.S95Y CDRL2<br>hu.9H5-L4.Q38E CDRL2<br>hu.9H5-L4.Q38E.H89V CDRL2<br>hu.9H5-L4.Q38E.S95Y CDRL2<br>hu.9H5-L4.Q38E.H89V.S95Y CDRL2 | SASTLAS |
| 75 | hu.9H5-H14L4 CDRL3<br>hu.9H5-L4.Q38E CDRL3 | HQDYTSSNVDNT |
| 76 | hu.9H5-L4.H89V CDRL3<br>hu.9H5-L4.Q38E.H89V CDRL3 | VQDYTSSNVDNT |
| 77 | hu.9H5-L4.S95Y CDRL3<br>hu.9H5-L4.Q38E.S95Y CDRL3 | HQDYTSYNVDNT |
| 78 | hu.9H5-L4.H89V.S95Y CDRL3<br>hu.9H5-L4.Q38E.H89V.S95Y CDRL3 | VQDYTSYNVDNT |
| 171 | hu.9H5-H14L4 VH FR1<br>hu.9H5-H14.G54A VH FR1<br>hu.9H5-H14.G98Q VH FR1<br>hu.9H5-H14.G54A.G98Q VH FR1<br>hu.9H5-H14.Q39K VH FR1<br>hu.9H5-H14.Q39K.G54A VH FR1<br>hu.9H5-H14.Q39K.G98Q VH FR1<br>hu.9H5-H14.Q39K.G54A.G98Q VH FR1 | EVQLVESGGGLIQPGGSLRLSCAASGFSLS |
| 172 | hu.9H5-H14L4 VH FR2<br>hu.9H5-H14.G54A VH FR2<br>hu.9H5-H14.G98Q VH FR2<br>hu.9H5-H14.G54A.G98Q VH FR2 | WVRQAPGKGLEYVG |
| 173 | hu.9H5-H14.Q39K VH FR2<br>hu.9H5-H14.Q39K.G54A VH FR2<br>hu.9H5-H14.Q39K.G98Q VH FR2<br>hu.9H5-H14.Q39K.G54A.G98Q VH FR2 | WVRKAPGKGLEYVG |
| 174 | hu.9H5-H14L4 VH FR3<br>hu.9H5-H14.G54A VH FR3 | RFTISRDNSKNTLYLQMNSLRAEDTAVYYCAR |

IV. Table of Certain Sequences

| SEQ ID NO | Description | Sequence |
|---|---|---|
| | hu.9H5-H14.G98Q VH FR3<br>hu.9H5-H14.G54A.G98Q VH FR3<br>hu.9H5-H14.Q39K VH FR3<br>hu.9H5-H14.Q39K.G54A VH FR3<br>hu.9H5-H14.Q39K.G98Q VH FR3<br>hu.9H5-H14.Q39K.G54A.G98Q VH FR3 | |
| 175 | hu.9H5-H14L4 VH FR4<br>hu.9H5-H14.G54A VH FR4<br>hu.9H5-H14.G98Q VH FR4<br>hu.9H5-H14.G54A.G98Q VH FR4<br>hu.9H5-H14.Q39K VH FR4<br>hu.9H5-H14.Q39K.G54A VH FR4<br>hu.9H5-H14.Q39K.G98Q VH FR4<br>hu.9H5-H14.Q39K.G54A.G98Q VH FR4 | WGQGTLVTVSS |
| 176 | hu.9H5-H14L4 VL FR1<br>hu.9H5-L4.H89V VL FR1<br>hu.9H5-L4.S95Y VL FR1<br>hu.9H5-L4.H89V.S95Y VL FR1<br>hu.9H5-L4.Q38E VL FR1<br>hu.9H5-L4.Q38E.H89V VL FR1<br>hu.9H5-L4.Q38E.S95Y VL FR1<br>hu.9H5-L4.Q38E.H89V.S95Y VL FR1 | DIQMTQSPSSLSASVGDRVTITC |
| 177 | hu.9H5-H14L4 VL FR2<br>hu.9H5-L4.H89V VL FR2<br>hu.9H5-L4.S95Y VL FR2<br>hu.9H5-L4.H89V.S95Y VL FR2 | WYQQKPGKAPKLLIY |
| 178 | hu.9H5-L4.Q38E VL FR2<br>hu.9H5-L4.Q38E.H89V VL FR2<br>hu.9H5-L4.Q38E.S95Y VL FR2<br>hu.9H5-L4.Q38E.H89V.S95Y VL FR2 | WYQEKPGKAPKLLIY |
| 179 | hu.9H5-H14L4 VL FR3<br>hu.9H5-L4.H89V VL FR3<br>hu.9H5-L4.S95Y VL FR3<br>hu.9H5-L4.H89V.S95Y VL FR3<br>hu.9H5-L4.Q38E VL FR3<br>hu.9H5-L4.Q38E.H89V VL FR3<br>hu.9H5-L4.Q38E.S95Y VL FR3<br>hu.9H5-L4.Q38E.H89V.S95Y VL FR3 | GVPSRFSGSGSGTDFTLTISSLQPEDFATYYC |
| 180 | hu.9H5-H14L4 VL FR4<br>hu.9H5-L4.H89V VL FR4<br>hu.9H5-L4.S95Y VL FR4<br>hu.9H5-L4.H89V.S95Y VL FR4<br>hu.9H5-L4.Q38E VL FR4<br>hu.9H5-L4.Q38E.H89V VL FR4<br>hu.9H5-L4.Q38E.S95Y VL FR4<br>hu.9H5-L4.Q38E.H89V.S95Y VL FR4 | FGGGTKVEIK |
| 79 | hu.9H5-H14L4 VH | EVQLVESGGG LIQPGGSLRL SCAASGFSLS SYGVSWVRQA PGKGLEYVGF IGSGGFAYYA SWAKSRFTIS RDNSKNTLYL QMNSLRAEDT AVYYCARDDV GGGKSLDIWG QGTLVTVSS |
| 80 | hu.9H5-H14L4 VL | DIQMTQSPSS LSASVGDRVT ITCQASQSIS SYLSWYQQKP |

IV. Table of Certain Sequences

| SEQ ID NO | Description | Sequence |
|---|---|---|
| | | GKAPKLLIYS ASTLASGVPS RFSGSGSGTD FTLTISSLQP<br>EDFATYYCHQ DYTSSNVDNT FGGGTKVEIK |
| 81 | hu.9H5-H14.G54A VH | EVQLVESGGG LIQPGGSLRL SCAASGFSLS SYGVSWVRQA<br>PGKGLEYVGF IGSAGFAYYA SWAKSRFTIS RDNSKNTLYL<br>QMNSLRAEDT AVYYCARDDV GGGKSLDIWG QGTLVTVSS |
| 82 | hu.9H5-H14.G98Q VH | EVQLVESGGG LIQPGGSLRL SCAASGFSLS SYGVSWVRQA<br>PGKGLEYVGF IGSGGFAYYA SWAKSRFTIS RDNSKNTLYL<br>QMNSLRAEDT AVYYCARDDV QGGKSLDIWG QGTLVTVSS |
| 83 | hu.9H5-H14.G54A.G98Q VH | EVQLVESGGG LIQPGGSLRL SCAASGFSLS SYGVSWVRQA<br>PGKGLEYVGF IGSAGFAYYA SWAKSRFTIS RDNSKNTLYL<br>QMNSLRAEDT AVYYCARDDV QGGKSLDIWG QGTLVTVSS |
| 84 | hu.9H5-H14.Q39K VH | EVQLVESGGG LIQPGGSLRL SCAASGFSLS SYGVSWVRKA<br>PGKGLEYVGF IGSGGFAYYA SWAKSRFTIS RDNSKNTLYL<br>QMNSLRAEDT AVYYCARDDV GGGKSLDIWG QGTLVTVSS |
| 85 | hu.9H5-H14.Q39K.G54A VH | EVQLVESGGG LIQPGGSLRL SCAASGFSLS SYGVSWVRKA<br>PGKGLEYVGF IGSAGFAYYA SWAKSRFTIS RDNSKNTLYL<br>QMNSLRAEDT AVYYCARDDV GGGKSLDIWG QGTLVTVSS |
| 86 | hu.9H5-H14.Q39K.G98Q VH | EVQLVESGGG LIQPGGSLRL SCAASGFSLS SYGVSWVRKA<br>PGKGLEYVGF IGSGGFAYYA SWAKSRFTIS RDNSKNTLYL<br>QMNSLRAEDT AVYYCARDDV QGGKSLDIWG QGTLVTVSS |
| 87 | hu.9H5-H14.Q39K.G54A.G98Q VH | EVQLVESGGG LIQPGGSLRL SCAASGFSLS SYGVSWVRKA<br>PGKGLEYVGF IGSAGFAYYA SWAKSRFTIS RDNSKNTLYL<br>QMNSLRAEDT AVYYCARDDV QGGKSLDIWG QGTLVTVSS |
| 88 | hu.9H5-L4.H89V VL | DIQMTQSPSS LSASVGDRVT ITCQASQSIS SYLSWYQQKP<br>GKAPKLLIYS ASTLASGVPS RFSGSGSGTD FTLTISSLQP<br>EDFATYYCVQ DYTSSNVDNT FGGGTKVEIK |
| 89 | hu.9H5-L4.S95Y VL | DIQMTQSPSS LSASVGDRVT ITCQASQSIS SYLSWYQQKP<br>GKAPKLLIYS ASTLASGVPS RFSGSGSGTD FTLTISSLQP<br>EDFATYYCHQ DYTSYNVDNT FGGGTKVEIK |
| 90 | hu.9H5-L4.H89V.S95Y VL | DIQMTQSPSS LSASVGDRVT ITCQASQSIS SYLSWYQQKP<br>GKAPKLLIYS ASTLASGVPS RFSGSGSGTD FTLTISSLQP<br>EDFATYYCVQ DYTSYNVDNT FGGGTKVEIK |
| 91 | hu.9H5-L4.Q38E VL | DIQMTQSPSS LSASVGDRVT ITCQASQSIS SYLSWYQEKP<br>GKAPKLLIYS ASTLASGVPS RFSGSGSGTD FTLTISSLQP<br>EDFATYYCHQ DYTSSNVDNT FGGGTKVEIK |
| 92 | hu.9H5-L4.Q38E.H89V VL | DIQMTQSPSS LSASVGDRVT ITCQASQSIS SYLSWYQEKP<br>GKAPKLLIYS ASTLASGVPS RFSGSGSGTD FTLTISSLQP<br>EDFATYYCVQ DYTSSNVDNT FGGGTKVEIK |
| 93 | hu.9H5-L4.Q38E.S95Y VL | DIQMTQSPSS LSASVGDRVT ITCQASQSIS SYLSWYQEKP<br>GKAPKLLIYS ASTLASGVPS RFSGSGSGTD FTLTISSLQP<br>EDFATYYCHQ DYTSYNVDNT FGGGTKVEIK |
| 94 | hu.9H5-L4.Q38E.H89V.S95Y VL | DIQMTQSPSS LSASVGDRVT ITCQASQSIS SYLSWYQEKP<br>GKAPKLLIYS ASTLASGVPS RFSGSGSGTD FTLTISSLQP<br>EDFATYYCVQ DYTSYNVDNT FGGGTKVEIK |
| 95 | Human IgG1 heavy chain constant region (hIgG1) | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVEP KSCDKTHTCP PCPAPELLGG<br>PSVFLFPPKP KDTLMISRTP EVTCVVVDVS HEDPEVKFNW<br>YVDGVEVHNA KTKPREEQYN STYRVVSVLT VLHQDWLNGK<br>EYKCKVSNKA LPAPIEKTIS KAKGQPREPQ VYTLPPSREE<br>MTKNQVSLTC LVKGFYPSDI AVEWESNGQP ENNYKTTPPV<br>LDSDGSFFLY SKLTVDKSRW QQGNVFSCSV MHEALHNHYT<br>QKSLSLSPGK |
| 183 | Human IgG1 heavy chain constant region (hIgG1) ΔGK | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVEP KSCDKTHTCP PCPAPELLGG<br>PSVFLFPPKP KDTLMISRTP EVTCVVVDVS HEDPEVKFNW<br>YVDGVEVHNA KTKPREEQYN STYRVVSVLT VLHQDWLNGK |

IV. Table of Certain Sequences

| SEQ ID NO | Description | Sequence |
|---|---|---|
| | | EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSP |
| 96 | hIgG1.N297G.Knob(T366W). S183K | ASTKGPSVFP LAPSSKSTSG GTAALGCLVK DYFPEPVTVS WNSGALTSGV HTFPAVLQSS GLYSLKSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLWC LVKGFYPSDI AVEWESNGQP ENNYKTTPPV LDSDGSFFLY SKLTVDKSRW QQGNVFSCSV MHEALHNHYT QKSLSLSPGK |
| 184 | hIgG1.N297G.Knob(T366W). S183K ΔGK | ASTKGPSVFP LAPSSKSTSG GTAALGCLVK DYFPEPVTVS WNSGALTSGV HTFPAVLQSS GLYSLKSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLWC LVKGFYPSDI AVEWESNGQP ENNYKTTPPV LDSDGSFFLY SKLTVDKSRW QQGNVFSCSV MHEALHNHYT QKSLSLSP |
| 97 | hIgG1.N297G.Hole(T366S. L368A.Y407V).S183E | ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV MHEALHNHYT QKSLSLSPGK |
| 185 | hIgG1.N297G.Hole(T366S. L368A.Y407V). S183E ΔGK | ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV MHEALHNHYT QKSLSLSP |
| 98 | hIgG1.N297G.Knob(T366W). S183K.M428L.N434S | ASTKGPSVFP LAPSSKSTSG GTAALGCLVK DYFPEPVTVS WNSGALTSGV HTFPAVLQSS GLYSLKSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLWC LVKGFYPSDI AVEWESNGQP ENNYKTTPPV LDSDGSFFLY SKLTVDKSRW QQGNVFSCSV LHEALHSHYT QKSLSLSPGK |
| 186 | hIgG1.N297G.Knob(T366W). S183K.M428L.N434S ΔGK | ASTKGPSVFP LAPSSKSTSG GTAALGCLVK DYFPEPVTVS WNSGALTSGV HTFPAVLQSS GLYSLKSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLWC LVKGFYPSDI AVEWESNGQP ENNYKTTPPV LDSDGSFFLY SKLTVDKSRW QQGNVFSCSV LHEALHSHYT QKSLSLSP |
| 99 | hIgG1.N297G.Hole(T366S. L368A.Y407V).S183E. M428L.N434S | ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV LHEALHSHYT QKSLSLSPGK |

IV. Table of Certain Sequences

| SEQ ID NO | Description | Sequence |
| --- | --- | --- |
| 187 | hIgG1.N297G.Hole(T366S.L368A.Y407V).S183E.M428L.N434S ΔGK | ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV LHEALHSHYT QKSLSLSP |
| 117 | hIgG1.N297G.Knob(T366W).S183E | ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLWC LVKGFYPSDI AVEWESNGQP ENNYKTTPPV LDSDGSFFLY SKLTVDKSRW QQGNVFSCSV MHEALHNHYT QKSLSLSPGK |
| 188 | hIgG1.N297G.Knob(T366W).S183E ΔGK | ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLWC LVKGFYPSDI AVEWESNGQP ENNYKTTPPV LDSDGSFFLY SKLTVDKSRW QQGNVFSCSV MHEALHNHYT QKSLSLSP |
| 118 | hIgG1.N297G.Hole(T366S.L368A.Y407V).S183K | ASTKGPSVFP LAPSSKSTSG GTAALGCLVK DYFPEPVTVS WNSGALTSGV HTFPAVLQSS GLYSLKSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV MHEALHNHYT QKSLSLSPGK |
| 189 | hIgG1.N297G.Hole(T366S.L368A.Y407V).S183K ΔGK | ASTKGPSVFP LAPSSKSTSG GTAALGCLVK DYFPEPVTVS WNSGALTSGV HTFPAVLQSS GLYSLKSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV MHEALHNHYT QKSLSLSP |
| 119 | hIgG1.N297G.Knob(T366W).S183E.M428L.N434S | ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLWC LVKGFYPSDI AVEWESNGQP ENNYKTTPPV LDSDGSFFLY SKLTVDKSRW QQGNVFSCSV LHEALHSHYT QKSLSLSPGK |
| 190 | hIgG1.N297G.Knob(T366W).S183E.M428L.N434S ΔGK | ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLWC LVKGFYPSDI AVEWESNGQP ENNYKTTPPV LDSDGSFFLY SKLTVDKSRW QQGNVFSCSV LHEALHSHYT QKSLSLSP |
| 120 | hIgG1.N297G.Hole(T366S.L368A.Y407V).S183K.M428L.N434S | ASTKGPSVFP LAPSSKSTSG GTAALGCLVK DYFPEPVTVS WNSGALTSGV HTFPAVLQSS GLYSLKSVVT VPSSSLGTQT YICNVNHKPS NTKVDKKVEP KSCDKTHTCP PCPAPELLGG |

| SEQ ID NO | Description | Sequence |
|---|---|---|
| | | PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV LHEALHSHYT QKSLSLSPGK |
| 191 | hIgG1.N297G.Hole(T366S. L368A.Y407V).S183K. M428L.N434S ΔGK | ASTKGPSVFP LAPSSKSTSG GTAALGCLVK DYFPEPVTVS WNSGALTSGV HTFPAVLQSS GLYSLKSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV LHEALHSHYT QKSLSLSP |
| 102 | Human kappa light chain contstant region (hKappa) | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 103 | hKappa.V133E | RTVAAPSVFI FPPSDEQLKS GTASVECLLN NFYPREAKVQ WKVDNALQSG NSQESVTEQD SKDSTYSLSS TLTLSKADYE KHKVYACEVT HQGLSSPVTK SFNRGEC |
| 104 | hKappa.V133K | RTVAAPSVFI FPPSDEQLKS GTASVKCLLN NFYPREAKVQ WKVDNALQSG NSQESVTEQD SKDSTYSLSS TLTLSKADYE KHKVYACEVT HQGLSSPVTK SFNRGEC |
| 108 | hu14H11c heavy chain (HC) in hu.10C5VY.hu14H11c.L2H11 WT | EQQLVESGGG LIQPGGSLRL SCAASGFSFS SSYYMSWVRE APGKGLEWVS SIYAGSSGAP YYAGWAKGRF TISRDNSKNT LYLQMNSLRA EDTAVYYCAR EGFAETGGYG YAAYFNLWGP GTLVTVSSAS TKGPSVFPLA PSSKSTSGGT AALGCLVKDY FPEPVTVSWN SGALTSGVHT FPAVLQSSGL YSLKSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYGST YRVVSVLTVL HQDWLNGKEY KCKVSNKALP APIEKTISKA KGQPREPQVY TLPPSREEMT KNQVSLWCLV KGFYPSDIAV EWESNGQPEN NYKTTPPVLD SDGSFFLYSK LTVDKSRWQQ GNVFSCSVMH EALHNHYTQK SLSLSPGK |
| 192 | hu14H11c heavy chain (HC) in hu.10C5VY.hu14H11c.L2H11 WT ΔGK | EQQLVESGGG LIQPGGSLRL SCAASGFSFS SSYYMSWVRE APGKGLEWVS SIYAGSSGAP YYAGWAKGRF TISRDNSKNT LYLQMNSLRA EDTAVYYCAR EGFAETGGYG YAAYFNLWGP GTLVTVSSAS TKGPSVFPLA PSSKSTSGGT AALGCLVKDY FPEPVTVSWN SGALTSGVHT FPAVLQSSGL YSLKSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYGST YRVVSVLTVL HQDWLNGKEY KCKVSNKALP APIEKTISKA KGQPREPQVY TLPPSREEMT KNQVSLWCLV KGFYPSDIAV EWESNGQPEN NYKTTPPVLD SDGSFFLYSK LTVDKSRWQQ GNVFSCSVMH EALHNHYTQK SLSLSP |
| 109 | hu14H11c light chain (LC) in hu.10C5VY.hu14H11c.L2H11 WT | DIQMTQSPSS LSASVGDRVT ITCLASEDIA SSVSWYQKKP GKAPKLLIYG ASNLESGVPS RFSGSGSGTD YTLTISSLQP EDFATYYCLG GYSYSSTGTA FGGGTKVEIK RTVAAPSVFI FPPSDEQLKS GTASVECLLN NFYPREAKVQ WKVDNALQSG NSQESVTEQD SKDSTYSLSS TLTLSKADYE KHKVYACEVT HQGLSSPVTK SFNRGEC |
| 110 | hu.10C5VY heavy chain (HC) in hu.10C5VY.hu14H11c.L2H11 WT | EVQLVESGGG LVQPGGSLRL SCAASGFSLS SYGVTWVRKA PGKGLEWIGY ITSVYGVSYY ASWAKSRSTI SRDTSKNTVY LQMGSLRAED MAVYYCAREN PDYGYAYDAW GQGTTVTVSS ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV MHEALHNHYT QKSLSLSPGK |

IV. Table of Certain Sequences

| SEQ ID NO | Description | Sequence |
| --- | --- | --- |
| 193 | hu.10C5VY heavy chain (HC) in hu.10C5VY.hu14H11c.L2H11 WT ΔGK | EVQLVESGGG LVQPGGSLRL SCAASGFSLS SYGVTWVRKA PGKGLEWIGY ITSVYGVSYY ASWAKSRSTI SRDTSKNTVY LQMGSLRAED MAVYYCAREN PDYGYAYDAW GQGTTVTVSS ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV MHEALHNHYT QKSLSLSP |
| 111 | hu.10C5VY light chain (LC) in hu.10C5VY.hu14H11c.L2H11 WT | AIRMTQSPSS FSASTGDRVT ITCQASESIS NELSWYQEKP GKAPKLLIYY ASTLASGVPS RFSGSGSGTD FTLTISSLQP EDFATYYCAQ GYGSSGVENV FGGGTKVEIK RTVAAPSVFI FPPSDEQLKS GTASVKCLLN NFYPREAKVQ WKVDNALQSG NSQESVTEQD SKDSTYSLSS TLTLSKADYE KHKVYACEVT HQGLSSPVTK SFNRGEC |
| 112 | hu14H11c heavy chain (HC) in hu.10C5VY.hu14H11c.L2H11 LS | EQQLVESGGG LIQPGGSLRL SCAASGFSFS SSYYMSWVRE APGKGLEWVS SIYAGSSGAP YYAGWAKGRF TISRDNSKNT LYLQMNSLRA EDTAVYYCAR EGFAETGGYG YAAYFNLWGP GTLVTVSSAS TKGPSVFPLA PSSKSTSGGT AALGCLVKDY FPEPVTVSWN SGALTSGVHT FPAVLQSSGL YSLKSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYGST YRVVSVLTVL HQDWLNGKEY KCKVSNKALP APIEKTISKA KGQPREPQVY TLPPSREEMT KNQVSLWCLV KGFYPSDIAV EWESNGQPEN NYKTTPPVLD SDGSFFLYSK LTVDKSRWQQ GNVFSCSVLH EALHSHYTQK SLSLSPGK |
| 194 | hu14H11c heavy chain (HC in hu.10C5VY.hu14H11c.L2H11 LS ΔGK | EQQLVESGGG LIQPGGSLRL SCAASGFSFS SSYYMSWVRE APGKGLEWVS SIYAGSSGAP YYAGWAKGRF TISRDNSKNT LYLQMNSLRA EDTAVYYCAR EGFAETGGYG YAAYFNLWGP GTLVTVSSAS TKGPSVFPLA PSSKSTSGGT AALGCLVKDY FPEPVTVSWN SGALTSGVHT FPAVLQSSGL YSLKSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYGST YRVVSVLTVL HQDWLNGKEY KCKVSNKALP APIEKTISKA KGQPREPQVY TLPPSREEMT KNQVSLWCLV KGFYPSDIAV EWESNGQPEN NYKTTPPVLD SDGSFFLYSK LTVDKSRWQQ GNVFSCSVLH EALHSHYTQK SLSLSP |
| 113 | hu14H11c light chain (LC) in hu.10C5VY.hu14H11c.L2H11 LS | DIQMTQSPSS LSASVGDRVT ITCLASEDIA SSVSWYQKKP GKAPKLLIYG ASNLESGVPS RFSGSGSGTD YTLTISSLQP EDFATYYCLG GYSYSSTGTA FGGGTKVEIK RTVAAPSVFI FPPSDEQLKS GTASVECLLN NFYPREAKVQ WKVDNALQSG NSQESVTEQD SKDSTYSLSS TLTLSKADYE KHKVYACEVT HQGLSSPVTK SFNRGEC |
| 114 | hu.10C5VY heavy chain (HC) in hu.10C5VY.hu14H11c.L2H11 LS | EVQLVESGGG LVQPGGSLRL SCAASGFSLS SYGVTWVRKA PGKGLEWIGY ITSVYGVSYY ASWAKSRSTI SRDTSKNTVY LQMGSLRAED MAVYYCAREN PDYGYAYDAW GQGTTVTVSS ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV LHEALHSHYT QKSLSLSPGK |
| 195 | hu.10C5VY heavy chain (HC in hu.10C5VY.hu14H11c.L2H11 LS ΔGK | EVQLVESGGG LVQPGGSLRL SCAASGFSLS SYGVTWVRKA PGKGLEWIGY ITSVYGVSYY ASWAKSRSTI SRDTSKNTVY LQMGSLRAED MAVYYCAREN PDYGYAYDAW GQGTTVTVSS ASTKGPSVFP LAPSSKSTSG GTAALGCLVK DYFPEPVTVS WNSGALTSGV HTFPAVLQSS GLYSLESVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW |

| | IV. Table of Certain Sequences | |
|---|---|---|
| SEQ ID NO | Description | Sequence |
| | | YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV LHEALHSHYT QKSLSLSP |
| 115 | hu.10C5VY light chain (LC) in hu.10C5VY.hu14H11c.L2H11 LS | AIRMTQSPSS FSASTGDRVT ITCQASESIS NELSWYQEKP GKAPKLLIYY ASTLASGVPS RFSGSGSGTD FTLTISSLQP EDFATYYCAQ GYGSSGVENV FGGGTKVEIK RTVAAPSVFI FPPSDEQLKS GTASVKCLLN NFYPREAKVQ WKVDNALQSG NSQESVTEQD SKDSTYSLSS TLTLSKADYE KHKVYACEVT HQGLSSPVTK SFNRGEC |
| 121 | KLK7 substrate; Nval is norvaline | RPKPVE-Nval-WRK |
| 181 | "dummy" hIgG1.N297G.Knob(T366W). S183K for one-armed constructs | DKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLWC LVKGFYPSDI AVEWESNGQP ENNYKTTPPV LDSDGSFFLY SKLTVDKSRW QQGNVFSCSV MHEALHNHYT QKSLSLSPGK |
| 182 | "dummy" hIgG1. N297G.Hole(T366S. L368A.Y407V). S183E for one-armed constructs | DKTHTCP PCPAPELLGG PSVFLFPPKP KDTLMISRTP EVTCVVVDVS HEDPEVKFNW YVDGVEVHNA KTKPREEQYG STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPPV LDSDGSFFLV SKLTVDKSRW QQGNVFSCSV MHEALHNHYT QKSLSLSPGK |
| 196 | SFTI 21705 (also referred to as SFTI-KLK7) | GKCLFSNPPICFPN |
| 197 | SPINK9.SRE.Fc | GSIESAKQTK QMVDCSHYKK LPPGQQRFCH REYDPICGSD GKTYKNDCFF CSKVKKTDGT LKFVHFGKCG NSRAQVTDKK IEPRGPTIKP CPPCKCPAPN LLGGPSVFIF PPKIKDVLMI SLSPIVTCVV VDVSEDDPDV QISWFVNNVE VHTAQTQTHR EDYNSTLRVV SALPIQHQDV MSGKEFKCKV NNKDLPAPIE RTISKPKGSV RAPQVYVLPP PEEEMTKKQV TLTCMVTDFM PEDIYVEWTN NGKTELNYKN TEPVLDSDGS YFMYSKLRVE KKNWVERNSY SCSVVHEGLH NHHTTKSFSR TPGK |

What is claimed is:

1. An antibody that binds to human KLK5, wherein the antibody comprises:
   a) a heavy chain variable domain (VH) comprising (a) CDR-H1 comprising the amino acid sequence of SEQ ID NO: 68, (b) CDR-H2 comprising the amino acid sequence of SEQ ID NO: 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78; or
   b) a heavy chain variable domain (VH) comprising (a) CDR-H1 comprising the amino acid sequence of SEQ ID NO: 68, (b) CDR-H2 comprising an amino acid sequence selected from SEQ ID NOs: 69 and 70, and (c) CDR-H3 comprising the amino acid sequence of SEQ ID NO: 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78; or
   c) a heavy chain variable domain (VH) comprising (a) CDR-H1 comprising the amino acid sequence of SEQ ID NO: 68, (b) CDR-H2 comprising an amino acid sequence selected from SEQ ID NOs: 69 and 70, and (c) CDR-H3 comprising an amino acid sequence selected from SEQ ID NOs: 71 and 72, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising an amino acid sequence selected from SEQ ID NOs: 75-78.

2. A pharmaceutical composition comprising the antibody of claim 1.

3. The pharmaceutical composition of claim 2, further comprising an additional therapeutic agent, wherein the additional therapeutic agent is an antibody that binds to human KLK7, wherein the antibody comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12.

4. The antibody of claim 1, wherein the antibody comprises a heavy chain variable domain (VH) comprising (a) CDR-H1 comprising the amino acid sequence of SEQ ID NO: 68, (b) CDR-H2 comprising the amino acid sequence of SEQ ID NO: 69, and (c) CDR-H3 comprising the amino acid sequence of SEQ ID NO: 71, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 75.

5. The antibody of claim 1, which is a monoclonal antibody.

6. The antibody of claim 4, which is a monoclonal antibody.

7. The antibody of claim 1, which is a humanized, or chimeric antibody.

8. The antibody of claim 4, which is a humanized, or chimeric antibody.

9. The antibody of claim 1, which is an antibody fragment that binds human KLK5.

10. The antibody of claim 4, which is an antibody fragment that binds human KLK5.

11. The antibody of claim 1, wherein the antibody binds human KLK5 with a KD of less than 1 nM as measured by surface plasmon resonance.

12. The antibody of claim 4, wherein the antibody binds human KLK5 with a KD of less than 1 nM as measured by surface plasmon resonance.

13. The antibody of claim 1, wherein the heavy chain variable region comprises an FR1 comprising the amino acid sequence of SEQ ID NO: 171, an FR2 comprising the amino acid sequence of SEQ ID NO: 172 or 173, an FR3 comprising the amino acid sequence of SEQ ID NO: 174, and/or an FR4 comprising the amino acid sequence of SEQ ID NO: 175.

14. The antibody of claim 4, wherein the heavy chain variable region comprises an FR1 comprising the amino acid sequence of SEQ ID NO: 171, an FR2 comprising the amino acid sequence of SEQ ID NO: 172 or 173, an FR3 comprising the amino acid sequence of SEQ ID NO: 174, and/or an FR4 comprising the amino acid sequence of SEQ ID NO: 175.

15. The antibody of claim 1, wherein the light chain variable region comprises an FR1 comprising the amino acid sequence of SEQ ID NO: 176, an FR2 comprising the amino acid sequence of SEQ ID NO: 177 or 178, an FR3 comprising the amino acid sequence of SEQ ID NO: 179, and/or an FR4 comprising the amino acid sequence of SEQ ID NO: 180.

16. The antibody of claim 4, wherein the light chain variable region comprises an FR1 comprising the amino acid sequence of SEQ ID NO: 176, an FR2 comprising the amino acid sequence of SEQ ID NO: 177 or 178, an FR3 comprising the amino acid sequence of SEQ ID NO: 179, and/or an FR4 comprising the amino acid sequence of SEQ ID NO: 180.

17. The antibody of claim 1, comprising:
 a) a VH sequence having at least 95% sequence identity to an amino acid sequence selected from the amino acid sequence of SEQ ID NOs: 79, or 81-87;
 b) a VL sequence having at least 95% sequence identity to an amino acid sequence selected from the amino acid sequence of SEQ ID NOs: 80 or 88-94; or
 c) a VH sequence as defined in (a) and a VL sequence as defined in (b).

18. The antibody of claim 4, comprising:
 a) a VH sequence having at least 95% sequence identity to an amino acid sequence selected from the amino acid sequence of SEQ ID NO: 79, or 81-87;
 b) a VL sequence having at least 95% sequence identity to an amino acid sequence selected from the amino acid sequence of SEQ ID NO: 80 and 88-94; or
 c) a VH sequence as defined in (a) and a VL sequence as defined in (b).

19. The antibody of claim 1, comprising:
 a) a VH sequence comprising an amino acid sequence selected from the amino acid sequence of SEQ ID NOs: 84-87;
 b) a VL sequence comprising an amino acid sequence selected from the amino acid sequence of SEQ ID NOs: 91-94; or
 c) a VH sequence as defined in (a) and a VL sequence as defined in (b).

20. The antibody of claim 1, wherein the antibody comprises a heavy chain constant region and a light chain constant region, wherein the heavy chain constant region comprises a S183K substitution (EU numbering) and/or an S183E substitution (EU numbering); and/or the light chain constant region comprises a V133K substitution (EU numbering) and/or a V133E substitution (EU numbering).

21. The antibody of claim 4, wherein the antibody comprises a heavy chain constant region and a light chain constant region, wherein the heavy chain constant region comprises a S183K substitution (EU numbering) and/or an S183E substitution (EU numbering); and/or the light chain constant region comprises a V133K substitution (EU numbering) and/or a V133E substitution (EU numbering).

22. The antibody of claim 1, which is a full length IgG1 antibody.

23. The antibody of claim 4, which is a full length IgG1 antibody.

24. The antibody of claim 22, wherein the antibody comprises a N297G substitution (EU numbering).

25. The antibody of claim 23, wherein the antibody comprises a N297G substitution (EU numbering).

26. The antibody of claim 22, wherein the antibody comprises a M428L substitution (EU numbering) and/or an N434S substitution (EU numbering).

27. The antibody of claim 23, wherein the antibody comprises a M428L substitution (EU numbering) and/or an N434S substitution (EU numbering).

28. The antibody of claim 1, wherein the antibody inhibits human KLK5 protease activity with an IC50 of less than 5 nM.

29. The antibody of claim 4, wherein the antibody inhibits human KLK5 protease activity with an IC50 of less than 5 nM.

30. The antibody of claim 1, wherein the antibody binds human KLK5 with a KD of less than 60 pM, as measured by surface plasmon resonance; and wherein the antibody inhibits human KLK5 protease activity with an IC50 of less than 5 nM.

31. The antibody of claim 4, wherein the antibody binds human KLK5 with a KD of less than 60 pM, as measured by surface plasmon resonance; and wherein the antibody inhibits human KLK5 protease activity with an IC50 of less than 5 nM.

32. The antibody of claim 28, wherein inhibition of human KLK5 protease activity is inhibition of human KLK5-mediated cleavage of the substrate Boc-Val-Pro-Arg-AMC.

33. The antibody of claim 29, wherein inhibition of human KLK5 protease activity is inhibition of human KLK5-mediated cleavage of the substrate Boc-Val-Pro-Arg-AMC.

34. The antibody of claim 30, wherein inhibition of human KLK5 protease activity is inhibition of human KLK5-mediated cleavage of the substrate Boc-Val-Pro-Arg-AMC.

35. The antibody of claim 31, wherein inhibition of human KLK5 protease activity is inhibition of human KLK5-mediated cleavage of the substrate Boc-Val-Pro-Arg-AMC.

36. The antibody of claim 1, wherein the antibody is a multispecific antibody.

37. The antibody of claim 4, wherein the antibody is a multispecific antibody.

38. The antibody of claim 20, wherein the antibody is a bispecific antibody.

39. The antibody of claim 21, wherein the antibody is a bispecific antibody.

40. The antibody of claim 36, wherein the antibody is a bispecific antibody.

41. The antibody of claim 37, wherein the antibody is a bispecific antibody.

42. A pharmaceutical composition comprising the antibody of claim 4.

43. The antibody of claim 38, wherein said antibody comprises a binding moiety that binds to human KLK7, wherein the antibody comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12.

44. The antibody of claim 39, wherein said antibody comprises a binding moiety that binds to human KLK7, wherein the antibody comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12.

45. The antibody of claim 40, wherein said antibody comprises a binding moiety that binds to human KLK7, wherein the antibody comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12.

46. The antibody of claim 41, wherein said antibody comprises a binding moiety that binds to human KLK7, wherein the antibody comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12.

47. The pharmaceutical composition of claim 42, further comprising an additional therapeutic agent.

48. The pharmaceutical composition of claim 47, wherein the additional therapeutic agent is an antibody that binds to human KLK7, wherein the antibody comprises a heavy chain variable domain (VH) comprising (a) CDR-H1 comprising the amino acid sequence of SEQ ID NO: 7, (b) CDR-H2 comprising the amino acid sequence of SEQ ID NO: 8, and (c) CDR-H3 comprising the amino acid sequence of SEQ ID NO: 9, and a light chain variable domain (VL) comprising (d) CDR-L1 comprising the amino acid sequence of SEQ ID NO: 10, (e) CDR-L2 comprising the amino acid sequence of SEQ ID NO: 11, and (f) CDR-L3 comprising the amino acid sequence of SEQ ID NO: 12.

* * * * *

```
                      SEQUENCE LISTING

Sequence total quantity: 199
SEQ ID NO: 1           moltype = AA  length = 293
FEATURE                Location/Qualifiers
source                 1..293
                       mol_type = protein
                       organism = Homo sapiens
SEQUENCE: 1
MATARPPWMW VLCALITALL LGVTEHVLAN NDVSCDHPSN TVPSGSNQDL GAGAGEDARS    60
DDSSSRIING SDCDMHTQPW QAALLLRPNQ LYCGAVLVHP QWLLTAAHCR KKVFRVRLGH   120
YSLSPVYESG QQMFQGVKSI PHPGYSHPGH SNDLMLIKLN RRIRPTKDVR PINVSSHCPS   180
AGTKCLVSGW GTTKSPQVHF PKVLQCLNIS VLSQKRCEDA YPRQIDDTMF CAGDKAGRDS   240
CQGDSGGPVV CNGSLQGLVS WGDYPCARPN RPGVYTNLCK FTKWIQETIQ ANS          293

SEQ ID NO: 2           moltype = AA  length = 227
FEATURE                Location/Qualifiers
source                 1..227
                       mol_type = protein
                       organism = Homo sapiens
SEQUENCE: 2
IINGSDCDMH TQPWQAALLL RPNQLYCGAV LVHPQWLLTA AHCRKKVFRV RLGHYSLSPV    60
YESGQQMFQG VKSIPHPGYS HPGHSNDLML IKLNRRIRPT KDVRPINVSS HCPSAGTKCL   120
VSGWGTTKSP QVHFPKVLQC LNISVLSQKR CEDAYPRQID DTMFCAGDKA GRDSCQGDSG   180
GPVVCNGSLQ GLVSWGDYPC ARPNRPGVYT NLCKFTKWIQ ETIQANS                 227

SEQ ID NO: 3           moltype = AA  length = 253
FEATURE                Location/Qualifiers
```

```
                              -continued
source                  1..253
                        mol_type = protein
                        organism = Homo sapiens
SEQUENCE: 3
MARSLLLPLQ  ILLLSLALET  AGEEAQGDKI  IDGAPCARGS  HPWQVALLSG  NQLHCGGVLV   60
NERWVLTAAH  CKMNEYTVHL  GSDTLGDRRA  QRIKASKSFR  HPGYSTQTHV  NDLMLVKLNS  120
QARLSSMVKK  VRLPSRCEPP  GTTCTVSGWG  TTTSPDVTFP  SDLMCVDVKL  ISPQDCTKVY  180
KDLLENSMLC  AGIPDSKKNA  CNGDSGGPLV  CRGTLQGLVS  WGTFPCGQPN  DPGVYTQVCK  240
FTKWINDTMK  KHR                                                         253

SEQ ID NO: 4            moltype = AA   length = 224
FEATURE                 Location/Qualifiers
source                  1..224
                        mol_type = protein
                        organism = Homo sapiens
SEQUENCE: 4
IIDGAPCARG  SHPWQVALLS  GNQLHCGGVL  VNERWVLTAA  HCKMNEYTVH  LGSDTLGDRR   60
AQRIKASKSF  RHPGYSTQTH  VNDLMLVKLN  SQARLSSMVK  KVRLPSRCEP  PGTTCTVSGW  120
GTTTSPDVTF  PSDLMCVDVK  LISPQDCTKV  YKDLLENSML  CAGIPDSKKN  ACNGDSGGPL  180
VCRGTLQGLV  SWGTFPCGQP  NDPGVYTQVC  KFTKWINDTM  KKHR                    224

SEQ ID NO: 5            moltype = AA   length = 253
FEATURE                 Location/Qualifiers
source                  1..253
                        mol_type = protein
                        organism = Macaca fascicularis
SEQUENCE: 5
MAGSLLLPLQ  ILLLSLALGT  AGQEAQGDKI  IDGAPCTRGS  HPWQVALLSG  NQLHCGGVLV   60
NERWVLTAAH  CKMNDYTVHL  GSDTLGDRKA  QRIKASRSFR  HPGYSTQTHV  NDLMLVKLNS  120
PARLSSTVKK  VRLPSRCEPP  GTTCTVSGWG  TTTSPDVTFP  SDLMCVDVKL  ISSQDCTKVY  180
KDMLGNSMLC  AGIPNSKKNA  CNGDSGGPLV  CRGTLQGLVS  WGTFPCGQPN  DPGVYTQVCK  240
FTKWINDTIK  KHR                                                         253

SEQ ID NO: 6            moltype = AA   length = 224
FEATURE                 Location/Qualifiers
source                  1..224
                        mol_type = protein
                        organism = Macaca fascicularis
SEQUENCE: 6
IIDGAPCTRG  SHPWQVALLS  GNQLHCGGVL  VNERWVLTAA  HCKMNDYTVH  LGSDTLGDRK   60
AQRIKASRSF  RHPGYSTQTH  VNDLMLVKLN  SPARLSSTVK  KVRLPSRCEP  PGTTCTVSGW  120
GTTTSPDVTF  PSDLMCVDVK  LISSQDCTKV  YKDMLGNSML  CAGIPNSKKN  ACNGDSGGPL  180
VCRGTLQGLV  SWGTFPCGQP  NDPGVYTQVC  KFTKWINDTI  KKHR                    224

SEQ ID NO: 7            moltype = AA   length = 6
FEATURE                 Location/Qualifiers
REGION                  1..6
                        note = 14H11c CDRH1
source                  1..6
                        mol_type = protein
                        organism = synthetic construct
SEQUENCE: 7
SSYYMS                                                                    6

SEQ ID NO: 8            moltype = AA   length = 18
FEATURE                 Location/Qualifiers
REGION                  1..18
                        note = 14H11c CDRH2
source                  1..18
                        mol_type = protein
                        organism = synthetic construct
SEQUENCE: 8
SIYAGSSGAP  YYAGWAKG                                                     18

SEQ ID NO: 9            moltype = AA   length = 17
FEATURE                 Location/Qualifiers
REGION                  1..17
                        note = 14H11c CDRH2
source                  1..17
                        mol_type = protein
                        organism = synthetic construct
SEQUENCE: 9
EGFAETGGYG  YAAYFNL                                                      17

SEQ ID NO: 10           moltype = AA   length = 11
FEATURE                 Location/Qualifiers
REGION                  1..11
                        note = 14H11c CDRL1
source                  1..11
```

```
                        mol_type = protein
                        organism = synthetic construct
SEQUENCE: 10
LASEDIASSV S                                                            11

SEQ ID NO: 11           moltype = AA   length = 7
FEATURE                 Location/Qualifiers
REGION                  1..7
                        note = 14H11c CDRL2
source                  1..7
                        mol_type = protein
                        organism = synthetic construct
SEQUENCE: 11
GASNLES                                                                 7

SEQ ID NO: 12           moltype = AA   length = 12
FEATURE                 Location/Qualifiers
REGION                  1..12
                        note = 14H11c CDRL3
source                  1..12
                        mol_type = protein
                        organism = synthetic construct
SEQUENCE: 12
LGGYSYSSTG TA                                                           12

SEQ ID NO: 13           moltype = AA   length = 126
FEATURE                 Location/Qualifiers
REGION                  1..126
                        note = rb.14H11c Heavy Chain Variable Region (VH)
source                  1..126
                        mol_type = protein
                        organism = synthetic construct
SEQUENCE: 13
QSLEESGGDL VKPGASLTLT CTASGFSFSS SYYMSWVRQA PGKGLEWIAS IYAGSSGAPY        60
YAGWAKGRFT ISKTSSTAVT LQMSSLTAAD TATYFCAREG FAETGGYGYA AYFNLWGPGT        120
LVTVSS                                                                  126

SEQ ID NO: 14           moltype = AA   length = 110
FEATURE                 Location/Qualifiers
REGION                  1..110
                        note = rb.14H11c Light Chain Variable Region (VL); rb.14H11
                         VL
source                  1..110
                        mol_type = protein
                        organism = synthetic construct
SEQUENCE: 14
AIEMTQSPPS LSASVGETVR IRCLASEDIA SSVSWYQQKP GKPPTLLIYG ASNLESGVPP        60
RFTGSGSGTD YTLTIGGVQA EDAATYYCLG GYSYSSTGTA FGAGTKVEIK                   110

SEQ ID NO: 15           moltype = AA   length = 128
FEATURE                 Location/Qualifiers
REGION                  1..128
                        note = hu.14H11c.V3-53*1.H1 VH
source                  1..128
                        mol_type = protein
                        organism = synthetic construct
SEQUENCE: 15
EQQLVESGGG LIQPGGSLRL SCAASGFSFS SSYYMSWVRQ APGKGLEWIA SIYAGSSGAP        60
YYAGWAKGRF TISKDSSKNT VYLQMNSLRA EDTAVYFCAR EGFAETGGYG YAAYFNLWGP        120
GTLVTVSS                                                                128

SEQ ID NO: 16           moltype = AA   length = 128
FEATURE                 Location/Qualifiers
REGION                  1..128
                        note = hu.14H11c.V3-53*1.H2 VH
source                  1..128
                        mol_type = protein
                        organism = synthetic construct
SEQUENCE: 16
EVQLVESGGG LIQPGGSLRL SCAASGFSFS SSYYMSWVRQ APGKGLEWIA SIYAGSSGAP        60
YYAGWAKGRF TISKDSSKNT VYLQMNSLRA EDTAVYFCAR EGFAETGGYG YAAYFNLWGP        120
GTLVTVSS                                                                128

SEQ ID NO: 17           moltype = AA   length = 128
FEATURE                 Location/Qualifiers
REGION                  1..128
                        note = hu.14H11c.V3-53*1.H3 VH
source                  1..128
                        mol_type = protein
```

```
                                      -continued
                         organism = synthetic construct
SEQUENCE: 17
EQQLVESGGG LIQPGGSLRL SCAASGFSFS SSYYMSWVRQ APGKGLEWVA SIYAGSSGAP    60
YYAGWAKGRF TISKDSSKNT VYLQMNSLRA EDTAVYFCAR EGFAETGGYG YAAYFNLWGP   120
GTLVTVSS                                                           128

SEQ ID NO: 18              moltype = AA  length = 128
FEATURE                    Location/Qualifiers
REGION                     1..128
                           note = hu.14H11c.V3-53*1.H4 VH
source                     1..128
                           mol_type = protein
                           organism = synthetic construct
SEQUENCE: 18
EQQLVESGGG LIQPGGSLRL SCAASGFSFS SSYYMSWVRQ APGKGLEWIS SIYAGSSGAP    60
YYAGWAKGRF TISKDSSKNT VYLQMNSLRA EDTAVYFCAR EGFAETGGYG YAAYFNLWGP   120
GTLVTVSS                                                           128

SEQ ID NO: 19              moltype = AA  length = 128
FEATURE                    Location/Qualifiers
REGION                     1..128
                           note = hu.14H11c.V3-53*1.H5 VH
source                     1..128
                           mol_type = protein
                           organism = synthetic construct
SEQUENCE: 19
EQQLVESGGG LIQPGGSLRL SCAASGFSFS SSYYMSWVRQ APGKGLEWIA SIYAGSSGAP    60
YYAGWAKGRF TISRDSSKNT VYLQMNSLRA EDTAVYFCAR EGFAETGGYG YAAYFNLWGP   120
GTLVTVSS                                                           128

SEQ ID NO: 20              moltype = AA  length = 128
FEATURE                    Location/Qualifiers
REGION                     1..128
                           note = hu.14H11c.V3-53*1.H6 VH
source                     1..128
                           mol_type = protein
                           organism = synthetic construct
SEQUENCE: 20
EQQLVESGGG LIQPGGSLRL SCAASGFSFS SSYYMSWVRQ APGKGLEWIA SIYAGSSGAP    60
YYAGWAKGRF TISKDNSKNT VYLQMNSLRA EDTAVYFCAR EGFAETGGYG YAAYFNLWGP   120
GTLVTVSS                                                           128

SEQ ID NO: 21              moltype = AA  length = 128
FEATURE                    Location/Qualifiers
REGION                     1..128
                           note = hu.14H11c.V3-53*1.H7 VH
source                     1..128
                           mol_type = protein
                           organism = synthetic construct
SEQUENCE: 21
EQQLVESGGG LIQPGGSLRL SCAASGFSFS SSYYMSWVRQ APGKGLEWIA SIYAGSSGAP    60
YYAGWAKGRF TISKDSSKNT LYLQMNSLRA EDTAVYFCAR EGFAETGGYG YAAYFNLWGP   120
GTLVTVSS                                                           128

SEQ ID NO: 22              moltype = AA  length = 128
FEATURE                    Location/Qualifiers
REGION                     1..128
                           note = hu.14H11c.V3-53*1.H8 VH
source                     1..128
                           mol_type = protein
                           organism = synthetic construct
SEQUENCE: 22
EQQLVESGGG LIQPGGSLRL SCAASGFSFS SSYYMSWVRQ APGKGLEWIA SIYAGSSGAP    60
YYAGWAKGRF TISKDSSKNT VYLQMNSLRA EDTAVYYCAR EGFAETGGYG YAAYFNLWGP   120
GTLVTVSS                                                           128

SEQ ID NO: 23              moltype = AA  length = 128
FEATURE                    Location/Qualifiers
REGION                     1..128
                           note = hu.14H11c.V3-53*1.H9 VH
source                     1..128
                           mol_type = protein
                           organism = synthetic construct
SEQUENCE: 23
EQQLVESGGG LIQPGGSLRL SCAASGFSFS SSYYMSWVRQ APGKGLEWIA SIYAGSSGAP    60
YYAGWAKGRF TISKDSSKNT VYLQMNSLRA EDTAVYFCAR EGFAETGGYG YAAYFNLWGQ   120
GTLVTVSS                                                           128

SEQ ID NO: 24              moltype = AA  length = 128
```

```
FEATURE                 Location/Qualifiers
REGION                  1..128
                        note = hu.14H11c.V3-53*1.H10 VH
source                  1..128
                        mol_type = protein
                        organism = synthetic construct
SEQUENCE: 24
EVQLVESGGG LIQPGGSLRL SCAASGFSFS SSYYMSWVRQ APGKGLEWVS SIYAGSSGAP    60
YYAGWAKGRF TISRDNSKNT LYLQMNSLRA EDTAVYYCAR EGFAETGGYG YAAYFNLWGQ   120
GTLVTVSS                                                           128

SEQ ID NO: 25           moltype = AA  length = 128
FEATURE                 Location/Qualifiers
REGION                  1..128
                        note = hu.14H11c.V3-53*4.H1 VH
source                  1..128
                        mol_type = protein
                        organism = synthetic construct
SEQUENCE: 25
EQQLVESGGG LVQPGGSLRL SCAASGFSFS SSYYMSWVRQ APGKGLEWIA SIYAGSSGAP    60
YYAGWAKGRF TISKHSSKNT VYLQMNSLRA EDTAVYFCAR EGFAETGGYG YAAYFNLWGP   120
GTLVTVSS                                                           128

SEQ ID NO: 26           moltype = AA  length = 128
FEATURE                 Location/Qualifiers
REGION                  1..128
                        note = hu.14H11c.V3-23.H1 VH
source                  1..128
                        mol_type = protein
                        organism = synthetic construct
SEQUENCE: 26
EQQLLESGGG LVQPGGSLRL SCAASGFSFS SSYYMSWVRQ APGKGLEWIA SIYAGSSGAP    60
YYAGWAKGRF TISKDSSKNT VYLQMNSLRA EDTAVYFCAR EGFAETGGYG YAAYFNLWGP   120
GTLVTVSS                                                           128

SEQ ID NO: 27           moltype = AA  length = 128
FEATURE                 Location/Qualifiers
REGION                  1..128
                        note = hu.14H11c.V3-33*2.H1 VH
source                  1..128
                        mol_type = protein
                        organism = synthetic construct
SEQUENCE: 27
EQQLVESGGG VVQPGRSLRL SCAASGFSFS SSYYMSWVRQ APGKGLEWIA SIYAGSSGAP    60
YYAGWAKGRF TISKDSSTNT VFLQMNSLRA EDTAVYFCAR EGFAETGGYG YAAYFNLWGP   120
GTLVTVSS                                                           128

SEQ ID NO: 28           moltype = AA  length = 128
FEATURE                 Location/Qualifiers
REGION                  1..128
                        note = hu.14H11c.V3-21.H1 VH
source                  1..128
                        mol_type = protein
                        organism = synthetic construct
SEQUENCE: 28
EQQLVESGGG LVKPGGSLRL SCAASGFSFS SSYYMSWVRQ APGKGLEWIA SIYAGSSGAP    60
YYAGWAKGRF TISKDTASTS VYLQMNSLRA EDTAVYFCAR EGFAETGGYG YAAYFNLWGP   120
GTLVTVSS                                                           128

SEQ ID NO: 29           moltype = AA  length = 128
FEATURE                 Location/Qualifiers
REGION                  1..128
                        note = hu.14H11c-H11 VH
source                  1..128
                        mol_type = protein
                        organism = synthetic construct
SEQUENCE: 29
EQQLVESGGG LIQPGGSLRL SCAASGFSFS SSYYMSWVRQ APGKGLEWVS SIYAGSSGAP    60
YYAGWAKGRF TISRDNSKNT LYLQMNSLRA EDTAVYYCAR EGFAETGGYG YAAYFNLWGP   120
GTLVTVSS                                                           128

SEQ ID NO: 30           moltype = AA  length = 128
FEATURE                 Location/Qualifiers
REGION                  1..128
                        note = hu.14H11c-H11.Q39E VH
source                  1..128
                        mol_type = protein
                        organism = synthetic construct
SEQUENCE: 30
```

| | | |
|---|---|---|
| EQQLVESGGG | LIQPGGSLRL SCAASGFSFS SSYYMSWVRE APGKGLEWVS SIYAGSSGAP | 60 |
| YYAGWAKGRF | TISRDNSKNT LYLQMNSLRA EDTAVYYCAR EGFAETGGYG YAAYFNLWGP | 120 |
| GTLVTVSS | | 128 |

SEQ ID NO: 31  moltype = AA  length = 110
FEATURE        Location/Qualifiers
REGION         1..110
               note = hu.14H11c.K1-39.L1 VL
source         1..110
               mol_type = protein
               organism = synthetic construct
SEQUENCE: 31

| | | |
|---|---|---|
| DIQMTQSPSS | LSASVGDRVT ITCLASEDIA SSVSWYQQKP GKPPKLLIYG ASNLESGVPS | 60 |
| RFSGSGSGTD | YTLTISSLQP EDFATYYCLG GYSYSSTGTA FGGGTKVEIK | 110 |

SEQ ID NO: 32  moltype = AA  length = 110
FEATURE        Location/Qualifiers
REGION         1..110
               note = hu.14H11c.K1-39.L2 VL
source         1..110
               mol_type = protein
               organism = synthetic construct
SEQUENCE: 32

| | | |
|---|---|---|
| DIQMTQSPSS | LSASVGDRVT ITCLASEDIA SSVSWYQQKP GKAPKLLIYG ASNLESGVPS | 60 |
| RFSGSGSGTD | YTLTISSLQP EDFATYYCLG GYSYSSTGTA FGGGTKVEIK | 110 |

SEQ ID NO: 33  moltype = AA  length = 110
FEATURE        Location/Qualifiers
REGION         1..110
               note = hu.14H11c.K1-39.L3 VL
source         1..110
               mol_type = protein
               organism = synthetic construct
SEQUENCE: 33

| | | |
|---|---|---|
| DIQMTQSPSS | LSASVGDRVT ITCLASEDIA SSVSWYQQKP GKPPKLLIYG ASNLESGVPS | 60 |
| RFSGSGSGTD | FTLTISSLQP EDFATYYCLG GYSYSSTGTA FGGGTKVEIK | 110 |

SEQ ID NO: 34  moltype = AA  length = 110
FEATURE        Location/Qualifiers
REGION         1..110
               note = hu.14H11c.K1-39.L4 VL
source         1..110
               mol_type = protein
               organism = synthetic construct
SEQUENCE: 34

| | | |
|---|---|---|
| DIQMTQSPSS | LSASVGDRVT ITCLASEDIA SSVSWYQQKP GKAPKLLIYG ASNLESGVPS | 60 |
| RFSGSGSGTD | FTLTISSLQP EDFATYYCLG GYSYSSTGTA FGGGTKVEIK | 110 |

SEQ ID NO: 35  moltype = AA  length = 110
FEATURE        Location/Qualifiers
REGION         1..110
               note = hu.14H11c.K1-5.L1 VL
source         1..110
               mol_type = protein
               organism = synthetic construct
SEQUENCE: 35

| | | |
|---|---|---|
| DIQMTQSPST | LSASVGDRVT ITCLASEDIA SSVSWYQQKP GKPPKLLIYG ASNLESGVPS | 60 |
| RFSGSGSGTE | YTLTISSLQP DDFATYYCLG GYSYSSTGTA FGGGTKVEIK | 110 |

SEQ ID NO: 36  moltype = AA  length = 110
FEATURE        Location/Qualifiers
REGION         1..110
               note = hu.14H11c.K1-8.L1 VL
source         1..110
               mol_type = protein
               organism = synthetic construct
SEQUENCE: 36

| | | |
|---|---|---|
| AIRMTQSPSS | FSASTGDRVT ITCLASEDIA SSVSWYQQKP GKPPKLLIYG ASNLESGVPS | 60 |
| RFSGSGSGTD | YTLTISSLQP EDFATYYCLG GYSYSSTGTA FGGGTKVEIK | 110 |

SEQ ID NO: 37  moltype = AA  length = 110
FEATURE        Location/Qualifiers
REGION         1..110
               note = hu.14H11c.K1-6.L1 VL
source         1..110
               mol_type = protein
               organism = synthetic construct
SEQUENCE: 37

| | | |
|---|---|---|
| AIQMTQSPSS | LSASVGDRVT ITCLASEDIA SSVSWYQQKP GKPPKLLIYG ASNLESGVPS | 60 |

-continued

```
RFSGSGSGTD YTLTISSLQP EDFATYYCLG GYSYSSTGTA FGGGTKVEIK            110

SEQ ID NO: 38           moltype = AA   length = 110
FEATURE                 Location/Qualifiers
REGION                  1..110
                        note = hu.14H11c-L2.Q38K VL
source                  1..110
                        mol_type = protein
                        organism = synthetic construct
SEQUENCE: 38
DIQMTQSPSS LSASVGDRVT ITCLASEDIA SSVSWYQKKP GKAPKLLIYG ASNLESGVPS  60
RFSGSGSGTD YTLTISSLQP EDFATYYCLG GYSYSSTGTA FGGGTKVEIK            110

SEQ ID NO: 39           moltype = AA   length = 5
FEATURE                 Location/Qualifiers
REGION                  1..5
                        note = CDRH1
source                  1..5
                        mol_type = protein
                        organism = synthetic construct
SEQUENCE: 39
SYGVT                                                             5

SEQ ID NO: 40           moltype = AA   length = 17
FEATURE                 Location/Qualifiers
REGION                  1..17
                        note = CDRH2
source                  1..17
                        mol_type = protein
                        organism = synthetic construct
SEQUENCE: 40
YITSNYGVSY YASWAKS                                                17

SEQ ID NO: 41           moltype = AA   length = 17
FEATURE                 Location/Qualifiers
REGION                  1..17
                        note = CDRH2
source                  1..17
                        mol_type = protein
                        organism = synthetic construct
SEQUENCE: 41
YITSVYGVSY YASWAKS                                                17

SEQ ID NO: 42           moltype = AA   length = 11
FEATURE                 Location/Qualifiers
REGION                  1..11
                        note = CDRH3
source                  1..11
                        mol_type = protein
                        organism = synthetic construct
SEQUENCE: 42
ENPDYGYAYD A                                                      11

SEQ ID NO: 43           moltype = AA   length = 11
FEATURE                 Location/Qualifiers
REGION                  1..11
                        note = CDRL1
source                  1..11
                        mol_type = protein
                        organism = synthetic construct
SEQUENCE: 43
QASESISNEL S                                                      11

SEQ ID NO: 44           moltype = AA   length = 11
FEATURE                 Location/Qualifiers
REGION                  1..11
                        note = CDRL1
source                  1..11
                        mol_type = protein
                        organism = synthetic construct
SEQUENCE: 44
QASESISNEL K                                                      11

SEQ ID NO: 45           moltype = AA   length = 7
FEATURE                 Location/Qualifiers
REGION                  1..7
                        note = CDRL2
source                  1..7
                        mol_type = protein
```

```
                        organism = synthetic construct
SEQUENCE: 45
YASTLAS                                                                  7

SEQ ID NO: 46           moltype = AA  length = 12
FEATURE                 Location/Qualifiers
REGION                  1..12
                        note = CDRL3
source                  1..12
                        mol_type = protein
                        organism = synthetic construct
SEQUENCE: 46
AQGFGSSGVE NV                                                           12

SEQ ID NO: 47           moltype = AA  length = 12
FEATURE                 Location/Qualifiers
REGION                  1..12
                        note = CDRL3
source                  1..12
                        mol_type = protein
                        organism = synthetic construct
SEQUENCE: 47
AQGYGSSGVE NV                                                           12

SEQ ID NO: 48           moltype = AA  length = 12
FEATURE                 Location/Qualifiers
REGION                  1..12
                        note = CDRL3
source                  1..12
                        mol_type = protein
                        organism = synthetic construct
SEQUENCE: 48
AQGFGSFGVE NV                                                           12

SEQ ID NO: 49           moltype = AA  length = 12
FEATURE                 Location/Qualifiers
REGION                  1..12
                        note = CDRL3
source                  1..12
                        mol_type = protein
                        organism = synthetic construct
SEQUENCE: 49
AQGYGSFGVE NV                                                           12

SEQ ID NO: 50           moltype = AA  length = 120
FEATURE                 Location/Qualifiers
REGION                  1..120
                        note = hu.10C5-H28L5 VH
source                  1..120
                        mol_type = protein
                        organism = synthetic construct
SEQUENCE: 50
EVQLVESGGG LVQPGGSLRL SCAASGFSLS SYGVTWVRQA PGKGLEWIGY ITSNYGVSYY        60
ASWAKSRSTI SRDTSKNTVY LQMGSLRAED MAVYYCAREN PDYGYAYDAW GQGTTVTVSS       120

SEQ ID NO: 51           moltype = AA  length = 110
FEATURE                 Location/Qualifiers
REGION                  1..110
                        note = hu.10C5-H28L5 VL
source                  1..110
                        mol_type = protein
                        organism = synthetic construct
SEQUENCE: 51
AIRMTQSPSS FSASTGDRVT ITCQASESIS NELSWYQQKP GKAPKLLIYY ASTLASGVPS        60
RFSGSGSGTD FTLTISSLQP EDFATYYCAQ GFGSSGVENV FGGGTKVEIK                 110

SEQ ID NO: 52           moltype = AA  length = 120
FEATURE                 Location/Qualifiers
REGION                  1..120
                        note = hu.10C5-H28.N53V VH
source                  1..120
                        mol_type = protein
                        organism = synthetic construct
SEQUENCE: 52
EVQLVESGGG LVQPGGSLRL SCAASGFSLS SYGVTWVRQA PGKGLEWIGY ITSVYGVSYY        60
ASWAKSRSTI SRDTSKNTVY LQMGSLRAED MAVYYCAREN PDYGYAYDAW GQGTTVTVSS       120

SEQ ID NO: 53           moltype = AA  length = 120
FEATURE                 Location/Qualifiers
```

```
REGION                  1..120
                        note = hu.10C5-H28.Q39K.N53V VH
source                  1..120
                        mol_type = protein
                        organism = synthetic construct
SEQUENCE: 53
EVQLVESGGG LVQPGGSLRL SCAASGFSLS SYGVTWVRKA PGKGLEWIGY ITSVYGVSYY    60
ASWAKSRSTI SRDTSKNTVY LQMGSLRAED MAVYYCAREN PDYGYAYDAW GQGTTVTVSS   120

SEQ ID NO: 54           moltype = AA  length = 110
FEATURE                 Location/Qualifiers
REGION                  1..110
                        note = hu.10C5-L5.S34K VL
source                  1..110
                        mol_type = protein
                        organism = synthetic construct
SEQUENCE: 54
AIRMTQSPSS FSASTGDRVT ITCQASESIS NELKWYQQKP GKAPKLLIYY ASTLASGVPS    60
RFSGSGSGTD FTLTISSLQP EDFATYYCAQ GFGSSGVENV FGGGTKVEIK              110

SEQ ID NO: 55           moltype = AA  length = 110
FEATURE                 Location/Qualifiers
REGION                  1..110
                        note = hu.10C5-L5.F92Y VL
source                  1..110
                        mol_type = protein
                        organism = synthetic construct
SEQUENCE: 55
AIRMTQSPSS FSASTGDRVT ITCQASESIS NELSWYQQKP GKAPKLLIYY ASTLASGVPS    60
RFSGSGSGTD FTLTISSLQP EDFATYYCAQ GYGSSGVENV FGGGTKVEIK              110

SEQ ID NO: 56           moltype = AA  length = 110
FEATURE                 Location/Qualifiers
REGION                  1..110
                        note = hu.10C5-L5.S95F VL
source                  1..110
                        mol_type = protein
                        organism = synthetic construct
SEQUENCE: 56
AIRMTQSPSS FSASTGDRVT ITCQASESIS NELSWYQQKP GKAPKLLIYY ASTLASGVPS    60
RFSGSGSGTD FTLTISSLQP EDFATYYCAQ GFGSFGVENV FGGGTKVEIK              110

SEQ ID NO: 57           moltype = AA  length = 110
FEATURE                 Location/Qualifiers
REGION                  1..110
                        note = hu.10C5-L5.S34K.F92Y VL
source                  1..110
                        mol_type = protein
                        organism = synthetic construct
SEQUENCE: 57
AIRMTQSPSS FSASTGDRVT ITCQASESIS NELKWYQQKP GKAPKLLIYY ASTLASGVPS    60
RFSGSGSGTD FTLTISSLQP EDFATYYCAQ GYGSSGVENV FGGGTKVEIK              110

SEQ ID NO: 58           moltype = AA  length = 110
FEATURE                 Location/Qualifiers
REGION                  1..110
                        note = hu.10C5-L5.S34K.S95F VL
source                  1..110
                        mol_type = protein
                        organism = synthetic construct
SEQUENCE: 58
AIRMTQSPSS FSASTGDRVT ITCQASESIS NELKWYQQKP GKAPKLLIYY ASTLASGVPS    60
RFSGSGSGTD FTLTISSLQP EDFATYYCAQ GFGSFGVENV FGGGTKVEIK              110

SEQ ID NO: 59           moltype = AA  length = 110
FEATURE                 Location/Qualifiers
REGION                  1..110
                        note = hu.10C5-L5.F92Y.S95F VL
source                  1..110
                        mol_type = protein
                        organism = synthetic construct
SEQUENCE: 59
AIRMTQSPSS FSASTGDRVT ITCQASESIS NELSWYQQKP GKAPKLLIYY ASTLASGVPS    60
RFSGSGSGTD FTLTISSLQP EDFATYYCAQ GYGSFGVENV FGGGTKVEIK              110

SEQ ID NO: 60           moltype = AA  length = 110
FEATURE                 Location/Qualifiers
REGION                  1..110
                        note = hu.10C5-L5.S34K.F92Y.S95F VL
```

```
source                   1..110
                         mol_type = protein
                         organism = synthetic construct
SEQUENCE: 60
AIRMTQSPSS FSASTGDRVT ITCQASESIS NELKWYQQKP GKAPKLLIYY ASTLASGVPS    60
RFSGSGSGTD FTLTISSLQP EDFATYYCAQ GYGSFGVENV FGGGTKVEIK              110

SEQ ID NO: 61            moltype = AA  length = 110
FEATURE                  Location/Qualifiers
REGION                   1..110
                         note = hu.10C5-L5.Q38E.S34K VL
source                   1..110
                         mol_type = protein
                         organism = synthetic construct
SEQUENCE: 61
AIRMTQSPSS FSASTGDRVT ITCQASESIS NELKWYQEKP GKAPKLLIYY ASTLASGVPS    60
RFSGSGSGTD FTLTISSLQP EDFATYYCAQ GFGSSGVENV FGGGTKVEIK              110

SEQ ID NO: 62            moltype = AA  length = 110
FEATURE                  Location/Qualifiers
REGION                   1..110
                         note = hu.10C5-L5.Q38E.F92Y VL
source                   1..110
                         mol_type = protein
                         organism = synthetic construct
SEQUENCE: 62
AIRMTQSPSS FSASTGDRVT ITCQASESIS NELSWYQEKP GKAPKLLIYY ASTLASGVPS    60
RFSGSGSGTD FTLTISSLQP EDFATYYCAQ GYGSSGVENV FGGGTKVEIK              110

SEQ ID NO: 63            moltype = AA  length = 110
FEATURE                  Location/Qualifiers
REGION                   1..110
                         note = hu.10C5-L5.Q38E.S95F VL
source                   1..110
                         mol_type = protein
                         organism = synthetic construct
SEQUENCE: 63
AIRMTQSPSS FSASTGDRVT ITCQASESIS NELSWYQEKP GKAPKLLIYY ASTLASGVPS    60
RFSGSGSGTD FTLTISSLQP EDFATYYCAQ GFGSFGVENV FGGGTKVEIK              110

SEQ ID NO: 64            moltype = AA  length = 110
FEATURE                  Location/Qualifiers
REGION                   1..110
                         note = hu.10C5-L5.Q38E.S34K.F92Y VL
source                   1..110
                         mol_type = protein
                         organism = synthetic construct
SEQUENCE: 64
AIRMTQSPSS FSASTGDRVT ITCQASESIS NELKWYQEKP GKAPKLLIYY ASTLASGVPS    60
RFSGSGSGTD FTLTISSLQP EDFATYYCAQ GYGSSGVENV FGGGTKVEIK              110

SEQ ID NO: 65            moltype = AA  length = 110
FEATURE                  Location/Qualifiers
REGION                   1..110
                         note = hu.10C5-L5.Q38E.S34K.S95F VL
source                   1..110
                         mol_type = protein
                         organism = synthetic construct
SEQUENCE: 65
AIRMTQSPSS FSASTGDRVT ITCQASESIS NELKWYQEKP GKAPKLLIYY ASTLASGVPS    60
RFSGSGSGTD FTLTISSLQP EDFATYYCAQ GFGSFGVENV FGGGTKVEIK              110

SEQ ID NO: 66            moltype = AA  length = 110
FEATURE                  Location/Qualifiers
REGION                   1..110
                         note = hu.10C5-L5.Q38E.F92Y.S95F VL
source                   1..110
                         mol_type = protein
                         organism = synthetic construct
SEQUENCE: 66
AIRMTQSPSS FSASTGDRVT ITCQASESIS NELSWYQEKP GKAPKLLIYY ASTLASGVPS    60
RFSGSGSGTD FTLTISSLQP EDFATYYCAQ GYGSFGVENV FGGGTKVEIK              110

SEQ ID NO: 67            moltype = AA  length = 110
FEATURE                  Location/Qualifiers
REGION                   1..110
                         note = hu.10C5-L5.Q38E.S34K.F92Y.S95F VL
source                   1..110
                         mol_type = protein
```

```
                            organism = synthetic construct
SEQUENCE: 67
AIRMTQSPSS FSASTGDRVT ITCQASESIS NELKWYQEKP GKAPKLLIYY ASTLASGVPS    60
RFSGSGSGTD FTLTISSLQP EDFATYYCAQ GYGSFGVENV FGGGTKVEIK              110

SEQ ID NO: 68           moltype = AA   length = 5
FEATURE                 Location/Qualifiers
REGION                  1..5
                        note = CDRH1
source                  1..5
                        mol_type = protein
                        organism = synthetic construct
SEQUENCE: 68
SYGVS                                                                 5

SEQ ID NO: 69           moltype = AA   length = 16
FEATURE                 Location/Qualifiers
REGION                  1..16
                        note = CDRH2
source                  1..16
                        mol_type = protein
                        organism = synthetic construct
SEQUENCE: 69
FIGSGGFAYY ASWAKS                                                    16

SEQ ID NO: 70           moltype = AA   length = 16
FEATURE                 Location/Qualifiers
REGION                  1..16
                        note = CDRH2
source                  1..16
                        mol_type = protein
                        organism = synthetic construct
SEQUENCE: 70
FIGSAGFAYY ASWAKS                                                    16

SEQ ID NO: 71           moltype = AA   length = 11
FEATURE                 Location/Qualifiers
REGION                  1..11
                        note = CDRH3
source                  1..11
                        mol_type = protein
                        organism = synthetic construct
SEQUENCE: 71
DDVGGGKSLD I                                                         11

SEQ ID NO: 72           moltype = AA   length = 11
FEATURE                 Location/Qualifiers
REGION                  1..11
                        note = CDRH3
source                  1..11
                        mol_type = protein
                        organism = synthetic construct
SEQUENCE: 72
DDVQGGKSLD I                                                         11

SEQ ID NO: 73           moltype = AA   length = 11
FEATURE                 Location/Qualifiers
REGION                  1..11
                        note = CDRL1
source                  1..11
                        mol_type = protein
                        organism = synthetic construct
SEQUENCE: 73
QASQSISSYL S                                                         11

SEQ ID NO: 74           moltype = AA   length = 7
FEATURE                 Location/Qualifiers
REGION                  1..7
                        note = CDRL2
source                  1..7
                        mol_type = protein
                        organism = synthetic construct
SEQUENCE: 74
SASTLAS                                                               7

SEQ ID NO: 75           moltype = AA   length = 12
FEATURE                 Location/Qualifiers
REGION                  1..12
                        note = CDRL3
```

```
source                     1..12
                           mol_type = protein
                           organism = synthetic construct
SEQUENCE: 75
HQDYTSSNVD NT                                                                    12

SEQ ID NO: 76              moltype = AA  length = 12
FEATURE                    Location/Qualifiers
REGION                     1..12
                           note = CDRL3
source                     1..12
                           mol_type = protein
                           organism = synthetic construct
SEQUENCE: 76
VQDYTSSNVD NT                                                                    12

SEQ ID NO: 77              moltype = AA  length = 12
FEATURE                    Location/Qualifiers
REGION                     1..12
                           note = CDRL3
source                     1..12
                           mol_type = protein
                           organism = synthetic construct
SEQUENCE: 77
HQDYTSYNVD NT                                                                    12

SEQ ID NO: 78              moltype = AA  length = 12
FEATURE                    Location/Qualifiers
REGION                     1..12
                           note = CDRL3
source                     1..12
                           mol_type = protein
                           organism = synthetic construct
SEQUENCE: 78
VQDYTSYNVD NT                                                                    12

SEQ ID NO: 79              moltype = AA  length = 119
FEATURE                    Location/Qualifiers
REGION                     1..119
                           note = hu.9H5-H14L4 VH
source                     1..119
                           mol_type = protein
                           organism = synthetic construct
SEQUENCE: 79
EVQLVESGGG LIQPGGSLRL SCAASGFSLS SYGVSWVRQA PGKGLEYVGF IGSGGFAYYA                 60
SWAKSRFTIS RDNSKNTLYL QMNSLRAEDT AVYYCARDDV GGGKSLDIWG QGTLVTVSS                 119

SEQ ID NO: 80              moltype = AA  length = 110
FEATURE                    Location/Qualifiers
REGION                     1..110
                           note = hu.9H5-H14L4 VL
source                     1..110
                           mol_type = protein
                           organism = synthetic construct
SEQUENCE: 80
DIQMTQSPSS LSASVGDRVT ITCQASQSIS SYLSWYQQKP GKAPKLLIYS ASTLASGVPS                 60
RFSGSGSGTD FTLTISSLQP EDFATYYCHQ DYTSSNVDNT FGGGTKVEIK                          110

SEQ ID NO: 81              moltype = AA  length = 119
FEATURE                    Location/Qualifiers
REGION                     1..119
                           note = hu.9H5-H14.G54A VH
source                     1..119
                           mol_type = protein
                           organism = synthetic construct
SEQUENCE: 81
EVQLVESGGG LIQPGGSLRL SCAASGFSLS SYGVSWVRQA PGKGLEYVGF IGSAGFAYYA                 60
SWAKSRFTIS RDNSKNTLYL QMNSLRAEDT AVYYCARDDV GGGKSLDIWG QGTLVTVSS                 119

SEQ ID NO: 82              moltype = AA  length = 119
FEATURE                    Location/Qualifiers
REGION                     1..119
                           note = hu.9H5-H14.G98Q VH
source                     1..119
                           mol_type = protein
                           organism = synthetic construct
SEQUENCE: 82
EVQLVESGGG LIQPGGSLRL SCAASGFSLS SYGVSWVRQA PGKGLEYVGF IGSGGFAYYA                 60
SWAKSRFTIS RDNSKNTLYL QMNSLRAEDT AVYYCARDDV QGGKSLDIWG QGTLVTVSS                 119
```

```
SEQ ID NO: 83            moltype = AA   length = 119
FEATURE                  Location/Qualifiers
REGION                   1..119
                         note = hu.9H5-H14.G54A.G98Q VH
source                   1..119
                         mol_type = protein
                         organism = synthetic construct
SEQUENCE: 83
EVQLVESGGG LIQPGGSLRL SCAASGFSLS SYGVSWVRQA PGKGLEYVGF IGSAGFAYYA    60
SWAKSRFTIS RDNSKNTLYL QMNSLRAEDT AVYYCARDDV QGGKSLDIWG QGTLVTVSS    119

SEQ ID NO: 84            moltype = AA   length = 119
FEATURE                  Location/Qualifiers
REGION                   1..119
                         note = hu.9H5-H14.Q39K VH
source                   1..119
                         mol_type = protein
                         organism = synthetic construct
SEQUENCE: 84
EVQLVESGGG LIQPGGSLRL SCAASGFSLS SYGVSWVRKA PGKGLEYVGF IGSGGFAYYA    60
SWAKSRFTIS RDNSKNTLYL QMNSLRAEDT AVYYCARDDV GGGKSLDIWG QGTLVTVSS    119

SEQ ID NO: 85            moltype = AA   length = 119
FEATURE                  Location/Qualifiers
REGION                   1..119
                         note = hu.9H5-H14.Q39K.G54A VH
source                   1..119
                         mol_type = protein
                         organism = synthetic construct
SEQUENCE: 85
EVQLVESGGG LIQPGGSLRL SCAASGFSLS SYGVSWVRKA PGKGLEYVGF IGSAGFAYYA    60
SWAKSRFTIS RDNSKNTLYL QMNSLRAEDT AVYYCARDDV GGGKSLDIWG QGTLVTVSS    119

SEQ ID NO: 86            moltype = AA   length = 119
FEATURE                  Location/Qualifiers
REGION                   1..119
                         note = hu.9H5-H14.Q39K.G98Q VH
source                   1..119
                         mol_type = protein
                         organism = synthetic construct
SEQUENCE: 86
EVQLVESGGG LIQPGGSLRL SCAASGFSLS SYGVSWVRKA PGKGLEYVGF IGSGGFAYYA    60
SWAKSRFTIS RDNSKNTLYL QMNSLRAEDT AVYYCARDDV QGGKSLDIWG QGTLVTVSS    119

SEQ ID NO: 87            moltype = AA   length = 119
FEATURE                  Location/Qualifiers
REGION                   1..119
                         note = hu.9H5-H14.Q39K.G54A.G98Q VH
source                   1..119
                         mol_type = protein
                         organism = synthetic construct
SEQUENCE: 87
EVQLVESGGG LIQPGGSLRL SCAASGFSLS SYGVSWVRKA PGKGLEYVGF IGSAGFAYYA    60
SWAKSRFTIS RDNSKNTLYL QMNSLRAEDT AVYYCARDDV QGGKSLDIWG QGTLVTVSS    119

SEQ ID NO: 88            moltype = AA   length = 110
FEATURE                  Location/Qualifiers
REGION                   1..110
                         note = hu.9H5-L4.H89V VL
source                   1..110
                         mol_type = protein
                         organism = synthetic construct
SEQUENCE: 88
DIQMTQSPSS LSASVGDRVT ITCQASQSIS SYLSWYQQKP GKAPKLLIYS ASTLASGVPS    60
RFSGSGSGTD FTLTISSLQP EDFATYYCVQ DYTSSNVDNT FGGGTKVEIK              110

SEQ ID NO: 89            moltype = AA   length = 110
FEATURE                  Location/Qualifiers
REGION                   1..110
                         note = hu.9H5-L4.S95Y VL
source                   1..110
                         mol_type = protein
                         organism = synthetic construct
SEQUENCE: 89
DIQMTQSPSS LSASVGDRVT ITCQASQSIS SYLSWYQQKP GKAPKLLIYS ASTLASGVPS    60
RFSGSGSGTD FTLTISSLQP EDFATYYCHQ DYTSYNVDNT FGGGTKVEIK              110

SEQ ID NO: 90            moltype = AA   length = 110
```

```
FEATURE                 Location/Qualifiers
REGION                  1..110
                        note = hu.9H5-L4.H89V.S95Y VL
source                  1..110
                        mol_type = protein
                        organism = synthetic construct
SEQUENCE: 90
DIQMTQSPSS LSASVGDRVT ITCQASQSIS SYLSWYQQKP GKAPKLLIYS ASTLASGVPS    60
RFSGSGSGTD FTLTISSLQP EDFATYYCVQ DYTSYNVDNT FGGGTKVEIK              110

SEQ ID NO: 91           moltype = AA  length = 110
FEATURE                 Location/Qualifiers
REGION                  1..110
                        note = hu.9H5-L4.Q38E VL
source                  1..110
                        mol_type = protein
                        organism = synthetic construct
SEQUENCE: 91
DIQMTQSPSS LSASVGDRVT ITCQASQSIS SYLSWYQEKP GKAPKLLIYS ASTLASGVPS    60
RFSGSGSGTD FTLTISSLQP EDFATYYCHQ DYTSSNVDNT FGGGTKVEIK              110

SEQ ID NO: 92           moltype = AA  length = 110
FEATURE                 Location/Qualifiers
REGION                  1..110
                        note = hu.9H5-L4.Q38E.H89V VL
source                  1..110
                        mol_type = protein
                        organism = synthetic construct
SEQUENCE: 92
DIQMTQSPSS LSASVGDRVT ITCQASQSIS SYLSWYQEKP GKAPKLLIYS ASTLASGVPS    60
RFSGSGSGTD FTLTISSLQP EDFATYYCVQ DYTSSNVDNT FGGGTKVEIK              110

SEQ ID NO: 93           moltype = AA  length = 110
FEATURE                 Location/Qualifiers
REGION                  1..110
                        note = hu.9H5-L4.Q38E.S95Y VL
source                  1..110
                        mol_type = protein
                        organism = synthetic construct
SEQUENCE: 93
DIQMTQSPSS LSASVGDRVT ITCQASQSIS SYLSWYQEKP GKAPKLLIYS ASTLASGVPS    60
RFSGSGSGTD FTLTISSLQP EDFATYYCHQ DYTSYNVDNT FGGGTKVEIK              110

SEQ ID NO: 94           moltype = AA  length = 110
FEATURE                 Location/Qualifiers
REGION                  1..110
                        note = hu.9H5-L4.Q38E.H89V.S95Y VL
source                  1..110
                        mol_type = protein
                        organism = synthetic construct
SEQUENCE: 94
DIQMTQSPSS LSASVGDRVT ITCQASQSIS SYLSWYQEKP GKAPKLLIYS ASTLASGVPS    60
RFSGSGSGTD FTLTISSLQP EDFATYYCVQ DYTSYNVDNT FGGGTKVEIK              110

SEQ ID NO: 95           moltype = AA  length = 330
FEATURE                 Location/Qualifiers
REGION                  1..330
                        note = Human IgG1 heavy chain constant region (hIgG1)
source                  1..330
                        mol_type = protein
                        organism = synthetic construct
SEQUENCE: 95
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 96           moltype = AA  length = 330
FEATURE                 Location/Qualifiers
REGION                  1..330
                        note = hIgG1.N297G.Knob(T366W).S183K
source                  1..330
                        mol_type = protein
                        organism = synthetic construct
SEQUENCE: 96
ASTKGPSVFP LAPSSKSTSG GTAALGCLVK DYFPEPVTVS WNSGALTSGV HTFPAVLQSS    60
GLYSLKSVVT VPSSSLGTQT YICNVNHKPS NTKVDKKVEP KSCDKTHTCP PCAPELLGG   120
```

```
PSVFLFPPKP KDTLMISRTP EVTCVVVDVS HEDPEVKFNW YVDGVEVHNA KTKPREEQYG     180
STYRVVSVLT VLHQDWLNGK EYKCKVSNKA LPAPIEKTIS KAKGQPREPQ VYTLPPSREE     240
MTKNQVSLWC LVKGFYPSDI AVEWESNGQP ENNYKTTPPV LDSDGSFFLY SKLTVDKSRW     300
QQGNVFSCSV MHEALHNHYT QKSLSLSPGK                                     330

SEQ ID NO: 97            moltype = AA   length = 330
FEATURE                  Location/Qualifiers
REGION                   1..330
                         note = hIgG1.N297G.Hole(T366S. L368A.Y407V). S183E
source                   1..330
                         mol_type = protein
                         organism = synthetic construct
SEQUENCE: 97
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPELLGG     120
PSVFLFPPKP KDTLMISRTP EVTCVVVDVS HEDPEVKFNW YVDGVEVHNA KTKPREEQYG     180
STYRVVSVLT VLHQDWLNGK EYKCKVSNKA LPAPIEKTIS KAKGQPREPQ VYTLPPSREE     240
MTKNQVSLSC AVKGFYPSDI AVEWESNGQP ENNYKTTPPV LDSDGSFFLV SKLTVDKSRW     300
QQGNVFSCSV MHEALHNHYT QKSLSLSPGK                                     330

SEQ ID NO: 98            moltype = AA   length = 330
FEATURE                  Location/Qualifiers
REGION                   1..330
                         note = hIgG1.N297G.Knob(T366W). S183K.M428L.N434S
source                   1..330
                         mol_type = protein
                         organism = synthetic construct
SEQUENCE: 98
ASTKGPSVFP LAPSSKSTSG GTAALGCLVK DYFPEPVTVS WNSGALTSGV HTFPAVLQSS      60
GLYSLKSVVT VPSSSLGTQT YICNVNHKPS NTKVDKKVEP KSCDKTHTCP PCPAPELLGG     120
PSVFLFPPKP KDTLMISRTP EVTCVVVDVS HEDPEVKFNW YVDGVEVHNA KTKPREEQYG     180
STYRVVSVLT VLHQDWLNGK EYKCKVSNKA LPAPIEKTIS KAKGQPREPQ VYTLPPSREE     240
MTKNQVSLWC LVKGFYPSDI AVEWESNGQP ENNYKTTPPV LDSDGSFFLY SKLTVDKSRW     300
QQGNVFSCSV LHEALHSHYT QKSLSLSPGK                                     330

SEQ ID NO: 99            moltype = AA   length = 330
FEATURE                  Location/Qualifiers
REGION                   1..330
                         note = hIgG1.N297G.Hole(T366S. L368A.Y407V).S183E.
                         M428L.N434S
source                   1..330
                         mol_type = protein
                         organism = synthetic construct
SEQUENCE: 99
ASTKGPSVFP LAPSSKSTSG GTAALGCLVK DYFPEPVTVS WNSGALTSGV HTFPAVLQSS      60
GLYSLESVVT VPSSSLGTQT YICNVNHKPS NTKVDKKVEP KSCDKTHTCP PCPAPELLGG     120
PSVFLFPPKP KDTLMISRTP EVTCVVVDVS HEDPEVKFNW YVDGVEVHNA KTKPREEQYG     180
STYRVVSVLT VLHQDWLNGK EYKCKVSNKA LPAPIEKTIS KAKGQPREPQ VYTLPPSREE     240
MTKNQVSLSC AVKGFYPSDI AVEWESNGQP ENNYKTTPPV LDSDGSFFLV SKLTVDKSRW     300
QQGNVFSCSV LHEALHSHYT QKSLSLSPGK                                     330

SEQ ID NO: 100           moltype = AA   length = 291
FEATURE                  Location/Qualifiers
source                   1..291
                         mol_type = protein
                         organism = Macaca fascicularis
SEQUENCE: 100
MATARTPWMW VLCALITALL LGVTEHVLAN DDVSCDNPSN TVPSGSNRDV GAGDDARSDD      60
SSSRIINGSD CDEHTQPWQA ALLLGPNQLY CGGVLVHPQW LLTAAHCRKK VFRVRLGHYS     120
LSPVYESGQQ MFQGIKSIPH PGYSHPGHSN DLMLIKLNRR IHSTKDVRPI NVSSHCPSAG     180
TKCLVSGWGT TRSPQVHFPK VLQCLNISVL SQKRCEDAYP RQIDDTMFCA GDEAGRDSCQ     240
GDSGGPVVCN GSLQGLVSWG DYPCAKPNRP GVYTNLCKFT KWIQETIQAN S              291

SEQ ID NO: 101           moltype = AA   length = 227
FEATURE                  Location/Qualifiers
source                   1..227
                         mol_type = protein
                         organism = Macaca fascicularis
SEQUENCE: 101
IINGSDCDEH TQPWQAALLL GPNQLYCGGV LVHPQWLLTA AHCRKKVFRV RLGHYSLSPV      60
YESGQQMFQG IKSIPHPGYS HPGHSNDLML IKLNRRIHST KDVRPINVSS HCPSAGTKCL     120
VSGWGTTRSP QVHFPKVLQC LNISVLSQKR CEDAYPRQID DTMFCAGDEA GRDSCQGDSG     180
GPVVCNGSLQ GLVSWGDYPC AKPNRPGVYT NLCKFTKWIQ ETIQANS                   227

SEQ ID NO: 102           moltype = AA   length = 107
FEATURE                  Location/Qualifiers
REGION                   1..107
                         note = Human kappa light chain contstant region (hKappa)
source                   1..107
```

```
                              mol_type = protein
                              organism = synthetic construct
SEQUENCE: 102
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 103                moltype = AA   length = 107
FEATURE                       Location/Qualifiers
REGION                        1..107
                              note = hKappa.V133E
source                        1..107
                              mol_type = protein
                              organism = synthetic construct
SEQUENCE: 103
RTVAAPSVFI FPPSDEQLKS GTASVECLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 104                moltype = AA   length = 107
FEATURE                       Location/Qualifiers
REGION                        1..107
                              note = hKappa.V133K
source                        1..107
                              mol_type = protein
                              organism = synthetic construct
SEQUENCE: 104
RTVAAPSVFI FPPSDEQLKS GTASVKCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 105                moltype = AA   length = 120
FEATURE                       Location/Qualifiers
REGION                        1..120
                              note = hu.10C5-H28.G33P VH
source                        1..120
                              mol_type = protein
                              organism = synthetic construct
SEQUENCE: 105
EVQLVESGGG LVQPGGSLRL SCAASGFSLS SYPVTWVRQA PGKGLEWIGY ITSNYGVSYY    60
ASWAKSRSTI SRDTSKNTVY LQMGSLRAED MAVYYCAREN PDYGYAYDAW GQGTTVTVSS   120

SEQ ID NO: 106                moltype = AA   length = 120
FEATURE                       Location/Qualifiers
REGION                        1..120
                              note = hu.10C5-H28.G33P.N53V VH
source                        1..120
                              mol_type = protein
                              organism = synthetic construct
SEQUENCE: 106
EVQLVESGGG LVQPGGSLRL SCAASGFSLS SYPVTWVRQA PGKGLEWIGY ITSVYGVSYY    60
ASWAKSRSTI SRDTSKNTVY LQMGSLRAED MAVYYCAREN PDYGYAYDAW GQGTTVTVSS   120

SEQ ID NO: 107                moltype = AA   length = 5
FEATURE                       Location/Qualifiers
REGION                        1..5
                              note = CDRH1
source                        1..5
                              mol_type = protein
                              organism = synthetic construct
SEQUENCE: 107
SYPVT                                                                  5

SEQ ID NO: 108                moltype = AA   length = 458
FEATURE                       Location/Qualifiers
REGION                        1..458
                              note = hu14H11c heavy chain (HC) in
                                 hu.10C5VY.hu14H11c.L2H11 WT
source                        1..458
                              mol_type = protein
                              organism = synthetic construct
SEQUENCE: 108
EQQLVESGGG LIQPGGSLRL SCAASGFSFS SSYYMSWVRE APGKGLEWVS SIYAGSSGAP    60
YYAGWAKGRF TISRDNSKNT LYLQMNSLRA EDTAVYYCAR EGFAETGGYG YAAYFNLWGP   120
GTLVTVSSAS TKGPSVFPLA PSSKSTSGGT AALGCLVKDY FPEPVTVSWN SGALTSGVHT   180
FPAVLQSSGL YSLKSVVTVP SSSLGTQTYI CNVNHKPSNT KVDKKVEPKS CDKTHTCPPC   240
PAPELLGGPS VFLFPPKPKD TLMISRTPEV TCVVVDVSHE DPEVKFNWYV DGVEVHNAKT   300
KPREEQYGST YRVVSVLTVL HQDWLNGKEY KCKVSNKALP APIEKTISKA KGQPREPQVY   360
TLPPSREEMT KNQVSLWCLV KGFYPSDIAV EWESNGQPEN NYKTTPPVLD SDGSFFLYSK   420
LTVDKSRWQQ GNVFSCSVMH EALHNHYTQK SLSLSPGK                           458

SEQ ID NO: 109                moltype = AA   length = 217
```

```
FEATURE                     Location/Qualifiers
REGION                      1..217
                            note = hu14H11c light chain (LC) in
                              hu.10C5VY.hu14H11c.L2H11 WT
source                      1..217
                            mol_type = protein
                            organism = synthetic construct
SEQUENCE: 109
DIQMTQSPSS LSASVGDRVT ITCLASEDIA SSVSWYQKKP GKAPKLLIYG ASNLESGVPS    60
RFSGSGSGTD YTLTISSLQP EDFATYYCLG GYSYSSTGTA FGGGTKVEIK RTVAAPSVFI   120
FPPSDEQLKS GTASVECLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 110              moltype = AA   length = 450
FEATURE                     Location/Qualifiers
REGION                      1..450
                            note = hu.10C5VY heavy chain (HC) in
                              hu.10C5VY.hu14H11c.L2H11 WT
source                      1..450
                            mol_type = protein
                            organism = synthetic construct
SEQUENCE: 110
EVQLVESGGG LVQPGGSLRL SCAASGFSLS SYGVTWVRKA PGKGLEWIGY ITSVYGVSYY    60
ASWAKSRSTI SRDTSKNTVY LQMGSLRAED MAVYYCAREN PDYGYAYDAW GQGTTVTVSS   120
ASTKGPSVFP LAPSSKSTSG GTAALGCLVK DYFPEPVTVS WNSGALTSGV HTFPAVLQSS   180
GLYSLESVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYG   300
STYRVVSVLT VLHQDWLNGK EYKCKVSNKA LPAPIEKTIS KAKGQPREPQ VYTLPPSREE   360
MTKNQVSLSC AVKGFYPSDI AVEWESNGQP ENNYKTTPPV LDSDGSFFLV SKLTVDKSRW   420
QQGNVFSCSV MHEALHNHYT QKSLSLSPGK                                    450

SEQ ID NO: 111              moltype = AA   length = 217
FEATURE                     Location/Qualifiers
REGION                      1..217
                            note = hu.10C5VY light chain (LC) in
                              hu.10C5VY.hu14H11c.L2H11 WT
source                      1..217
                            mol_type = protein
                            organism = synthetic construct
SEQUENCE: 111
AIRMTQSPSS FSASTGDRVT ITCQASESIS NELSWYQEKP GKAPKLLIYY ASTLASGVPS    60
RFSGSGSGTD FTLTISSLQP EDFATYYCAQ GYGSSGVENV FGGGTKVEIK RTVAAPSVFI   120
FPPSDEQLKS GTASVKCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 112              moltype = AA   length = 458
FEATURE                     Location/Qualifiers
REGION                      1..458
                            note = hu14H11c heavy chain (HC) in
                              hu.10C5VY.hu14H11c.L2H11 LS
source                      1..458
                            mol_type = protein
                            organism = synthetic construct
SEQUENCE: 112
EQQLVESGGG LIQPGGSLRL SCAASGFSFS SSYYMSWVRE APGKGLEWVS SIYAGSSGAP    60
YYAGWAKGRF TISRDNSKNT LYLQMNSLRA EDTAVYYCAR EGFAETGGYG YAAYFNLWGP   120
GTLVTVSSAS TKGPSVFPLA PSSKSTSGGT AALGCLVKDY FPEPVTVSWN SGALTSGVHT   180
FPAVLQSSGL YSLKSVVTVP SSSLGTQTYI CNVNHKPSNT KVDKKVEPKS CDKTHTCPPC   240
PAPELLGGPS VFLFPPKPKD TLMISRTPEV TCVVVDVSHE DPEVKFNWYV DGVEVHNAKT   300
KPREEQYGST YRVVSVLTVL HQDWLNGKEY KCKVSNKALP APIEKTISKA KGQPREPQVY   360
TLPPSREEMT KNQVSLWCLV KGFYPSDIAV EWESNGQPEN NYKTTPPVLD SDGSFFLYSK   420
LTVDKSRWQQ GNVFSCSVLH EALHSHYTQK SLSLSPGK                           458

SEQ ID NO: 113              moltype = AA   length = 217
FEATURE                     Location/Qualifiers
REGION                      1..217
                            note = hu14H11c light chain (LC) in
                              hu.10C5VY.hu14H11c.L2H11 LS
source                      1..217
                            mol_type = protein
                            organism = synthetic construct
SEQUENCE: 113
DIQMTQSPSS LSASVGDRVT ITCLASEDIA SSVSWYQKKP GKAPKLLIYG ASNLESGVPS    60
RFSGSGSGTD YTLTISSLQP EDFATYYCLG GYSYSSTGTA FGGGTKVEIK RTVAAPSVFI   120
FPPSDEQLKS GTASVECLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 114              moltype = AA   length = 450
FEATURE                     Location/Qualifiers
```

| | | |
|---|---|---|
| REGION | 1..450 | |
| | note = hu.10C5VY heavy chain (HC) in hu.10C5VY.hu14H11c.L2H11 LS | |
| source | 1..450 | |
| | mol_type = protein | |
| | organism = synthetic construct | |

SEQUENCE: 114
```
EVQLVESGGG LVQPGGSLRL SCAASGFSLS SYGVTWVRKA PGKGLEWIGY ITSVYGVSYY   60
ASWAKSRSTI SRDTSKNTVY LQMGSLRAED MAVYYCAREN PDYGYAYDAW GQGTTVTVSS  120
ASTKGPSVFP LAPSSKSTSG GTAALGCLVK DYFPEPVTVS WNSGALTSGV HTFPAVLQSS  180
GLYSLESVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYG  300
STYRVVSVLT VLHQDWLNGK EYKCKVSNKA LPAPIEKTIS KAKGQPREPQ VYTLPPSREE  360
MTKNQVSLSC AVKGFYPSDI AVEWESNGQP ENNYKTTPPV LDSDGSFFLV SKLTVDKSRW  420
QQGNVFSCSV LHEALHSHYT QKSLSLSPGK                                  450
```

| | | |
|---|---|---|
| SEQ ID NO: 115 | moltype = AA  length = 217 | |
| FEATURE | Location/Qualifiers | |
| REGION | 1..217 | |
| | note = hu.10C5VY light chain (LC) in hu.10C5VY.hu14H11c.L2H11 LS | |
| source | 1..217 | |
| | mol_type = protein | |
| | organism = synthetic construct | |

SEQUENCE: 115
```
AIRMTQSPSS FSASTGDRVT ITCQASESIS NELSWYQEKP GKAPKLLIYY ASTLASGVPS   60
RFSGSGSGTD FTLTISSLQP EDFATYYCAQ GYGSSGVENV FGGGTKVEIK RTVAAPSVFI  120
FPPSDEQLKS GTASVKCLLN NFYPREAKVQ WKVDNALQSG NSQESVTEQD SKDSTYSLSS  180
TLTLSKADYE KHKVYACEVT HQGLSSPVTK SFNRGEC                          217
```

| | | |
|---|---|---|
| SEQ ID NO: 116 | moltype = AA  length = 126 | |
| FEATURE | Location/Qualifiers | |
| REGION | 1..126 | |
| | note = rb.14H11 Heavy Chain Variable Region (VH) | |
| source | 1..126 | |
| | mol_type = protein | |
| | organism = synthetic construct | |

SEQUENCE: 116
```
QSLEESGGDL VKPGASLTLT CTASGFSFSS SYYMCWVRQA PGKGLEWIAS IYAGSSGAPY   60
YAGWAKGRFT ISKTSSTAVT LQMSSLTAAD TATYFCAREG FAETGGYGYA AYFNLWGPGT  120
LVTVSS                                                            126
```

| | | |
|---|---|---|
| SEQ ID NO: 117 | moltype = AA  length = 330 | |
| FEATURE | Location/Qualifiers | |
| REGION | 1..330 | |
| | note = hIgG1.N297G.Knob(T366W). S183E | |
| source | 1..330 | |
| | mol_type = protein | |
| | organism = synthetic construct | |

SEQUENCE: 117
```
ASTKGPSVFP LAPSSKSTSG GTAALGCLVK DYFPEPVTVS WNSGALTSGV HTFPAVLQSS   60
GLYSLESVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYG  180
STYRVVSVLT VLHQDWLNGK EYKCKVSNKA LPAPIEKTIS KAKGQPREPQ VYTLPPSREE  240
MTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                  330
```

| | | |
|---|---|---|
| SEQ ID NO: 118 | moltype = AA  length = 330 | |
| FEATURE | Location/Qualifiers | |
| REGION | 1..330 | |
| | note = hIgG1.N297G.Hole(T366S. L368A.Y407V). S183K | |
| source | 1..330 | |
| | mol_type = protein | |
| | organism = synthetic construct | |

SEQUENCE: 118
```
ASTKGPSVFP LAPSSKSTSG GTAALGCLVK DYFPEPVTVS WNSGALTSGV HTFPAVLQSS   60
GLYSLKVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYG  180
STYRVVSVLT VLHQDWLNGK EYKCKVSNKA LPAPIEKTIS KAKGQPREPQ VYTLPPSREE  240
MTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330
```

| | | |
|---|---|---|
| SEQ ID NO: 119 | moltype = AA  length = 330 | |
| FEATURE | Location/Qualifiers | |
| REGION | 1..330 | |
| | note = hIgG1.N297G.Knob(T366W). S183E.M428L.N434S | |
| source | 1..330 | |
| | mol_type = protein | |
| | organism = synthetic construct | |

```
SEQUENCE: 119
ASTKGPSVFP LAPSSKSTSG GTAALGCLVK DYFPEPVTVS WNSGALTSGV HTFPAVLQSS    60
GLYSLESVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
MTKNQVSLWC LVKGFYPSDI AVEWESNGQP ENNYKTTPPV LDSDGSFFLY SKLTVDKSRW   300
QQGNVFSCSV LHEALHSHYT QKSLSLSPGK                                   330

SEQ ID NO: 120              moltype = AA  length = 330
FEATURE                     Location/Qualifiers
REGION                      1..330
                            note = hIgG1.N297G.Hole(T366S. L368A.Y407V).S183K.
                              M428L.N434S
source                      1..330
                            mol_type = protein
                            organism = synthetic construct
SEQUENCE: 120
ASTKGPSVFP LAPSSKSTSG GTAALGCLVK DYFPEPVTVS WNSGALTSGV HTFPAVLQSS    60
GLYSLKSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
MTKNQVSLSC AVKGFYPSDI AVEWESNGQP ENNYKTTPPV LDSDGSFFLV SKLTVDKSRW   300
QQGNVFSCSV LHEALHSHYT QKSLSLSPGK                                   330

SEQ ID NO: 121              moltype = AA  length = 10
FEATURE                     Location/Qualifiers
REGION                      1..10
                            note = KLK7 substrate
MOD_RES                     7
                            note = Nva
source                      1..10
                            mol_type = protein
                            organism = synthetic construct
SEQUENCE: 121
RPKPVEXWRK                                                          10

SEQ ID NO: 122              moltype = AA  length = 29
FEATURE                     Location/Qualifiers
REGION                      1..29
                            note = rb.14H11c VH FR1
source                      1..29
                            mol_type = protein
                            organism = synthetic construct
SEQUENCE: 122
QSLEESGGDL VKPGASLTLT CTASGFSFS                                     29

SEQ ID NO: 123              moltype = AA  length = 30
FEATURE                     Location/Qualifiers
REGION                      1..30
                            note = FR1
source                      1..30
                            mol_type = protein
                            organism = synthetic construct
SEQUENCE: 123
EQQLVESGGG LIQPGGSLRL SCAASGFSFS                                    30

SEQ ID NO: 124              moltype = AA  length = 30
FEATURE                     Location/Qualifiers
REGION                      1..30
                            note = FR1
source                      1..30
                            mol_type = protein
                            organism = synthetic construct
SEQUENCE: 124
EVQLVESGGG LIQPGGSLRL SCAASGFSFS                                    30

SEQ ID NO: 125              moltype = AA  length = 30
FEATURE                     Location/Qualifiers
REGION                      1..30
                            note = hu.14H11c.V3-53*4.H1 VH FR1
source                      1..30
                            mol_type = protein
                            organism = synthetic construct
SEQUENCE: 125
EQQLVESGGG LVQPGGSLRL SCAASGFSFS                                    30

SEQ ID NO: 126              moltype = AA  length = 30
FEATURE                     Location/Qualifiers
REGION                      1..30
```

```
                        note = hu.14H11c.V3-23.H1 VH FR1
source                  1..30
                        mol_type = protein
                        organism = synthetic construct
SEQUENCE: 126
EQQLLESGGG LVQPGGSLRL SCAASGFSFS                                              30

SEQ ID NO: 127          moltype = AA  length = 30
FEATURE                 Location/Qualifiers
REGION                  1..30
                        note = hu.14H11c.V3-33*2.H1 VH FR1
source                  1..30
                        mol_type = protein
                        organism = synthetic construct
SEQUENCE: 127
EQQLVESGGG VVQPGRSLRL SCAASGFSFS                                              30

SEQ ID NO: 128          moltype = AA  length = 30
FEATURE                 Location/Qualifiers
REGION                  1..30
                        note = hu.14H11c.V3-21.H1 VH FR1
source                  1..30
                        mol_type = protein
                        organism = synthetic construct
SEQUENCE: 128
EQQLVESGGG LVKPGGSLRL SCAASGFSFS                                              30

SEQ ID NO: 129          moltype = AA  length = 14
FEATURE                 Location/Qualifiers
REGION                  1..14
                        note = FR2
source                  1..14
                        mol_type = protein
                        organism = synthetic construct
SEQUENCE: 129
WVRQAPGKGL EWIA                                                               14

SEQ ID NO: 130          moltype = AA  length = 14
FEATURE                 Location/Qualifiers
REGION                  1..14
                        note = hu.14H11c.V3-53*1.H3 VH FR2
source                  1..14
                        mol_type = protein
                        organism = synthetic construct
SEQUENCE: 130
WVRQAPGKGL EWVA                                                               14

SEQ ID NO: 131          moltype = AA  length = 14
FEATURE                 Location/Qualifiers
REGION                  1..14
                        note = hu.14H11c.V3-53*1.H4 VH FR2
source                  1..14
                        mol_type = protein
                        organism = synthetic construct
SEQUENCE: 131
WVRQAPGKGL EWIS                                                               14

SEQ ID NO: 132          moltype = AA  length = 14
FEATURE                 Location/Qualifiers
REGION                  1..14
                        note = FR2
source                  1..14
                        mol_type = protein
                        organism = synthetic construct
SEQUENCE: 132
WVRQAPGKGL EWVS                                                               14

SEQ ID NO: 133          moltype = AA  length = 14
FEATURE                 Location/Qualifiers
REGION                  1..14
                        note = hu.14H11c-H11.Q39E VH FR2
source                  1..14
                        mol_type = protein
                        organism = synthetic construct
SEQUENCE: 133
WVREAPGKGL EWVS                                                               14

SEQ ID NO: 134          moltype = AA  length = 31
FEATURE                 Location/Qualifiers
```

```
REGION                  1..31
                        note = rb.14H11c VH FR3
source                  1..31
                        mol_type = protein
                        organism = synthetic construct
SEQUENCE: 134
RFTISKTSST AVTLQMSSLT AADTATYFCA R                                      31

SEQ ID NO: 135          moltype = AA  length = 32
FEATURE                 Location/Qualifiers
REGION                  1..32
                        note = FR3
source                  1..32
                        mol_type = protein
                        organism = synthetic construct
SEQUENCE: 135
RFTISKDSSK NTVYLQMNSL RAEDTAVYFC AR                                     32

SEQ ID NO: 136          moltype = AA  length = 32
FEATURE                 Location/Qualifiers
REGION                  1..32
                        note = hu.14H11c.V3-53*1.H5 VH FR3
source                  1..32
                        mol_type = protein
                        organism = synthetic construct
SEQUENCE: 136
RFTISRDSSK NTVYLQMNSL RAEDTAVYFC AR                                     32

SEQ ID NO: 137          moltype = AA  length = 32
FEATURE                 Location/Qualifiers
REGION                  1..32
                        note = hu.14H11c.V3-53*1.H6 VH FR3
source                  1..32
                        mol_type = protein
                        organism = synthetic construct
SEQUENCE: 137
RFTISKDNSK NTVYLQMNSL RAEDTAVYFC AR                                     32

SEQ ID NO: 138          moltype = AA  length = 32
FEATURE                 Location/Qualifiers
REGION                  1..32
                        note = hu.14H11c.V3-53*1.H7 VH FR3
source                  1..32
                        mol_type = protein
                        organism = synthetic construct
SEQUENCE: 138
RFTISKDSSK NTLYLQMNSL RAEDTAVYFC AR                                     32

SEQ ID NO: 139          moltype = AA  length = 32
FEATURE                 Location/Qualifiers
REGION                  1..32
                        note = hu.14H11c.V3-53*1.H8 VH FR3
source                  1..32
                        mol_type = protein
                        organism = synthetic construct
SEQUENCE: 139
RFTISKDSSK NTVYLQMNSL RAEDTAVYYC AR                                     32

SEQ ID NO: 140          moltype = AA  length = 32
FEATURE                 Location/Qualifiers
REGION                  1..32
                        note = FR3
source                  1..32
                        mol_type = protein
                        organism = synthetic construct
SEQUENCE: 140
RFTISRDNSK NTLYLQMNSL RAEDTAVYYC AR                                     32

SEQ ID NO: 141          moltype = AA  length = 32
FEATURE                 Location/Qualifiers
REGION                  1..32
                        note = hu.14H11c.V3-53*4.H1 VH FR3
source                  1..32
                        mol_type = protein
                        organism = synthetic construct
SEQUENCE: 141
RFTISKHSSK NTVYLQMNSL RAEDTAVYFC AR                                     32

SEQ ID NO: 142          moltype = AA  length = 32
```

```
FEATURE                 Location/Qualifiers
REGION                  1..32
                        note = hu.14H11c.V3-33*2.H1 VH FR3
source                  1..32
                        mol_type = protein
                        organism = synthetic construct
SEQUENCE: 142
RFTISKDSST NTVFLQMNSL RAEDTAVYFC AR                                    32

SEQ ID NO: 143          moltype = AA  length = 32
FEATURE                 Location/Qualifiers
REGION                  1..32
                        note = hu.14H11c.V3-21.H1 VH FR3
source                  1..32
                        mol_type = protein
                        organism = synthetic construct
SEQUENCE: 143
RFTISKDTAS TSVYLQMNSL RAEDTAVYFC AR                                    32

SEQ ID NO: 144          moltype = AA  length = 11
FEATURE                 Location/Qualifiers
REGION                  1..11
                        note = FR4
source                  1..11
                        mol_type = protein
                        organism = synthetic construct
SEQUENCE: 144
WGPGTLVTVS S                                                           11

SEQ ID NO: 145          moltype = AA  length = 11
FEATURE                 Location/Qualifiers
REGION                  1..11
                        note = FR4
source                  1..11
                        mol_type = protein
                        organism = synthetic construct
SEQUENCE: 145
WGQGTLVTVS S                                                           11

SEQ ID NO: 146          moltype = AA  length = 23
FEATURE                 Location/Qualifiers
REGION                  1..23
                        note = rb.14H11c VL FR1
source                  1..23
                        mol_type = protein
                        organism = synthetic construct
SEQUENCE: 146
AIEMTQSPPS LSASVGETVR IRC                                              23

SEQ ID NO: 147          moltype = AA  length = 23
FEATURE                 Location/Qualifiers
REGION                  1..23
                        note = FR1
source                  1..23
                        mol_type = protein
                        organism = synthetic construct
SEQUENCE: 147
DIQMTQSPSS LSASVGDRVT ITC                                              23

SEQ ID NO: 148          moltype = AA  length = 23
FEATURE                 Location/Qualifiers
REGION                  1..23
                        note = hu.14H11c.K1-5.L1 VL FR1
source                  1..23
                        mol_type = protein
                        organism = synthetic construct
SEQUENCE: 148
DIQMTQSPST LSASVGDRVT ITC                                              23

SEQ ID NO: 149          moltype = AA  length = 23
FEATURE                 Location/Qualifiers
REGION                  1..23
                        note = hu.14H11c.K1-8.L1 VL FR1
source                  1..23
                        mol_type = protein
                        organism = synthetic construct
SEQUENCE: 149
AIRMTQSPSS FSASTGDRVT ITC                                              23
```

```
SEQ ID NO: 150           moltype = AA   length = 23
FEATURE                  Location/Qualifiers
REGION                   1..23
                         note = hu.14H11c.K1-6.L1 VL FR1
source                   1..23
                         mol_type = protein
                         organism = synthetic construct
SEQUENCE: 150
AIQMTQSPSS LSASVGDRVT ITC                                                 23

SEQ ID NO: 151           moltype = AA   length = 15
FEATURE                  Location/Qualifiers
REGION                   1..15
                         note = rb.14H11c VL FR2
source                   1..15
                         mol_type = protein
                         organism = synthetic construct
SEQUENCE: 151
WYQQKPGKPP TLLIY                                                          15

SEQ ID NO: 152           moltype = AA   length = 15
FEATURE                  Location/Qualifiers
REGION                   1..15
                         note = FR2
source                   1..15
                         mol_type = protein
                         organism = synthetic construct
SEQUENCE: 152
WYQQKPGKPP KLLIY                                                          15

SEQ ID NO: 153           moltype = AA   length = 15
FEATURE                  Location/Qualifiers
REGION                   1..15
                         note = FR2
source                   1..15
                         mol_type = protein
                         organism = synthetic construct
SEQUENCE: 153
WYQQKPGKAP KLLIY                                                          15

SEQ ID NO: 154           moltype = AA   length = 15
FEATURE                  Location/Qualifiers
REGION                   1..15
                         note = hu.14H11c-L2.Q38K VL FR2
source                   1..15
                         mol_type = protein
                         organism = synthetic construct
SEQUENCE: 154
WYQKKPGKAP KLLIY                                                          15

SEQ ID NO: 155           moltype = AA   length = 32
FEATURE                  Location/Qualifiers
REGION                   1..32
                         note = rb.14H11c VL FR3
source                   1..32
                         mol_type = protein
                         organism = synthetic construct
SEQUENCE: 155
GVPPRFTGSG SGTDYTLTIG GVQAEDAATY YC                                       32

SEQ ID NO: 156           moltype = AA   length = 32
FEATURE                  Location/Qualifiers
REGION                   1..32
                         note = FR3
source                   1..32
                         mol_type = protein
                         organism = synthetic construct
SEQUENCE: 156
GVPSRFSGSG SGTDYTLTIS SLQPEDFATY YC                                       32

SEQ ID NO: 157           moltype = AA   length = 32
FEATURE                  Location/Qualifiers
REGION                   1..32
                         note = FR3
source                   1..32
                         mol_type = protein
                         organism = synthetic construct
SEQUENCE: 157
GVPSRFSGSG SGTDFTLTIS SLQPEDFATY YC                                       32
```

```
SEQ ID NO: 158           moltype = AA  length = 32
FEATURE                  Location/Qualifiers
REGION                   1..32
                         note = hu.14H11c.K1-5.L1 VL FR3
source                   1..32
                         mol_type = protein
                         organism = synthetic construct
SEQUENCE: 158
GVPSRFSGSG SGTEYTLTIS SLQPDDFATY YC                                32

SEQ ID NO: 159           moltype = AA  length = 10
FEATURE                  Location/Qualifiers
REGION                   1..10
                         note = rb.14H11c VL FR4
source                   1..10
                         mol_type = protein
                         organism = synthetic construct
SEQUENCE: 159
FGAGTKVEIK                                                         10

SEQ ID NO: 160           moltype = AA  length = 10
FEATURE                  Location/Qualifiers
REGION                   1..10
                         note = FR4
source                   1..10
                         mol_type = protein
                         organism = synthetic construct
SEQUENCE: 160
FGGGTKVEIK                                                         10

SEQ ID NO: 161           moltype = AA  length = 30
FEATURE                  Location/Qualifiers
REGION                   1..30
                         note = FR1
source                   1..30
                         mol_type = protein
                         organism = synthetic construct
SEQUENCE: 161
EVQLVESGGG LVQPGGSLRL SCAASGFSLS                                   30

SEQ ID NO: 162           moltype = AA  length = 14
FEATURE                  Location/Qualifiers
REGION                   1..14
                         note = FR2
source                   1..14
                         mol_type = protein
                         organism = synthetic construct
SEQUENCE: 162
WVRQAPGKGL EWIG                                                    14

SEQ ID NO: 163           moltype = AA  length = 14
FEATURE                  Location/Qualifiers
REGION                   1..14
                         note = hu.10C5-H28.Q39K.N54V VH FR2
source                   1..14
                         mol_type = protein
                         organism = synthetic construct
SEQUENCE: 163
WVRKAPGKGL EWIG                                                    14

SEQ ID NO: 164           moltype = AA  length = 32
FEATURE                  Location/Qualifiers
REGION                   1..32
                         note = FR3
source                   1..32
                         mol_type = protein
                         organism = synthetic construct
SEQUENCE: 164
RSTISRDTSK NTVYLQMGSL RAEDMAVYYC AR                                32

SEQ ID NO: 165           moltype = AA  length = 11
FEATURE                  Location/Qualifiers
REGION                   1..11
                         note = FR4
source                   1..11
                         mol_type = protein
                         organism = synthetic construct
SEQUENCE: 165
```

```
WGQGTTVTVS S                                                                  11

SEQ ID NO: 166          moltype = AA   length = 23
FEATURE                 Location/Qualifiers
REGION                  1..23
                        note = Exemplary LC-FR1 sequence
source                  1..23
                        mol_type = protein
                        organism = synthetic construct
SEQUENCE: 166
AIRMTQSPSS FSASTGDRVT ITC                                                     23

SEQ ID NO: 167          moltype = AA   length = 15
FEATURE                 Location/Qualifiers
REGION                  1..15
                        note = FR2
source                  1..15
                        mol_type = protein
                        organism = synthetic construct
SEQUENCE: 167
WYQQKPGKAP KLLIY                                                              15

SEQ ID NO: 168          moltype = AA   length = 15
FEATURE                 Location/Qualifiers
REGION                  1..15
                        note = FR2
source                  1..15
                        mol_type = protein
                        organism = synthetic construct
SEQUENCE: 168
WYQEKPGKAP KLLIY                                                              15

SEQ ID NO: 169          moltype = AA   length = 32
FEATURE                 Location/Qualifiers
REGION                  1..32
                        note = FR3
source                  1..32
                        mol_type = protein
                        organism = synthetic construct
SEQUENCE: 169
GVPSRFSGSG SGTDFTLTIS SLQPEDFATY YC                                           32

SEQ ID NO: 170          moltype = AA   length = 10
FEATURE                 Location/Qualifiers
REGION                  1..10
                        note = FR4
source                  1..10
                        mol_type = protein
                        organism = synthetic construct
SEQUENCE: 170
FGGGTKVEIK                                                                    10

SEQ ID NO: 171          moltype = AA   length = 30
FEATURE                 Location/Qualifiers
REGION                  1..30
                        note = FR1
source                  1..30
                        mol_type = protein
                        organism = synthetic construct
SEQUENCE: 171
EVQLVESGGG LIQPGGSLRL SCAASGFSLS                                              30

SEQ ID NO: 172          moltype = AA   length = 14
FEATURE                 Location/Qualifiers
REGION                  1..14
                        note = FR2
source                  1..14
                        mol_type = protein
                        organism = synthetic construct
SEQUENCE: 172
WVRQAPGKGL EYVG                                                               14

SEQ ID NO: 173          moltype = AA   length = 14
FEATURE                 Location/Qualifiers
REGION                  1..14
                        note = FR2
source                  1..14
                        mol_type = protein
                        organism = synthetic construct
```

```
SEQUENCE: 173
WVRKAPGKGL EYVG                                                                         14

SEQ ID NO: 174          moltype = AA  length = 32
FEATURE                 Location/Qualifiers
REGION                  1..32
                        note = FR3
source                  1..32
                        mol_type = protein
                        organism = synthetic construct
SEQUENCE: 174
RFTISRDNSK NTLYLQMNSL RAEDTAVYYC AR                                                      32

SEQ ID NO: 175          moltype = AA  length = 11
FEATURE                 Location/Qualifiers
REGION                  1..11
                        note = FR4
source                  1..11
                        mol_type = protein
                        organism = synthetic construct
SEQUENCE: 175
WGQGTLVTVS S                                                                            11

SEQ ID NO: 176          moltype = AA  length = 23
FEATURE                 Location/Qualifiers
REGION                  1..23
                        note = FR1
source                  1..23
                        mol_type = protein
                        organism = synthetic construct
SEQUENCE: 176
DIQMTQSPSS LSASVGDRVT ITC                                                               23

SEQ ID NO: 177          moltype = AA  length = 15
FEATURE                 Location/Qualifiers
REGION                  1..15
                        note = FR2
source                  1..15
                        mol_type = protein
                        organism = synthetic construct
SEQUENCE: 177
WYQQKPGKAP KLLIY                                                                        15

SEQ ID NO: 178          moltype = AA  length = 15
FEATURE                 Location/Qualifiers
REGION                  1..15
                        note = FR2
source                  1..15
                        mol_type = protein
                        organism = synthetic construct
SEQUENCE: 178
WYQEKPGKAP KLLIY                                                                        15

SEQ ID NO: 179          moltype = AA  length = 32
FEATURE                 Location/Qualifiers
REGION                  1..32
                        note = FR3
source                  1..32
                        mol_type = protein
                        organism = synthetic construct
SEQUENCE: 179
GVPSRFSGSG SGTDFTLTIS SLQPEDFATY YC                                                      32

SEQ ID NO: 180          moltype = AA  length = 10
FEATURE                 Location/Qualifiers
REGION                  1..10
                        note = FR4
source                  1..10
                        mol_type = protein
                        organism = synthetic construct
SEQUENCE: 180
FGGGTKVEIK                                                                              10

SEQ ID NO: 181          moltype = AA  length = 227
FEATURE                 Location/Qualifiers
REGION                  1..227
                        note = dummy hIgG1.N297G.Knob(T366W). S183K for one-armed
                         constructs
source                  1..227
```

```
                        mol_type = protein
                        organism = synthetic construct
SEQUENCE: 181
DKTHTCPPCP APELLGGPSV FLFPPKPKDT LMISRTPEVT CVVVDVSHED PEVKFNWYVD    60
GVEVHNAKTK PREEQYGSTY RVVSVLTVLH QDWLNGKEYK CKVSNKALPA PIEKTISKAK   120
GQPREPQVYT LPPSREEMTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 182          moltype = AA  length = 227
FEATURE                 Location/Qualifiers
REGION                  1..227
                        note = dummy hIgG1.N297G.Hole(T366S.L368A.Y407V).S183E
                         for one-armed constructs
source                  1..227
                        mol_type = protein
                        organism = synthetic construct
SEQUENCE: 182
DKTHTCPPCP APELLGGPSV FLFPPKPKDT LMISRTPEVT CVVVDVSHED PEVKFNWYVD    60
GVEVHNAKTK PREEQYGSTY RVVSVLTVLH QDWLNGKEYK CKVSNKALPA PIEKTISKAK   120
GQPREPQVYT LPPSREEMTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                 227

SEQ ID NO: 183          moltype = AA  length = 328
FEATURE                 Location/Qualifiers
REGION                  1..328
                        note = Human IgG1 heavy chain constant region (hIgG1) GK
source                  1..328
                        mol_type = protein
                        organism = synthetic construct
SEQUENCE: 183
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 184          moltype = AA  length = 328
FEATURE                 Location/Qualifiers
REGION                  1..328
                        note = hIgG1.N297G.Knob(T366W).S183K GK
source                  1..328
                        mol_type = protein
                        organism = synthetic construct
SEQUENCE: 184
ASTKGPSVFP LAPSSKSTSG GTAALGCLVK DYFPEPVTVS WNSGALTSGV HTFPAVLQSS    60
GLYSLKSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
MTKNQVSLWC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 185          moltype = AA  length = 328
FEATURE                 Location/Qualifiers
REGION                  1..328
                        note = hIgG1.N297G.Hole(T366S.L368A.Y407V).S183EGK
source                  1..328
                        mol_type = protein
                        organism = synthetic construct
SEQUENCE: 185
ASTKGPSVFP LAPSSKSTSG GTAALGCLVK DYFPEPVTVS WNSGALTSGV HTFPAVLQSS    60
GLYSLESVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
MTKNQVSLSC AVKGFYPSDI AVEWESNGQP ENNYKTTPPV LDSDGSFFLV SKLTVDKSRW   300
QQGNVFSCSV MHEALHNHYT QKSLSLSP                                     328

SEQ ID NO: 186          moltype = AA  length = 328
FEATURE                 Location/Qualifiers
REGION                  1..328
                        note = hIgG1.N297G.Knob(T366W).S183K.M428L.N434S GK
source                  1..328
                        mol_type = protein
                        organism = synthetic construct
SEQUENCE: 186
ASTKGPSVFP LAPSSKSTSG GTAALGCLVK DYFPEPVTVS WNSGALTSGV HTFPAVLQSS    60
GLYSLKSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
```

```
MTKNQVSLWC LVKGFYPSDI AVEWESNGQP ENNYKTTPPV LDSDGSFFLY SKLTVDKSRW    300
QQGNVFSCSV LHEALHSHYT QKSLSLSP                                      328

SEQ ID NO: 187           moltype = AA  length = 328
FEATURE                  Location/Qualifiers
REGION                   1..328
                         note = hIgG1.N297G.Hole(T366S. L368A.Y407V).S183E.
                           M428L.N434S GK
source                   1..328
                         mol_type = protein
                         organism = synthetic construct
SEQUENCE: 187
ASTKGPSVFP LAPSSKSTSG GTAALGCLVK DYFPEPVTVS WNSGALTSGV HTFPAVLQSS    60
GLYSLESVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
MTKNQVSLSC AVKGFYPSDI AVEWESNGQP ENNYKTTPPV LDSDGSFFLV SKLTVDKSRW   300
QQGNVFSCSV LHEALHSHYT QKSLSLSP                                      328

SEQ ID NO: 188           moltype = AA  length = 328
FEATURE                  Location/Qualifiers
REGION                   1..328
                         note = hIgG1.N297G.Knob(T366W). S183E GK
source                   1..328
                         mol_type = protein
                         organism = synthetic construct
SEQUENCE: 188
ASTKGPSVFP LAPSSKSTSG GTAALGCLVK DYFPEPVTVS WNSGALTSGV HTFPAVLQSS    60
GLYSLESVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
MTKNQVSLWC LVKGFYPSDI AVEWESNGQP ENNYKTTPPV LDSDGSFFLY SKLTVDKSRW   300
QQGNVFSCSV MHEALHNHYT QKSLSLSP                                      328

SEQ ID NO: 189           moltype = AA  length = 328
FEATURE                  Location/Qualifiers
REGION                   1..328
                         note = hIgG1.N297G.Hole(T366S. L368A.Y407V). S183K GK
source                   1..328
                         mol_type = protein
                         organism = synthetic construct
SEQUENCE: 189
ASTKGPSVFP LAPSSKSTSG GTAALGCLVK DYFPEPVTVS WNSGALTSGV HTFPAVLQSS    60
GLYSLKSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
MTKNQVSLSC AVKGFYPSDI AVEWESNGQP ENNYKTTPPV LDSDGSFFLV SKLTVDKSRW   300
QQGNVFSCSV MHEALHNHYT QKSLSLSP                                      328

SEQ ID NO: 190           moltype = AA  length = 328
FEATURE                  Location/Qualifiers
REGION                   1..328
                         note = hIgG1.N297G.Knob(T366W). S183E.M428L.N434S GK
source                   1..328
                         mol_type = protein
                         organism = synthetic construct
SEQUENCE: 190
ASTKGPSVFP LAPSSKSTSG GTAALGCLVK DYFPEPVTVS WNSGALTSGV HTFPAVLQSS    60
GLYSLESVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
MTKNQVSLWC LVKGFYPSDI AVEWESNGQP ENNYKTTPPV LDSDGSFFLY SKLTVDKSRW   300
QQGNVFSCSV LHEALHSHYT QKSLSLSP                                      328

SEQ ID NO: 191           moltype = AA  length = 328
FEATURE                  Location/Qualifiers
REGION                   1..328
                         note = hIgG1.N297G.Hole(T366S. L368A.Y407V).S183K.
                           M428L.N434S GK
source                   1..328
                         mol_type = protein
                         organism = synthetic construct
SEQUENCE: 191
ASTKGPSVFP LAPSSKSTSG GTAALGCLVK DYFPEPVTVS WNSGALTSGV HTFPAVLQSS    60
GLYSLKSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSREE   240
MTKNQVSLSC AVKGFYPSDI AVEWESNGQP ENNYKTTPPV LDSDGSFFLV SKLTVDKSRW   300
QQGNVFSCSV LHEALHSHYT QKSLSLSP                                      328
```

```
SEQ ID NO: 192          moltype = AA  length = 456
FEATURE                 Location/Qualifiers
REGION                  1..456
                        note = hu14H11c heavy chain (HC) in
                         hu.10C5VY.hu14H11c.L2H11 WT GK
source                  1..456
                        mol_type = protein
                        organism = synthetic construct
SEQUENCE: 192
EQQLVESGGG LIQPGGSLRL SCAASGFSFS SSYYMSWVRE APGKGLEWVS SIYAGSSGAP   60
YYAGWAKGRF TISRDNSKNT LYLQMNSLRA EDTAVYYCAR EGFAETGGYG YAAYFNLWGP  120
GTLVTVSSAS TKGPSVFPLA PSSKSTSGGT AALGCLVKDY FPEPVTVSWN SGALTSGVHT  180
FPAVLQSSGL YSLKSVVTVP SSSLGTQTYI CNVNHKPSNT KVDKKVEPKS CDKTHTCPPC  240
PAPELLGGPS VFLFPPKPKD TLMISRTPEV TCVVVDVSHE DPEVKFNWYV DGVEVHNAKT  300
KPREEQYGST YRVVSVLTVL HQDWLNGKEY KCKVSNKALP APIEKTISKA KGQPREPQVY  360
TLPPSREEMT KNQVSLWCLV KGFYPSDIAV EWESNGQPEN NYKTTPPVLD SDGSFFLYSK  420
LTVDKSRWQQ GNVFSCSVMH EALHNHYTQK SLSLSP                            456

SEQ ID NO: 193          moltype = AA  length = 448
FEATURE                 Location/Qualifiers
REGION                  1..448
                        note = hu.10C5VY heavy chain (HC) in
                         hu.10C5VY.hu14H11c.L2H11 WT GK
source                  1..448
                        mol_type = protein
                        organism = synthetic construct
SEQUENCE: 193
EVQLVESGGG LVQPGGSLRL SCAASGFSLS SYGVTWVRKA PGKGLEWIGY ITSVYGVSYY   60
ASWAKSRSTI SRDTSKNTVY LQMGSLRAED MAVYYCAREN PDYGYAYDAW GQGTTVTVSS  120
ASTKGPSVFP LAPSSKSTSG GTAALGCLVK DYFPEPVTVS WNSGALTSGV HTFPAVLQSS  180
GLYSLESVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYG  300
STYRVVSVLT VLHQDWLNGK EYKCKVSNKA LPAPIEKTIS KAKGQPREPQ VYTLPPSREE  360
MTKNQVSLSC AVKGFYPSDI AVEWESNGQP ENNYKTTPPV LDSDGSFFLV SKLTVDKSRW  420
QQGNVFSCSV MHEALHNHYT QKSLSLSP                                     448

SEQ ID NO: 194          moltype = AA  length = 456
FEATURE                 Location/Qualifiers
REGION                  1..456
                        note = hu14H11c heavy chain (HC) in
                         hu.10C5VY.hu14H11c.L2H11 LS GK
source                  1..456
                        mol_type = protein
                        organism = synthetic construct
SEQUENCE: 194
EQQLVESGGG LIQPGGSLRL SCAASGFSFS SSYYMSWVRE APGKGLEWVS SIYAGSSGAP   60
YYAGWAKGRF TISRDNSKNT LYLQMNSLRA EDTAVYYCAR EGFAETGGYG YAAYFNLWGP  120
GTLVTVSSAS TKGPSVFPLA PSSKSTSGGT AALGCLVKDY FPEPVTVSWN SGALTSGVHT  180
FPAVLQSSGL YSLKSVVTVP SSSLGTQTYI CNVNHKPSNT KVDKKVEPKS CDKTHTCPPC  240
PAPELLGGPS VFLFPPKPKD TLMISRTPEV TCVVVDVSHE DPEVKFNWYV DGVEVHNAKT  300
KPREEQYGST YRVVSVLTVL HQDWLNGKEY KCKVSNKALP APIEKTISKA KGQPREPQVY  360
TLPPSREEMT KNQVSLWCLV KGFYPSDIAV EWESNGQPEN NYKTTPPVLD SDGSFFLYSK  420
LTVDKSRWQQ GNVFSCSVLH EALHSHYTQK SLSLSP                            456

SEQ ID NO: 195          moltype = AA  length = 448
FEATURE                 Location/Qualifiers
REGION                  1..448
                        note = hu.10C5VY heavy chain (HC) in
                         hu.10C5VY.hu14H11c.L2H11 LS GK
source                  1..448
                        mol_type = protein
                        organism = synthetic construct
SEQUENCE: 195
EVQLVESGGG LVQPGGSLRL SCAASGFSLS SYGVTWVRKA PGKGLEWIGY ITSVYGVSYY   60
ASWAKSRSTI SRDTSKNTVY LQMGSLRAED MAVYYCAREN PDYGYAYDAW GQGTTVTVSS  120
ASTKGPSVFP LAPSSKSTSG GTAALGCLVK DYFPEPVTVS WNSGALTSGV HTFPAVLQSS  180
GLYSLESVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYG  300
STYRVVSVLT VLHQDWLNGK EYKCKVSNKA LPAPIEKTIS KAKGQPREPQ VYTLPPSREE  360
MTKNQVSLSC AVKGFYPSDI AVEWESNGQP ENNYKTTPPV LDSDGSFFLV SKLTVDKSRW  420
QQGNVFSCSV LHEALHSHYT QKSLSLSP                                     448

SEQ ID NO: 196          moltype = AA  length = 14
FEATURE                 Location/Qualifiers
REGION                  1..14
                        note = SFTI 21705 (also referred to as SFTI-KLK7)
source                  1..14
                        mol_type = protein
```

```
                        organism = synthetic construct
SEQUENCE: 196
GKCLFSNPPI CFPN                                                         14

SEQ ID NO: 197          moltype = AA  length = 314
FEATURE                 Location/Qualifiers
REGION                  1..314
                        note = SPINK9.SRE.Fc
source                  1..314
                        mol_type = protein
                        organism = synthetic construct
SEQUENCE: 197
GSIESAKQTK QMVDCSHYKK LPPGQQRFCH REYDPICGSD GKTYKNDCFF CSKVKKTDGT         60
LKFVHFGKCG NSRAQVTDKK IEPRGPTIKP CPPCKCPAPN LLGGPSVFIF PPKIKDVLMI        120
SLSPIVTCVV VDVSEDDPDV QISWFVNNVE VHTAQTQTHR EDYNSTLRVV SALPIQHQDW        180
MSGKEFKCKV NNKDLPAPIE RTISKPKGSV RAPQVYVLPP PEEEMTKKQV TLTCMVTDFM        240
PEDIYVEWTN NGKTELNYKN TEPVLDSDGS YFMYSKLRVE KKNWVERNSY SCSVVHEGLH        300
NHHTTKSFSR TPGK                                                         314

SEQ ID NO: 198          moltype = AA  length = 237
FEATURE                 Location/Qualifiers
REGION                  1..237
                        note = rb.14H11c Heavy Chain Fab
source                  1..237
                        mol_type = protein
                        organism = synthetic construct
SEQUENCE: 198
QSLEESGGDL VKPGASLTLT CTASGFSFSS SYYMSWVRQA PGKGLEWIAS IYAGSSGAPY         60
YAGWAKGRFT ISKTSSTAVT LQMSSLTAAD TATYFCAREG FAETGGYGYA AYFNLWGPGT        120
LVTVSSGQPK APSVFPLAPC CGDTPSSTVT LGCLVKGYLP EPVTVTWNSG TLTNGVRTFP        180
SVRQSSGLYS LSSVVSVTSS SQPVTCNVAH PATNTKVDKT VAPSTCSKPT HHHHHHP           237

SEQ ID NO: 199          moltype = AA  length = 215
FEATURE                 Location/Qualifiers
REGION                  1..215
                        note = rb.14H11c Light Chain Fab
source                  1..215
                        mol_type = protein
                        organism = synthetic construct
SEQUENCE: 199
AIEMTQSPPS LSASVGETVR IRCLASEDIA NSVSWYQQKP GKPPTLLIYG ASNLESGVPP         60
RFTGSGSGTD YTLTIGGVQA EDAATYYCLG GYSYSSTGTA FGAGTKVEIN RDPVAPSVLL        120
FPPSKEELTT GTATIVCVAN KFYPSDITVT WKVDGTTQQS GIENSKTPQS PEDNTYNLSS        180
TLTLTSTQYN SHKEYTCKVT QGTTSVVQSF NRGDC                                  215
```